(12) United States Patent
Novak et al.

(10) Patent No.: US 7,579,441 B2
(45) Date of Patent: Aug. 25, 2009

(54) CYTOKINE ZALPHA11 LIGAND FUSION PROTEINS

(75) Inventors: Julia E. Novak, Bainbridge Island, WA (US); Scott R. Presnell, Tacoma, WA (US); Cindy A. Sprecher, Seattle, WA (US); Donald C. Foster, Lake Forest Park, WA (US); Richard D. Holly, Seattle, WA (US); Jane A. Gross, Seattle, WA (US); Janet V. Johnston, Seattle, WA (US); Andrew J. Nelson, Shoreline, WA (US); Stacey R. Dillon, Seattle, WA (US); Angela K. Hammond, Maple Valley, WA (US)

(73) Assignee: ZymoGenetics, Inc., Seattle, WA (US)

( * ) Notice: Subject to any disclaimer, the term of this patent is extended or adjusted under 35 U.S.C. 154(b) by 195 days.

(21) Appl. No.: 11/551,811

(22) Filed: Oct. 23, 2006

(65) Prior Publication Data

US 2007/0166794 A1    Jul. 19, 2007

Related U.S. Application Data

(60) Division of application No. 10/787,442, filed on Feb. 26, 2004, now Pat. No. 7,491,800, which is a continuation of application No. 10/659,684, filed on Sep. 10, 2003, now Pat. No. 7,473,765, which is a continuation of application No. 10/295,723, filed on Nov. 15, 2002, now Pat. No. 6,686,178, which is a division of application No. 09/923,246, filed on Aug. 3, 2001, now Pat. No. 6,605,272, which is a division of application No. 09/522,217, filed on Mar. 9, 2000, now Pat. No. 6,307,024.

(60) Provisional application No. 60/123,547, filed on Mar. 9, 1999, provisional application No. 60/123,904, filed on Mar. 11, 1999, provisional application No. 60/142,013, filed on Jul. 1, 1999.

(51) Int. Cl.
*C07K 17/00* (2006.01)
*C07K 14/00* (2006.01)
*A61K 39/00* (2006.01)

(52) U.S. Cl. .................... 530/351; 530/350; 424/185.1
(58) Field of Classification Search ....................... None
See application file for complete search history.

(56) References Cited

U.S. PATENT DOCUMENTS

| | | | | |
|---|---|---|---|---|
| 6,057,128 | A | 5/2000 | Donaldson et al. | 435/69.1 |
| 6,307,024 | B1 * | 10/2001 | Novak et al. | 530/351 |
| 6,605,272 | B2 | 8/2003 | Novak et al. | 424/85.2 |
| 6,686,178 | B2 | 2/2004 | Novak et al. | 435/69.52 |
| 2003/0219433 | A1 | 11/2003 | Hansen et al. | 424/141.1 |
| 2004/0009150 | A1 | 1/2004 | Nelson et al. | |
| 2004/0016010 | A1 | 1/2004 | Kasaian et al. | |
| 2004/0110932 | A1 | 6/2004 | Novak et al. | |
| 2004/0260065 | A1 | 12/2004 | Novak et al. | |
| 2005/0265966 | A1 | 12/2005 | Kindsvogel et al. | |
| 2006/0134754 | A1 | 6/2006 | Chan et al. | |
| 2006/0269973 | A1 | 11/2006 | Yee | |
| 2007/0014800 | A1 | 1/2007 | Novak et al. | |
| 2007/0041940 | A1 | 2/2007 | Nelson et al. | |
| 2007/0041974 | A1 | 2/2007 | Novak et al. | |
| 2007/0048260 | A1 | 3/2007 | Novak et al. | |
| 2007/0048263 | A1 | 3/2007 | Meyer | |
| 2007/0048264 | A1 | 3/2007 | Kindsvogel et al. | |
| 2007/0048266 | A1 | 3/2007 | Nelson et al. | |
| 2007/0048267 | A1 | 3/2007 | Nelson et al. | |
| 2007/0048268 | A1 | 3/2007 | Nelson et al. | |
| 2007/0048269 | A1 | 3/2007 | Nelson et al. | |
| 2007/0048270 | A1 | 3/2007 | Nelson et al. | |
| 2007/0048271 | A1 | 3/2007 | Nelson et al. | |
| 2007/0048272 | A1 | 3/2007 | Nelson et al. | |
| 2007/0048273 | A1 | 3/2007 | Nelson et al. | |
| 2007/0048798 | A1 | 3/2007 | Zamost et al. | |
| 2007/0048842 | A1 | 3/2007 | Zamost et al. | |
| 2007/0048845 | A1 | 3/2007 | Novak et al. | |
| 2007/0049529 | A1 | 3/2007 | Novak et al. | |
| 2007/0049548 | A1 | 3/2007 | Nelson et al. | |
| 2007/0049549 | A1 | 3/2007 | Nelson et al. | |
| 2007/0054320 | A1 | 3/2007 | Novak et al. | |
| 2007/0059284 | A1 | 3/2007 | Nelson et al. | |
| 2007/0059825 | A1 | 3/2007 | Novak et al. | |
| 2007/0066807 | A1 | 3/2007 | Novak et al. | |
| 2007/0066808 | A1 | 3/2007 | Novak et al. | |
| 2007/0086980 | A1 | 4/2007 | Nelson et al. | |
| 2007/0092485 | A1 | 4/2007 | Novak et al. | |
| 2007/0098682 | A1 | 5/2007 | Novak et al. | |

(Continued)

FOREIGN PATENT DOCUMENTS

| | | |
|---|---|---|
| WO | 03/103589 | 12/2003 |
| WO | 2004/032857 | 4/2004 |
| WO | 2004/056392 | 7/2004 |
| WO | 2005/037306 | 4/2005 |

OTHER PUBLICATIONS

Clegg et al., "Therapeutic opportunities for IL-21," *European Cytokine Network* 14(3):28, 2003.

(Continued)

*Primary Examiner*—Christine J Saoud
*Assistant Examiner*—Jegatheesan Seharaseyon
(74) *Attorney, Agent, or Firm*—Deborah A. Sawislak

(57) ABSTRACT

Antibodies that bind to polypeptides and peptides comprising the sequence of zalpha11 Ligand as shown in SEQ ID NO: 2 are described. The antibodies may bind the full length sequence of 162 amino acid residues or a fragment thereof, including a mature polypeptide of 131 amino acid residues and smaller polypeptide and peptide sequences. The antibodies may include antibodies that are polyclonal, monoclonal, murine, humanized or neutralizing. Methods for producing the antibodies are also described.

4 Claims, 5 Drawing Sheets

U.S. PATENT DOCUMENTS

| | | |
|---|---|---|
| 2007/0098683 A1 | 5/2007 | Novak et al. |
| 2007/0099269 A1 | 5/2007 | Novak et al. |
| 2007/0122382 A1 | 5/2007 | Kindsvogel et al. |
| 2007/0128161 A1 | 6/2007 | Nelson et al. |
| 2007/0178063 A1 | 8/2007 | Kindsvogel et al. |

OTHER PUBLICATIONS

Nelson et al., "Interleukin 21 has anti-tumor activity in animal models without the toxicity of IL-2," Proceedings of the American Association for Cancer Research Annual Meeting 44:562, 2003.

Funaro et al., "Monoclonal antibodies and therapy of human cancers," *Biotechnology Advances* 18(5):385-401, 2000.

Ozaki et al., "Regulation of B cell differentiation and plasma cell generation by IL-21, a novel inducer of Blimp-1 and Bcl-6," *J Immunol.* 173(9):5361-71, 2004.

Aklulu et al., "Depletion of normal B cells with rituximab as an adjunet to IL-2 therapy for renal cell carcinoma and melanoma," *Ann Oncol.* 15(7):1109-14, 2004.

Moroz et al., "IL-21 enhances and sustains CD8+ T cell responses to achieve duragble tumor immunity: comparative evaluation of IL-2, IL-15, and IL-21," *J Immunol.* 173(2):900-9, 2004.

O'Shea et al., "Jak3 and the phatogenesis of severe combined immunodeficiency," *Mol Immunol.* 737-37, 2004.

Sivakumar et al., Interleukin-21 is a T-helper cytokine that regulates humoral immunity and cell-mediated anti-tumor responses,: *Immunology* 112(2):177-82, 2004.

Munshi, "Recent advances in the management of multiple myeloma," *Semin Hematol.* 2(4):21-6, 2004.

Rowshani et al., "Effects of CD25 monoclonal antibody on proliferative and effector functions of alloactivated human T cells in vitro," *Eur J Immunol.* 34(3):882-99, 2004.

Sievers et al., "IL-21 enhances trastuzumab-mediated killing of breast cancer cell lines in vitro," *Breast Cancer Res. And Treatment* S1(0):6075, 2004.

Kindsvogel et al., "IL-21 enhances rituximab-mediated killing of B-lymphoma cell lines in vitro and in vivo," *J. Clin. Oncol.* 22(14S):2581, 2004.

Hughes et al., "Interleukin 21 efficacy in a mouse model of metastatic renal cell carcinoma," *J. Clin. Oncol.* 22(14S)2598, 2004.

Sivakumar et al., "Interleukin-21 Elicits Durable T and NK Cytotoxicity: Basic Biology to Clinical Trials," *J. Immunother.* 27(6):S56, 2004.

Hughes et al., "Mechanisms of IL-21 Enhancement of Rituximap Efficacy in a Lymphoma Xenograft Model," *Blood* 104(11):394A, 2004.

Rastetter et al., "Rituximab: expanding role in therapy for lymphomas and autoimmume diseases," *Annu Rev Med.* 55:477-503, 2004.

Akamatsu et al., "Selected IL-21R Expression and Apoptosis Induction by IL-21 in Follicular Lymphoma," *Blood* 104(11):629A, 2004.

Ueda et al., "Expression of Functional IL-21 Receptor on adult T-cell Leukemia Cells," *Blood* 102(11), 2003.

Gitlitz et al., "Cytokine-based therapy for metastatic renal cell cancer," *Urol Clin North Am.* (3):589-600, 2003.

Ma et al., IL-21 activates both innate and adpative immunity to generate potent antitumor responses that require perforin but are independent of IFN-gamms, *J. Immunol.* 171(2):608-15, 2003.

Mehta et al., "IL-21 induces the apoptosis of resting and activated primary B cells," *J. Immunol..* 170(8):4111-8, 2003.

Strengell et al., "IL-21 up-regulates the expression of genes associated with innate immunity and Th1 response," *J Immunol.* 169(7):3600-5, 2002.

Nelson et al., "Anti-tumor Effects of Interleukin 21," Immounobiology of Lymphomna abstr. 593, 2002.

Parrish-Novak et al., "Interleukin 21 and its receptor are involved in NK cell expansion and regulation of lymphocyte function," *Nature* 408(6808):57-63, 2000.

Ro et al., "IL-21 is a Growth and Survival Factor for Human Myeloma Cells," *Blood* 98(11):abst. 3216, 2001.

U.S. Appl. No. 11/553,367, Oct. 26, 2006, Nelson et al.
U.S. Appl. No. 11/553,395, Oct. 26, 2006, Nelson et al.

* cited by examiner

```
          1            15 16            30 31            45 46            60 61            75 76            90
hIL-2     --------------- ------APTSSSTKK TQLQLEHLLLDLQMILNGINNYKN------ ---PKLTRMLTFKFY MPKKATE---LKHLQ
hIL-15    -----------AGIH VFILGCFSAGLPKTE ANWVNVISDLKKI-EDLIQSMHIDAT---- -------------LY TESDVHPSCKVTAMK
za11-Lig  --------------- --sSSQGQDRHMIRM RQLIDIVDQLKNYVNDLVPEF--------- -------------LP APEDVETNCEWSAFS
hIL-4     --------------- ----------HKCD- ITLQEIIKTLNSLTEQKTLCTELTVTDI-- -------------FA ASKNTTE----KETF
mIL-4     --------------- --------HIHGCDK NHLREIIGILNEVTGEGTPCTEMDVPNV-- -------------LT ATKNTTE----SELV
hGM-CSF   --------------- ---SPSPSTQPWEHV NAIQEARRLLNLSRDTAAEMNETV------ --------------E VISEMFD---LQEPT
mGM-CSF   --------------- -----IIVTRPWKHV EAIKEALNLLDDMPVTL---NEEV------ --------------E VVSNEFS---FKKLT 91          105 106          120 121          135 136          150 151          165 166          180
hIL-2     CLEEELKPLEEVLNL AQSKNFHLRPRDLIS NINVIVLGLKGSE----------------- --------TTFMCE- YADETATIVEFLNRW
hIL-15    CFLLELQVISLESGD ASIHDTVENLIILAN NSLSSNGNVTESG----------------- ---------CKECEE LEEK--NIKEFLQSF
za11-Lig  CFQKAQLKSANTGNN ERIINVSIKKLKRKP PSTNAGRRQKHRL----------------- --------TCPSCDS YEKK--PPKEFLERF
hIL-4     CRAATVLRQFYSHHE KDTRCLGATAQQFHR HKQLIRFLKRLDRNLWGLAGL--------- ----------NSCPV KEANQSTLENFLERL
mIL-4     CRASKVLRIFYLKHG K-TPCLKKNSSVLME LQRLFRAFRCLDS----------------- ---------SISCTM NESKSTSLKDFLESL
hGM-CSF   CLQTRLELYKQGLRG SLTKLKGPLTMMASH YKQHCPPTPE-------------------- ----------TSCA- --TQIITFESFKENL
mGM-CSF   CVQTRLKIFEQGLRG NFTKLKGALNMTASY YQTYCPPTPE-------------------- ----------TDCE- --TQVTTYADFIDSL hIL-2     ITFCQSIISTL    132
hIL-15    VHIVQMFINTS1    134
za11-Lig  KSLLQKMIHQHLSSR THGSEDS    136
hIL-4     KTIMREKYSKCSS    129
mIL-4     KSIMQMDYS    120
hGM-CSF   KDFLLVIPFDC--WE    119
mGM-CSF   KTFLTDIPFEC--KK PSQK    118
```

CYTOKINE ZALPHA11 LIGAND FUSION PROTEINS

CROSS-REFERENCE TO RELATED APPLICATIONS

This application is a divisional of U.S. patent application Ser. No. 10/787,442, filed on Feb. 26, 2004, now U.S. Pat. No. 7,491,800 which is a continuation of U.S. patent application Ser. No. 10/659,684, filed Sep. 10, 2003 now U.S. Pat. No. 7,437,765; which is a continuation of U.S. patent application Ser. No. 10/295,723, filed Nov. 15, 2002, issued as U.S. Pat. No. 6,686,178 on Feb. 3, 2004 which has been filed as reissue U.S. patent application Ser. No. 11/346,580, filed Feb. 2, 2006; which are incorporated herein by reference; which is a divisional of U.S. patent application Ser. No. 09/923,246, filed Aug. 3, 2001, issued as U.S. Pat. No. 6,605,272 on Aug. 12, 2003; which is a divisional of U.S. patent application Ser. No. 09/522,217, filed Mar. 9, 2000, issued as U.S. Pat. No. 6,307,024 on Oct. 23, 2001; which claims the benefit of U.S. Provisional Application Ser. Nos. 60/123,547, filed Mar. 9, 1999; 60/123,904, filed Mar. 11, 1999; and 60/142,013, filed Jul. 1, 1999.

BACKGROUND OF THE INVENTION

Proliferation and differentiation of cells of multicellular organisms are controlled by hormones and polypeptide growth factors. These diffusable molecules allow cells to communicate with each other and act in concert to form cells, tissues and organs, and to repair damaged tissue. Examples of hormones and growth factors include the steroid hormones (e.g. estrogen, testosterone), parathyroid hormone, follicle stimulating hormone, the interleukins, platelet derived growth factor (PDGF), epidermal growth factor (EGF), granulocyte-macrophage colony stimulating factor (GM-CSF), erythropoietin (EPO) and calcitonin.

Hormones and growth factors influence cellular metabolism by binding to receptors. Receptors may be integral membrane proteins that are linked to signaling pathways within the cell, such as second messenger systems. Other classes of receptors are soluble molecules, such as the transcription factors.

Cytokines generally stimulate proliferation or differentiation of cells of the hematopoietic lineage or participate in the immune and inflammatory response mechanisms of the body. Examples of cytokines which affect hematopoiesis are erythropoietin (EPO), which stimulates the development of red blood cells; thrombopoietin (TPO), which stimulates development of cells of the megakaryocyte lineage; and granulocyte-colony stimulating factor (G-CSF), which stimulates development of neutrophils. These cytokines are useful in restoring normal blood cell levels in patients suffering from anemia, thrombocytopenia, and neutropenia or receiving chemotherapy for cancer.

The interleukins are a family of cytokines that mediate immunological responses, including inflammation. The interleukins mediate a variety of inflammatory pathologies. Central to an immune response is the T cell, which produce many cytokines and adaptive immunity to antigens. Cytokines produced by the T cell have been classified as type 1 and type 2 (Kelso, A. *Immun. Cell Biol.* 76:300-317, 1998). Type 1 cytokines include IL-2, IFN-γ, LT-α, and are involved in inflammatory responses, viral immunity, intracellular parasite immunity and allograft rejection. Type 2 cytokines include IL-4, IL-5, IL-6, IL-10 and IL-13, and are involved in humoral responses, helminth immunity and allergic response. Shared cytokines between Type 1 and 2 include IL-3, GM-CSF and TNF-α. There is some evidence to suggest that Type 1 and Type 2 producing T cell populations preferentially migrate into different types of inflamed tissue.

Mature T cells may be activated, i.e., by an antigen or other stimulus, to produce, for example, cytokines, biochemical signaling molecules, or receptors that further influence the fate of the T cell population.

B cells can be activated via receptors on their cell surface including B cell receptor and other accessory molecules to perform accessory cell functions, such as production of cytokines.

Natural killer (NK) cells have a common progenitor cell with T cells and B cells, and play a role in immune surveillance. NK cells, which comprise up to 15% of blood lymphocytes, do not express antigen receptors, and therefore do not use MHC recognition as requirement for binding to a target cell. NK cells are involved in the recognition and killing of certain tumor cells and virally infected cells. In vivo, NK cells are believed to require activation, however, in vitro, NK cells have been shown to kill some types of tumor cells without activation.

The demonstrated in vivo activities of the cytokine family illustrate the enormous clinical potential of, and need for, other cytokines, cytokine agonists, and cytokine antagonists. The present invention addresses these needs by providing a new cytokine that stimulates cells of the hematopoietic cell lineage, as well as related compositions and methods.

The present invention provides such polypeptides for these and other uses that should be apparent to those skilled in the art from the teachings herein.

BRIEF DESCRIPTION OF THE DRAWINGS

FIG. 1 is an illustration of a multiple alignment of human IL-2, human IL-15, zalpha11 Ligand (SEQ ID NO: 2), human IL-4, mouse IL-4, human GM-CSF and mouse GM-CSF.

SUMMARY OF THE INVENTION

Figure 2A:
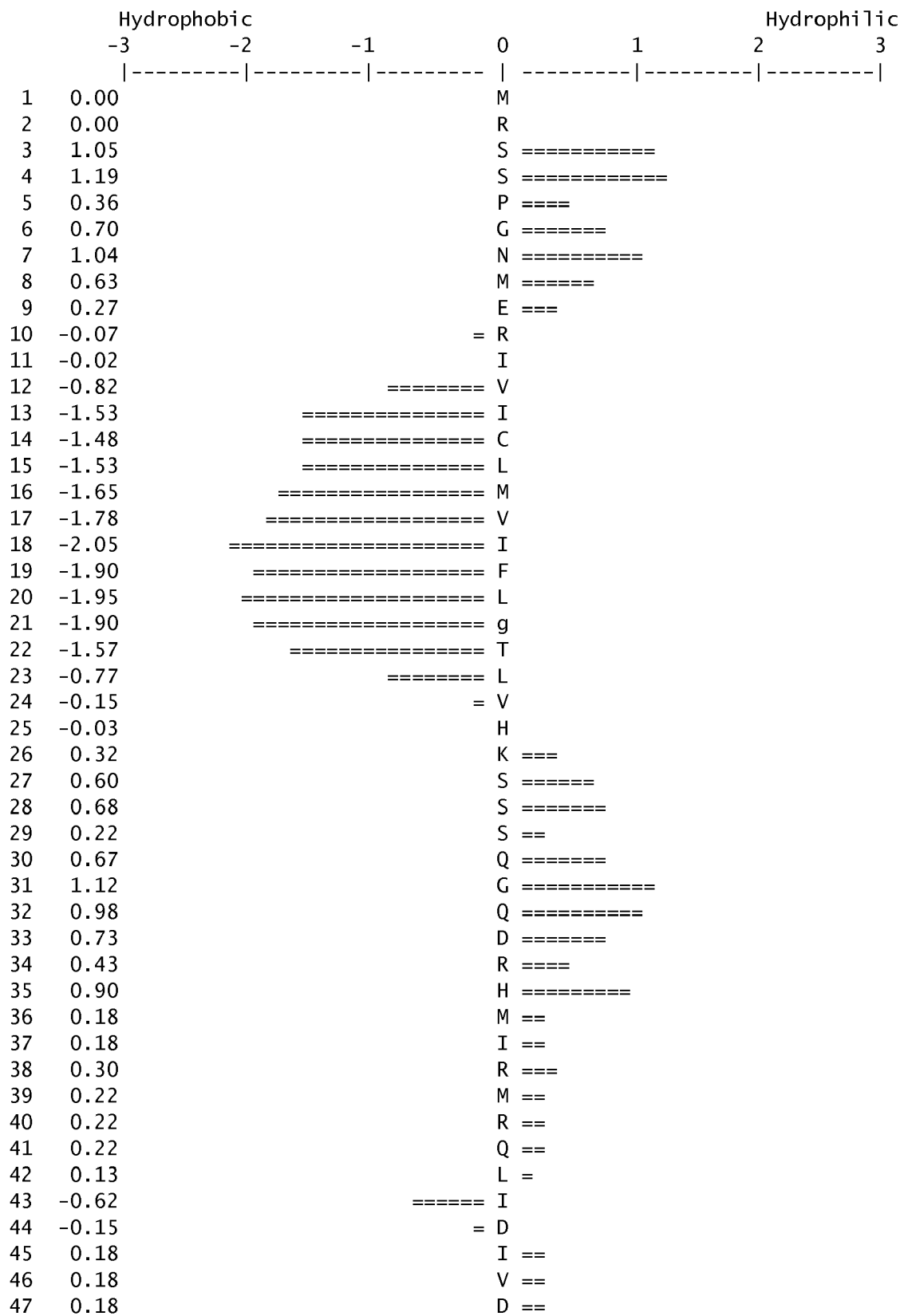
FIG. 2 is a Hopp/Woods hydrophilicity plot of human zalpha11 Ligand.
Figure 2D:
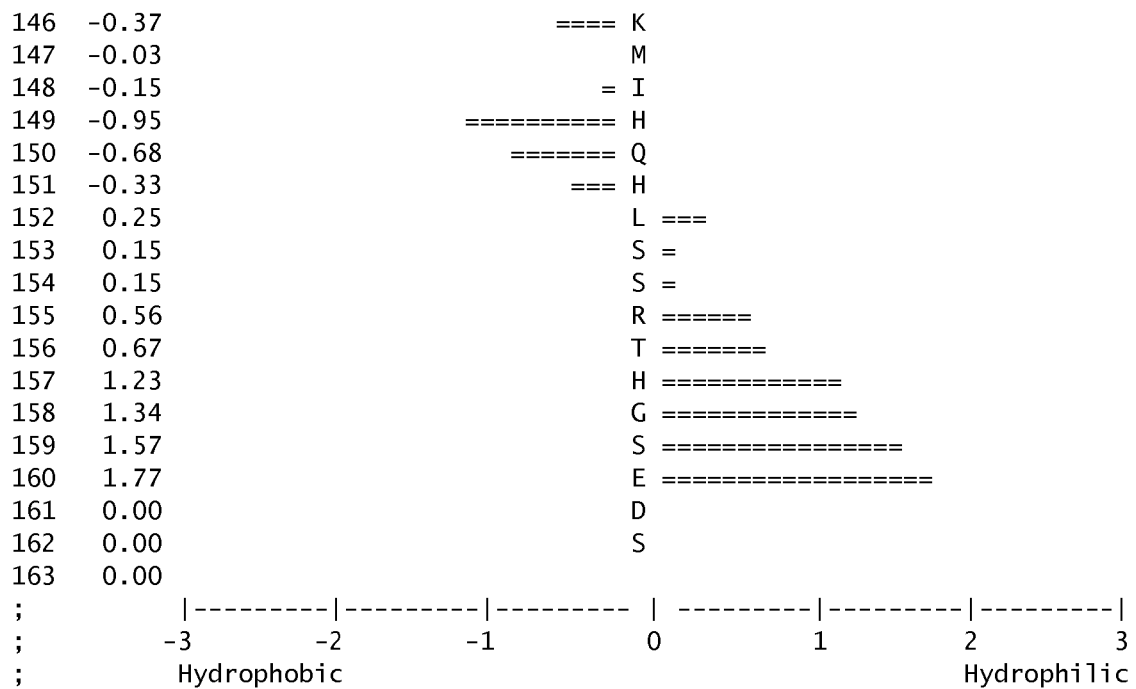

In one aspect, the present invention provides an antibody which binds to a polypeptide comprising a sequence of amino acid residues as shown in SEQ ID NO: 2 from residue 1 to residue 162. Additional embodiments of the invention include antibodies that are polyclonal, monoclonal, murine, humaninzed murine antibodies and antibodies which are neutralizing.

In another aspect, the antibody binds a polypeptide comprising residues 32 to 162 as shown in SEQ ID NO: 2. Additional embodiments of the invention include antibodies that are polyclonal, monoclonal, murine, humaninzed murine antibodies and antibodies which are neutralizing.

The present invention also provides an antibody fragment which binds to a polypeptide comprising a sequence of amino acid residues as shown in SEQ ID NO: 2 from residue 1 to residue 162.

Other aspects of the present invention provide antibodies that bind to peptides comprising a sequence of amino acid residues as shown in SEQ ID NO: 2 from residues 114 to 119, 101 to 105, 126 to 131, 113 to 118 or 158 to 162. In certain embodiments, these antibodies are polyclonal, monoclonal, murine, humaninzed murine antibodies and antibodies which are neutralizing.

Another aspect of the present invention provides a method of producing an antibody to a polypeptide comprising: inoculating an animal with a polypeptide selected from the group consisting of: (a) a polypeptide consisting of 9 to 131 amino acids, wherein the polypeptide is identical to a contiguous sequence of amino acid residues in SEQ ID NO:2 from amino acid number 32 (Gln) to amino acid number 162 (Ser); (b) a polypeptide according to claim 1; (c) a polypeptide comprising the amino acid sequence of SEQ ID NO:2 from amino acid number 41 (Gln) to amino acid number 148 (Ile); (d) a polypeptide comprising the amino acid sequence of SEQ ID NO:2 from amino acid number 41 (Gln) to amino acid number 56 (Val); (e) a polypeptide comprising the amino acid sequence of SEQ ID NO:2 from amino acid number 69 (Thr) to amino acid number 84 (Leu); (f) a polypeptide comprising the amino acid sequence of SEQ ID NO:2 from amino acid number 92 (Asn) to amino acid number 105 (Arg); (g) a polypeptide comprising the amino acid sequence of SEQ ID NO:2 from amino acid number 135 (Glu) to amino acid number 148 (Ile); (h) a polypeptide comprising the amino acid sequence of SEQ ID NO:72; (i) a polypeptide comprising the amino acid sequence of SEQ ID NO:73; (j) a polypeptide comprising the amino acid sequence of SEQ ID NO:2 from amino acid number 32 (Gln) to amino acid number 162 (Ser); (k) a polypeptide comprising the amino acid sequence of SEQ ID NO:2 from amino acid number 1 (Met) to amino acid number 162 (Ser); (l) a polypeptide comprising the amino acid sequence of SEQ ID NO:2 from amino acid number 114 to amino acid number 119; (m) a polypeptide comprising the amino acid sequence of SEQ ID NO:2 from amino acid number 101 to amino acid number 105; (n) a polypeptide comprising the amino acid sequence of SEQ ID NO:2 from amino acid number 126 to amino acid number 131; (o) a polypeptide comprising the amino acid sequence of SEQ ID NO:2 from amino acid number 113 to amino acid number 118; (p) a polypeptide comprising the amino acid sequence of SEQ ID NO:2 from amino acid number 158 to amino acid number 162; and wherein the polypeptide elicits an immune response in the animal to produce the antibody; and isolating the antibody from the animal. The present invention also includes antibodies produced by the methods described above, wherein the antibody binds to a zalpha11 Ligand polypeptide.

DESCRIPTION OF THE INVENTION

Prior to setting forth the invention in detail, it may be helpful to the understanding thereof to define the following terms:

The term "affinity tag" is used herein to denote a polypeptide segment that can be attached to a second polypeptide to provide for purification or detection of the second polypeptide or provide sites for attachment of the second polypeptide to a substrate. In principal, any peptide or protein for which an antibody or other specific binding agent is available can be used as an affinity tag. Affinity tags include a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), Glu-Glu affinity tag (Grussenmeyer et al., *Proc. Natl. Acad. Sci. USA* 82:7952-4, 1985), substance P, Flag* peptide (Hopp et al., *Biotechnology* 6:1204-10, 1988), streptavidin binding peptide, or other antigenic epitope or binding domain. See, in general, Ford et al., *Protein Expression and Purification* 2: 95-107, 1991. DNAs encoding affinity tags are available from commercial suppliers (e.g., Pharmacia Biotech, Piscataway, N.J.).

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The terms "amino-terminal" and "carboxyl-terminal" are used herein to denote positions within polypeptides. Where the context allows, these terms are used with reference to a particular sequence or portion of a polypeptide to denote proximity or relative position. For example, a certain sequence positioned carboxyl-terminal to a reference sequence within a polypeptide is located proximal to the carboxyl terminus of the reference sequence, but is not necessarily at the carboxyl terminus of the complete polypeptide.

The term "complement/anti-complement pair" denotes non-identical moieties that form a non-covalently associated, stable pair under appropriate conditions. For instance, biotin and avidin (or streptavidin) are prototypical members of a complement/anti-complement pair. Other exemplary complement/anti-complement pairs include receptor/ligand pairs, antibody/antigen (or hapten or epitope) pairs, sense/antisense polynucleotide pairs, and the like. Where subsequent dissociation of the complement/anti-complement pair is desirable, the complement/anti-complement pair preferably has a binding affinity of <109 M−1.

The term "complements of a polynucleotide molecule" denotes a polynucleotide molecule having a complementary base sequence and reverse orientation as compared to a reference sequence. For example, the sequence 5' ATGCACGGG 3' is complementary to 5' CCCGTGCAT 3'.

The term "degenerate nucleotide sequence" denotes a sequence of nucleotides that includes one or more degenerate codons (as compared to a reference polynucleotide molecule that encodes a polypeptide). Degenerate codons contain different triplets of nucleotides, but encode the same amino acid residue (i.e., GAU and GAC triplets each encode Asp).

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated, but may include naturally occurring 5' and 3' untranslated regions such as promoters and terminators. The identification of associated regions will be evident to one of ordinary skill in the art (see for example, Dynan and Tijan, *Nature* 316:774-78, 1985).

An "isolated" polypeptide or protein is a polypeptide or protein that is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. When used in this context, the term "isolated" does not exclude the presence of the same polypeptide in alternative physical forms, such as dimers or alternatively glycosylated or derivatized forms.

The term "neoplastic", when referring to cells, indicates cells undergoing new and abnormal proliferation, particularly in a tissue where in the proliferation is uncontrolled and progressive, resulting in a neoplasm. The neoplastic cells can be either malignant, i.e. invasive and metastatic, or benign.

The term "operably linked", when referring to DNA segments, indicates that the segments are arranged so that they function in concert for their intended purposes, e.g., transcription initiates in the promoter and proceeds through the coding segment to the terminator.

The term "ortholog" denotes a polypeptide or protein obtained from one species that is the functional counterpart of a polypeptide or protein from a different species. Sequence differences among orthologs are the result of speciation.

"Paralogs" are distinct but structurally related proteins made by an organism. Paralogs are believed to arise through gene duplication. For example, *-globin, *-globin, and myoglobin are paralogs of each other.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules. Sizes of polynucleotides are expressed as base pairs (abbreviated "bp"), nucleotides ("nt"), or kilobases ("kb"). Where the context allows, the latter two terms may describe polynucleotides that are single-stranded or double-stranded. When the term is applied to double-stranded molecules it is used to denote overall length and will be understood to be equivalent to the term "base pairs". It will be recognized by those skilled in the art that the two strands of a double-stranded polynucleotide may differ slightly in length and that the ends thereof may be staggered as a result of enzymatic cleavage; thus all nucleotides within a double-stranded polynucleotide molecule may not be paired.

A "polypeptide" is a polymer of amino acid residues joined by peptide bonds, whether produced naturally or synthetically. Polypeptides of less than about 10 amino acid residues are commonly referred to as "peptides".

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

A "protein" is a macromolecule comprising one or more polypeptide chains. A protein may also comprise non-peptidic components, such as carbohydrate groups. Carbohydrates and other non-peptidic substituents may be added to a protein by the cell in which the protein is produced, and will vary with the type of cell. Proteins are defined herein in terms of their amino acid backbone structures; substituents such as carbohydrate groups are generally not specified, but may be present nonetheless.

The term "receptor" denotes a cell-associated protein that binds to a bioactive molecule (i.e., a ligand) and mediates the effect of the ligand on the cell. Membrane-bound receptors are characterized by a multi-peptide structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. In general, receptors can be membrane bound, cytosolic or nuclear; monomeric (e.g., thyroid stimulating hormone receptor, beta-adrenergic receptor) or multimeric (e.g., PDGF receptor, growth hormone receptor, IL-3 receptor, GM-CSF receptor, G-CSF receptor, erythropoietin receptor and IL-6 receptor).

The term "secretory signal sequence" denotes a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "splice variant" is used herein to denote alternative forms of RNA transcribed from a gene. Splice variation arises naturally through use of alternative splicing sites within a transcribed RNA molecule, or less commonly between separately transcribed RNA molecules, and may result in several mRNAs transcribed from the same gene. Splice variants may encode polypeptides having altered amino acid sequence. The term splice variant is also used herein to denote a protein encoded by a splice variant of an mRNA transcribed from a gene.

Molecular weights and lengths of polymers determined by imprecise analytical methods (e.g., gel electrophoresis) will be understood to be approximate values. When such a value is expressed as "about" X or "approximately" X, the stated value of X will be understood to be accurate to ±10%.

All references cited herein are incorporated by reference in their entirety.

The present invention is based in part upon the discovery of a novel DNA sequence that encodes a protein having the structure of a four-helical-bundle cytokine. Through processes of cloning, proliferation assays and binding studies described in detail herein, a polynucleotide sequence encoding a novel ligand polypeptide has been identified that is a ligand with high specificity for the previously orphan receptor zalpha11. This polypeptide ligand, designated zalpha11 Ligand, was isolated from a cDNA library generated from activated human peripheral blood cells (hPBCs), which were selected for CD3. CD3 is a cell surface marker unique to cells of lymphoid origin, particularly T cells.

In the examples which follow, a cell line that is dependent on the zalpha11 orphan receptor-linked pathway for survival and growth in the absence of other growth factors was used to screen for a source of the cDNA encoding the zalpha11 Ligand. The preferred growth factor-dependent cell line that was used for transfection and expression of zalpha11 receptor was BaF3 (Palacios and Steinmetz, *Cell* 41: 727-734, 1985; Mathey-Prevot et al., *Mol. Cell. Biol.* 6: 4133-4135, 1986). However, other growth factor-dependent cell lines, such as FDC-P1 (Hapel et al., *Blood* 64: 786-790, 1984), and MO7e (Kiss et al., *Leukemia* 7: 235-240, 1993) are suitable for this purpose.

The amino acid sequence for the zalpha11 receptor indicated that the encoded receptor belonged to the Class I cytokine receptor subfamily that includes, but is not limited to, the receptors for IL-2, IL-4, IL-7, IL-15, EPO, TPO, GM-CSF and G-CSF (for a review see, Cosman, "The Hematopoietin Receptor Superfamily" in *Cytokine* 5(2): 95-106, 1993). The zalpha11 receptor is fully described in commonly-owned PCT Patent Application No. US99/22149. Analysis of the tissue distribution of the mRNA of the zalpha11 receptor revealed expression in lymph node, peripheral blood leukocytes (PBLs), spleen, bone marrow, and thymus. Moreover, the mRNA was abundant in the Raji cell line (ATCC No. CCL-86) derived from a Burkitt's lymphoma. The tissue distribution of the receptor suggests that a target for the predicted zalpha11 Ligand is hematopoietic lineage cells, in particular lymphoid progenitor cells and lymphoid cells. Other known four-helical-bundle cytokines that act on lymphoid cells include IL-2, IL-4, IL-7, and IL-15. For a review of four-helical-bundle cytokines, see, Nicola et al., *Advances in Protein Chemistry* 52:1-65, 1999 and Kelso, A., *Immunol. Cell Biol.* 76:300-317, 1998.

Conditioned media (CM) from CD3+ selected, PMA/Ionomycin-stimulated human peripheral blood cells supported the growth of BaF3 cells that expressed the zalpha11 receptor and were otherwise dependent on IL-3. Conditioned medias from cells that were not: 1) PMA/Ionomycin-stimulated; or were not: 2) CD3 selected (with or without PMA/Ionomycin stimulation) did not support the growth of BaF3/zalpha11 receptor cells. Control experiments demonstrated that this proliferative activity was not attributable to other known growth factors, and that the ability of such conditioned media to stimulate proliferation of zalpha11 receptor-expressing cells could be neutralized by a soluble form of the receptor.

Proliferation of zalpha11 receptor-expressing BaF3 cells exposed to CM from CD3+ selected, PMA/Ionomycin-stimulated human peripheral blood cells were identified by visual inspection of the cultures and/or by proliferation assay. Many suitable proliferation assays are known in the art, and include assays for reduction of a dye such as ALAMAR BLUE™ (AccuMed International, Inc. Westlake, Ohio), 3-(4, 5-dimethylthiazol-2-yl)-2,5-diphenyl tetrazolium bromide (Mosman, *J. Immunol. Meth.* 65: 55-63, 1983); 3,(4,5 dimethyl thiazol-2yl)-5-3-carboxymethoxyphenyl-2H-tetrazolium; 2,3-bis(2-methoxy-4-nitro-5-sulfophenyl)-5-[(phenylamino)carbonyl]-2H-tetrazolium hydroxide; and cyanoditolyl-tetrazolium chloride (which are commercially available from Polysciences, Inc., Warrington, Pa.); mitogenesis assays, such as measurement of incorporation of $^3$H-thymidine; dye exclusion assays using, for example, naphthalene black or trypan blue; dye uptake using diacetyl fluorescein; and chromium release. See, in general, Freshney, *Culture of Animal Cells: A Manual of Basic Technique,* 3rd ed., Wiley-Liss, 1994, which is incorporated herein by reference.

A cDNA library was prepared from CD3+ selected, PMA- and Ionomycin-stimulated primary human peripheral blood cells. The CD3+ selected, PMA- and Ionomycin-stimulated human peripheral blood cells cDNA library was divided into pools containing multiple cDNA molecules and was transfected into a host cell line, for example, BHK 570 cells (ATCC accession no. 10314). The transfected host cells were cultured in a medium that did not contain exogenous growth factors and conditioned medium was collected. The conditioned media were assayed for the ability to stimulate proliferation of BaF3 cells transfected with the zalpha11 receptor. CDNA pools producing conditioned medium that stimulated BaF3/zalpha11 receptor cells were identified. This pooled plasmid cDNA was electroporated into *E. coli*. CDNA was isolated from single colonies and transfected individually into BHK 570 cells. Positive clones were identified by a positive result in the BaF3/zalpha11 receptor proliferation assay, and specificity was tested by neutralization of proliferation using the soluble zalpha11 receptor.

A positive clone was isolated, and sequence analysis revealed that the polynucleotide sequence contained within the plasmid DNA was novel. The secretory signal sequence is comprised of amino acid residues 1 (Met) to 31 (Gly), and the mature polypeptide is comprised of amino acid residues 32 (Gln) to 162 (Ser) (as shown in SEQ ID NO: 2).

In general, cytokines are predicted to have a four-alpha helix structure, with helices A, C and D being most important in ligand-receptor interactions, and are more highly conserved among members of the family. Referring to the human zalpha11 Ligand amino acid sequence shown in SEQ ID NO:2, alignment of human zalpha11 Ligand, human IL-15, human IL-4, and human GM-CSF amino acid sequences it is predicted that zalpha11 Ligand helix A is defined by amino acid residues 41-56; helix B by amino acid residues 69-84; helix C by amino acid residues 92-105; and helix D by amino acid residues 135-148; as shown in SEQ ID NO: 2. Structural analysis suggests that the A/B loop is long, the B/C loop is short and the C/D loop is parallel long. This loop structure results in an up-up-down-down helical organization. The cysteine residues are absolutely conserved between zalpha11 Ligand and IL-15, as shown in FIG. 1. The cysteine residues that are conserved between IL-15 and zalpha11 Ligand correspond to amino acid residues 71, 78, 122 and 125 of SEQ ID NO: 2. Conservation of some of the cysteine residues is also found in IL-2, IL-4, GM-CSF and zalpha11 Ligand corresponding to amino acid residues 78 and 125 of SEQ ID NO: 2, as shown in FIG. 1. Consistent cysteine placement is further confirmation of the four-helical-bundle structure. Also highly conserved in the family comprising IL-15, IL-2, IL-4, GM-CSF and zalpha11 Ligand is the Glu-Phe-Leu sequence as shown in SEQ ID NO: 2 at residues 136-138, as in FIG. 1.

Further analysis of zalpha11 Ligand based on multiple alignments (as shown in FIG. 1) predicts that amino acid residues 44, 47 and 135 (as shown in SEQ ID NO: 2) play an important role in zalpha11 Ligand binding to its cognate receptor. Moreover, the predicted amino acid sequence of murine zalpha11 Ligand shows 57% identity to the predicted human protein. Based on comparison between sequences of human and murine zalpha11 Ligand well-conserved residues were found in the regions predicted to encode alpha helices A and D. The corresponding polynucleotides encoding the zalpha11 Ligand polypeptide regions, domains, motifs, residues and sequences described herein are as shown in SEQ ID NO:1.

Detailed mutational analysis has been performed for IL-4 and IL-2, both of which are highly related to zalpha11 ligand. Analysis of murine IL-2 (Zurawski et al., *EMBO J.* 12:5113-5119, 1993) shows residues in helices A and C are important for binding to IL-2Rβ; critical residues are Asp34, Asn99, and Asn 103. Multiple residues within murine IL-2 loop A/B and helix B are important for IL-2Rα binding, while only a single residue, Gln141 in helix D, is vital for binding with IL-2Rα. Similarly, helices A and C are sites of interaction between IL-4 and IL-4Rα (the structurally similar to IL-2Rα), and residues within helix D are vital for IL-2Rα interaction (Wang et al., *Proc. Natl. Acad. Sci. USA* 94:1657-1662, 1997; Kruse et al., *EMBO J.* 11:3237-3244, 1992). In particular, the mutation Tyr124 to Asp in human IL-4 creates an antagonist, which binds with IL-4Rα but not IL-2Rα and therefore cannot signal (Kruse et al. ibid. 1992).

While helix A is relatively well-conserved between human and murine zalpha11 Ligand, helix C is more divergent. While both species have predominant acidic amino acids in this region, the differences may account for species specificity in interaction between zalpha11 Ligand and its "beta" type receptor, zalpha11. Loop A/B and helix B of zalpha11 Ligand are well-conserved between species; although no receptor subunit corresponding to IL-2R* has yet been identified, conservation through this region suggests that it is functionally significant. The D helices of human and murine zalpha11 Ligand are also highly conserved. Zalpha11 receptor antagonists may be designed through mutations within zalpha11 Ligand helix D. These may include truncation of the protein from residue Gln145 (SEQ ID NO: 2), or mutations of Gln145 or Ile148 (of SEQ ID NO: 2; corresponding to Tyr124 in human IL-4) to residues such as Ala or Asp. Any mutation which disrupts the zalpha11 Ligand helical structure may abolish binding with its receptor and thus inhibit signaling.

Four-helical bundle cytokines are also grouped by the length of their component helices. "Long-helix" form cytokines generally consist of between 24-30 residue helices, and include IL-6, ciliary neutrotrophic factor (CNTF), leukemia inhibitory factor (LIF) and human growth hormone (hGH). "Short-helix" form cytokines generally consist of between 18-21 residue helices and include IL-2, IL-4 and GM-CSF. Zalpha11 Ligand is believed to be a new member of the short-helix form cytokine group. Studies using CNTF and IL-6 demonstrated that a CNTF helix can be exchanged for the equivalent helix in IL-6, conferring CTNF-binding properties to the chimera. Thus, it appears that functional domains of four-helical cytokines are determined on the basis of structural homology, irrespective of sequence identity, and can maintain functional integrity in a chimera (Kallen et al., *J. Biol. Chem.* 274:11859-11867, 1999). Therefore, the helical domains of zalpha11 Ligand will be useful for preparing chimeric fusion molecules, particularly with other short-helix form cytokines to determine and modulate receptor binding specificity. Of particular interest are fusion proteins engineered with helix A and/or helix D, and fusion proteins that combine helical and loop domains from other short-form cytokines such as IL-2, IL-4, IL-15 and GM-CSF. The amino acid residues comprising helices A, B, C, and D, and loops A/B, B/C and C/D for zalpha11 Ligand, IL-2, IL-4, IL-15 and GM-CSF are shown in Table 1.

TABLE 1

| | Helix A | A/B Loop | Helix B | B/C Loop | Helix C | C/D Loop | Helix D | |
|---|---|---|---|---|---|---|---|---|
| zalpha 11 Ligand residues | 41-56 | 57-68 | 69-84 | 85-91 | 92-105 | 106-134 | 135-148 | SEQ ID NO: 2 |
| IL-2 residues | 36-46 | 47-52 | 53-75 | 76-86 | 87-99 | 100-102 | 103-121 | SEQ ID NO: 111 |
| IL-4 residues | 29-43 | 44-64 | 65-83 | 84-94 | 95-118 | 119-133 | 134-151 | SEQ ID NO: 112 |
| IL-15 residues | 45-68 | 69-83 | 84-101 | 102-106 | 107-119 | 120-133 | 134-160 | SEQ ID NO: 113 |
| GM-CSF residues | 30-44 | 45-71 | 72-81 | 82-90 | 91-102 | 103-119 | 120-131 | SEQ ID NO: 114 |

The present invention provides polynucleotide molecules, including DNA and RNA molecules, that encode the zalpha11 Ligand polypeptides disclosed herein. Those skilled in the art will readily recognize that, in view of the degeneracy of the genetic code, considerable sequence variation is possible among these polynucleotide molecules. SEQ ID NO:3 is a degenerate DNA sequence that encompasses all DNAs that encode the zalpha11 Ligand polypeptide of SEQ ID NO:2. Those skilled in the art will recognize that the degenerate sequence of SEQ ID NO:3 also provides all RNA sequences encoding SEQ ID NO:2 by substituting U for T. Thus, zalpha11 Ligand polypeptide-encoding polynucleotides comprising nucleotide 1 or 97 to nucleotide 486 of SEQ ID NO:3 and their RNA equivalents are contemplated by the present invention. Table 2 sets forth the one-letter codes used within SEQ ID NO:3 to denote degenerate nucleotide positions. "Resolutions" are the nucleotides denoted by a code letter. "Complement" indicates the code for the complementary nucleotide(s). For example, the code Y denotes either C or T, and its complement R denotes A or G, with A being complementary to T, and G being complementary to C.

TABLE 2

| Nucleotide | Resolution | Complement | Resolution |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| W | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO:3, encompassing all possible codons for a given amino acid, are set forth in Table 3.

TABLE 3

| Amino Acid | One Letter Code | Codons | Degenerate Codon |
|---|---|---|---|
| Cys | C | TGC TGT | TGY |
| Ser | S | AGC AGT TCA TCC TCG TCT | WSN |

TABLE 3-continued

| Amino Acid | One Letter Code | Codons | Degenerate Codon |
|---|---|---|---|
| Thr | T | ACA ACC ACG ACT | ACN |
| Pro | P | CCA CCC CCG CCT | CCN |
| Ala | A | GCA GCC GCG GCT | GCN |

TABLE 3-continued

| Amino Acid | One Letter Code | Codons | Degenerate Codon |
|---|---|---|---|
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | * | TAA TAG TGA | TRR |
| Asn\|Asp | B | | RAY |
| Glu\|Gln | Z | | SAR |
| Any | X | | NNN |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may encode variant amino acid sequences, but one of ordinary skill in the art can easily identify such variant sequences by reference to the amino acid sequence of SEQ ID NO:2. Variant sequences can be readily tested for functionality as described herein.

One of ordinary skill in the art will also appreciate that different species can exhibit "preferential codon usage." In general, see, Grantham, et al., Nuc. Acids Res. 8:1893-912, 1980; Haas, et al. Curr. Biol. 6:315-24, 1996; Wain-Hobson, et al., Gene 13:355-64, 1981; Grosjean and Fiers, Gene 18:199-209, 1982; Holm, Nuc. Acids Res. 14:3075-87, 1986; Ikemura, J. Mol. Biol. 158:573-97, 1982. As used herein, the term "preferential codon usage" or "preferential codons" is a term of art referring to protein translation codons that are most frequently used in cells of a certain species, thus favoring one or a few representatives of the possible codons encoding each amino acid (See Table 3). For example, the amino acid Threonine (Thr) may be encoded by ACA, ACC, ACG, or ACT, but in mammalian cells ACC is the most commonly used codon; in other species, for example, insect cells, yeast, viruses or bacteria, different Thr codons may be preferential.

Preferential codons for a particular species can be introduced into the polynucleotides of the present invention by a variety of methods known in the art. Introduction of preferential codon sequences into recombinant DNA can, for example, enhance production of the protein by making protein translation more efficient within a particular cell type or species. Therefore, the degenerate codon sequence disclosed in SEQ ID NO:3 serves as a template for optimizing expression of polynucleotides in various cell types and species commonly used in the art and disclosed herein. Sequences containing preferential codons can be tested and optimized for expression in various species, and tested for functionality as disclosed herein.

As previously noted, the isolated polynucleotides of the present invention include DNA and RNA. Methods for preparing DNA and RNA are well known in the art. In general, RNA is isolated from a tissue or cell that produces large amounts of zalpha11 Ligand RNA. Such tissues and cells are identified by Northern blotting (Thomas, Proc. Natl. Acad. Sci. USA 77:5201, 1980), or by screening conditioned medium from various cell types for activity on target cells or tissue. Once the activity or RNA producing cell or tissue is identified, total RNA can be prepared using guanidinium isothiocyanate extraction followed by isolation by centrifugation in a CsCl gradient (Chirgwin et al., Biochemistry 18:52-94, 1979). Poly(A)+ RNA is prepared from total RNA using the method of Aviv and Leder (Proc. Natl. Acad. Sci. USA 69:1408-12, 1972). Complementary DNA (cDNA) is prepared from poly(A)+ RNA using known methods. In the alternative, genomic DNA can be isolated. Polynucleotides encoding zalpha11 Ligand polypeptides are then identified and isolated by, for example, hybridization or PCR.

A full-length clone encoding zalpha11 Ligand can be obtained by conventional cloning procedures. Complementary DNA (cDNA) clones are preferred, although for some applications (e.g., expression in transgenic animals) it may be preferable to use a genomic clone, or to modify a cDNA clone to include at least one genomic intron. Methods for preparing cDNA and genomic clones are well known and within the level of ordinary skill in the art, and include the use of the sequence disclosed herein, or parts thereof, for probing or priming a library. Expression libraries can be probed with antibodies to zalpha11 receptor fragments, or other specific binding partners.

Zalpha11 Ligand polynucleotide sequences disclosed herein can also be used as probes or primers to clone 5' non-coding regions of a zalpha11 Ligand gene. In view of the tissue-specific expression observed for zalpha11 Ligand this gene region is expected to provide for hematopoietic- and lymphoid-specific expression. Promoter elements from a zalpha11 Ligand gene could thus be used to direct the tissue-specific expression of heterologous genes in, for example, transgenic animals or patients treated with gene therapy. Cloning of 5' flanking sequences also facilitates production of zalpha11 Ligand proteins by "gene activation" as disclosed in U.S. Pat. No. 5,641,670. Briefly, expression of an endogenous zalpha11 Ligand gene in a cell is altered by introducing into the zalpha11 Ligand locus a DNA construct comprising at least a targeting sequence, a regulatory sequence, an exon, and an unpaired splice donor site. The targeting sequence is a zalpha11 Ligand 5' non-coding sequence that permits homologous recombination of the construct with the endogenous zalpha11 Ligand locus, whereby the sequences within the construct become operably linked with the endogenous zalpha11 Ligand coding sequence. In this way, an endogenous zalpha11 Ligand promoter can be replaced or supplemented with other regulatory sequences to provide enhanced, tissue-specific, or otherwise regulated expression.

The present invention further provides counterpart polypeptides and polynucleotides from other species (orthologs). These species include, but are not limited to mammalian, avian, amphibian, reptile, fish, insect and other vertebrate and invertebrate species. Of particular interest are zalpha11 Ligand polypeptides from other mammalian species, including murine, porcine, ovine, bovine, canine, feline, equine, and other primate polypeptides. Orthologs of human zalpha11 Ligand can be cloned using information and compositions provided by the present invention in combination with conventional cloning techniques. For example, a cDNA can be cloned using mRNA obtained from a tissue or cell type that expresses zalpha11 Ligand as disclosed herein. Suitable sources of mRNA can be identified by probing Northern blots with probes designed from the sequences disclosed herein. A library is then prepared from mRNA of a positive tissue or cell line. A zalpha11 Ligand-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the representative human zalpha11 Ligand sequence disclosed herein. Within an additional method, the cDNA library can be used to transform or transfect host cells, and expression of the cDNA of interest can be detected with an antibody to zalpha11 Ligand polypeptide, binding studies or activity assays. Similar techniques can also be applied to the isolation of genomic clones.

The polynucleotide sequence for the mouse ortholog of zalpha11 Ligand has been identified and is shown in SEQ ID NO: 55 and the corresponding amino acid sequence shown in SEQ ID NO: 56. There is 62% identity between the mouse and human sequences over a 124 amino acid region that corresponds to residues 30 to 153 in SEQ ID NO: 2 and residues 23 to 146 of SEQ ID NO: 56 of zalpha11 Ligand. Mature sequence for the mouse zalpha11 Ligand putatively begins at His18 (as shown in SEQ ID NO: 56), which corresponds to His25 (as shown in SEQ ID NO: 2) in the human sequence. Because a truncated form of the human polypeptide is active, it is likely that an equivalent polypeptide of the mouse zalpha11 Ligand (i.e. without residues His18 to Pro22 of SEQ ID NO: 56) is active as well. Tissue analysis revealed that expression of mouse zalpha11 Ligand is found in testis, spleen and thymus.

Those skilled in the art will recognize that the sequence disclosed in SEQ ID NO:1 represents a single allele of human zalpha11 Ligand and that allelic variation and alternative splicing are expected to occur. Allelic variants of this sequence can be cloned by probing cDNA or genomic libraries from different individuals according to standard procedures. Allelic variants of the DNA sequence shown in SEQ ID NO:1, including those containing silent mutations and those in which mutations result in amino acid sequence changes, are within the scope of the present invention, as are proteins which are allelic variants of SEQ ID NO:2. cDNAs generated from alternatively spliced mRNAs, which retain the properties of the zalpha11 Ligand polypeptide, are included within the scope of the present invention, as are polypeptides encoded by such cDNAs and mRNAs. Allelic variants and splice variants of these sequences can be cloned by probing cDNA or genomic libraries from different individuals or tissues according to standard procedures known in the art.

The zalpha11 Ligand gene has been mapped to the IL-2 framework marker SHGC-12342, positioning zalpha11 Ligand approximately 180 kb from the IL-2 marker. The use of surrounding markers positions the zalpha11 Ligand gene in the 4q27 region on the integrated LDB chromosome 4 map (The Genetic Location Database, University of Southhampton,). The present invention also provides reagents which will find use in diagnostic applications. For example, the zalpha11 Ligand gene, a probe comprising zalpha11 Ligand DNA or RNA or a subsequence thereof can be used to determine if the zalpha11 Ligand gene is present on a human chromosome, such as chromosome 4, or if a gene mutation has occurred. Based on annotation of a fragment of human genomic DNA containing a part of zalpha11 Ligand genomic DNA (Genbank Accession No. AC007458), zalpha11 Ligand is located at the 4q27 region of chromosome 4. Detectable chromosomal aberrations at the zalpha11 Ligand gene locus include, but are not limited to, aneuploidy, gene copy number changes, loss of heterogeneity (LOH), translocations, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; Marian, *Chest* 108:255-65, 1995).

The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

As stated previously, human zalpha11 Ligand gene resides near the IL-2 gene, which is in a region of chromosome 4q that has been shown to have linkage with susceptibility to inflammatory bowel disease (IBD) (including Crohn's disease (CD) and ulcerative colitis) in some families (Hampe et al. *Am. J. Hum. Genet.* 64:808-816, 1999; Cho et al. *Proc. Natl. Acad. Sci.* 95:7502-7507, 1998). In addition, the zalpha11 receptor gene maps to 16p11, another genomic region which is associated with susceptibility to CD (Hugot et al., *Nature* 379:821-823, 1996; Ohmen et al., *Hum. Mol. Genet.* 5:1679-1683, 1996). CD is a chronic inflammation of the gut with frequent systemic involvement; while the exact etiology is unknown, immunoregulatory dysfunction involving failure of tolerance to ordinary gut antigens is a major component (for reviews, see (Braegger et al., *Annals Allergy* 72:135-141, 1994; Sartor, *Am. J. Gastroenterol.* 92:5S-11S, 1997)). Several studies have found abnormal NK activity in CD patients (see, for example, (Egawa et. al., *J. Clin. Lab. Immunol.* 20:187-192, 1986; Aparicio-Pagés et al. *J. Clin. Lab. Immunol.* 29:119-124, 1989; van Tol et al., *Scand. J. Gastroenterol.* 27:999-1005, 1992)), and defective memory B cell formation has also been documented (Brogan et al., *J. Clin. Lab. Immunol.* 24:69-74, 1987). Since zalpha11 Ligand plays a role in immune regulation, and since the genes for both receptor and ligand lie within CD susceptibility regions, both receptor and ligand are candidate genes for genetic predisposition to Crohn's disease.

Determination of the involvement of zalpha11 receptor and/or zalpha11 Ligand in the pathology of IBD can be accomplished by several methods. Sequencing of exons from genomic DNA can reveal coding mutations (including missense, nonsense, and frameshift mutations), as can sequencing of cDNAs. An additional advantage of sequencing from genomic DNA is that splice junctions are also contained within the sequenced fragments and may reveal splicing abnormalities, which might not appear in cDNA samples if, for example, misspliced RNAs were rapidly degraded. The genomic structure of zalpha11 Ligand has been determined. Other methods for analysis of zalpha11 Ligand and receptor in IBD patients include: (1) assessment of ligand production from activated T cells from patients vs. normal controls (i.e. by bioassay); (2) in situ hybridization of zalpha11 receptor or zalpha11 Ligand RNA to sections of inflamed intestine from IBD patients, compared to similar sections from normal controls; (3) immunohistochemistry on sections from IBD patients vs. normal controls; and (4) assessment of the responsiveness of patients' peripheral B cells to zalpha11 Ligand, as measured by mitogenesis assays.

A diagnostic could assist physicians in determining the type of disease and appropriate associated therapy, or could assist in genetic counseling. As such, the inventive anti-zalpha11 Ligand antibodies, polynucleotides, and polypeptides can be used for the detection of zalpha11 Ligand polypeptide, mRNA or anti-zalpha11 Ligand antibodies, thus serving as markers and be directly used for detecting or genetic diseases or cancers, as described herein, using methods known in the art and described herein. Further, zalpha11 Ligand polynucleotide probes can be used to detect abnormalities involving chromosome 4q27 as described herein. These abnormalities may be associated with human diseases, or tumorigenesis, spontaneous abortion or other genetic disorders. Thus, zalpha11 Ligand polynucleotide probes can be used to detect abnormalities or genotypes associated with these defects.

As discussed above, defects in the zalpha11 Ligand gene itself may result in a heritable human disease state. Molecules of the present invention, such as the polypeptides, antagonists, agonists, polynucleotides and antibodies of the present invention would aid in the detection, diagnosis prevention, and treatment of diseases associated with a zalpha11 Ligand genetic defect. In addition, zalpha11 Ligand polynucleotide probes can be used to detect allelic differences between diseased or non-diseased individuals at the zalpha11 Ligand chromosomal locus. As such, the zalpha11 Ligand sequences can be used as diagnostics in forensic DNA profiling.

In general, the diagnostic methods used in genetic linkage analysis, to detect a genetic abnormality or aberration in a patient, are known in the art. Most diagnostic methods comprise the steps of (i) obtaining a genetic sample from a potentially diseased patient, diseased patient or potential non-diseased carrier of a recessive disease allele; (ii) producing a first reaction product by incubating the genetic sample with a zalpha11 Ligand polynucleotide probe wherein the polynucleotide will hybridize to complementary polynucleotide sequence, such as in RFLP analysis or by incubating the genetic sample with sense and antisense primers in a PCR reaction under appropriate PCR reaction conditions; (iii) Visualizing the first reaction product by gel electrophoresis and/or other known method such as visualizing the first reaction product with a zalpha11 Ligand polynucleotide probe wherein the polynucleotide will hybridize to the complementary polynucleotide sequence of the first reaction; and (iv) comparing the visualized first reaction product to a second control reaction product of a genetic sample from a normal or control individual. A difference between the first reaction product and the control reaction product is indicative of a genetic abnormality in the diseased or potentially diseased patient, or the presence of a heterozygous recessive carrier phenotype for a non-diseased patient, or the presence of a genetic defect in a tumor from a diseased patient, or the presence of a genetic abnormality in a fetus or pre-implantation embryo. For example, a difference in restriction fragment pattern, length of PCR products, length of repetitive sequences at the zalpha11 Ligand genetic locus, and the like, are indicative of a genetic abnormality, genetic aberration, or allelic difference in comparison to the normal control. Controls can be from unaffected family members, or unrelated individuals, depending on the test and availability of samples. Genetic samples for use within the present invention include genomic DNA, mRNA, and cDNA isolated from any tissue or other biological sample from a patient, such as but not limited to, blood, saliva, semen, embryonic cells, amniotic fluid, and the like. The polynucleotide probe or primer can be RNA or DNA, and will comprise a portion of SEQ ID NO:1, the complement of SEQ ID NO:1, or an RNA equivalent thereof. Such methods of showing genetic linkage analysis to human disease phenotypes are well known in the art. For reference to PCR based methods in diagnostics see, generally, Mathew (ed.), *Protocols in Human Molecular Genetics* (Humana Press, Inc. 1991), White (ed.), *PCR Protocols: Current Methods and Applications* (Humana Press, Inc. 1993), Cotter (ed.), *Molecular Diagnosis of Cancer* (Humana Press, Inc. 1996), Hanausek and Walaszek (eds.), *Tumor Marker Protocols* (Humana Press, Inc. 1998), Lo (ed.), *Clinical Applications of PCR* (Humana Press, Inc. 1998), and Meltzer (ed.), *PCR in Bioanalysis* (Humana Press, Inc. 1998)).

Mutations associated with the zalpha11 Ligand locus can be detected using nucleic acid molecules of the present invention by employing standard methods for direct mutation analysis, such as restriction fragment length polymorphism analysis, short tandem repeat analysis employing PCR techniques, amplification-refractory mutation system analysis, single-strand conformation polymorphism detection, RNase cleavage methods, denaturing gradient gel electrophoresis, fluorescence-assisted mismatch analysis, and other genetic analysis techniques known in the art (see, for example, Mathew (ed.), *Protocols in Human Molecular Genetics* (Humana Press, Inc. 1991), Marian, *Chest* 108:255 (1995), Coleman and Tsongalis, *Molecular Diagnostics* (Human Press, Inc. 1996), Elles (ed.) *Molecular Diagnosis of Genetic Diseases* (Humana Press, Inc. 1996), Landegren (ed.), *Laboratory Protocols for Mutation Detection* (Oxford University Press 1996), Birren et al. (eds.), *Genome Analysis, Vol. 2: Detecting Genes* (Cold Spring Harbor Laboratory Press 1998), Dracopoli et al. (eds.), *Current Protocols in Human Genetics* (John Wiley & Sons 1998), and Richards and Ward, "Molecular Diagnostic Testing," in *Principles of Molecular Medicine*, pages 83-88 (Humana Press, Inc. 1998). Direct analysis of an zalpha11 Ligand gene for a mutation can be performed using a subject's genomic DNA. Methods for amplifying genomic DNA, obtained for example from peripheral blood lymphocytes, are well-known to those of skill in the art (see, for example, Dracopoli et al. (eds.), *Current Protocols in Human Genetics*, at pages 7.1.6 to 7.1.7 (John Wiley & Sons 1998)).

Positions of introns in the zalpha11 Ligand gene were determined by identification of genomic clones, followed by sequencing the intron/exon junctions. The first intron lies between amino acid residue 56 (Leu) and residue 57 (Val) in Seq. ID. No. 2, and is 115 base pairs in length. The second intron is the largest at 4.4 kilobases, and lies between amino acid residue 68 (Glu) and residue 69 (Thr) in Seq. ID. No. 2. The third intron is 2.6 kilobases, and lies between amino acid residue 120 (Leu) and residue 121 (Thr) in Seq. ID. No. 2. The final intron, 89 base pairs, lies between amino acid residue 146 (Lys) and residue 147 (Met) in Seq. ID. No. 2. The complete gene spans about 8 kb.

The structure of the zalpha11 Ligand gene is similar to that of the IL-2 gene (Fujita et al. *Proc. Natl. Acad. Sci.* 80:7437-7441, 1983), though the zalpha11 Ligand gene contains one additional intron (intron 4). The pattern of a short first intron and long second and third introns is conserved between the two genes, though the IL-2 gene is slightly smaller overall (about 6 kb). The IL-15 gene, on the other hand, consists of 8 exons and spans at least 34 kb (Anderson et al. *Genomics* 25:701-706, 1995). Thus the zalpha11 Ligand gene is more similar in structure to the IL-2 gene than to the IL-15 gene.

Within embodiments of the invention, isolated zalpha11 Ligand-encoding nucleic acid molecules can hybridize under stringent conditions to nucleic acid molecules having the nucleotide sequence of SEQ ID NO:1, to nucleic acid molecules having the nucleotide sequence of nucleotides 47 to 532 of SEQ ID NO:1, or to nucleic acid molecules having a nucleotide sequence complementary to SEQ ID NO:1. In general, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe.

A pair of nucleic acid molecules, such as DNA-DNA, RNA-RNA and DNA-RNA, can hybridize if the nucleotide sequences have some degree of complementarity. Hybrids can tolerate mismatched base pairs in the double helix, but the stability of the hybrid is influenced by the degree of mismatch. The Tm of the mismatched hybrid decreases by 1° C. for every 1-1.5% base pair mismatch. Varying the stringency of the hybridization conditions allows control over the degree of mismatch that will be present in the hybrid. The degree of stringency increases as the hybridization temperature increases and the ionic strength of the hybridization buffer decreases.

It is well within the abilities of one skilled in the art to adapt these conditions for use with a particular polynucleotide hybrid. The Tm for a specific target sequence is the temperature (under defined conditions) at which 50% of the target sequence will hybridize to a perfectly matched probe sequence. Those conditions which influence the Tm include, the size and base pair content of the polynucleotide probe, the ionic strength of the hybridization solution, and the presence of destabilizing agents in the hybridization solution. Numerous equations for calculating Tm are known in the art, and are specific for DNA, RNA and DNA-RNA hybrids and polynucleotide probe sequences of varying length (see, for example, Sambrook et al., *Molecular Cloning: A Laboratory Manual*, Second Edition (Cold Spring Harbor Press 1989); Ausubel et al., (eds.), *Current Protocols in Molecular Biology* (John Wiley and Sons, Inc. 1987); Berger and Kimmel (eds.), *Guide to Molecular Cloning Techniques*, (Academic Press, Inc. 1987); and Wetmur, *Crit. Rev. Biochem. Mol. Biol.* 26:227 (1990)). Sequence analysis software such as OLIGO 6.0 (LSR; Long Lake, Minn.) and Primer Premier 4.0 (Premier Biosoft International; Palo Alto, Calif.), as well as sites on the Internet, are available tools for analyzing a given sequence and calculating Tm based on user defined criteria. Such programs can also analyze a given sequence under defined conditions and identify suitable probe sequences. Typically, hybridization of longer polynucleotide sequences, >50 base pairs, is performed at temperatures of about 20-25° C. below the calculated Tm. For smaller probes, <50 base pairs, hybridization is typically carried out at the Tm or 5-10° C. below the calculated Tm. This allows for the maximum rate of hybridization for DNA-DNA and DNA-RNA hybrids.

Following hybridization, the nucleic acid molecules can be washed to remove non-hybridized nucleic acid molecules under stringent conditions, or under highly stringent conditions. Typical stringent washing conditions include washing in a solution of 0.5×-2×SSC with 0.1% sodium dodecyl sulfate (SDS) at 55-65° C. That is, nucleic acid molecules encoding a variant zalpha11 Ligand polypeptide hybridize with a nucleic acid molecule having the nucleotide sequence of SEQ ID NO:1 (or its complement) under stringent washing conditions, in which the wash stringency is equivalent to 0.5×-2× SSC with 0.1% SDS at 55-65° C., including 0.5×SSC with 0.1% SDS at 55° C., or 2×SSC with 0.1% SDS at 65° C. One of skill in the art can readily devise equivalent conditions, for example, by substituting SSPE for SSC in the wash solution.

Typical highly stringent washing conditions include washing in a solution of 0.1×-0.2×SSC with 0.1% sodium dodecyl sulfate (SDS) at 50-65° C. In other words, nucleic acid molecules encoding a variant zalpha11 Ligand polypeptide hybridize with a nucleic acid molecule having the nucleotide sequence of SEQ ID NO:1 (or its complement) under highly stringent washing conditions, in which the wash stringency is equivalent to 0.1×-0.2×SSC with 0.1% SDS at 50-65° C., including 0.1×SSC with 0.1% SDS at 50° C., or 0.2×SSC with 0.1% SDS at 65° C.

The present invention also provides isolated zalpha11 Ligand polypeptides that have a substantially similar sequence identity to the polypeptides of SEQ ID NO:2, or their orthologs. The term "substantially similar sequence identity" is used herein to denote polypeptides comprising at least 70%, at least 80%, at least 90%, at least 95%, or greater than 95% sequence identity to the sequences shown in SEQ ID NO:2, or their orthologs. The present invention also includes polypeptides that comprise an amino acid sequence having at least 70%, at least 80%, at least 90%, at least 95% or greater than 95% sequence identity to the sequence of amino acid residues 1 to 162 or 32 to 162 of SEQ ID NO:2. The present invention further includes nucleic acid molecules that encode such polypeptides. Methods for determining percent identity are described below.

The present invention also contemplates variant zalpha11 Ligand nucleic acid molecules that can be identified using two criteria: a determination of the similarity between the encoded polypeptide with the amino acid sequence of SEQ ID NO:2, and/or a hybridization assay, as described above. Such zalpha11 Ligand variants include nucleic acid molecules: (1) that hybridize with a nucleic acid molecule having the nucleotide sequence of SEQ ID NO:1 (or its complement) under stringent washing conditions, in which the wash stringency is equivalent to 0.5×-2×SSC with 0.1% SDS at 55-65° C.; or (2) that encode a polypeptide having at least 70%, at least 80%, at least 90%, at least 95% or greater than 95% sequence identity to the amino acid sequence of SEQ ID NO:2. Alternatively, zalpha11 Ligand variants can be characterized as nucleic acid molecules: (1) that hybridize with a nucleic acid molecule having the nucleotide sequence of SEQ ID NO:1 (or its complement) under highly stringent washing conditions, in which the wash stringency is equivalent to 0.1×-0.2×SSC with 0.1% SDS at 50-65° C.; and (2) that encode a polypeptide having at least 70%, at least 80%, at least 90%, at least 95% or greater than 95% sequence identity to the amino acid sequence of SEQ ID NO:2.

Percent sequence identity is determined by conventional methods. See, for example, Altschul et al., Bull. Math. Bio. 48:603 (1986), and Henikoff and Henikoff, Proc. Natl. Acad. Sci. USA 89:10915 (1992). Briefly, two amino acid sequences are aligned to optimize the alignment scores using a gap opening penalty of 10, a gap extension penalty of 1, and the "BLOSUM62" scoring matrix of Henikoff and Henikoff (ibid.) as shown in Table 4 (amino acids are indicated by the standard one-letter codes).

modifying the scoring matrix file ("SMATRIX"), as explained in Appendix 2 of Pearson, *Meth. Enzymol.* 183:63 (1990).

TABLE 4

$$\frac{\text{Total number of identical matches}}{[\text{length of the longer sequence plus the number of gaps introduced into the longer sequence in order to align the two sequences}]} \times 100$$

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

Those skilled in the art appreciate that there are many established algorithms available to align two amino acid sequences. The "FASTA" similarity search algorithm of Pearson and Lipman is a suitable protein alignment method for examining the level of identity shared by an amino acid sequence disclosed herein and the amino acid sequence of a putative variant zalpha11 Ligand. The FASTA algorithm is described by Pearson and Lipman, *Proc. Nat'l Acad. Sci. USA* 85:2444 (1988), and by Pearson, *Meth. Enzymol.* 183:63 (1990).

Briefly, FASTA first characterizes sequence similarity by identifying regions shared by the query sequence (e.g., SEQ ID NO:2) and a test sequence that have either the highest density of identities (if the ktup variable is 1) or pairs of identities (if ktup=2), without considering conservative amino acid substitutions, insertions, or deletions. The ten regions with the highest density of identities are then rescored by comparing the similarity of all paired amino acids using an amino acid substitution matrix, and the ends of the regions are "trimmed" to include only those residues that contribute to the highest score. If there are several regions with scores greater than the "cutoff" value (calculated by a predetermined formula based upon the length of the sequence and the ktup value), then the trimmed initial regions are examined to determine whether the regions can be joined to form an approximate alignment with gaps. Finally, the highest scoring regions of the two amino acid sequences are aligned using a modification of the Needleman-Wunsch-Sellers algorithm (Needleman and Wunsch, *J. Mol. Biol.* 48:444 (1970); Sellers, *SIAM J. Appl. Math.* 26:787 (1974)), which allows for amino acid insertions and deletions. Preferred parameters for FASTA analysis are: ktup=1, gap opening penalty=10, gap extension penalty=1, and substitution matrix=BLOSUM62. These parameters can be introduced into a FASTA program by FASTA can also be used to determine the sequence identity of nucleic acid molecules using a ratio as disclosed above. For nucleotide sequence comparisons, the ktup value can range between one to six, preferably from three to six, most preferably three, with other parameters set as default.

Variant zalpha11 Ligand polypeptides or polypeptides with substantially similar sequence identity are characterized as having one or more amino acid substitutions, deletions or additions. These changes are preferably of a minor nature, that is conservative amino acid substitutions (see Table 5) and other substitutions that do not significantly affect the folding or activity of the polypeptide; small deletions, typically of one to about 30 amino acids; and amino- or carboxyl-terminal extensions, such as an amino-terminal methionine residue, a small linker peptide of up to about 20-25 residues, or an affinity tag. The present invention thus includes polypeptides of from about 108 to 216 amino acid residues that comprise a sequence that is at least 70%, preferably at least 90%, and more preferably 95% or more identical to the corresponding region of SEQ ID NO:2. Polypeptides comprising affinity tags can further comprise a proteolytic cleavage site between the zalpha11 Ligand polypeptide and the affinity tag. Preferred such sites include thrombin cleavage sites and factor Xa cleavage sites.

TABLE 5

| Conservative amino acid substitutions | |
|---|---|
| Basic: | arginine |
|  | lysine |
|  | histidine |
| Acidic: | glutamic acid |
|  | aspartic acid |
| Polar: | glutamine |
|  | asparagine |

TABLE 5-continued

Conservative amino acid substitutions

| | |
|---|---|
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Determination of amino acid residues that comprise regions or domains that are critical to maintaining structural integrity can be determined. Within these regions one can determine specific residues that will be more or less tolerant of change and maintain the overall tertiary structure of the molecule. Methods for analyzing sequence structure include, but are not limited to alignment of multiple sequences with high amino acid or nucleotide identity, secondary structure propensities, binary patterns, complementary packing and buried polar interactions (Barton, *Current Opin. Struct. Biol.* 5:372-376, 1995 and Cordes et al., *Current Opin. Struct. Biol.* 6:3-10, 1996). In general, when designing modifications to molecules or identifying specific fragments determination of structure will be accompanied by evaluating activity of modified molecules.

Amino acid sequence changes are made in zalpha11 Ligand polypeptides so as to minimize disruption of higher order structure essential to biological activity. For example, where the zalpha11 Ligand polypeptide comprises one or more helices, changes in amino acid residues will be made so as not to disrupt the helix geometry and other components of the molecule where changes in conformation abate some critical function, for example, binding of the molecule to its binding partners, e.g., A and D helices, residues 44, 47 and 135 of SEQ ID NO: 2. The effects of amino acid sequence changes can be predicted by, for example, computer modeling as disclosed above or determined by analysis of crystal structure (see, e.g., Lapthorn et al., *Nat. Struct. Biol.* 2:266-268, 1995). Other techniques that are well known in the art compare folding of a variant protein to a standard molecule (e.g., the native protein). For example, comparison of the cysteine pattern in a variant and standard molecules can be made. Mass spectrometry and chemical modification using reduction and alkylation provide methods for determining cysteine residues which are associated with disulfide bonds or are free of such associations (Bean et al., *Anal. Biochem.* 201:216-226, 1992; Gray, *Protein Sci.* 2:1732-1748, 1993; and Patterson et al., *Anal. Chem.* 66:3727-3732, 1994). It is generally believed that if a modified molecule does not have the same cysteine pattern as the standard molecule folding would be affected. Another well known and accepted method for measuring folding is circular dichrosism (CD). Measuring and comparing the CD spectra generated by a modified molecule and standard molecule is routine (Johnson, *Proteins* 7:205-214, 1990). Crystallography is another well known method for analyzing folding and structure. Nuclear magnetic resonance (NMR), digestive peptide mapping and epitope mapping are also known methods for analyzing folding and structurally similarities between proteins and polypeptides (Schaanan et al., *Science* 257:961-964, 1992).

A Hopp/Woods hydrophilicity profile of the zalpha11 Ligand protein sequence as shown in SEQ ID NO:2 can be generated (Hopp et al., *Proc. Natl. Acad. Sci.* 78:3824-3828, 1981; Hopp, *J. Immun. Meth.* 88:1-18, 1986 and Triquier et al., *Protein Engineering* 11:153-169, 1998). The profile is based on a sliding six-residue window. Buried G, S, and T residues and exposed H, Y, and W residues were ignored. For example, in zalpha11 Ligand, hydrophilic regions include amino acid residues 114-119 of SEQ ID NO: 2, amino acid residues 101-105 of SEQ ID NO: 2, amino acid residues 126-131 of SEQ ID NO: 2, amino acid residues 113-118 of SEQ ID NO: 2, and amino acid residues 158-162 of SEQ ID NO: 2.

Those skilled in the art will recognize that hydrophilicity or hydrophobicity will be taken into account when designing modifications in the amino acid sequence of a zalpha11 Ligand polypeptide, so as not to disrupt the overall structural and biological profile. Of particular interest for replacement are hydrophobic residues selected from the group consisting of Val, Leu and Ile or the group consisting of Met, Gly, Ser, Ala, Tyr and Trp. For example, residues tolerant of substitution could include residues 100 and 103 as shown in SEQ ID NO: 2. Cysteine residues at positions 71, 78, 122 and 125 of SEQ ID NO: 2, will be relatively intolerant of substitution.

The identities of essential amino acids can also be inferred from analysis of sequence similarity between IL-15, IL-2, IL-4 and GM-CSF with zalpha11 Ligand. Using methods such as "FASTA" analysis described previously, regions of high similarity are identified within a family of proteins and used to analyze amino acid sequence for conserved regions. An alternative approach to identifying a variant zalpha11 Ligand polynucleotide on the basis of structure is to determine whether a nucleic acid molecule encoding a potential variant zalpha11 Ligand gene can hybridize to a nucleic acid molecule having the nucleotide sequence of SEQ ID NO:1, as discussed above.

Other methods of identifying essential amino acids in the polypeptides of the present invention are procedures known in the art, such as site-directed mutagenesis or alanine-scanning mutagenesis (Cunningham and Wells, *Science* 244:1081 (1989), Bass et al., *Proc. Natl. Acad. Sci. USA* 88:4498 (1991), Coombs and Corey, "Site-Directed Mutagenesis and Protein Engineering," in *Proteins: Analysis and Design*, Angeletti (ed.), pages 259-311 (Academic Press, Inc. 1998)). In the latter technique, single alanine mutations are introduced at every residue in the molecule, and the resultant mutant molecules are tested for biological or biochemical activity as disclosed below to identify amino acid residues that are critical to the activity of the molecule. See also, Hilton et al., *J. Biol. Chem.* 271:4699 (1996).

The present invention also includes functional fragments of zalpha11 Ligand polypeptides and nucleic acid molecules encoding such functional fragments. A "functional" zalpha11 Ligand or fragment thereof as defined herein is characterized by its proliferative or differentiating activity, by its ability to induce or inhibit specialized cell functions, or by its ability to bind specifically to an anti-zalpha11 Ligand antibody or zalpha11 receptor (either soluble or immobilized). As previously described herein, zalpha11 Ligand is characterized by a four-helical-bundle structure comprising helix A (amino acid residues 41-56), helix B (amino acid residues 69-84), helix C (amino acid residues 92-105) and helix D (amino acid residues 135-148), as shown in SEQ ID NO: 2. Thus, the present invention further provides fusion proteins encompassing: (a) polypeptide molecules comprising one or more of the helices described above; and (b) functional fragments comprising one or more of these helices. The other polypeptide portion of the fusion protein may be contributed by another four-helical-bundle cytokine, such as IL-15, IL-2, IL-4 and GM-CSF, or by a non-native and/or an unrelated secretory signal peptide that facilitates secretion of the fusion protein.

Thus the present invention provides fusion proteins comprising at least four polypeptides, wherein the order of polypeptides from N-terminus to C-terminus are: a first polypeptide comprises amino acids selected from a group consisting of: (a) IL-2 helix A amino acid residues 36-46 of SEQ ID NO: 111; (b) IL-15 helix A amino acid residues 29-43 of SEQ ID NO: 112; (c) IL-4 helix A amino acid residues 45-68 of SEQ ID NO: 113; (d) GMCSF helix A amino acid residues 30-44 of SEQ ID NO: 114; and (e) amino acids residues 41 to 56 of SEQ ID NO: 2; a first spacer of 6-27 amino acids; and a second polypeptide that comprises amino acid residues selected from the group consisting of: (a) IL-2 helix B amino acid residues 53-75 of SEQ ID NO: 111; (b) IL-4 helix B amino acid residues 65-83 of SEQ ID NO: 112; (c) IL-15 helix B amino acid residues 84-101 of SEQ ID NO: 113; (d) GMCSF helix B amino acid residues 72-81 of SEQ ID NO: 114; and (e) amino acid residues 69-84 of SEQ ID NO: 2; a second spacer of 5-11 amino acid residues; a third polypeptide that comprises a sequence of amino acid residues selected from the group consisting of: (a) IL-2 helix C residues 87-99 of SEQ ID NO: 111; (b) IL-4 helix C residues 95-118 of SEQ ID NO: 112; (c) IL-15 helix C residues 107-119 of SEQ ID NO: 113; (d) GMCSF helix C residues 91-102 of SEQ ID NO: 114; and (e) amino acid residues 92-105 of SEQ ID NO: 2; a third spacer of 3-29 amino acid residues; and a fourth polypeptide that comprises amino acid residues selected from the group consisting of: (a) IL-2 helix D amino acid residues 103-121 of SEQ ID NO: 111; (b) IL-15 helix D amino acid residues 134-157 of SEQ ID NO: 112; (c) IL-4 helix D amino acid residues 134-160 of SEQ ID NO: 113; (d) GMCSF helix D amino acid residues 120-131 of SEQ ID NO: 114; and (e) amino acid residues 135-148 of SEQ ID NO: 2, wherein at least one of the four polypeptides is from zalpha11 Ligand. In other embodiments that the spacer peptides will be selected from the A/B, B/C and C/D loops of zalpha11 Ligand, IL-2, IL-4, IL-15 or GM-CSF, as shown in Table 1.

Routine deletion analyses of nucleic acid molecules can be performed to obtain functional fragments of a nucleic acid molecule that encodes a zalpha11 Ligand polypeptide. As an illustration, DNA molecules having the nucleotide sequence of SEQ ID NO:1 or fragments thereof, can be digested with Bal31 nuclease to obtain a series of nested deletions. These DNA fragments are then inserted into expression vectors in proper reading frame, and the expressed polypeptides are isolated and tested for zalpha11 Ligand activity, or for the ability to bind anti-zalpha11 Ligand antibodies or zalpha11 receptor. One alternative to exonuclease digestion is to use oligonucleotide-directed mutagenesis to introduce deletions or stop codons to specify production of a desired zalpha11 Ligand fragment. Alternatively, particular fragments of a zalpha11 Ligand gene can be synthesized using the polymerase chain reaction.

Standard methods for identifying functional domains are well-known to those of skill in the art. For example, studies on the truncation at either or both termini of interferons have been summarized by Horisberger and Di Marco, *Pharmac. Ther.* 66:507 (1995). Moreover, standard techniques for functional analysis of proteins are described by, for example, Treuter et al., *Molec. Gen. Genet.* 240:113 (1993); Content et al., "Expression and preliminary deletion analysis of the 42 kDa 2 5A synthetase induced by human interferon," in *Biological Interferon Systems, Proceedings of ISIR TNO Meeting on Interferon Systems*, Cantell (ed.), pages 65 72 (Nijhoff 1987); Herschman, "The EGF Receptor," in *Control of Animal Cell Proliferation* 1, Boynton et al., (eds.) pages 169-199 (Academic Press 1985); Coumailleau et al., *J. Biol. Chem.* 270:29270 (1995); Fukunaga et al., *J. Biol. Chem.* 270:25291 (1995); Yamaguchi et al., *Biochem. Pharmacol.* 50:1295 (1995); and Meisel et al., *Plant Molec. Biol.* 30:1 (1996).

Multiple amino acid substitutions can be made and tested using known methods of mutagenesis and screening, such as those disclosed by Reidhaar-Olson and Sauer (*Science* 241: 53 (1988)) or Bowie and Sauer (*Proc. Nat'l Acad. Sci. USA* 86:2152 (1989)). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832 (1991), Ladner et al., U.S. Pat. No. 5,223,409, Huse, international publication No. WO 92/06204), and region-directed mutagenesis (Derbyshire et al., *Gene* 46:145 (1986), and Ner et al., *DNA* 7:127, (1988)).

Variants of the disclosed zalpha11 Ligand nucleotide and polypeptide sequences can also be generated through DNA shuffling as disclosed by Stemmer, *Nature* 370:389 (1994), Stemmer, *Proc. Natl. Acad. Sci. USA* 91:10747 (1994), and international publication No. WO 97/20078. Briefly, variant DNA molecules are generated by in vitro homologous recombination by random fragmentation of a parent DNA followed by reassembly using PCR, resulting in randomly introduced point mutations. This technique can be modified by using a family of parent DNA molecules, such as allelic variants or DNA molecules from different species, to introduce additional variability into the process. Selection or screening for the desired activity, followed by additional iterations of mutagenesis and assay provides for rapid "evolution" of sequences by selecting for desirable mutations while simultaneously selecting against detrimental changes.

Mutagenesis methods as disclosed herein can be combined with high-throughput, automated screening methods to detect activity of cloned, mutagenized polypeptides in host cells. Mutagenized DNA molecules that encode biologically active polypeptides, or polypeptides that bind with anti-zalpha11 Ligand antibodies or soluble zalpha11 receptor, can be recovered from the host cells and rapidly sequenced using modern equipment. These methods allow the rapid determination of the importance of individual amino acid residues in a polypeptide of interest, and can be applied to polypeptides of unknown structure.

In addition, the proteins of the present invention (or polypeptide fragments thereof) can be joined to other bioactive molecules, particularly other cytokines, to provide multi-functional molecules. For example, one or more helices from zalpha11 Ligand can be joined to other cytokines to enhance their biological properties or efficiency of production.

The present invention thus provides a series of novel, hybrid molecules in which a segment comprising one or more of the helices of zalpha11 Ligand is fused to another polypeptide. Fusion is preferably done by splicing at the DNA level to allow expression of chimeric molecules in recombinant production systems. The resultant molecules are then assayed for such properties as improved solubility, improved stability, prolonged clearance half-life, improved expression and secretion levels, and pharmacodynamics. Such hybrid molecules may further comprise additional amino acid residues (e.g. a polypeptide linker) between the component proteins or polypeptides.

Non-naturally occurring amino acids include, without limitation, trans-3-methylproline, 2,4-methanoproline, cis-4-hydroxyproline, trans-4-hydroxyproline, N-methylglycine, allo-threonine, methylthreonine, hydroxyethylcysteine, hydroxyethylhomocysteine, nitroglutamine, homoglutamine, pipecolic acid, thiazolidine carboxylic acid, dehydroproline, 3- and 4-methylproline, 3,3-dimethylproline, tert-leucine, norvaline, 2-azaphenylalanine, 3-azaphenylalanine, 4-azaphenylalanine, and 4-fluorophenylalanine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations is typically carried out in a cell-free system comprising an E. coli S30 extract and commercially available enzymes and other reagents. Proteins are purified by chromatography. See, for example, Robertson et al., J. Am. Chem. Soc. 113:2722 (1991), Ellman et al., Methods Enzymol. 202: 301 (1991), Chung et al., Science 259:806 (1993), and Chung et al., Proc. Nat'l Acad. Sci. USA 90:10145 (1993).

In a second method, translation is carried out in Xenopus oocytes by microinjection of mutated mRNA and chemically aminoacylated suppressor tRNAs (Turcatti et al., J. Biol. Chem. 271:19991 (1996)). Within a third method, E. coli cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., Biochem. 33:7470 (1994). Naturally occurring amino acid residues can be converted to non-naturally occurring species by in vitro chemical modification. Chemical modification can be combined with site-directed mutagenesis to further expand the range of substitutions (Wynn and Richards, Protein Sci. 2:395 (1993). It may be advantageous to stabilize zalpha11 Ligand to extend the half-life of the molecule, particularly for extending metabolic persistence in an active state. To achieve extended half-life, zalpha11 Ligand molecules can be chemically modified using methods described herein. PEGylation is one method commonly used that has been demonstrated to increase plasma half-life, increased solubility, and decreased antigenicity and immunogenicity (Nucci et al., *Advanced Drug Delivery Reviews* 6:133-155, 1991 and Lu et al., *Int. J. Peptide Protein Res.* 43:127-138, 1994).

A limited number of non-conservative amino acids, amino acids that are not encoded by the genetic code, non-naturally occurring amino acids, and unnatural amino acids may be substituted for zalpha11 Ligand amino acid residues.

The present invention also provides polypeptide fragments or peptides comprising an epitope-bearing portion of a zalpha11 Ligand polypeptide described herein. Such fragments or peptides may comprise an "immunogenic epitope," which is a part of a protein that elicits an antibody response when the entire protein is used as an immunogen. Immunogenic epitope-bearing peptides can be identified using standard methods (see, for example, Geysen et al., *Proc. Nat'l Acad. Sci. USA* 81:3998 (1983)).

In contrast, polypeptide fragments or peptides may comprise an "antigenic epitope," which is a region of a protein molecule to which an antibody can specifically bind. Certain epitopes consist of a linear or contiguous stretch of amino acids, and the antigenicity of such an epitope is not disrupted by denaturing agents. It is known in the art that relatively short synthetic peptides that can mimic epitopes of a protein can be used to stimulate the production of antibodies against the protein (see, for example, Sutcliffe et al., *Science* 219:660 (1983)). Accordingly, antigenic epitope-bearing peptides and polypeptides of the present invention are useful to raise antibodies that bind with the polypeptides described herein. Hopp/Woods hydrophilicity profiles can be used to determine regions that have the most antigenic potential (Hopp et al., 1981, ibid. and Hopp, 1986, ibid.). In zalpha11 Ligand these regions include: amino acid residues 114-119, 101-105, 126-131, 113-118, and 158-162 of SEQ ID NO: 2.

Antigenic epitope-bearing peptides and polypeptides preferably contain at least four to ten amino acids, at least ten to fourteen amino acids, or about fourteen to about thirty amino acids of SEQ ID NO:2 or SEQ ID NO:56. Such epitope-bearing peptides and polypeptides can be produced by fragmenting a zalpha11 Ligand polypeptide, or by chemical peptide synthesis, as described herein. Moreover, epitopes can be selected by phage display of random peptide libraries (see, for example, Lane and Stephen, *Curr. Opin. Immunol.* 5:268 (1993); and Cortese et al., *Curr. Opin. Biotechnol.* 7:616 (1996)). Standard methods for identifying epitopes and producing antibodies from small peptides that comprise an epitope are described, for example, by Mole, "Epitope Mapping," in *Methods in Molecular Biology, Vol.* 10, Manson (ed.), pages 105-116 (The Humana Press, Inc. 1992); Price, "Production and Characterization of Synthetic Peptide-Derived Antibodies," in *Monoclonal Antibodies: Production, Engineering, and Clinical Application*, Ritter and Ladyman (eds.), pages 60-84 (Cambridge University Press 1995), and Coligan et al. (eds.), *Current Protocols in Immunology*, pages 9.3.1-9.3.5 and pages 9.4.1-9.4.11 (John Wiley & Sons 1997).

Regardless of the particular nucleotide sequence of a variant zalpha11 Ligand polynucleotide, the polynucleotide encodes a polypeptide that is characterized by its proliferative or differentiating activity, its ability to induce or inhibit specialized cell functions, or by the ability to bind specifically to an anti-zalpha11 Ligand antibody or zalpha11 receptor. More specifically, variant zalpha11 Ligand polynucleotides will encode polypeptides which exhibit at least 50% and preferably, greater than 70%, 80% or 90%, of the activity of the polypeptide as shown in SEQ ID NO: 2.

For any zalpha11 Ligand polypeptide, including variants and fusion proteins, one of ordinary skill in the art can readily generate a fully degenerate polynucleotide sequence encoding that variant using the information set forth in Tables 1 and 2 above.

The present invention further provides a variety of other polypeptide fusions (and related multimeric proteins comprising one or more polypeptide fusions). For example, a zalpha11 Ligand polypeptide can be prepared as a fusion to a dimerizing protein as disclosed in U.S. Pat. Nos. 5,155,027 and 5,567,584. Preferred dimerizing proteins in this regard include immunoglobulin constant region domains. Immunoglobulin-zalpha11 Ligand polypeptide fusions can be expressed in genetically engineered cells (to produce a variety of multimeric zalpha11 Ligand analogs). Auxiliary domains can be fused to zalpha11 Ligand polypeptides to target them to specific cells, tissues, or macromolecules. For example, a zalpha11 Ligand polypeptide or protein could be targeted to a predetermined cell type by fusing a zalpha11 Ligand polypeptide to a ligand that specifically binds to a receptor on the surface of that target cell. In this way, polypeptides and proteins can be targeted for therapeutic or diagnostic purposes. A zalpha11 Ligand polypeptide can be fused to two or more moieties, such as an affinity tag for purification and a targeting domain. Polypeptide fusions can also comprise one or more cleavage sites, particularly between domains. See, Tuan et al., *Connective Tissue Research* 34:1-9, 1996.

Using the methods discussed herein, one of ordinary skill in the art can identify and/or prepare a variety of polypeptides that have substantially similar sequence identity to residues 1-162 or 32-162 of SEQ ID NO: 2, or functional fragments and fusions thereof, wherein such polypeptides or fragments or fusions retain the properties of the wild-type protein such as the ability to stimulate proliferation, differentiation, induce specialized cell function or bind the zalpha11 receptor or zalpha11 Ligand antibodies.

The zalpha11 Ligand polypeptides of the present invention, including full-length polypeptides, functional fragments, and fusion polypeptides, can be produced in genetically engineered host cells according to conventional techniques. Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells are disclosed by Sambrook et al., *Molecular Cloning: A Laboratory Manual* 2nd ed., Cold Spring Harbor Laboratory Press, Cold Spring Harbor, N.Y., 1989, and Ausubel et al., eds., *Current Protocols in Molecular Biology*, John Wiley and Sons, Inc., NY, 1987.

In general, a DNA sequence encoding a zalpha11 Ligand polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zalpha11 Ligand polypeptide into the secretory pathway of a host cell, a secretory signal sequence (also known as a leader sequence, prepro sequence or pre sequence) is provided in the expression vector. The secretory signal sequence may be that of zalpha11 Ligand, or may be derived from another secreted protein (e.g., t-PA) or synthesized de novo. The secretory signal sequence is operably linked to the zalpha11 Ligand DNA sequence, i.e., the two sequences are joined in the correct reading frame and positioned to direct the newly synthesized polypeptide into the secretory pathway of the host cell. Secretory signal sequences are commonly positioned 5' to the DNA sequence encoding the polypeptide of interest, although certain secretory signal sequences may be positioned elsewhere in the DNA sequence of interest (see, e.g., Welch et al., U.S. Pat. No. 5,037,743; Holland et al., U.S. Pat. No. 5,143,830).

Alternatively, the secretory signal sequence contained in the polypeptides of the present invention is used to direct other polypeptides into the secretory pathway. The present invention provides for such fusion polypeptides. A signal fusion polypeptide can be made wherein a secretory signal sequence derived from amino acid residue 1-31 of SEQ ID NO:2 is be operably linked to a DNA sequence encoding another polypeptide using methods known in the art and disclosed herein. The secretory signal sequence contained in the fusion polypeptides of the present invention is preferably fused amino-terminally to an additional peptide to direct the additional peptide into the secretory pathway. Such constructs have numerous applications known in the art. For example, these novel secretory signal sequence fusion constructs can direct the secretion of an active component of a normally non-secreted protein. Such fusions may be used in vivo or in vitro to direct peptides through the secretory pathway.

Cultured mammalian cells are suitable hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841-5, 1982), DEAE-dextran mediated transfection (Ausubel et al., ibid.), and liposome-mediated transfection (Hawley-Nelson et al., *Focus* 15:73, 1993; Ciccarone et al., *Focus* 15:80, 1993, and viral vectors (Miller and Rosman, *BioTechniques* 7:980-90, 1989; Wang and Finer, *Nature Med.* 2:714-6, 1996). The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., J. Gen. Virol. 36:59-72, 1977) and Chinese hamster ovary (e.g. CHO-K1; ATCC No. CCL 61) cell lines. Additional suitable cell lines are known in the art and available from public depositories such as the American Type Culture Collection, Manassas, Va. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems can also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used. Alternative markers that introduce an altered phenotype, such as green fluorescent protein, or cell surface proteins such as CD4, CD8, Class I MHC, placental alkaline phosphatase may be used to sort transfected cells from untransfected cells by such means as FACS sorting or magnetic bead separation technology.

Other higher eukaryotic cells can also be used as hosts, including plant cells, insect cells and avian cells. The use of *Agrobacterium rhizogenes* as a vector for expressing genes in plant cells has been reviewed by Sinkar et al., *J. Biosci.* (*Bangalore*) 11:47-58, 1987. Transformation of insect cells and production of foreign polypeptides therein is disclosed by Guarino et al., U.S. Pat. No. 5,162,222 and WIPO publication WO 94/06463. Insect cells can be infected with recombinant baculovirus, commonly derived from *Autographa californica* nuclear polyhedrosis virus (AcNPV). See, King, L. A. and Possee, R. D., *The Baculovirus Expression System: A Laboratory Guide*, London, Chapman & Hall; O'Reilly, D. R. et al., Baculovirus Expression Vectors: A Laboratory Manual, New York, Oxford University Press, 1994; and, Richardson, C. D., Ed., *Baculovirus Expression Protocols, Methods in Molecular Biology*, Totowa, N.J., Humana Press, 1995. The second method of making recombinant baculovirus utilizes a transposon-based system described by Luckow (Luckow, V. A, et al., *J Virol* 67:4566-79, 1993). This system is sold in the Bac-to-Bac kit (Life Technologies, Rockville, Md.). This system utilizes a transfer vector, pFastBac1™ (Life Technologies) containing a Tn7 transposon to move the DNA encoding the zalpha11 Ligand polypeptide into a baculovirus genome maintained in *E. coli* as a large plasmid called a "bacmid." The pFastBac1™ transfer vector utilizes the AcNPV polyhedrin promoter to drive the expression of the gene of interest, in this case zalpha11 Ligand. However, pFastBac1™ can be modified to a considerable degree. The polyhedrin promoter can be removed and substituted with the baculovirus basic protein promoter (also known as Pcor, p6.9 or MP promoter) which is expressed earlier in the baculovirus infection, and has been shown to be advantageous for expressing secreted proteins. See, Hill-Perkins, M. S. and Possee, R. D., *J. Gen. Virol.* 71:971-6, 1990; Bonning, B. C. et al., *J. Gen. Virol.* 75:1551-6, 1994; and, Chazenbalk, G. D., and Rapoport, B., *J. Biol. Chem.* 270:1543-9, 1995. In such transfer vector constructs, a short or long version of the basic protein promoter can be used. Moreover, transfer vectors can be constructed which replace the native zalpha11 Ligand secretory signal sequences with secretory signal sequences derived from insect proteins. For example, a secretory signal sequence from Ecdysteroid Glucosyltransferase (EGT), honey bee Melittin (Invitrogen, Carlsbad, Calif.), or baculovirus gp67 (PharMingen, San Diego, Calif.) can be used in constructs to replace the native zalpha11 Ligand secretory signal sequence. In addition, transfer vectors can include an in-frame fusion with DNA encoding an epitope tag at the C- or N-terminus of the expressed zalpha11 Ligand polypeptide, for example, a Glu-Glu epitope tag (Grussenmeyer, T. et al., *Proc. Natl. Acad. Sci.* 82:7952-4, 1985). Using techniques known in the art, a transfer vector containing zalpha11 Ligand is transformed into *E. Coli*, and screened for bacmids which contain an interrupted lacZ gene indicative of recombinant baculovirus. The bacmid DNA containing the recombinant baculovirus genome is isolated, using common techniques, and used to transfect *Spodoptera frugiperda* cells, e.g. Sf9 cells. Recombinant virus that expresses zalpha11 Ligand is subsequently produced. Recombinant viral stocks are made by methods commonly used the art.

The recombinant virus is used to infect host cells, typically a cell line derived from the fall armyworm, *Spodoptera frugiperda*. See, in general, Glick and Pasternak, *Molecular Biotechnology: Principles and Applications of Recombinant DNA*, ASM Press, Washington, D.C., 1994. Another suitable cell line is the High FiveO™ cell line (Invitrogen) derived from *Trichoplusia ni* (U.S. Pat. No. 5,300,435).

Fungal cells, including yeast cells, can also be used within the present invention. Yeast species of particular interest in this regard include *Saccharomyces cerevisiae*, *Pichia pastoris*, and *Pichia methanolica*. Methods for transforming *S. cerevisiae* cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in *Saccharomyces cerevisiae* is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092) and alcohol dehydrogenase genes. See also U.S. Pat. Nos. 4,990,446; 5,063,154; 5,139,936 and 4,661,454. Transformation systems for other yeasts, including *Hansenula polymorpha*, *Schizosaccharomyces pombe*, *Kluyveromyces lactis*, *Kluyveromyces fragilis*, *Ustilago maydis*, *Pichia pastoris*, *Pichia methanolica*, *Pichia guillermondii* and *Candida maltosa* are known in the art. See, for example, Gleeson et al., *J. Gen. Microbiol.* 132:3459-65, 1986 and Cregg, U.S. Pat. No. 4,882,279. *Aspergillus* cells may be utilized according to the methods of McKnight et al., U.S. Pat. No. 4,935,349. Methods for transforming *Acremonium chrysogenum* are disclosed by Sumino et al., U.S. Pat. No. 5,162,228. Methods for transforming *Neurospora* are disclosed by Lambowitz, U.S. Pat. No. 4,486,533.

The use of *Pichia methanolica* as host for the production of recombinant proteins is disclosed in WIPO Publications WO 97/17450, WO 97/17451, WO 98/02536, and WO 98/02565. DNA molecules for use in transforming *P. methanolica* will commonly be prepared as double-stranded, circular plasmids, which are preferably linearized prior to transformation. For polypeptide production in *P. methanolica*, it is preferred that the promoter and terminator in the plasmid be that of a *P. methanolica* gene, such as a *P. methanolica* alcohol utilization gene (AUG1 or AUG2). Other useful promoters include those of the dihydroxyacetone synthase (DHAS), formate dehydrogenase (FMD), and catalase (CAT) genes. To facilitate integration of the DNA into the host chromosome, it is preferred to have the entire expression segment of the plasmid flanked at both ends by host DNA sequences. A preferred selectable marker for use in *Pichia methanolica* is a *P. methanolica* ADE2 gene, which encodes phosphoribosyl-5-aminoimidazole carboxylase (AIRC; EC 4.1.1.21), which allows ade2 host cells to grow in the absence of adenine. For large-scale, industrial processes where it is desirable to minimize the use of methanol, it is preferred to use host cells in which both methanol utilization genes (AUG1 and AUG2) are deleted. For production of secreted proteins, host cells deficient in vacuolar protease genes (PEP4 and PRB1) are preferred. Electroporation is used to facilitate the introduction of a plasmid containing DNA encoding a polypeptide of interest into *P. methanolica* cells. It is preferred to transform *P. methanolica* cells by electroporation using an exponentially decaying, pulsed electric field having a field strength of from 2.5 to 4.5 kV/cm, preferably about 3.75 kV/cm, and a time constant ($\Omega$) of from 1 to 40 milliseconds, most preferably about 20 milliseconds.

Prokaryotic host cells, including strains of the bacteria *Escherichia coli*, *Bacillus* and other genera are also useful host cells within the present invention. Techniques for transforming these hosts and expressing foreign DNA sequences cloned therein are well known in the art (see, e.g., Sambrook et al., ibid.). When expressing a zalpha11 Ligand polypeptide in bacteria such as *E. coli*, the polypeptide may be retained in the cytoplasm, typically as insoluble granules, or may be directed to the periplasmic space by a bacterial secretion sequence. In the former case, the cells are lysed, and the granules are recovered and denatured using, for example, guanidine isothiocyanate or urea. The denatured polypeptide can then be refolded and dimerized by diluting the denaturant, such as by dialysis against a solution of urea and a combination of reduced and oxidized glutathione, followed by dialysis against a buffered saline solution. In the latter case, the polypeptide can be recovered from the periplasmic space in a soluble and functional form by disrupting the cells (by, for example, sonication or osmotic shock) to release the contents of the periplasmic space and recovering the protein, thereby obviating the need for denaturation and refolding.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell. *P. methanolica* cells are cultured in a medium comprising adequate sources of carbon, nitrogen and trace nutrients at a temperature of about 25° C. to 35° C. Liquid cultures are provided with sufficient aeration by conventional means, such as shaking of small flasks or sparging of fermentors. A preferred culture medium for *P. methanolica* is YEPD (2% D-glucose, 2% Bacto™ Peptone (Difco Laboratories, Detroit, Mich.), 1% Bacto™ yeast extract (Difco Laboratories), 0.004% adenine and 0.006% L-leucine).

It is preferred to purify the polypeptides of the present invention to ≧80% purity, more preferably to ≧90% purity, even more preferably ≧95% purity, and particularly preferred is a pharmaceutically pure state, that is greater than 99.9% pure with respect to contaminating macromolecules, particularly other proteins and nucleic acids, and free of infectious and pyrogenic agents. Preferably, a purified polypeptide is substantially free of other polypeptides, particularly other polypeptides of animal origin.

Expressed recombinant zalpha11 Ligand polypeptides (or chimeric zalpha11 Ligand polypeptides) can be purified using fractionation and/or conventional purification methods and media. Ammonium sulfate precipitation and acid or chaotrope extraction may be used for fractionation of samples. Exemplary purification steps may include hydroxyapatite, size exclusion, FPLC and reverse-phase high performance liquid chromatography. Suitable chromatographic media include derivatized dextrans, agarose, cellulose, polyacrylamide, specialty silicas, and the like. PEI, DEAE, QAE and Q derivatives are preferred. Exemplary chromatographic media include those media derivatized with phenyl, butyl, or octyl groups, such as Phenyl-Sepharose FF (Pharmacia), Toyopearl butyl 650 (Toso Haas, Montgomeryville, Pa.), Octyl-Sepharose (Pharmacia) and the like; or polyacrylic resins, such as Amberchrom CG 71 (Toso Haas) and the like. Suitable solid supports include glass beads, silica-based resins, cellulosic resins, agarose beads, cross-linked agarose beads, polystyrene beads, cross-linked polyacrylamide resins and the like that are insoluble under the conditions in which they are to be used. These supports may be modified with reactive groups that allow attachment of proteins by amino groups, carboxyl groups, sulfhydryl groups, hydroxyl groups and/or carbohydrate moieties. Examples of coupling chemistries include cyanogen bromide activation, N-hydroxysuccinimide activation, epoxide activation, sulfhydryl activation, hydrazide activation, and carboxyl and amino derivatives for carbodiimide coupling chemistries. These and other solid media are well known and widely used in the art, and are available from commercial suppliers. Methods for binding receptor polypeptides to support media are well known in the art. Selection of a particular method is a matter of routine design and is determined in part by the properties of the chosen support. See, for example, *Affinity Chromatography: Principles & Methods*, Pharmacia LKB Biotechnology, Uppsala, Sweden, 1988.

The polypeptides of the present invention can be isolated by exploitation of their physical or biochemical properties. For example, immobilized metal ion adsorption (IMAC) chromatography can be used to purify histidine-rich proteins, including those comprising polyhistidine tags. Briefly, a gel is first charged with divalent metal ions to form a chelate (Sulkowski, *Trends in Biochem.* 3:1-7, 1985). Histidine-rich proteins will be adsorbed to this matrix with differing affinities, depending upon the metal ion used, and will be eluted by competitive elution, lowering the pH, or use of strong chelating agents. Other methods of purification include purification of glycosylated proteins by lectin affinity chromatography and ion exchange chromatography (*Methods in Enzymol.*, Vol. 182, "Guide to Protein Purification", M. Deutscher, (ed.), Acad. Press, San Diego, 1990, pp. 529-39) and use of the soluble zalpha11 receptor. Within additional embodiments of the invention, a fusion of the polypeptide of interest and an affinity tag (e.g., maltose-binding protein, an immunoglobulin domain) may be constructed to facilitate purification.

Moreover, using methods described in the art, polypeptide fusions, or hybrid zalpha11 Ligand proteins, are constructed using regions or domains of the inventive zalpha11 Ligand in combination with those of other human cytokine family proteins (e.g. interleukins or GM-CSF), or heterologous proteins (Sambrook et al., ibid., Altschul et al., ibid., Picard, *Cur. Opin. Biology,* 5:511-5, 1994, and references therein). These methods allow the determination of the biological importance of larger domains or regions in a polypeptide of interest. Such hybrids may alter reaction kinetics, binding, constrict or expand the substrate specificity, or alter tissue and cellular localization of a polypeptide, and can be applied to polypeptides of unknown structure.

Fusion proteins can be prepared by methods known to those skilled in the art by preparing each component of the fusion protein and chemically conjugating them. Alternatively, a polynucleotide encoding both components of the fusion protein in the proper reading frame can be generated using known techniques and expressed by the methods described herein. For example, part or all of a helix conferring a biological function may be swapped between zalpha11 Ligand of the present invention with the functionally equivalent helices from another family member, such as IL-15, IL-2, IL-4 or GM-CSF. Such components include, but are not limited to, the secretory signal sequence; helices A, B, C, D; loops A/B, B/C, C/D; of four-helical-bundle cytokines. Such fusion proteins would be expected to have a biological functional profile that is the same or similar to polypeptides of the present invention or other known four-helical-bundle cytokine family proteins, depending on the fusion constructed. Moreover, such fusion proteins may exhibit other properties as disclosed herein.

Standard molecular biological and cloning techniques can be used to swap the equivalent domains between the zalpha11 Ligand polypeptide and those polypeptides to which they are fused. Generally, a DNA segment that encodes a domain of interest, e.g., zalpha11 Ligand helices A through D, or other domain described herein, is operably linked in frame to at least one other DNA segment encoding an additional polypeptide (for instance a domain or region from another cytokine, such as the IL-2, or the like), and inserted into an appropriate expression vector, as described herein. Generally DNA constructs are made such that the several DNA segments that encode the corresponding regions of a polypeptide are operably linked in frame to make a single construct that encodes the entire fusion protein, or a functional portion thereof. For example, a DNA construct would encode from N-terminus to C-terminus a fusion protein comprising a signal polypeptide followed by a mature four helical bundle cytokine fusion protein containing helix A, followed by helix B, followed by helix C, followed by helix D. Such fusion proteins can be expressed, isolated, and assayed for activity as described herein.

Zalpha11 Ligand polypeptides or fragments thereof may also be prepared through chemical synthesis. zalpha11 Ligand polypeptides may be monomers or multimers; glycosylated or non-glycosylated; pegylated or non-pegylated; and may or may not include an initial methionine amino acid residue. For example, the polypeptides can be prepared by solid phase peptide synthesis, for example as described by Merrifield, *J. Am. Chem. Soc.* 85:2149, 1963.

The activity of molecules of the present invention can be measured using a variety of assays that measure proliferation of and/or binding to cells expressing the zalpha11 receptor. Of particular interest are changes in zalpha11 Ligand-dependent cells. Suitable cell lines to be engineered to be zalpha11 Ligand-dependent include the IL-3-dependent BaF3 cell line (Palacios and Steinmetz, *Cell* 41: 727-734, 1985; Mathey-Prevot et al., *Mol. Cell. Biol.* 6: 4133-4135, 1986), FDC-P1 (Hapel et al., *Blood* 64: 786-790, 1984), and MO7e (Kiss et al., *Leukemia* 7: 235-240, 1993). Growth factor-dependent cell lines can be established according to published methods (e.g. Greenberger et al., *Leukemia Res.* 8: 363-375, 1984; Dexter et al., in Baum et al. Eds., *Experimental Hematology Today*, 8th Ann. Mtg. Int. Soc. Exp. Hematol. 1979, 145-156, 1980).

Proteins of the present invention are useful for stimulating proliferation, activation, differentiation and/or induction or inhibition of specialized cell function of cells of the involved homeostasis of the hematopoiesis and immune function. In particular, zalpha11 Ligand polypeptides are useful for stimulating proliferation, activation, differentiation, induction or inhibition of specialized cell functions of cells of the hematopoietic lineages, including, but not limited to, T cells, B cells, NK cells, dendritic cells, monocytes, and macrophages, as well as epithelial cells. Proliferation and/or differentiation of hematopoietic cells can be measured in vitro using cultured cells or in vivo by administering molecules of the claimed invention to the appropriate animal model. Assays measuring cell proliferation or differentiation are well known in the art. For example, assays measuring proliferation include such assays as chemosensitivity to neutral red dye (Cavanaugh et al., *Investigational New Drugs* 8:347-354, 1990, incorporated herein by reference), incorporation of radiolabelled nucleotides (Cook et al., *Analytical Biochem.* 179:1-7, 1989, incorporated herein by reference), incorporation of 5-bromo-2'-deoxyuridine (BrdU) in the DNA of proliferating cells (Porstmann et al., *J. Immunol. Methods* 82:169-179, 1985, incorporated herein by reference), and use of tetrazolium salts (Mosmann, *J. Immunol. Methods* 65:55-63, 1983; Alley et al., *Cancer Res.* 48:589-601, 1988; Marshall et al., *Growth Reg.* 5:69-84, 1995; and Scudiero et al., *Cancer Res.* 48:4827-4833, 1988; all incorporated herein by reference). Assays measuring differentiation include, for example, measuring cell-surface markers associated with stage-specific expression of a tissue, enzymatic activity, functional activity or morphological changes (Watt, *FASEB*, 5:281-284, 1991; Francis, *Differentiation* 57:63-75, 1994; Raes, *Adv. Anim. Cell Biol. Technol. Bioprocesses*, 161-171, 1989; all incorporated herein by reference).

The molecules of the present invention can be assayed in vivo using viral delivery systems. Exemplary viruses for this purpose include adenovirus, herpesvirus, retroviruses, vaccinia virus, and adeno-associated virus (AAV). Adenovirus, a double-stranded DNA virus, is currently the best studied gene transfer vector for delivery of heterologous nucleic acid (for review, see T. C. Becker et al., *Meth. Cell Biol.* 43:161-89, 1994; and J. T. Douglas and D. T. Curiel, *Science & Medicine* 4:44-53, 1997).

As a ligand, the activity of zalpha11 Ligand polypeptide can be measured by a silicon-based biosensor microphysiometer which measures the extracellular acidification rate or proton excretion associated with receptor binding and subsequent physiologic cellular responses. An exemplary device is the Microphysiometer CYTOSENSOR® manufactured by Molecular Devices, Sunnyvale, Calif. A variety of cellular responses, such as cell proliferation, ion transport, energy production, inflammatory response, regulatory and receptor activation, and the like, can be measured by this method. See, for example, McConnell, H. M. et al., *Science* 257:1906-1912, 1992; Pitchford, S. et al., *Meth. Enzymol.* 228:84-108, 1997; Arimilli, S. et al., *J. Immunol. Meth.* 212:49-59, 1998; Van Liefde, I. et al., *Eur. J. Pharmacol.* 346:87-95, 1998.

Moreover, zalpha11 Ligand can be used to identify cells, tissues, or cell lines which respond to a zalpha11 Ligand-stimulated pathway. The microphysiometer, described above, can be used to rapidly identify ligand-responsive cells, such as cells responsive to zalpha11 Ligand of the present invention. Cells can be cultured in the presence or absence of zalpha11 Ligand polypeptide. Those cells which elicit a measurable change in extracellular acidification in the presence of zalpha11 Ligand are responsive to zalpha11 Ligand. Such cells or cell lines, can be used to identify antagonists and agonists of zalpha11 Ligand polypeptide as described above.

In view of the tissue distribution observed for zalpha11 receptor agonists (including the natural zalpha11 Ligand substrate/cofactor/etc.) and/or antagonists have enormous potential in both in vitro and in vivo applications. Compounds identified as zalpha11 Ligand agonists are useful for expansion, proliferation, activation, differentiation, and/or induction or inhibition of specialized cell functions of cells involved in homeostasis of hematopoiesis and immune function. For example, zalpha11 Ligand and agonist compounds are useful as components of defined cell culture media, and may be used alone or in combination with other cytokines and hormones to replace serum that is commonly used in cell culture. Agonists are thus useful in specifically promoting the growth and/or development of T-cells, B-cells, NK cells, cytotoxic lymphocytes, and other cells of the lymphoid and myeloid lineages in culture.

Antagonists are also useful as research reagents for characterizing sites of ligand-receptor interaction. Antagonists are useful to inhibit expansion, proliferation, activation, and/or differentiation of cells involved in regulating hematopoiesis. Inhibitors of zalpha11 Ligand activity (zalpha11 Ligand antagonists) include anti-zalpha11 Ligand antibodies and soluble zalpha11 Ligand receptors, as well as other peptidic and non-peptidic agents (including ribozymes).

zalpha11 Ligand can also be used to identify inhibitors (antagonists) of its activity. Test compounds are added to the assays disclosed herein to identify compounds that inhibit the activity of zalpha11 Ligand. In addition to those assays disclosed herein, samples can be tested for inhibition of zalpha11 Ligand activity within a variety of assays designed to measure receptor binding, the stimulation/inhibition of zalpha11 Ligand-dependent cellular responses or proliferation of zalpha11 receptor-expressing cells.

A zalpha11 Ligand polypeptide can be expressed as a fusion with an immunoglobulin heavy chain constant region, typically an Fc fragment, which contains two constant region domains and lacks the variable region. Methods for preparing such fusions are disclosed in U.S. Pat. Nos. 5,155,027 and 5,567,584. Such fusions are typically secreted as multimeric molecules wherein the Fc portions are disulfide bonded to each other and two non-Ig polypeptides are arrayed in closed proximity to each other. Fusions of this type can be used for example, for dimerization, increasing stability and in vivo half-life, to affinity purify ligand, as in vitro assay tool or antagonist. For use in assays, the chimeras are bound to a support via the Fc region and used in an ELISA format.

A zalpha11 Ligand-binding polypeptide can also be used for purification of ligand. The polypeptide is immobilized on a solid support, such as beads of agarose, cross-linked agarose, glass, cellulosic resins, silica-based resins, polystyrene, cross-linked polyacrylamide, or like materials that are stable under the conditions of use. Methods for linking polypeptides to solid supports are known in the art, and include amine chemistry, cyanogen bromide activation, N-hydroxysuccinimide activation, epoxide activation, sulfhydryl activation, and hydrazide activation. The resulting medium will generally be configured in the form of a column, and fluids containing ligand are passed through the column one or more times to allow ligand to bind to the receptor polypeptide. The ligand is then eluted using changes in salt concentration, chaotropic agents (guanidine HCl), or pH to disrupt ligand-receptor binding.

An assay system that uses a ligand-binding receptor (or an antibody, one member of a complement/anti-complement pair) or a binding fragment thereof, and a commercially available biosensor instrument (BIAcore, Pharmacia Biosensor, Piscataway, N.J.) may be advantageously employed. Such receptor, antibody, member of a complement/anti-complement pair or fragment is immobilized onto the surface of a receptor chip. Use of this instrument is disclosed by Karlsson, J. *Immunol. Methods* 145:229-40, 1991 and Cunningham and Wells, *J. Mol. Biol.* 234:554-63, 1993. A receptor, antibody, member or fragment is covalently attached, using amine or sulfhydryl chemistry, to dextran fibers that are attached to gold film within the flow cell. A test sample is passed through the cell. If a ligand, epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding. Alternatively, ligand/receptor binding can be analyzed using SELDI™ technology (Ciphergen, Inc., Palo Alto, Calif.).

Ligand-binding receptor polypeptides can also be used within other assay systems known in the art. Such systems include Scatchard analysis for determination of binding affinity (see Scatchard, *Ann. NY Acad. Sci.* 51:660-72, 1949) and calorimetric assays (Cunningham et al., *Science* 253:545-48, 1991; Cunningham et al., *Science* 245:821-25, 1991).

Zalpha11 Ligand polypeptides can also be used to prepare antibodies that bind to zalpha11 Ligand epitopes, peptides or polypeptides. The zalpha11 Ligand polypeptide or a fragment thereof serves as an antigen (immunogen) to inoculate an animal and elicit an immune response. One of skill in the art would recognize that antigenic, epitope-bearing polypeptides contain a sequence of at least 6, preferably at least 9, and more preferably at least 15 to about 30 contiguous amino acid residues of a zalpha11 Ligand polypeptide (e.g., SEQ ID NO:2). Polypeptides comprising a larger portion of a zalpha11 Ligand polypeptide, i.e., from 30 to 100 residues up to the entire length of the amino acid sequence are included. Antigens or immunogenic epitopes can also include attached tags, adjuvants and carriers, as described herein. Suitable antigens include the zalpha11 Ligand polypeptide encoded by SEQ ID NO:2 from amino acid number 32 to amino acid number 162, or a contiguous 9 to 131 amino acid fragment thereof. Other suitable antigens include, the full length and the mature zalpha11 Ligand, helices A-D, and individual or multiple helices A, B, C, and D, of the zalpha11 Ligand four-helical-bundle structure, as described herein. Preferred peptides to use as antigens are hydrophilic peptides such as those predicted by one of skill in the art from a hydrophobicity plot, as described herein, for example, amino acid residues 114-119, 101-105, 126-131, 113-118, and 158-162 of SEQ ID NO:2.

Antibodies from an immune response generated by inoculation of an animal with these antigens can be isolated and purified as described herein. Methods for preparing and isolating polyclonal and monoclonal antibodies are well known in the art. See, for example, *Current Protocols in Immunology*, Cooligan, et al. (eds.), National Institutes of Health, John Wiley and Sons, Inc., 1995; Sambrook et al., *Molecular Cloning: A Laboratory Manual*, Second Edition, Cold Spring Harbor, N.Y., 1989; and Hurrell, J. G. R., Ed., *Monoclonal Hybridoma Antibodies: Techniques and Applications*, CRC Press, Inc., Boca Raton, Fla., 1982.

As would be evident to one of ordinary skill in the art, polyclonal antibodies can be generated from inoculating a variety of warm-blooded animals such as horses, cows, goats, sheep, dogs, chickens, rabbits, mice, and rats with a zalpha11 Ligand polypeptide or a fragment thereof. The immunogenicity of a zalpha11 Ligand polypeptide may be increased through the use of an adjuvant, such as alum (aluminum hydroxide) or Freund's complete or incomplete adjuvant. Polypeptides useful for immunization also include fusion polypeptides, such as fusions of zalpha11 Ligand or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')2 and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Moreover, human antibodies can be produced in transgenic, non-human animals that have been engineered to contain human immunoglobulin genes as disclosed in WIPO Publication WO 98/24893. It is preferred that the endogenous immunoglobulin genes in these animals be inactivated or eliminated, such as by homologous recombination.

Antibodies are considered to be specifically binding if: 1) they exhibit a threshold level of binding activity, and 2) they do not significantly cross-react with related polypeptide molecules. A threshold level of binding is determined if anti-zalpha11 Ligand antibodies herein bind to a zalpha11 Ligand polypeptide, peptide or epitope with an affinity at least 10-fold greater than the binding affinity to control (non-zalpha11 Ligand) polypeptide. It is preferred that the antibodies exhibit a binding affinity (Ka) of $10^6$ $M^{-1}$ or greater, preferably $10^7$ $M^{-1}$ or greater, more preferably $10^8$ $M^{-1}$ or greater, and most preferably $10^9$ $M^{-1}$ or greater. The binding affinity of an antibody can be readily determined by one of ordinary skill in the art, for example, by Scatchard analysis (Scatchard, G., *Ann. NY Acad. Sci.* 51: 660-672, 1949).

Whether anti-zalpha11 Ligand antibodies do not significantly cross-react with related polypeptide molecules is shown, for example, by the antibody detecting zalpha11 Ligand polypeptide but not known related polypeptides using a standard Western blot analysis (Ausubel et al., ibid.). Examples of known related polypeptides are those disclosed in the prior art, such as known orthologs, and paralogs, and similar known members of a protein family. Screening can also be done using non-human zalpha11 Ligand, and zalpha11 Ligand mutant polypeptides. Moreover, antibodies can be "screened against" known related polypeptides, to isolate a population that specifically binds to the zalpha11 Ligand polypeptides. For example, antibodies raised to zalpha11 Ligand are adsorbed to related polypeptides adhered to insoluble matrix; antibodies specific to zalpha11 Ligand will flow through the matrix under the proper buffer conditions. Screening allows isolation of polyclonal and monoclonal antibodies non-crossreactive to known closely related polypeptides (*Antibodies: A Laboratory Manual*, Harlow and Lane (eds.), Cold Spring Harbor Laboratory Press, 1988; *Current Protocols in Immunology*, Cooligan, et al. (eds.), National Institutes of Health, John Wiley and Sons, Inc., 1995). Screening and isolation of specific antibodies is well known in the art. See, *Fundamental Immunology*, Paul (eds.), Raven Press, 1993; Getzoff et al., *Adv. in Immunol.* 43: 1-98, 1988; *Monoclonal Antibodies: Principles and Practice*, Goding, J. W. (eds.), Academic Press Ltd., 1996; Benjamin et al., *Ann. Rev. Immunol.* 2: 67-101, 1984. Specifically binding anti-zalpha11 Ligand antibodies can be detected by a number of methods in the art, and disclosed below.

A variety of assays known to those skilled in the art can be utilized to detect antibodies which bind to zalpha11 Ligand proteins or polypeptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmuno-precipitation, enzyme-linked immunosorbent assay (ELISA), dot blot or Western blot assay, inhibition or competition assay, and sandwich assay. In addition, antibodies can be screened for binding to wild-type versus mutant zalpha11 Ligand protein or polypeptide.

Antibodies to zalpha11 Ligand may be used for tagging cells that express zalpha11 Ligand; for isolating zalpha11 Ligand by affinity purification; for diagnostic assays for determining circulating levels of zalpha11 Ligand polypeptides; for detecting or quantitating soluble zalpha11 Ligand as a marker of underlying pathology or disease; in analytical methods employing FACS; for screening expression libraries; for generating anti-idiotypic antibodies; and as neutralizing antibodies or as antagonists to block zalpha11 Ligand activity in vitro and in vivo. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anti-complement pairs as intermediates. Antibodies herein may also be directly or indirectly conjugated to drugs, toxins, radionuclides and the like, and these conjugates used for in vivo diagnostic or therapeutic applications. Moreover, antibodies to zalpha11 Ligand or fragments thereof may be used in vitro to detect denatured zalpha11 Ligand or fragments thereof in assays, for example, Western Blots or other assays known in the art.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria, toxin, saporin, *Pseudomonas* exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule can be conjugated with a member of a complementary/anticomplementary pair, where the other member is bound to the polypeptide or antibody portion. For these purposes, biotin/streptavidin is an exemplary complementary/anticomplementary pair.

Binding polypeptides can also act as zalpha11 Ligand "antagonists" to block zalpha11 Ligand binding and signal transduction in vitro and in vivo. These anti-zalpha11 Ligand binding polypeptides would be useful for inhibiting zalpha11 Ligand activity or protein-binding.

Polypeptide-toxin fusion proteins or antibody-toxin fusion proteins can be used for targeted cell or tissue inhibition or ablation (for instance, to treat cancer cells or tissues). Alternatively, if the polypeptide has multiple functional domains (i.e., an activation domain or a receptor binding domain, plus a targeting domain), a fusion protein including only the targeting domain may be suitable for directing a detectable molecule, a cytotoxic molecule or a complementary molecule to a cell or tissue type of interest. In instances where the domain only fusion protein includes a complementary molecule, the anti-complementary molecule can be conjugated to a detectable or cytotoxic molecule. Such domain-complementary molecule fusion proteins thus represent a generic targeting vehicle for cell/tissue-specific delivery of generic anti-complementary-detectable/cytotoxic molecule conjugates.

Zalpha11 Ligand cytokine fusion proteins or antibody-cytokine fusion proteins can be used for enhancing in vivo killing of target tissues (for example, blood and bone marrow cancers), if the zalpha11 Ligand polypeptide or anti-zalpha11 Ligand antibody targets the hyperproliferative blood or bone marrow cell (See, generally, Hornick et al., *Blood* 89:4437-47, 1997). The described fusion proteins enable targeting of a cytokine to a desired site of action, thereby providing an elevated local concentration of cytokine. Suitable zalpha11 Ligand polypeptides or anti-zalpha11 Ligand antibodies target an undesirable cell or tissue (i.e., a tumor or a leukemia), and the fused cytokine mediated improved target cell lysis by effector cells. Suitable cytokines for this purpose include interleukin 2 and granulocyte-macrophage colony-stimulating factor (GM-CSF), for instance.

Differentiation is a progressive and dynamic process, beginning with pluripotent stem cells and ending with terminally differentiated cells. Pluripotent stem cells that can regenerate without commitment to a lineage express a set of differentiation markers that are lost when commitment to a cell lineage is made. Progenitor cells express a set of differentiation markers that may or may not continue to be expressed as the cells progress down the cell lineage pathway toward maturation. Differentiation markers that are expressed exclusively by mature cells are usually functional properties such as cell products, enzymes to produce cell products, and receptors. The stage of a cell population's differentiation is monitored by identification of markers present in the cell population.

There is evidence to suggest that factors that stimulate specific cell types down a pathway towards terminal differentiation or dedifferentiation affect the entire cell population originating from a common precursor or stem cell. Thus, the present invention includes stimulating or inhibiting the proliferation of lymphoid cells, hematopoietic cells and epithelial cells.

Zalpha11 Ligand was isolated from tissue known to have important immunological function and which contain cells that play a role in the immune system. Zalpha11 Ligand is expressed in CD3+ selected, activated peripheral blood cells, and it has been shown that zalpha11 Ligand expression increases after T cell activation. Moreover, results of experiments described in the Examples section herein demonstrate that polypeptides of the present invention have an effect on the growth/expansion and/or differentiated state of NK cells or NK progenitors. Additional evidence demonstrates that zalpha11 Ligand affects proliferation and/or differentiation of T cells and B cells in vivo. Factors that both stimulate proliferation of hematopoietic progenitors and activate mature cells are generally known. NK cells are responsive to IL-2 alone, but proliferation and activation generally require additional growth factors. For example, it has been shown that IL-7 and Steel Factor (c-kit ligand) were required for colony formation of NK progenitors. IL-15+IL-2 in combination with IL-7 and Steel Factor was more effective (Mrózek et al., *Blood* 87:2632-2640, 1996). However, unidentified cytokines may be necessary for proliferation of specific subsets of NK cells and/or NK progenitors (Robertson et. al., *Blood* 76:2451-2438, 1990). A composition comprising zalpha11 Ligand and IL-15 stimulates NK progenitors and NK cells, with evidence that this composition is more potent than previously described factors and combinations of factors.

Assays measuring differentiation include, for example, measuring cell markers associated with stage-specific expression of a tissue, enzymatic activity, functional activity or morphological changes (Watt, *FASEB*, 5:281-284, 1991; Francis, *Differentiation* 57:63-75, 1994; Raes, *Adv. Anim. Cell Biol. Technol. Bioprocesses,* 161-171, 1989; all incorporated herein by reference). Alternatively, zalpha11 Ligand polypeptide itself can serve as an additional cell-surface or secreted marker associated with stage-specific expression of a tissue. As such, direct measurement of zalpha11 Ligand polypeptide, or its loss of expression in a tissue as it differentiates, can serve as a marker for differentiation of tissues.

Similarly, direct measurement of zalpha11 Ligand polypeptide, or its loss of expression in a tissue can be determined in a tissue or in cells as they undergo tumor progression. Increases in invasiveness and motility of cells, or the gain or loss of expression of zalpha11 Ligand in a pre-cancerous or cancerous condition, in comparison to normal tissue, can serve as a diagnostic for transformation, invasion and metastasis in tumor progression. As such, knowledge of a tumor's stage of progression or metastasis will aid the physician in choosing the most proper therapy, or aggressiveness of treatment, for a given individual cancer patient. Methods of measuring gain and loss of expression (of either mRNA or protein) are well known in the art and described herein and can be applied to zalpha11 Ligand expression. For example, appearance or disappearance of polypeptides that regulate cell motility can be used to aid diagnosis and prognosis of prostate cancer (Banyard, J. and Zetter, B. R., *Cancer and Metast. Rev.* 17:449-458, 1999). As an effector of cell motility, zalpha11 Ligand gain or loss of expression may serve as a diagnostic for lymphoid, B-cell, epithelial, hematopoietic and other cancers.

Moreover, the activity and effect of zalpha11 Ligand on tumor progression and metastasis can be measured in vivo. Several syngeneic mouse models have been developed to study the influence of polypeptides, compounds or other treatments on tumor progression. In these models, tumor cells passaged in culture are implanted into mice of the same strain as the tumor donor. The cells will develop into tumors having similar characteristics in the recipient mice, and metastasis will also occur in some of the models. Appropriate tumor models for our studies include the Lewis lung carcinoma (ATCC No. CRL-1642) and B16 melanoma (ATCC No. CRL-6323), amongst others. These are both commonly used tumor lines, syngeneic to the C57BL6/J mouse, that are readily cultured and manipulated in vitro. Tumors resulting from implantation of either of these cell lines are capable of metastasis to the lung in C57BL6/J mice. The Lewis lung carcinoma model has recently been used in mice to identify an inhibitor of angiogenesis (O'Reilly M S, et al. *Cell* 79: 315-328, 1994). C57BL6/J mice are treated with an experimental agent either through daily injection of recombinant protein, agonist or antagonist or a one time injection of recombinant adenovirus. Three days following this treatment, $10^5$ to $10^6$ cells are implanted under the dorsal skin. Alternatively, the cells themselves may be infected with recombinant adenovirus, such as one expressing zalpha11 Ligand, before implantation so that the protein is synthesized at the tumor site or intracellularly, rather than systemically. The mice normally develop visible tumors within 5 days. The tumors are allowed to grow for a period of up to 3 weeks, during which time they may reach a size of 1500-1800 mm3 in the control treated group. Tumor size and body weight are carefully monitored throughout the experiment. At the time of sacrifice, the tumor is removed and weighed along with the lungs and the liver. The lung weight has been shown to correlate well with metastatic tumor burden. As an additional measure, lung surface metastases are counted. The resected tumor, lungs and liver are prepared for histopathological examination, immunohistochemistry, and in situ hybridization, using methods known in the art and described herein. The influence of the expressed polypeptide in question, e.g., zalpha11 Ligand, on the ability of the tumor to recruit vasculature and undergo metastasis can thus be assessed. In addition, aside from using adenovirus, the implanted cells can be transiently transfected with zalpha11 Ligand. Use of stable zalpha11 Ligand transfectants as well as use of induceable promoters to activate zalpha11 Ligand expression in vivo are known in the art and can be used in this system to assess zalpha11 Ligand induction of metastasis. Moreover, purified zalpha11 Ligand or zalpha11 Ligand conditioned media can be directly injected in to this mouse model, and hence be used in this system. For general reference see, O'Reilly M S, et al. *Cell* 79:315-328, 1994; and Rusciano D, et al. *Murine Models of Liver Metastasis. Invasion Metastasis* 14:349-361, 1995.

Zalpha11 Ligand will be useful in treating tumorgenesis, and therefore would be useful in the treatment of cancer. Zalpha11 Ligand inhibits IL-4 stimulated proliferation of anti-IgM stimulated normal B-cells and a similar effect is observed in B-cell tumor lines suggesting that there may be therapeutic benefit in treating patients with the zalpha11 Ligand in order to induce the B cell tumor cells into a less proliferative state. The ligand could be administered in combination with other agents already in use including both conventional chemotherapeutic agents as well as immune modulators such as interferon alpha. Alpha/beta interferons have been shown to be effective in treating some leukemias and animal disease models, and the growth inhibitory effects of interferon-alpha and zalpha11 Ligand are additive for at least one B-cell tumor-derived cell line.

The present invention provides a method of reducing proliferation of a neoplastic B or T cells comprising administering to a mammal with a B or T cell neoplasm an amount of a composition of zalpha11 Ligand sufficient to reduce proliferation of the neoplastic B or T cells. In other embodiments, the composition can comprise at least one other cytokine selected from the group consisting of IL-2, IL-15, IL-4, GM-CSF, Flt3 ligand or stem cell factor.

In another aspect, the present invention provides a method of reducing proliferation of a neoplastic B or T cells comprising administering to a mammal with a B or T cell neoplasm an amount of a composition of zalpha11 Ligand antagonist sufficient to reducing proliferation of the neoplastic B or T cells. In other embodiments, the composition can comprise at least one other cytokine selected from the group consisting of IL-2, IL-15, IL-4, GM-CSF, Flt3 ligand or stem cell factor. Furthermore, the zalpha11 Ligand antagonist can be a ligand/toxin fusion protein.

A zalpha11 Ligand-saporin fusion toxin may be employed against a similar set of leukemias and lymphomas, extending the range of leukemias that can be treated with zalpha11 Ligand. Fusion toxin mediated activation of the zalpha11 receptor provides two independent means to inhibit the growth of the target cells, the first being identical to the effects seen by the ligand alone, and the second due to delivery of the toxin through receptor internalization. The lymphoid restricted expression pattern of the zalpha11 receptor suggests that the ligand-saporin conjugate can be tolerated by patients.

When treatment for malignancies includes allogeneic bone marrow or stem cell transplantation, zalpha11 Ligand may be valuable in enhancement of the graft-vs-tumor effect. zalpha11 Ligand stimulates the generation of lytic NK cells from marrow progenitors and stimulates the proliferation of T-cells following activation of the antigen receptors. Therefore, when patients receive allogenic marrow transplants, zalpha11 Ligand will enhance the generation of anti-tumor responses, with or without the infusion of donor lymphocytes.

The tissue distribution of a receptor for a given cytokine offers a strong indication of the potential sites of action of that cytokine. Northern analysis of zalpha11 receptor revealed transcripts in human spleen, thymus, lymph node, bone marrow, and peripheral blood leukocytes. Specific cell types were identified as expressing zalpha11 receptors, and strong signals were seen in a mixed lymphocyte reaction (MLR) and in the Burkitt's lymphoma Raji. The two monocytic cell lines, THP-1 (Tsuchiya et al., *Int. J. Cancer* 26:171-176, 1980) and U937 (Sundstrom et al., *Int. J. Cancer* 17:565-577, 1976), were negative.

Zalpha11 receptor is expressed at relatively high levels in the MLR, in which peripheral blood mononuclear cells (PB-MNC) from two individuals are mixed, resulting in mutual activation. Detection of high levels of transcript in the MLR but not in resting T or B cell populations suggests that zalpha11 receptor expression may be induced in one or more cell types during activation. Activation of isolated populations of T and B cells can be artificially achieved by stimulating cells with PMA and ionomycin. When sorted cells were subjected to these activation conditions, levels of zalpha11 receptor transcript increased in both cell types, supporting a role for this receptor and zalpha11 Ligand in immune responses, especially in autocrine and paracrine T and B cell expansions during activation. Zalpha11 Ligand may also play a role in the expansion of more primitive progenitors involved in lymphopoiesis.

zalpha11 receptor was found to be present at low levels in resting T and B cells, and was upregulated during activation in both cell types. Interestingly, the B cells also down-regulate the message more quickly than do T cells, suggesting that amplitude of signal and timing of quenching of signal are important for the appropriate regulation of B cell responses.

In addition, a large proportion of intestinal lamina propria cells show positive hybridization signals with zalpha11 receptor. This tissue consists of a mixed population of lymphoid cells, including activated CD4+ T cells and activated B cells. Immune dysfunction, in particular chronic activation of the mucosal immune response, plays an important role in the etiology of Crohn's disease; abnormal response to and/or production of proinflammatory cytokines is also a suspected factor (Braegger et al., *Annals Allergy* 72:135-141, 1994; Sartor R B *Am. J. Gastroenterol.* 92:5S-11S, 1997. zalpha11 Ligand in concert with IL-15 expands NK cells from bone marrow progenitors and augments NK cell effector function. zalpha11 Ligand also co-stimulates mature B cells stimulated with anti-CD40 antibodies, but inhibits B cell proliferation to signals through IgM. zalpha11 Ligand enhances T cell proliferation in concert with a signal through the T cell receptor, and overexpression in transgenic mice leads to lymphopenia and an expansion of monocytes and granulocytes. These pleiotropic effects of zalpha11 Ligand suggest that it can provide therapeutic utility for a wide range of diseases arising from defects in the immune system, including (but not limited to) systemic lupus erythematosus (SLE), rheumatoid arthritis (RA), multiple sclerosis (MS), myasthenia gravis, and diabetes. It is important to note that these diseases are the result of a complex network of immune dysfunction (SLE, for example, is the manifestation of defects in both T and B cells), and that immune cells are dependent upon interaction with one another to elicit a potent immune response. Therefore, zalpha11 Ligand (or an antagonist of the Ligand) that can be used to manipulate more than one type of immune cell is an attractive therapeutic candidate for intervention at multiple stages of disease.

The polypeptides and proteins of the present invention can also be used ex vivo, such as in autologous marrow culture. Briefly, bone marrow is removed from a patient prior to chemotherapy or organ transplant and treated with zalpha11 Ligand, optionally in combination with one or more other cytokines. The treated marrow is then returned to the patient after chemotherapy to speed the recovery of the marrow or after transplant to suppress graft vs. Host disease. In addition, the proteins of the present invention can also be used for the ex vivo expansion of marrow or peripheral blood progenitor (PBPC) cells. Prior to treatment, marrow can be stimulated with stem cell factor (SCF) to release early progenitor cells into peripheral circulation. These progenitors can be collected and concentrated from peripheral blood and then treated in culture with zalpha11 Ligand, optionally in combination with one or more other cytokines, including but not limited to SCF, IL-2, IL-4, IL-7 or IL-15, to differentiate and proliferate into high-density lymphoid cultures, which can then be returned to the patient following chemotherapy or transplantation.

The present invention provides a method for expansion of hematopoietic cells and hematopoietic cell progenitors comprising culturing bone marrow or peripheral blood cells with a composition comprising an amount of zalpha11 Ligand sufficient to produce an increase in the number of lymphoid cells in the bone marrow or peripheral blood cells as compared to bone marrow or peripheral blood cells cultured in the absence of zalpha11 Ligand. In other embodiments, the hematopoietic cells and hematopoietic progenitor cells are lymphoid cells. In another embodiment, the lymphoid cells are NK cells or cytotoxic T cells. Furthermore, the composition can also comprise at least one other cytokine selected from the group consisting of IL-2, IL-15, IL-4, GM-CSF, Flt3 ligand and stem cell factor.

Alternatively, zalpha11 Ligand may activate the immune system which would be important in boosting immunity to infectious diseases, treating immunocompromised patients, such as HIV+ patients, or in improving vaccines. In particular, zalpha11 Ligand stimulation or expansion of NK cells, or their progenitors, would provide therapeutic value in treatment of viral infection, and as an anti-neoplastic factor. NK cells are thought to play a major role in elimination of metastatic tumor cells and patients with both metastases and solid tumors have decreased levels of NK cell activity (Whiteside et. al., *Curr. Top. Microbiol. Immunol.* 230:221-244, 1998). Similarly, zalpha11 Ligand stimulation of the immune response against viral and non-viral pathogenic agents (including bacteria, protozoa, and fungi) would provide therapeutic value in treatment of such infections by inhibiting the growth of such infections agents. Determining directly or indirectly the levels of a pathogen or antigen, such as a tumor cell, present in the body can be achieved by a number of methods known in the art and described herein.

The present invention include a method of stimulating an immune response in a mammal exposed to an antigen or pathogen comprising the steps of: (1) determining directly or indirectly the level of antigen or pathogen present in said mammal; (2) administering a composition comprising zalpha11 Ligand polypeptide in an acceptable pharmaceutical vehicle; (3) determining directly or indirectly the level of antigen or pathogen in said mammal; and (4) comparing the level of the antigen or pathogen in step 1 to the antigen or pathogen level in step 3, wherein a change in the level is indicative of stimulating an immune response. In another embodiment the zalpha11 Ligand composition is re-administered. In other embodiments, the antigen is a B cell tumor; a virus; a parasite or a bacterium.

In another aspect, the present invention provides a method of stimulating an immune response in a mammal exposed to an antigen or pathogen comprising: (1) determining a level of an antigen- or pathogen-specific antibody; (2) administering a composition comprising zalpha11 Ligand polypeptide in an acceptable pharmaceutical vehicle; (3) determining a post administration level of antigen- or pathogen-specific antibody; (4) comparing the level of antibody in step (1) to the level of antibody in step (3), wherein an increase in antibody level is indicative of stimulating an immune response.

Polynucleotides encoding zalpha11 Ligand polypeptides are useful within gene therapy applications where it is desired to increase or inhibit zalpha11 Ligand activity. If a mammal has a mutated or absent zalpha11 Ligand gene, the zalpha11 Ligand gene can be introduced into the cells of the mammal. In one embodiment, a gene encoding a zalpha11 Ligand polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320-30, 1991); an attenuated adenovirus vector, such as the vector described by Stratford-Perricaudet et al., *J. Clin. Invest.* 90:626-30, 1992; and a defective adeno-associated virus vector (Samulski et al., *J. Virol.* 61:3096-101, 1987; Samulski et al., *J. Virol.* 63:3822-8, 1989).

A zalpha11 Ligand gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413-7, 1987; Mackey et al., *Proc. Natl. Acad. Sci. USA* 85:8027-31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the immune system, pancreas, liver, kidney, and brain. Lipids may be chemically coupled to other molecules for the purpose of targeting. Targeted peptides (e.g., hormones or neurotransmitters), proteins such as antibodies, or non-peptide molecules can be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963-7, 1992; Wu et al., *J. Biol. Chem.* 263:14621-4, 1988.

Antisense methodology can be used to inhibit zalpha11 Ligand gene transcription, such as to inhibit cell proliferation in vivo. Polynucleotides that are complementary to a segment of a zalpha11 Ligand-encoding polynucleotide (e.g., a polynucleotide as set froth in SEQ ID NO:1) are designed to bind to zalpha11 Ligand-encoding mRNA and to inhibit translation of such mRNA. Such antisense polynucleotides are used to inhibit expression of zalpha11 Ligand polypeptide-encoding genes in cell culture or in a subject.

Mice engineered to express the zalpha11 Ligand gene, referred to as "transgenic mice," and mice that exhibit a complete absence of zalpha11 Ligand gene function, referred to as "knockout mice," may also be generated (Snouwaert et al., *Science* 257:1083, 1992; Lowell et al., *Nature* 366:740-42, 1993; Capecchi, M. R., *Science* 244: 1288-1292, 1989; Palmiter, R. D. et al. *Annu Rev Genet.* 20: 465-499, 1986). For example, transgenic mice that over-express zalpha11 Ligand, either ubiquitously or under a tissue-specific or tissue-restricted promoter can be used to ask whether over-expression causes a phenotype. For example, over-expression of a wild-type zalpha11 Ligand polypeptide, polypeptide fragment or a mutant thereof may alter normal cellular processes, resulting in a phenotype that identifies a tissue in which zalpha11 Ligand expression is functionally relevant and may indicate a therapeutic target for the zalpha11 Ligand, its agonists or antagonists. For example, a preferred transgenic mouse to engineer is one that over-expresses the zalpha11 Ligand (amino acid residues 32-162 of SEQ ID NO:2). Moreover, such over-expression may result in a phenotype that shows similarity with human diseases. Similarly, knockout zalpha11 Ligand mice can be used to determine where zalpha11 Ligand is absolutely required in vivo. The phenotype of knockout mice is predictive of the in vivo effects of that a zalpha11 Ligand antagonist, such as those described herein, may have. The human or mouse zalpha11 Ligand cDNA can be used to generate knockout mice. These mice may be employed to study the zalpha11 Ligand gene and the protein encoded thereby in an in vivo system, and can be used as in vivo models for corresponding human diseases. Moreover, transgenic mice expression of zalpha11 Ligand antisense polynucleotides or ribozymes directed against zalpha11 Ligand, described herein, can be used analogously to transgenic mice described above. Studies may be carried out by administration of purified zalpha11 Ligand protein, as well.

For pharmaceutical use, the proteins of the present invention are formulated for parenteral, particularly intravenous or subcutaneous, delivery according to conventional methods. The bioactive polypeptide or antibody conjugates described herein can be delivered intravenously, intraarterially or intraductally, or may be introduced locally at the intended site of action. Intravenous administration will be by bolus injection or infusion over a typical period of one to several hours. In general, pharmaceutical formulations will include a zalpha11 Ligand protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in Remington: *The Science and Practice of Pharmacy*, Gennaro, ed., Mack Publishing Co., Easton, Pa., 19th ed., 1995. Therapeutic doses will generally be in the range of 0.1 to 100 µg/kg of patient weight per day, preferably 0.5-20 µg/kg per day, with the exact dose determined by the clinician according to accepted standards, taking into account the nature and severity of the condition to be treated, patient traits, etc. Determination of dose is within the level of ordinary skill in the art. The proteins may be administered for acute treatment, over one week or less, often over a period of one to three days or may be used in chronic treatment, over several months or years. In general, a therapeutically effective amount of zalpha11 Ligand is an amount sufficient to produce a clinically significant change in hematopoietic or immune function.

The invention is further illustrated by the following non-limiting examples.

EXAMPLES

Example 1

Construction of MPL-zalpha11 Polypeptide Chimera: MPL Extracellular and TM Domain Fused to the Zalpha11 Intracellular Signaling Domain The extracellular and transmembrane domains of the murine MPL receptor were isolated from a plasmid containing the murine MPL receptor (PHZ1/MPL plasmid) using PCR with primers ZC17,212 (SEQ ID NO:5) and ZC19,914 (SEQ ID NO:6). The reaction conditions were as follows: 95° C. for 1 min.; 35 cycles at 95° C. for 1 min., 45° C. for 1 min., 72° C. for 2 min.; followed by 72° C. at 10 min.; then a 10° C. soak. The PCR product was run on a 1% low melting point agarose (Boerhinger Mannheim, Indianapolis, Ind.) and the approximately 1.5 kb MPL receptor fragment isolated using PCR purification reagents QIAQUICK® gel extraction kit (Qiagen) as per manufacturer's instructions.

The intracellular domains of human zalpha11 were isolated from a plasmid containing zalpha11 receptor cDNA using PCR with primers ZC19,913 (SEQ ID NO:8) and ZC20,097 (SEQ ID NO:9). The polynucleotide sequence corresponding to the zalpha11 receptor coding sequence is shown in SEQ ID NO:7, and the corresponding amino acid sequence shown in SEQ ID NO:115. The reaction conditions were as per above. The PCR product was run on a 1% low melting point agarose (Boerhinger Mannheim) and the approximately 900 bp zalpha11 fragment isolated using PCR purification reagents QIAQUICK® gel extraction kit as per manufacturer's instructions.

Each of the isolated fragments described above were mixed at a 1:1 volumetric ratio and used in a PCR reaction using ZC17,212 (SEQ ID NO:5) and ZC20,097 (SEQ ID NO:9) to create the MPL-zalpha11 chimera. The reaction conditions were as follows: 95° C. for 1 min.; 35 cycles at 95° C. for 1 min., 55° C. for 1 min., 72° C. for 2 min.; followed by 72° C. at 10 min.; then a 10° C. soak. The entire PCR product was run on a 1% low melting point agarose (Boehringer Mannheim) and the approximately 2.4 kb MPL-zalpha11 chimera fragment isolated using PCR purification reagents QIAQUICK® gel extraction kit (Qiagen) as per manufacturer's instructions. The MPL-zalpha11 chimera fragment was digested with EcoRI (BRL) and XbaI (Boerhinger Mannheim) as per manufacturer's instructions. The entire digest was run on a 1% low melting point agarose (Boehringer Mannheim) and the cleaved MPL-zalpha11 chimera isolated using PCR purification reagents QIAQUICK® gel extraction kit (Qiagen) as per manufacturer's instructions. The resultant cleaved MPL-zalpha11 chimera was inserted into an expression vector as described below.

Recipient expression vector pZP-5N was digested with EcoRI (BRL) and HindIII (BRL) as per manufacturer's instructions, and gel purified as described above. This vector fragment was combined with the EcoRI and XbaI cleaved MPL-zalpha11 chimera isolated above and a XbaI/HindIII linker fragment in a ligation reaction. The ligation was run using T4 Ligase (BRL), at 15° C. overnight. A sample of the ligation was electroporated in to *E. coli* DH10b™ competent cells ELECTROMAX™ electrocompetent *E. coli* cells (25 µF, 200Ω, 2.3V). Transformants were plated on LB+Ampicillin plates and single colonies screened by PCR to check for the MPL-zalpha11 chimera using ZC17,212 (SEQ ID NO:5) and ZC20,097 (SEQ ID NO:9) using the PCR conditions as described above.

Confirmation of the MPL-zalpha11 chimera sequence was made by sequence analyses using the following primers: ZC12,700 (SEQ ID NO:10), ZC5,020 (SEQ ID NO:11), ZC6,675 (SEQ ID NO:12), ZC7,727 (SEQ ID NO:13), ZC8,290 (SEQ ID NO:14), ZC19,572 (SEQ ID NO:15), ZC6,622 (SEQ ID NO:16), ZC7,736 (SEQ ID NO:17), and ZC9,273 (SEQ ID NO:18). The insert was approximately 2.4 bp, and was full-length.

Example 2

MPL-zalpha11 Chimera Based Proliferation in BAF3 Assay using Alamar Blue

A. Construction of BaF3 Cells Expressing MPL-zalpha11 Chimera

BaF3, an interleukin-3 (IL-3) dependent pre-lymphoid cell line derived from murine bone marrow (Palacios and Steinmetz, *Cell* 41: 727-734, 1985; Mathey-Prevot et al., *Mol. Cell. Biol.* 6: 4133-4135, 1986), was maintained in complete media (RPMI medium (JRH Bioscience Inc., Lenexa, Kans.) supplemented with 10% heat-inactivated fetal calf serum, 2 ng/ml murine IL-3 (mIL-3) (R & D, Minneapolis, Minn.), 2 mM L-glutaMax-1™ (Gibco BRL), 1 mM Sodium Pyruvate (Gibco BRL), and PSN antibiotics (GIBCO BRL)). Prior to electroporation, pZP-5N/MPL-zalpha11 plasmid DNA (Example 1) was prepared and purified using a QIAGEN® Maxi Prep kit (Qiagen) as per manufacturer's instructions. BaF3 cells for electroporation were washed once in RPMI media and then resuspended in RPMI media at a cell density of $10^7$ cells/ml. One ml of resuspended BaF3 cells was mixed with 30 µg of the pZP-5N/MPL-zalpha11 plasmid DNA and transferred to separate disposable electroporation chambers (GIBCO BRL). Following a 15 minute incubation at room temperature the cells were given two serial shocks (800 lFad/300 V.; 1180 lFad/300 V.) delivered by an electroporation apparatus (CELL-PORATOR™; GIBCO BRL). After a 5 minute recovery time, the electroporated cells were transferred to 50 ml of complete media and placed in an incubator for 15-24 hours (37° C., 5% CO2). The cells were then spun down and resuspended in 50 ml of complete media containing (Gibco) selection (500 µg/ml G418) in a T-162 flask to isolate the G418-resistant pool. Pools of the transfected BaF3 cells, hereinafter called BaF3/MPL-zalpha11 cells, were assayed for signaling capability as described below.

B. Testing the Signaling Capability of the BaF3/MPL-zalpha11 Cells Using an Alamar Blue Proliferation Assay BaF3/MPL-zalpha11 cells were spun down and washed in the complete media, described above, but without mIL-3 (hereinafter referred to as "mIL-3 free media"). The cells were spun and washed 3 times to ensure the removal of the mIL-3. Cells were then counted in a hemacytometer. Cells were plated in a 96-well format at 5000 cells per well in a volume of 100 µl per well using the mIL-3 free media.

Proliferation of the BaF3/MPL-zalpha11 cells was assessed using murine mthrombopoietin (mTPO) diluted with mIL-3 free media to 500 ng/ml, 250 ng/ml, 125 ng/ml, 62 ng/ml, 30 ng/ml, 15 ng/ml, 7.5 ng/ml, 3.75 ng/ml, 1.8 ng/ml, 0.9 ng/ml, 0.5 ng/ml and 0.25 ng/ml concentrations. 100 µl of the diluted mTPO was added to the BaF3/MPL-zalpha11 cells. The total assay volume is 200 µl. Negative controls were run in parallel using mIL-3 free media only, without the addition of mTPO. The assay plates were incubated at 37° C., 5% CO2 for 3 days at which time ALAMAR BLUE™ (Accumed, Chicago, Ill.) was added at 20 µl/well. ALAMAR BLUE™ gives a fluourometric readout based on the metabolic activity of cells, and is thus a direct measurement of cell proliferation in comparison to a negative control. Plates were again incubated at 37° C., 5% $CO_2$ for 24 hours. Plates were read on the Fmax™ plate reader (Molecular Devices Sunnyvale, Calif.) using the SOFTMAX™ Pro program, at wavelengths 544 (Excitation) and 590 (Emmission).

Results confirmed the signaling capability of the intracellular portion of the zalpha11 receptor, as the thrombopoietin induced proliferation at approximately 10 fold over back ground at mTPO concentrations of 62 ng/ml and greater.

Example 3

Construction of Expression Vector Expressing Full-length Zalpha11

The entire zalpha11 receptor was isolated from a plasmid containing zalpha11 receptor cDNA (SEQ ID NO:7) using PCR with primers ZC19,905 (SEQ ID NO:19) and ZC19,906 (SEQ ID NO:20). The reaction conditions were as follows: 95° C. for 1 min; 35 cycles at 95° C. for 1 min, 55° C. for 1 min, 72° C. for 2 min; followed by 72° C. at 10 min; then a 10° C. soak. The PCR product was run on a 1% low melting point agarose (Boerhinger Mannheim) gel and the approximately 1.5 kb zalpha11 cDNA isolated using PCR purification reagents QIAQUICK® gel extraction kit (Qiagen) as per manufacturer's instructions.

The purified zalpha11 cDNA was digested with BamHI (Boerhinger Mannheim) and EcoRI (BRL) as per manufacturer's instructions. The entire digest was run on a 1% low melting point agarose (Boerhinger Mannheim) gel and the cleaved zalpha11 fragment was purified the using PCR purification reagents QIAQUICK® gel extraction kit as per manufacturer's instructions. The resultant cleaved zalpha11 fragment was inserted into an expression vector as described below.

Recipient expression vector pZP-5N was digested with BamHI (Boerhinger Mannheim) and EcoRI (BRL) as per manufacturer's instructions, and gel purified as described above. This vector fragment was combined with the BamHI and EcoRI cleaved zalpha11 fragment isolated above in a ligation reaction using T4 Ligase (BRL). The ligation was incubated at 15° C. overnight. A sample of the ligation was electroporated in to *E. coli* DH10b™ competent cells ELECTROMAX™ electrocompetent *E. coli* cells (25 µF, 200Ω, 2.3V). Transformants were plated on LB+Ampicillin plates and single colonies screened by PCR to check for the zalpha11 sequence using ZC19,905 (SEQ ID NO:19) and ZC19,906 (SEQ ID NO:20) using the PCR conditions as described above.

Confirmation of the zalpha11 sequence was made by sequence analyses using the following primers: ZC12,700 (SEQ ID NO:10), ZC5,020 (SEQ ID NO:11), ZC20,114 (SEQ ID NO:21), ZC19,459 (SEQ ID NO:22), ZC19,954 (SEQ ID NO:23), and ZC20,116 (SEQ ID NO:24). The insert was approximately 1.6 kb, and was full-length.

Example 4

Zalpha11 based proliferation in BAF3 assay using ALAMAR BLUE™

A. Construction of BaF3 Cells Expressing Zalpha11 Receptor

BaF3 cells expressing the full-length zalpha11 receptor was constructed as per Example 2A above, using 30 µg of the zalpha11 expression vector, described in Example 3 above. The BaF3 cells expressing the zalpha11 receptor mRNA were designated as BaF3/zalpha11. These cells were used to screen for zalpha11 Ligand as described below in Examples 5 and 6.

Example 5

Screening for Zalpha11 Ligand Using BaF3/Zalpha11 cells Using an ALAMAR BLUE™ Proliferation Assay A. Activation of Primary Monkey Splenocytes to Test for Presence of Zalpha11 Ligand Monkey splenocytes were stimulated in vitro to produce conditioned media to test for the presence of zalpha11 Ligand activity as described below. Monkey spleens were obtained from 8 year old female *M. nesestrian* monkeys. The spleens were teased part to produce a single cell suspension. The mononuclear cells were isolated by FICOLL PAQUE PLUS™ (Pharmacia Biotech, Uppsala, Sweden) density gradient. The mononuclear cells were seeded at $2\times10^6$ cells/ml in RPMI-1640 media supplemented with 10% FBS and activated with 5 ng/ml Phorbol-12-myristate-13-acetate (PMA) (Calbiochem, San Diego, Calif.), and 0.5 mg/ml Ionomycin™ (Calbiochem) for 48 hrs. The supernatant from the stimulated monkey spleen cells was used to assay proliferation of the BaF3/zalpha11 cells as described below.

B. Screening for Zalpha11 Ligand Using BaF3/Zalpha11 Cells Using an ALAMAR BLUE™ Proliferation Assay BaF3/Zalpha11 cells were spun down and washed in mIL-3 free media. The cells were spun and washed 3 times to ensure the removal of the mIL-3. Cells were then counted in a hemacytometer. Cells were plated in a 96-well format at 5000 cells per well in a volume of 100 µl per well using the mIL-3 free media.

Proliferation of the BaF3/Zalpha11 cells was assessed using conditioned media from activated monkey spleen (see Example 5A). Conditioned media was diluted with mIL-3 free media to 50%, 25%, 12.5%, 6.25%, 3.125%, 1.5%, 0.75% and 0.375% concentrations. 100 µl of the diluted conditioned media was added to the BaF3/Zalpha11 cells. The total assay volume is 200 µl. The assay plates were incubated at 37° C., 5% $CO_2$ for 3 days at which time Alamar Blue™ (Accumed, Chicago, Ill.) was added at 20 µl/well. Plates were again incubated at 37° C., 5% $CO_2$ for 24 hours. Plates were read on the Fmax™ plate reader (Molecular devices) as described above (Example 2).

Results confirmed the proliferative response of the BaF3/Zalpha11 cells to a factor present in the activated monkey spleen conditioned media. The response, as measured, was approximately 4-fold over background at the 50% concentration. The untransfected BaF3 cells did not proliferate in response to this factor, showing that this factor is specific for the Zalpha11 receptor.

C. Human Primary Source used to Isolate Zalpha11 Ligand 100 ml blood draws were taken from each of six donors. The blood was drawn using 10×10 ml vacutainer tubes containing heparin. Blood was pooled from six donors (600 ml), diluted 1:1 in PBS, and separated using a FICOLL-PLEAUE PLUS™ (Pharmacia Biotech). The isolated primary human cell yield after separation on the ficoll gradient was $1.2\times10^9$ cells.

Cells were suspended in 9.6 ml MACS buffer (PBS, 0.5% EDTA, 2 mM EDTA). 1.6 ml of cell suspension was removed and 0.4 ml CD3 microbeads (Miltenyi Biotec, Auburn, Calif.) added. The mixture was incubated for 15 min. at 4° C. These cells labeled with CD3 beads were washed with 30 ml MACS buffer, and then resuspended in 2 ml MACS buffer.

A VS+ column (Miltenyi) was prepared according to the manufacturer's instructions. The VS+ column was then placed in a VarioMACS™ magnetic field (Miltenyi). The column was equilibrated with 5 ml MACS buffer. The isolated primary human cells were then applied to the column. The CD3 negative cells were allowed to pass through. The column was rinsed with 9 ml (3×3 ml) MACS buffer. The column was then removed from the magnet and placed over a 15 ml falcon tube. CD3+ cells were eluted by adding 5 ml MACS buffer to the column and bound cells flushed out using the plunger provided by the manufacturer. The incubation of the cells with the CD3 magnetic beads, washes, and VS+ column steps (incubation through elution) above were repeated five more times. The resulting CD3+ fractions from the six column separations were pooled. The yield of CD3+ selected human cells were $3\times10^8$ total cells.

A sample of the pooled CD3+ selected human cells was removed for staining and sorting on a fluorescent antibody cell sorter (FACS) to assess their purity. The human CD3+ selected cells were 91% CD3+ cells.

The human CD3+ selected cells were activated by incubating in RPMI+5% FBS+PMA 10 ng/ml and Ionomycin 0.5 µg/ml (Calbiochem) for 13 hours 37° C. The supernatant from these activated CD3+ selected human cells was tested for zalpha11 Ligand activity as described below. Moreover, the activated CD3+ selected human cells were used to prepare a cDNA library, as described in Example 6, below.

D. Testing Supernatant from Activated CD3+ Selected Human Cells for Zalpha11 Ligand Using BaF3/Zalpha11 Cells and an ALAMAR BLUE™ Proliferation Assay BaF3/Zalpha11 cells were spun down and washed in mIL-3 free media. The cells were spun and washed 3 times to ensure the removal of the mIL-3. Cells were then counted in a hemacytometer. Cells were plated in a 96-well format at 5000 cells per well in a volume of 100 µl per well using the mIL-3 free media.

Proliferation of the BaF3/Zalpha11 cells was assessed using conditioned media from activated CD3+ selected human cells (see Example 5C) diluted with mIL-3 free media to 50%, 25%, 12.5%, 6.25%, 3.125%, 1.5%, 0.75% and 0.375% concentrations. 100 µl of the diluted conditioned media was added to the BaF3/Zalpha11 cells. The total assay volume is 200 µl. The assay plates were incubated and assayed as described in Example 5B.

Results confirmed the proliferative response of the BaF3/Zalpha11 cells to a factor present in the activated CD3+ selected human Cell conditioned media. The response, as measured, was approximately 10-fold over background at the 50% concentration. The untransfected BaF3 cells did not proliferate in response to this factor, showing that this factor is specific for the Zalpha11 receptor. Moreover soluble alpha 11 receptor blocked this proliferative activity in the BaF3/Zalpha11 cells (see, Example 11).

Example 6

Cloning of Human Zalpha11 Ligand from a Human CD3+ Selected Cell Library

Screening of a primary human activated CD3+ selected cell cDNA library revealed an isolated cDNA that is a novel member of the four-helix bundle cytokine family. This cDNA encoded the zalpha11 Ligand. The cDNA was identified by screening for activity of the zalpha11 Ligand using the zalpha11 receptor.

A. The Vector for CD3+ Selected Library Construction

The vector for CD3+ selected library construction was pZP7NX. The pZP7NX vector was constructed as follows: The coding region for the DHFR selective marker in vector pZP7 was removed by DNA digestion with NcoI and PstI restriction enzymes (Boehringer Mannheim). The digested DNA was run on 1% agarose gel, cut out and gel purified using the Qiagen Gel Extraction Kit (Qiagen) as per manufacturer's instructions. A DNA fragment representing the coding region of Zeocin selective marker was amplified by PCR method with primers ZC13,946 (SEQ ID NO:25) and ZC13,945 (SEQ ID NO:26), and pZeoSV2(+) as a template. There are additional PstI and BclI restriction sites in primer ZC13,946 (SEQ ID NO:25), and additional NcoI and SfuI sites in primer ZC13,945 (SEQ ID NO:26). The PCR fragment was cut with PstI and NcoI restriction enzymes and cloned into pZP7 vector prepared by cleaving with the same two enzymes and subsequent gel purification. This vector was named pZP7Z. Then the Zeocin coding region was removed by DNA digestion of vector pZP7Z with BclI and SfuI restriction enzymes. The digested DNA was run on 1% agarose gel, cut out and gel purified, and then ligated with a DNA fragment of Neomycin coding region cut from pZem228 vector (deposited at the American Type Culture Collection (ATCC), Manassas, Va.; ATCC Deposit No. 69446) with the same restriction enzymes (BclI and SfuI).

This new vector was named pZP7N, in which the coding region for DHFR selective marker was replaced by the coding region for a Neomycin selective marker from vector pZem228. A stuffer fragment including an Xho1 site was added to pZP7N to create a vector suitable for high efficiency directional cloning of cDNA; this new vector was called pZP7NX. To prepare the vector for cDNA, 20 µg of pZP7NX was digested with 20 units of EcoR1 (Life Technologies Gaithersberg, Md.) and 20 units of Xho1 (Boehringer Mannheim Indianapolis, Ind.) for 5 hours at 37° C., then 68° C. for 15 minutes. The digest was then run on a 0.8% low melt agarose 1×TAE gel to separate the stuffer from the vector. The vector band was excised and digested with "beta-Agarase" (New England Biolabs, Beverly, Mass.) following the manufacturer's recommendations. After ethanol precipitation the digested vector was resuspended in water to 45 ng/ml in preparation for ligation of CD3+ selected cDNA library described below.

B. Preparation of Primary Human Activated CD3+ Selected Cell cDNA Library

Approximately $1.5 \times 10^8$ primary human CD3+ selected cells stimulated in ionomycin/PMA were isolated by centrifugation after culturing at 37° C. for 13 hours (Example 5C). Total RNA was isolated from the cell pellet using the RNA isolation kit RNEASY® MIDI kit from Qiagen, Inc. (Valencia, Calif.). mRNA was isolated from 225 micrograms of total RNA using the MPG®mRNA purification kit from CPG Inc. (Lincoln Park, N.J.). 3.4 micrograms of mRNA was isolated and converted to double stranded cDNA using the following procedure.

First strand cDNA from stimulated human CD3+ selected cells was synthesized as follows. Nine µl Oligo d(T)-selected poly(A) CD3+ RNA at a concentration of 0.34 µg/µl and 1.0 µl of 1 µg/µl first strand primer ZC18,698 (SEQ ID NO:27) containing an XhoI restriction site were mixed and heated at 65° C. for 4 minutes and cooled by chilling on ice. First strand cDNA synthesis was initiated by the addition of 9 µl of first strand buffer (5× SUPERSCRIPT® buffer; (Life Technologies), 4 µl of 100 mM dithiothreitol and 2 µl of a deoxynucleotide triphosphate solution containing 10 mM each of dATP, dGTP, dTTP and 5-methyl-dCTP (Pharmacia Biotech Inc.) to the RNA-primer mixture. The reaction mixture was incubated at 45° C. for 4 minutes followed by the addition of 8 µl of 200 U/µl SUPERSCRIPT®II, RNase H-reverse transcriptase (Life technologies). The reaction was incubated at 45° C. for 45 minutes followed by an incubation ramp of 1° C. every 2 minutes to 50° C. where the reaction was held for 10 minutes. To denature any secondary structure and allow for additional extension of the cDNA the reaction was then heated to 70° C. for 2 minutes then dropped to 55° C. for 4 minutes after which 2 µl of SUPERSCRIPT®II RT was added and incubated an additional 15 minutes followed by a ramp up to 70° C. 1 minute/1° C. Unincorporated nucleotides were removed from the cDNA by twice precipitating in the presence of 2 µg of glycogen carrier, 2.0 M ammonium acetate and 2.5 volume ethanol, followed by a 100 µl wash with 70% ethanol. The cDNA was resuspended in 98 µl water for use in second strand synthesis.

Second strand synthesis was performed on the first strand cDNA under conditions that promoted first strand priming of second strand synthesis resulting in DNA hairpin formation. The second strand reaction contained 98 µl of the first strand cDNA, 30 µl of 5× polymerase I buffer (100 mM Tris: HCl, pH 7.5, 500 mM KCl, 25 mM MgCl$_2$, 50 mM (NH$_4$)$_2$SO$_4$), 2 µl of 100 mM dithiothreitol, 6 µl of a solution containing 10 mM of each deoxynucleotide triphosphate, 5 µl of 5 mM b-NAD, 1 µl of 3 U/µl E. coli DNA ligase (New England Biolabs Inc.) and 4 µl of 10 U/µl E. coli DNA polymerase I (New England Biolabs Inc.). The reaction was assembled at room temperature and was incubated at room temperature for 2 minutes followed by the addition of 4 µl of 3.8 U/µl RNase H (Life Technologies). The reaction was incubated at 15° C. for two hours followed by a 15 minute incubation at room temperature. 10 µl of 1M TRIS pH7.4 was added to the reaction and extracted twice with phenol/chloroform and once with chloroform, the organic phases were then back extracted with 50 µl of TE (10 mM TRIS pH 7.4, 1 mM EDTA), pooled with the other aqueous and ethanol precipitated in the presence of 0.3 M sodium acetate. The pellet was washed with 100 µl 70% ethanol air dried and resuspended in 40 µl water.

The single-stranded DNA of the hairpin structure was cleaved using mung bean nuclease. The reaction mixture contained 40 µl of second strand cDNA, 5 µl of 10× mung bean nuclease buffer (Life technologies), 5 µl of mung bean nuclease (Pharmacia Biotech Corp.) diluted to 1 U/µl in 1× mung bean nuclease buffer. The reaction was incubated at 37° C. for 45 minutes. The reaction was terminated by the addition of 10 µl of 1 M Tris: HCl, pH 7.4 followed by sequential phenol/chloroform and chloroform extractions as described above. Following the extractions, the cDNA was ethanol precipitated in the presence of 0.3 M sodium acetate. The pellet was washed with 100 µl 70% ethanol air dried and resuspended in 38 µl water.

The resuspended cDNA was blunt-ended with T4 DNA polymerase. The cDNA, which was resuspended in 38 µl of water, was mixed with 12 µl 5×T4 DNA polymerase buffer (250 mM Tris:HCl, pH 8.0, 250 mM KCl, 25 mM MgCl2), 2 µl 0.1 M dithiothreitol, 6 µl of a solution containing 10 mM of each deoxynucleotide triphosphate and 2 µl of 1 U/µl T4 DNA polymerase (Boehringer Mannheim Corp.). After an incubation of 45 minutes at 15° C., the reaction was terminated by the addition of 30 µl TE followed by sequential phenol/chloroform and chloroform extractions and back extracted with 20 µl TE as described above. The DNA was ethanol precipitated in the presence of 2 µl PELLET PAINT® (Novagen) carrier and 0.3 M sodium acetate and was resuspended 11 µl of water.

Eco RI adapters were ligated onto the 5' ends of the cDNA described above to enable cloning into an expression vector. 11 µl of cDNA and 4 µl of 65 pmole/µl of Eco RI hemiphosphorylated adaptor (Pharmacia Biotech Corp) were mixed with 5 µl 5× ligase buffer (Life Technologies), 2 µl of 10 mM ATP and 3 µl of 1 U/µl T4 DNA ligase (Life Technologies), 1

μl 10× ligation buffer (Promega Corp), 9 μl water. The extra dilution with 1× buffer was to prevent the PELLET PAINT® from precipitating. The reaction was incubated 9 hours in a water bath temperature ramp from 10° C. to 22° C. over 9 hours, followed by 45 minutes at 25° C. The reaction was terminated by incubation at 68° C. for 15 minutes.

To facilitate the directional cloning of the cDNA into an expression vector, the cDNA was digested with XhoI, resulting in a cDNA having a 5' Eco RI cohesive end and a 3' XhoI cohesive end. The XhoI restriction site at the 3' end of the cDNA had been previously introduced using the ZC18698 (SEQ ID NO:27) primer. Restriction enzyme digestion was carried out in a reaction mixture containing 35 μl of the ligation mix described above, 6 μl of 10×H buffer (Boehringer Mannheim Corp.), 1 μl of 2 mg/ml BSA (Biolabs Corp.), 17 μl water and 1.0 μl of 40 U/μl XhoI (Boehringer Mannheim). Digestion was carried out at 37° C. for 1 hour. The reaction was terminated by incubation at 68° C. for 15 minutes followed by ethanol precipitation, washing drying as described above and resuspension in 30 μl water.

The resuspended cDNA was heated to 65° C. for 5 minutes and cooled on ice, 4 μl of 5× gel loading dye (Research Genetics Corp.) was added, the cDNA was loaded onto a 0.8% low melt agarose 1×TAE gel (SEA PLAQUE GTG™ low melt agarose; FMC Corp.) and electrophoresed. The contaminating adapters and cDNA below 0.6 Kb in length were excised from the gel. The electrodes were reversed, molten agarose was added to fill in the wells, the buffer was changed and the cDNA was electrophoresed until concentrated near the lane origin. The area of the gel containing the concentrated cDNA was excised and placed in a microfuge tube, and the agarose was melted by heating to 65° C. for 15 minutes. Following equilibration of the sample to 45° C., 2 μl of 1 U/μl Beta-agarase I (Biolabs, Inc.) was added, and the mixture was incubated for 90 min. at 45° C. to digest the agarose. After incubation, 1 tenth volume of 3 M Na acetate was added to the sample, and the mixture was incubated on ice for 15 minutes. The sample was centrifuged at 14,000×g for 15 minutes at room temperature to remove undigested agarose, the cDNA was ethanol precipitated, washed in 70% ethanol, air-dried and resuspended in 40 μl water.

To determine the optimum ratio of cDNA to vector several ligations were assembled and electroporated. Briefly, 2 μl of 5×T4 ligase buffer (Life Technologies), 1 μl of 10 mM ATP, 1 μl pZP7NX digested with EcoR1-Xho1, 1 ll T4 DNA ligase diluted to 0.25 u/μl (Life Technologies) water to 10 μl and 0.5, 1, 2 or 3 μl of cDNA were mixed in 4 separate ligations, incubated at 22° C. for 4 hours, 68° C. for 20 minutes, sodium acetate-ethanol precipitated, washed, dried and resuspended in 10 μl. A single microliter of each ligation was electroporated into 40 μl *E. coli* DH10b™ competent cells ELECTROMAX™ electrocompetent bacteria (Life Technologies) using a 0.1 cm cuvette (Biorad) and a Genepulser, pulse controller® (Biorad) set to 2.5 KV, 25 μF, 200 ohms. These cells were immediately resuspended in 1 ml. SOC broth (Manniatis, et al. supra.) followed by 500 μl of 50% glycerol-SOC as a preservative. These "glycerol stocks" were frozen in several aliquots at −70° C. An aliquot of each was thawed and plated serially on LB-agar plates supplemented with ampicillin at 100 μg/ml. Colony numbers indicated that the optimum ratio of CD3+ cDNA to pZP7NX vector was 1 μl to 45 ng; such a ligation yielded 4.5 million primary clones.

For the purpose of screening this library using a BaF3-zalpha11 based proliferation assay (Example 5) glycerol stocks from above were diluted into liquid cultures of 100 or 250 clones per pool in deep well microtiter plates, grown 24 hours at 37° C. with shaking and plasmid isolated using a Qiagen kit following the manufacturer's instructions. Such DNA was subsequently transfected into BHK cells, media conditioned 72 hours, harvested and placed on 5K BaF3-zalpha11 cells for 72 hours after which proliferation was assessed using an "ALAMAR BLUE™" fluorescence assay (Example 5B and Example 2B).

For the purpose of screening the library by secretion trap cloning, a complex, amplified form of the library was needed to transfect COS-7 cells. About 4.8 million clones were plated on 110 15 cm LB-agar plates supplemented with 100 μg/ml ampicillin, 10 μg/ml methicillin. After growing the plates overnight at 37° C. the bacteria were harvested by scraping and pelleted. Plasmid DNA was extracted from the pelleted bacteria using an anion exchange matrix plasmid purification method NUCLEOBOND® (Clonetech) following the manufacturer's instructions. This plasmid was then used to transfect COS-7 cells (ATCC No. CRL 1651) on slides and screened using the secretion trap technique described below (Example 12).

Example 7

Expression Cloning of Human Zalpha11 Ligand

The glycerol stocks from the activated human CD3+ selected cell library (Example 6) were added to enriched culture medium SUPER BROTH®II (Becton Dickinson, Cockeysville, Md.)+0.1 mg/ml ampicillin (amp) at a concentration of 250 cells per 800 microliters. The *E. coli* were allowed to equilibrate for 24 hours at room temperature. At the time of inoculation, 400 microliters was plated on LB+amp plates to determine the actual titer of the inoculation. After 24 hours the plates were counted and then the final concentration of the enriched culture medium Super Broth®II+*E. coli* was adjusted so that the final concentration was 250 cells per 1.2 ml. Three times 2 liters were inoculated for a total of 6 liters. The media were then plated into 96-well deep well blocks (Qiagen). Plating was done on the 8-channel Q-Fill2™ dispenser (Genetix, Christchurch, Dorset, UK). The *E. coli* were grown overnight at 37° C. shaking at 250 rotations/min. on a New Brunswick Scientific Innova 4900 multi-tier environment shaker. The *E. coli* were spun out of solution at 3000 rpm, using a Beckman GS-6KR centrifuge. These *E. coli* pellets were frozen at −20° C. or used fresh before miniprepping the plasmid DNA. Each pellet contains approximately 250 cDNA clones from the human CD3+ selected cell library.

These pools of 250 cDNA clones were then mini-prepped using QIAPREP® 96 Turbo Miniprep kit (Qiagen). Plasmid DNA was eluted using 125 μl of TE (10 mM Tris pH 8, 1 mM EDTA). This plasmid DNA was then used to transfect BHK cells.

BHK Transfection

BHK cells were plated in 96-well tissue culture plates at a density of 12,000 cells per well in a volume of 100 μl. per well. Culture media was DMEM (GibcoBRL), 5% heat-inactivated fetal bovine serum, 2 mM L-glutamine (Gibco-BRL), 1×PSN (GibcoBRL), 1 mM NaPyruvate (GibcoBRL).

The following day, BHK cells were washed once with 100 μl SFA. SFA is serum-free media which is DMEM/F12 (Gibco/BRL), 2 mM GlutaMax™ (Gibco/BRL), 1 mM NaPyruvate, 10 μg/ml transferrin, 5 μg/ml insulin, 10 μg/ml fetuin, 2 μg/ml selenium, 25 mM HEPES (Gibco/BRL), 100 μM non-essential amino acids (Gibco/BRL).

A DNA/LIPOFECTAMINE™ mix is made as follows: 2.2 μl LIPOFECTAMINE™ reagent (Gibco/BRL) is combined with 102.8 μl SFA at room temperature; approximately 5 μl of the plasmid DNA (200 ng/μl) is then added to the LIPO- FECTAMINE™/SFA to form the DNA/LIPOFECTAMINE™ mixture, which is incubated at room temperature for 30 minutes. The SFA was removed from the BHK cells and the cells were incubated with 50 µl of the DNA/LIPOFECTAMINE™ mix for 5 hours at 37° C. with 5% CO2. Fifty µl of the DNA/LIPOFECTAMINE™ mixture was added to each of two wells of the BHK cells, so that transfections were done in duplicate.

After BHK cells were incubated with DNA/LIPOFECTAMINE™ mix for 5 hours, the DNA/LIPOFECTAMINE™ mix was removed and 100 µl culture media was added. Cells were incubated overnight, the media was removed and replaced with 100 µl. culture media. After culturing cells for 72 hours, conditioned media was removed, frozen at −80° C. for a minimum of 20 minutes, thawed, and then 50 µl was assayed in the zalpha11/BaF3 proliferation assay, described in Examples 2B and Example 5, to identify pools of 250 clones with ligand activity.

Thirty-five 96-well plates were screened in a single assay. This represented approximately 250 cDNAs/well or 840,000 cDNAs total. Of these, conditioned media from 54 wells (representing 250 cDNAs per well) tested positive in the proliferation assay. The conditioned media from these positive pools was re-tested in a second assay (secretion trap) with and without the soluble receptor (see, Example 12). The zalpha11CEE soluble receptor (Example 10A) was used at a final concentration of about 1 µg/ml. For all 54 positive pools, essentially all of the activity was neutralized by addition of the soluble zalpha11 receptor, indicating that these pools contained a cDNA from the zalpha11 Ligand. Four of these positive pools were chosen to break-down and isolate a single cDNA that would encode the zalpha11 Ligand. These were 45C5, 46G11, 40H12, and 60A1.

For each of these 4 pools, 1 µl. of DNA was used to transform E. coli DH10b™ competents cells ELECTROMAX™ cells (Gibco/BRL) by electroporation. The transformants were plated on LB+amp (100 µg/ml)+methicillin (10 µg/ml) plates to give single colonies. For each electroporated pool, 960 individual colonies were toothpicked into ten 96-well plates containing 1.2 ml of SuperBrothII™ per well. These plates were numbered #1-10 for each of the breakdown pools (45C5, 46G11, 40H12, and 60A1). These were cultured overnight and the plasmid DNA miniprepped as above. For 46G11, 40H12, and 60A1, plasmid DNA from the breakdown plates was transfected into BHK cells as above.

For 45 C5, a "fast track" protocol was utilized to accelerate the identification of the zalpha11 Ligand cDNA. BHK cells were transfected with plasmid DNA from the breakdown plates as above, DNA/LIPOFECTAMINE™ mix was removed after a 5 hour incubation, and culture media was added. Since the transfections were done in duplicate, the culture media was harvested the following day after 24 hours from one of the transfected BHK plates, and harvested the following day after 48 hours from the remaining transfected plate. The 24 hour conditioned media was assayed as above for zalpha11 Ligand activity using the proliferation assay as described herein.

Plasmid DNA was pooled from 45C5 breakdown plates #1-4 and assayed for binding of zalpha11 soluble receptor to its ligand by the "secretion-trap" protocol (see, Example 12, below). Eight positive clones were identified from a total of 384 sequences. Results from the proliferation assay confirmed activity of the zalpha11 Ligand and correlated with results of the secretion trap assay (see Example 12). Concurrently, plasmid DNA miniprepped from plates #1-4 of the 45C5 pool breakdown was sequenced to determine the DNA sequence of each of the 384 clones.

Several clones that were positively identified in the proliferation and secretion trap assays were also sequenced using the following primers: ZC14,063 (SEQ ID NO:28), ZC7,764a (SEQ ID NO:38), ZC7,764b (SEQ ID NO:39), ZC22,034 (SEQ ID NO:40), and ZC22,035 (SEQ ID NO:41). The polynucleotide sequence of zalpha11 Ligand was full-length (SEQ ID NO:1) and its corresponding amino acid sequence is shown (SEQ ID NO:2).

Example 8

Construction of Mammalian Expression Vectors that Express Zalpha11 Soluble Receptors: Zalpha11CEE, Zalpha11CFLG, Zalpha11CHIS and Zalpha11-Fc4

A. Construction of Zalpha11 Mammalian Expression Vector Containing Zalpha11CEE, Zalpha11CFLG and Zalpha11CHIS An expression vector was prepared for the expression of the soluble, extracellular domain of the zalpha11 polypeptide, pC4zalpha11CEE, wherein the construct is designed to express a zalpha11 polypeptide comprised of the predicted initiating methionine and truncated adjacent to the predicted transmembrane domain, and with a C-terminal Glu-Glu tag (SEQ ID NO:29).

A 700 bp PCR generated zalpha11 DNA fragment was created using ZC19,931 (SEQ ID NO:30) and ZC19,932 (SEQ ID NO:31) as PCR primers to add Asp718 and BamHI restriction sites. A plasmid containing the zalpha11 receptor cDNA (SEQ ID NO:7) was used as a template. PCR amplification of the zalpha11 fragment was performed as follows: Twenty five cycles at 94 C for 0.5 minutes; five cycles at 94° C. for 10 seconds, 50° C. for 30 seconds, 68° C. for 45 seconds, followed by a 4° C. hold. The reaction was purified by chloroform/phenol extraction and isopropanol precipitation, and digested with Asp718 and BamHI (Gibco BRL) following manufacturer's protocol. A band of the predicted size, 700 bp, was visualized by 1% agarose gel electrophoresis, excised and the DNA was purified using a QIAEXII® purification system (Qiagen) according the manufacturer's instructions.

The excised DNA was subcloned into plasmid pC4EE which had been cut with BamHI and Asp718. The pC4zalpha11CEE expression vector uses the native zalpha11 signal peptide and attaches the Glu-Glu tag (SEQ ID NO:29) to the C-terminus of the extracellular portion of the zalpha11 polypeptide-encoding polynucleotide sequence. Plasmid pC4EE, is a mammalian expression vector containing an expression cassette having the mouse metallothionein-1 promoter, multiple restriction sites for insertion of coding sequences, a stop codon and a human growth hormone terminator. The plasmid also has an E. coli origin of replication, a mammalian selectable marker expression unit having an SV40 promoter, enhancer and origin of replication, a DHFR gene and the SV40 terminator.

About 30 ng of the restriction digested zalpha11 insert and about 12 ng of the digested vector were ligated overnight at 16° C. One microliter of each ligation reaction was independently electroporated into DH10B competent cells (GIBCO BRL, Gaithersburg, Md.) according to manufacturer's direction and plated onto LB plates containing 50 mg/ml ampicillin, and incubated overnight. Colonies were screened by restriction analysis of DNA prepared from 2 ml liquid cultures of individual colonies. The insert sequence of positive clones was verified by sequence analysis. A large scale plasmid preparation was done using a QIAGEN® Maxi prep kit (Qiagen) according to manufacturer's instructions.

The same process was used to prepare the zalpha11 soluble receptors with a C-terminal his tag, composed of 6 His residues in a row; and a C-terminal flag (SEQ ID NO:37) tag, zalpha11CFLAG. To prepare these constructs, the aforementioned vector has either the HIS or the FLAG® tag in place of the glu-glu tag (SEQ ID NO:29).

B. Mammalian Expression Construct of Soluble Zalpha11 Receptor Zalpha11-Fc4

An expression plasmid containing all or part of a polynucleotide encoding zalpha11 was constructed via homologous recombination. The extracellular domain of the zalpha11 receptor was fused to the Fc region derived from human IgG, called "Fc4" (SEQ ID NO:33) which contains a mutation so that it no longer binds the Fc receptor. A fragment of zalpha11 cDNA was isolated using PCR that includes the polynucleotide sequence from extracellular domain of the zalpha11 receptor. The two primers used in the production of the zalpha11 fragment were: (1) The primers for PCR each include from 5' to 3' end: 40 bp of the vector flanking sequence (5' of the insert) and 17 bp corresponding to the 5' end of the zalpha11 extracellular domain (SEQ ID NO:32); and (2) 40 bp of the 5' end of the Fc4 polynucleotide sequence (SEQ ID NO:33) and 17 bp corresponding to the 3' end of the zalpha11 extracellular domain (SEQ ID NO:34). The fragment of Fc-4 for fusion with the zalpha11 was generated by PCR in a similar fashion. The two primers used in the production of the Fc4 fragment were: (1) a 5' primer consisting of 40 bp of sequence from the 3' end of zalpha11 extracellular domain and 17 bp of the 5' end of Fc4 (SEQ ID NO:35); and (2) a 3' primer consisting of 40 bp of vector sequence (3' of the insert) and 17 bp of the 3' end of Fc4 (SEQ ID NO:36).

PCR amplification of the each of the reactions described above was performed as follows: one cycle at 94° C. for 2 minutes; twenty-five cycles at 94° C. for 30 seconds, 60° C. for 30 seconds, 72° C. for 1 minute; one cycle at 72° C. for 5 minutes; followed by a 4° C. hold. Ten µl of the 100 µl PCR reaction was run on a 0.8% LMP agarose gel (Seaplaque GTG) with 1×TBE buffer for analysis. The remaining 90 µl of the PCR reaction is precipitated with the addition of 5 µl 1 M NaCl and 250 µl of absolute ethanol. The expression vector used was derived from the plasmid pCZR199 derived from pZP9 (ATCC Deposit No. 98668), and was cut with SmaI (BRL). The expression vector was derived from the plasmid pCZR199, and is a mammalian expression vector containing an expression cassette having the CMV immediate early promoter, a consensus intron from the variable region of mouse immunoglobulin heavy chain locus, multiple restriction sites for insertion of coding sequences, a stop codon and a human growth hormone terminator. The expression vector also has an *E. coli* origin of replication, a mammalian selectable marker expression unit having an SV40 promoter, enhancer and origin of replication, a DHFR gene and the SV40 terminator. The expression vector used was constructed from pCZR199 by the replacement of the metallothionein promoter with the CMV immediate early promoter.

One hundred microliters of competent yeast cells (*S. cerevisiae*) were combined with 10 µl containing approximately 1 µg each of the zalpha11 and Fc4 inserts, and 100 ng of SmaI (BRL) digested expression vector and transferred to a 0.2 cm electroporation cuvette. The yeast/DNA mixtures were electropulsed at 0.75 kV (5 kV/cm), "infinite" ohms, 25 µF. To each cuvette is added 600 µl of 1.2 M sorbitol and the yeast was plated in two 300 µl aliquots onto two URA-D plates and incubated at 30° C.

After about 48 hours, the Ura+ yeast transformants from a single plate were resuspended in 1 ml H2O and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 µl acid washed glass beads and 200 µl phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 µl ethanol (EtOH), followed by centrifugation for 10 minutes at 4° C. The DNA pellet was resuspended in 100 µL H2O.

Transformation of electrocompetent *E. coli* cells (DH10B, GibcoBRL) is done with 0.5-2 ml yeast DNA prep and 40 µl of DH10B cells. The cells were electropulsed at 2.0 kV, 25 mF and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM MgCl$_2$, 10 mM MgSO$_4$, 20 mM glucose) was plated in 250 µl aliquots on four LB AMP plates (LB broth (Lennox), 1.8% Bacto Agar (Difco), 100 mg/L Ampicillin).

Individual clones harboring the correct expression construct for zalpha11-Fc4 were identified by restriction digest to verify the presence of the zalpha11-Fc4 insert and to confirm that the various DNA sequences have been joined correctly to one another. The insert of positive clones were subjected to sequence analysis. Larger scale plasmid DNA is isolated using the QIAGEN® Maxi kit (Qiagen) according to manufacturer's instructions.

Example 9

Transfection and Expression of Zalpha11 Soluble Receptor Polypeptides

A. Mammalian Expression of Soluble Zalpha11 Receptor Zalpha11CEE, Zalpha11CFLG, and Zalpha11CHIS BHK 570 cells (ATCC No. CRL-10314), passage 27, were plated at $1.2 \times 10^6$ cells/well (6-well plate) in 800 µl of serum free (SF) DMEM media (DMEM, Gibco/BRL High Glucose) (Gibco BRL, Gaithersburg, Md.). The cells were transfected with expression plasmids containing zalpha11CEE, zalpha11CFLG, or zalpha11CHIS described above (see, Example 8), using LIPOFECTIN™ (Gibco BRL), in serum free (SF) DMEM. Three micrograms of zalpha11CEE, zalpha11CFLG, or zalpha11CHIS each were separately diluted into 1.5 ml tubes to a total final volume of 100 µl SF DMEM. In separate tubes, 15 µl of Lipofectin™ (Gibco BRL) was mixed with 100 µl of SF DMEM. The Lipofectin™ mix was incubated at room temperature for 30-45 minutes then the DNA mix was added and allowed to incubate approximately 10-15 minutes at room temperature.

The entire DNA: Lipofectin™ mixture was added to the plated cells and distributed evenly over them. The cells were incubated at 37° C. for approximately five hours, then transferred to separate 150 mm MAXI plates in a final volume of 30 ml DMEM/5% fetal bovine serum (FBS) (Hyclone, Logan, Utah). The plates were incubated at 37° C., 5% CO$_2$, overnight and the DNA: Lipofectin™ mixture was replaced with selection media (5% FBS/DMEM with 1 µM methotrexate (MTX)) the next day.

Approximately 10-12 days post-transfection, the plates were washed with 10 ml SF DMEM. The wash media was aspirated and replaced with 7.25 ml serum-free DMEM. Sterile Teflon meshes (Spectrum Medical Industries, Los Angeles, Calif.) pre-soaked in SF DMEM were then placed over the clonal cell colonies. A sterile nitrocellulose filter pre-soaked in SF DMEM was then placed over the mesh. Orientation marks on the nitrocellulose were transferred to the culture dish. The plates were then incubated for 5-6 hours in a 37° C., 5% CO$_2$ incubator.

Following incubation, the filters/meshes were removed, and the media aspirated and replaced with 5% FBS/DMEM with 1 µM MTX. The filters were then blocked in 10% nonfat dry milk/Western A buffer (Western A: 50 mM Tris pH 7.4, 5 mM EDTA, 0.05% NP-40, 150 mM NaCl and 0.25% gelatin) for 15 minutes at room temperature on a rotating shaker. The filters were then incubated with an anti-Glu-Glu, anti-FLAG®, or anti-HIS antibody-HRP conjugates, respectively, in 2.5% nonfat dry milk/Western A buffer for one hour at room temperature on a rotating shaker. The filters were then washed three times at room temperature with Western A for 5-10 minutes per wash. The filters were developed with ultra ECL reagent (Amersham Corp., Arlington Heights, Ill.) according the manufacturer's directions and visualized on the Lumi-Imager (Roche Corp.)

Positive expressing clonal colonies were mechanically picked to 12-well plates in one ml of 5% FCS/DMEM with 5 µM MTX, then grown to confluence. Conditioned media samples were then tested for expression levels via SDS-PAGE and Western analysis. The three highest expressing clones for each construct were picked; two out of three were frozen down as back up and one was expanded for mycoplasma testing and large-scale factory seeding.

B. Mammalian Expression of Soluble Zalpha11 Receptor Zalpha11-Fc4

BHK 570 cells (ATCC NO: CRL-10314) were plated in 10 cm tissue culture dishes and allowed to grow to approximately 50 to 70% confluency overnight at 37° C., 5% CO$_2$, in DMEM/FBS media (DMEM, Gibco/BRL High Glucose, (Gibco BRL, Gaithersburg, Md.), 5% fetal bovine serum (Hyclone, Logan, Utah), 1 mM L-glutamine (JRH Biosciences, Lenexa, Kans.), 1 mM sodium pyruvate (Gibco BRL)). The cells were then transfected with the plasmid containing zalpha11-Fc4 (see, Example 8), using LIPOFECTAMINE™ (Gibco BRL), in serum free (SF) media formulation (DMEM, 10 mg/ml transferrin, 5 mg/ml insulin, 2 mg/ml fetuin, 1% L-glutamine and 1% sodium pyruvate). The plasmid containing zalpha11-Fc4 was diluted into 15 ml tubes to a total final volume of 640 ml with SF media. 35 ml of LIPOFECTAMINE™ (Gibco BRL) was mixed with 605 ml of SF medium. The Lipofectamine™ mix was added to the DNA mix and allowed to incubate approximately 30 minutes at room temperature. Five milliliters of SF media was added to the DNA:LIPOFECTAMINE™ mixture. The cells were rinsed once with 5 ml of SF media, aspirated, and the DNA:LIPOFECTAMINE™ mixture is added. The cells were incubated at 37° C. for five hours, then 6.4 ml of DMEM/10% FBS, 1% PSN media was added to each plate. The plates were incubated at 37° C. overnight and the DNA:Lipofectamine™ mixture was replaced with fresh 5% FBS/DMEM media the next day. On day 2 post-transfection, the cells were split into the selection media (DMEM/FBS media from above with the addition of 1 µM methotrexate (Sigma Chemical Co., St. Louis, Mo.)) in 150 mm plates at 1:10, 1:20 and 1:50. The media on the cells was replaced with fresh selection media at day 5 post-transfection. Approximately 10 days post-transfection, two 150 mm culture dishes of methotrexate resistant colonies from each transfection were trypsinized and the cells are pooled and plated into a T-162 flask and transferred to large scale culture.

Example 10

Purification of Zalpha11 Soluble Receptors from BHK 570 Cells

A. Purification of Zalpha11CEE Polypeptide from BHK 570

Unless otherwise noted, all operations were carried out at 4° C. The following procedure was used for purifying zalpha11 polypeptide containing C-terminal GluGlu (EE) tags. Thirty liters of cell factory conditioned media was concentrated to 1.6 liters with an Amicon S10Y3 spiral cartridge on a ProFlux A30. A Protease inhibitor solution was added to the concentrated 1.6 liters of cell factory conditioned media from transfected BHK 570 cells (see, Example 9) to final concentrations of 2.5 mM ethylenediaminetetraacetic acid (EDTA, Sigma Chemical Co. St. Louis, Mo.), 0.003 mM leupeptin (Boehringer-Mannheim, Indianapolis, Ind.), 0.001 mM pepstatin (Boehringer-Mannheim) and 0.4 mM Pefabloc (Boehringer-Mannheim). Samples were removed for analysis and the bulk volume was frozen at −80° C. until the purification was started. Total target protein concentrations of the concentrated cell factory conditioned media was determined via SDS-PAGE and Western blot analysis with the anti-EE HRP conjugated antibody.

A 100 ml column of anti-EE G-Sepharose (prepared as described below) was poured in a Waters AP-5, 5 cm×10 cm glass column. The column was flow packed and equilibrated on a BioCad Sprint (PerSeptive BioSystems, Framingham, Mass.) with phosphate buffered saline (PBS) pH 7.4. The concentrated cell factory conditioned media was thawed, 0.2 micron sterile filtered, pH adjusted to 7.4, then loaded on the column overnight with 1 ml/minute flow rate. The column was washed with 10 column volumes (CVs) of phosphate buffered saline (PBS, pH 7.4), then plug eluted with 200 ml of PBS (pH 6.0) containing 0.5 mg/ml EE peptide (Anaspec, San Jose, Calif.) at 5 ml/minute. The EE peptide used has the sequence EYMPME (SEQ ID NO:29). The column was washed for 10 CVs with PBS, then eluted with 5 CVs of 0.2M glycine, pH 3.0. The pH of the glycine-eluted column was adjusted to 7.0 with 2 CVs of 5×PBS, then equilibrated in PBS (pH 7.4). Five ml fractions were collected over the entire elution chromatography and absorbance at 280 and 215 nM were monitored; the pass through and wash pools were also saved and analyzed. The EE-polypeptide elution peak fractions were analyzed for the target protein via SDS-PAGE Silver staining and Western Blotting with the anti-EE HRP conjugated antibody. The polypeptide elution fractions of interest were pooled and concentrated from 60 ml to 5.0 ml using a 10,000 Dalton molecular weight cutoff membrane spin concentrator (Millipore, Bedford, Mass.) according to the manufacturer's instructions.

To separate zalpha11CEE from other co-purifying proteins, the concentrated polypeptide elution pooled fractions were subjected to a POROS HQ-50 (strong anion exchange resin from PerSeptive BioSystems, Framingham, Mass.) at pH 8.0. A 1.0×6.0 cm column was poured and flow packed on a BioCad Sprint. The column was counter ion charged then equibrated in 20 mM TRIS pH 8.0 (Tris(Hydroxymethyl Aminomethane)). The sample was diluted 1:13 (to reduce the ionic strength of PBS) then loaded on the Poros HQ column at 5 ml/minute. The column was washed for 10 CVs with 20 mM Tris pH 8.0 then eluted with a 40 CV gradient of 20 mM Tris/1 M sodium chloride (NaCl) at 10 ml/minute. 1.5 ml fractions were collected over the entire chromatography and absorbance at 280 and 215 nM were monitored. The elution peak fractions were analyzed via SDS-PAGE Silver staining. Fractions of interest were pooled and concentrated to 1.5-2 ml using a 10,000 Dalton molecular weight cutoff membrane spin concentrator (Millipore, Bedford, Mass.) according to the manufacturer's instructions.

To separate zalpha11CEE polypeptide from free EE peptide and any contaminating co-purifying proteins, the pooled concentrated fractions were subjected to chromatography on a 1.5×90 cm Sephadex S200 (Pharmacia, Piscataway, N.J.) column equilibrated and loaded in PBS at a flow rate of 1.0 ml/min using a BioCad Sprint. 1.5 ml fractions were collected across the entire chromatography and the absorbance at 280 and 215 nM were monitored. The peak fractions were characterized via SDS-PAGE Silver staining, and only the most pure fractions were pooled. This material represented purified zalpha11CEE polypeptide.

This purified material was finally subjected to a 4 ml Acti-Clean Etox (Sterogene) column to remove any remaining endotoxins. The sample was passed over the PBS equilibrated gravity column four times then the column was washed with a single 3 ml volume of PBS, which was pooled with the "cleaned" sample. The material was then 0.2 micron sterile filtered and stored at −80° C. until it was aliquoted.

On Western blotted, Coomassie Blue and Silver stained SDS-PAGE gels, the zalpha11CEE polypeptide was one major band of an apparent molecular weight of about 50,000 Daltons. The mobility of this band was the same on reducing and non-reducing gels.

The protein concentration of the purified material was performed by BCA analysis (Pierce, Rockford, Ill.) and the protein was aliquoted, and stored at −80° C. according to our standard procedures. On IEF (isoelectric focusing) gels the protein runs with a PI of less than 4.5. The concentration of zalpha11CEE polypeptide was 1.0 mg/ml.

To prepare anti-EE Sepharose, a 100 ml bed volume of protein G-Sepharose (Pharmacia, Piscataway, N.J.) was washed 3 times with 100 ml of PBS containing 0.02% sodium azide using a 500 ml Nalgene 0.45 micron filter unit. The gel was washed with 6.0 volumes of 200 mM triethanolamine, pH 8.2 (TEA, Sigma, St. Louis, Mo.), and an equal volume of EE antibody solution containing 900 mg of antibody was added. After an overnight incubation at 4° C., unbound antibody was removed by washing the resin with 5 volumes of 200 mM TEA as described above. The resin was resuspended in 2 volumes of TEA, transferred to a suitable container, and dimethylpimilimidate-2HCl (Pierce, Rockford, Ill.) dissolved in TEA, was added to a final concentration of 36 mg/ml of protein G-Sepharose gel. The gel was rocked at room temperature for 45 min and the liquid was removed using the filter unit as described above. Nonspecific sites on the gel were then blocked by incubating for 10 min. at room temperature with 5 volumes of 20 mM ethanolamine in 200 mM TEA. The gel was then washed with 5 volumes of PBS containing 0.02% sodium azide and stored in this solution at B. Purification of Zalpha11CFLAG Polypeptide from BHK 570

Unless otherwise noted, all operations were carried out at 4° C. The following procedure was used for purifying zalpha11 polypeptide containing C-terminal FLAG® (FLG) (Sigma-Aldrich Co.) tags. Thirty liters of cell factory conditioned media was concentrated to 1.7 liters with an Amicon S10Y3 spiral cartridge on a ProFlux A30. A Protease inhibitor solution was added to the 1.7 liters of concentrated cell factory conditioned media from transfected BHK 570 cells (see, Example 9) to final concentrations of 2.5 mM ethylenediaminetetraacetic acid (EDTA, Sigma Chemical Co. St. Louis, Mo.), 0.003 mM leupeptin (Boehringer-Mannheim, Indianapolis, Ind.), 0.001 mM pepstatin (Boehringer-Mannheim) and 0.4 mM Pefabloc (Boehringer-Mannheim). Samples were removed for analysis and the bulk volume was frozen at −80° C. until the purification was started. Total target protein concentrations of the cell factory conditioned media was determined via SDS-PAGE and Western blot analysis with the anti-FLAG (Kodak) HRP conjugated antibody. A 125 ml column of anti-FLAG® M2-Agarose affinity gel (Sigma-Aldrich Co.) was poured in a Waters AP-5, 5 cm×10 cm glass column. The column was flow packed and equilibrated on a BioCad Sprint (PerSeptive BioSystems, Framingham, Mass.) with phosphate buffered saline (PBS) pH 7.4. The concentrated cell factory conditioned media was thawed, 0.2 micron sterile filtered, pH adjusted to 7.4, then loaded on the column overnight with 1 ml/minute flow rate. The column was washed with 10 column volumes (CVs) of phosphate buffered saline (PBS, pH 7.4), then plug eluted with 250 ml of PBS (pH 6.0) containing 0.5 mg/ml FLAG® (Sigma-Aldrich Co.) peptide at 5 ml/minute. The FLAG® peptide used has the sequence DYKDDDDK (SEQ ID NO:37). The column was washed for 10 CVs with PBS, then eluted with 5 CVs of 0.2M glycine, pH 3.0. The pH of the glycine-eluted column was adjusted to 7.0 with 2 CVs of 5×PBS, then equilibrated in PBS (pH 7.4). Five ml fractions were collected over the entire elution chromatography and absorbence at 280 and 215 nM were monitored; the pass through and wash pools were also saved and analyzed. The FLAG®-polypeptide elution peak fractions were analyzed for the target protein via SDS-PAGE Silver staining and Western Blotting with the anti-FLAG HRP conjugated antibody. The polypeptide elution fractions of interest were pooled and concentrated from 80 ml to 12 ml using a 10,000 Dalton molecular weight cutoff membrane spin concentrator (Millipore, Bedford, Mass.) according to the manufacturer's instructions.

To separate zalpha11CFLG from other co-purifying proteins, the polypeptide elution pooled fractions were subjected to a POROS HQ-50 (strong anion exchange resin from PerSeptive BioSystems, Framingham, Mass.) at pH 8.0. A 1.0× 6.0 cm column was poured and flow packed on a BioCad Sprint. The column was counter ion charged then equilibrated in 20 mM TRIS pH 8.0 (Tris (Hydroxymethyl Aminomethane)). The sample was diluted 1:13 (to reduce the ionic strength of PBS) then loaded on the Poros HQ-50 column at 5 ml/minute. The column was washed for 10 column volumes (CVs) with 20 mM Tris pH 8.0 then eluted with a 40 CV gradient of 20 mM Tris/1 M sodium chloride (NaCl) at 10 ml/minute. 1.5 ml fractions were collected over the entire chromatography and absorbance at 280 and 215 nM were monitored. The elution peak fractions were analyzed via SDS-PAGE Silver staining. Fractions of interest were pooled and concentrated to 1.5-2 ml using a 10,000 Dalton molecular weight cutoff membrane spin concentrator (Millipore, Bedford, Mass.) according to the manufacturer's instructions.

To separate zalpha11CFLG polypeptide from free FLAG® peptide and any contaminating co-purifying proteins, the pooled concentrated fractions were subjected to chromatography on a 1.5×90 cm Sephacryl S200 (Pharmacia, Piscataway, N.J.) column equilibrated and loaded in PBS at a flow rate of 1.0 ml/min using a BioCad Sprint. 1.5 ml fractions were collected across the entire chromatography and the absorbance at 280 and 215 nM were monitored. The peak fractions were characterized via SDS-PAGE Silver staining, and only the most pure fractions were pooled. This material represented purified zalpha11CFLG polypeptide.

This purified material was finally subjected to a 4 ml Acti-Clean Etox (Sterogene) column to remove any remaining endotoxins. The sample was passed over the PBS equilibrated gravity column four times then the column was washed with a single 3 ml volume of PBS, which was pooled with the "cleaned" sample. The material was then 0.2 micron sterile filtered and stored at −80° C. until it was aliquoted.

On Western blotted, Coomassie Blue and Silver stained SDS-PAGE gels, the zalpha11CFLG polypeptide was one major band of an apparent molecular weight of about 50,000 Daltons. The mobility of this band was the same on reducing and non-reducing gels.

The protein concentration of the purified material was performed by BCA analysis (Pierce, Rockford, Ill.) and the protein was aliquoted, and stored at −80° C. according to our standard procedures. On IEF (isoelectric focusing) gels the protein runs with a PI of less than 4.5. The concentration of zalpha11CFLG polypeptide was 1.2 mg/ml.

C. Purification of zalpha11-Fc4 Polypeptide from Transfected BHK 570 Cells

Unless otherwise noted, all operations were carried out at 4° C. The following procedure was used for purifying zalpha11 polypeptide containing C-terminal fusion to human IgG/Fc (zalpha11-Fc4; Examples 8 and 9). 12,000 ml of conditioned media from BHK 570 cells transfected with zalpha11-Fc4 (Example 9) was filtered through a 0.2 mm sterilizing filter and then supplemented with a solution of protease inhibitors, to final concentrations of, 0.001 mM leupeptin (Boerhinger-Mannheim, Indianapolis, Ind.), 0.001 mM pepstatin (Boerhinger-Mannheim) and 0.4 mM Pefabloc (Boerhinger-Mannheim). A protein G sepharose (6 ml bed volume, Pharmacia Biotech) was packed and washed with 500 ml PBS (Gibco/BRL) The supplemented conditioned media was passed over the column with a flow rate of 10 ml/minute, followed by washing with 1000 ml PBS (BRL/Gibco). zalpha11-Fc4 was eluted from the column with 0.1 M Glycine pH 3.5 and 2 ml fractions were collected directly into 0.2 ml 2M Tris pH 8.0, to adjust the final pH to 7.0 in the fractions.

The eluted fractions were characterized by SDS-PAGE and western blotting with anti-human Fc (Amersham) antibodies. Western blot analysis of reducing SDS-PAGE gels reveal an immunoreactive protein of about 80,000 KDa in fractions 2-10. Silver stained SDS-PAGE gels also revealed an 80,000 KDa zalpha11:Fc polypeptide in fractions 2-10. Fractions 2-10 were pooled.

The protein concentration of the pooled fractions was performed by BCA analysis (Pierce, Rockford, Ill.) and the material was aliquoted, and stored at −80° C. according to our standard procedures. The concentration of the pooled fractions was 0.26 mg/ml.

Example 11

Assay Using Zalpha11 Soluble Receptor Zalpha11CEE, Zalpha11CFLG and Zalpha11-Fc4 (Mutant) Soluble Receptors in Competitive Inhibition Assay BaF3/Zalpha11 cells were spun down and washed in mIL-3 free media. The cells were spun and washed 3 times to ensure the removal of the mIL-3. Cells were then counted in a hemacytometer. Cells were plated in a 96-well format at 5000 cells per well in a volume of 100 µl per well using the mIL-3 free media.

Both conditioned media from the monkey spleen cell activation and the human CD3+ selected cells, described in Example 5, were added in separate experiments at 50%, 25%, 12.5%, 6.25%, 3.125%, 1.5%, 0.75% and 0.375% concentrations, with or without zalpha11 soluble receptors (CEE, C-flag, and Fc4 constructs; See, Example 9 and 10) at 10 µg/ml. The total assay volume was 200 µl.

The assay plates were incubated 37° C., 5% $CO_2$ for 3 days at which time ALAMAR BLUE™ (Accumed) was added at 20 µl/well. Plates were again incubated at 37° C., 5% $CO_2$ for 24 hours. Plates were read on the Fmax™ plate reader (Molecular Devices) as described in Example 2. Results demonstrated complete inhibition of cell growth from each of the different zalpha11 soluble receptor constructs at 10 µg/ml, confirming that the factor in each sample was specific for the zalpha11 receptor.

Titration curves, diluting out the soluble receptors, were also run using the above stated assay. Both the zalpha11CEE and zalpha11CFLG soluble zalpha11 receptors were able to completely inhibit growth at concentrations as low as 20 ng/ml. The mutant zalpha11-Fc4 soluble zalpha11 receptor was only as effective at 1.5 µg/ml.

Example 12

Secretion Trap Assay

A secretion trap assay was used to identify the cDNA by for the zalpha11 Ligand. The positive DNA pools obtained from the expression cloning effort described in Example 7.

The DNA pools of 250 clones were transfected into BHK cells in 96-well format, and the condition medium were put into the proliferation assay using BaF3/zalpha11 cells described in Examples 4 and Example 5. Several DNA pools gave positive activities which were repeated and neutralized with zalpha11 soluble receptors (see Example 11).

One of the positive DNA pools, 45C5, was transfected into COS cells in 12-well format, using the transfection reagents LIPOFECTAMINE™ method described below. A secretion trap assay was then performed using zalpha11 soluble receptors (C-terminal Glu-Glu tagged either with or without biotinylation; C-terminal Flag tagged; or Fc4 zalpha11 soluble receptor fusions) (Example 9) to test the direct binding between potential ligand of zalpha11 receptor in pool 45C5 and zalpha11 soluble receptor (see below). The result was positive. Thus, the DNA of pool 45C5 was electroporated into *E. coli*, and single colonies were picked into ten 96-well plates. Plates were shaken at 37° C. for 24 hours, and then DNA minipreps QIAPREP® 96 Turbo Miniprep Kit; Qiagen) were prepared in 96-well format using a TomTech Quadra 9600. The plasmid DNA was then pooled in the format of rows and columns, transfected into COS cells, and then the positive pools were determined by secretion trap as described below.

COS Cell Transfections

The COS cell transfection was performed as follows: Mix 3 ul pooled DNA and 5 ul transfection LIPOFECTAMINE™ in 92 ul serum free DMEM media (55 mg sodium pyruvate, 146 mg L-glutamine, 5 mg transferrin, 2.5 mg insulin, 1 µg selenium and 5 mg fetuin in 500 ml DMEM), incubate at room temperature for 30 minutes and then add 400 ul serum free DMEM media. Add this 500 ul mixture onto $1.5 \times 10^5$ COS cells/well plated on 12-well tissue culture plate and incubate for 5 hours at 37° C. Add 500 ul 20% FBS DMEM media (100 ml FBS, 55 mg sodium pyruvate and 146 mg L-glutamine in 500 ml DMEM) and incubate overnight.

Secretion Trap Assay

The secretion trap was performed as follows: Media was rinsed off cells with PBS and then fixed for 15 minutes with 1.8% Formaldehyde in PBS. Cells were then washed with TNT (0.1M Tris-HCL, 0.15M NaCl, and 0.05% Tween-20 in $H_2O$), and permeated with 0.1% Triton-X in PBS for 15 minutes, and again washed with TNT. Cells were blocked for 1 hour with TNB (0.1M Tris-HCL, 0.15M NaCl and 0.5% Blocking Reagent (NEN Renaissance TSA-Direct Kit) in H$_2$O), and washed again with TNT. If using the biotinylated protein, the cells were blocked for 15 minute incubations with Avidin and then Biotin (Vector Labs) washing in-between with TNT. Depending on which soluble receptor was used, the cells were incubated for 1 hour with: (A) 1-3 μg/ml zalpha11 soluble receptor zalpha11-Fc4 fusion protein (Example 10); (B) 3 μg/ml zalpha11 soluble receptor C-terminal FLAG tagged, zalpha11CFLG (Example 10); (C) 3 μg/ml zalpha11 soluble receptor C-terminal GluGlu tagged, zalpha11CEE (Example 10); or (D) 3 μg/ml biotinylated zalpha11 soluble receptor zalpha11CEE in TNB. Cells were then washed with TNT. Depending on which soluble receptor was used, cells were incubated for another hour with: (A) 1:200 diluted goat-anti-human Ig-HRP (Fc specific); (B) 1:1000 diluted M2-HRP; (C) 1:1000 diluted anti-GluGlu antibody-HRP; or (D) 1:300 diluted streptavidin-HRP (NEN kit) in TNB. Again cells were washed with TNT.

Positive binding was detected with fluorescein tyramide reagent diluted 1:50 in dilution buffer (NEN kit) and incubated for 4-6 minutes, and washed with TNT. Cells were preserved with VECTASHIELD® Mounting Media (Vector Labs Burlingame, Calif.) diluted 1:5 in TNT. Cells were visualized using a FITC filter on fluorescent microscope.

Example 13

Chromosomal Assignment and Placement of the Gene for the Zalpha11 Ligand.

The gene for the zalpha11 Ligand was mapped to chromosome 4 using the commercially available version of the "Stanford G3 Radiation Hybrid Mapping Panel" (Research Genetics, Inc., Huntsville, Ala.). The "Stanford G3 RH Panel" contains DNAs from each of 83 radiation hybrid clones of the whole human genome, plus two control DNAs (the RM donor and the A3 recipient).

For the mapping of the zalpha11 Ligand gene with the "Stanford G3 RH Panel", 20 μl reactions were set up in a 96-well microtiter plate (Stratagene, La Jolla, Calif.) and used in a "ROBOCYCLER®GRADIENT 96" thermal cycler (Stratagene). Each of the 85 PCR reactions consisted of 2 μl 10× KlenTaq PCR reaction buffer (CLONTECH Laboratories, Inc., Palo Alto, Calif.), 1.6 μl dNTPs mix (2.5 mM each, PERKIN-ELMER, Foster City, Calif.), 1 μl sense primer, ZC 22,050 (SEQ ID NO:42), 1 μl antisense primer, ZC 22,051 (SEQ ID NO:43), 2 μl "REDILOAD™" (Research Genetics, Inc., Huntsville, Ala.), 0.4 μl 50× ADVANTAGE® KlenTaq Polymerase Mix (Clontech Laboratories, Inc.), 25 ng of DNA from an individual hybrid clone or control and ddH2O for a total volume of 20 μl. The reactions were overlaid with an equal amount of mineral oil and sealed. The PCR cycler conditions were as follows: an initial 1 cycle 5 minute denaturation at 94° C., 35 cycles of a 45 seconds denaturation at 94° C., 45 seconds annealing at 60° C. and 1 minute AND 15 seconds extension at 72° C., followed by a final 1 cycle extension of 7 minutes at 72° C. The reactions were separated by electrophoresis on a 2% agarose gel (Life Technologies, Gaithersburg, Md.).

The results showed linkage of the zalpha11 Ligand gene to the IL2 framework marker SHGC-12342 with a LOD score of >12 and at a distance of 6 cR__10000 (approximately 180 kb) from the marker. The use of surrounding markers positions the zalpha11 Ligand gene in the 4q27 region on the integrated LDB chromosome 4 map.

Example 14

Identification and Cloning of Murine Zalpha11 Ligand
Using an EST Sequence to Obtain Full-length Murine Zalpha11 Ligand A. EST Sequence of Mouse Zalpha11 Ligand By searching the database with human zalpha11 Ligand cDNA sequence (SEQ ID NO:1) as a query, a mouse EST (EST1483966) was identified as potential partial sequence for mouse zalpha11 Ligand. The EST1483966 represents a mouse genomic fragment, in which a peptide sequence derived from two potential exons shared high sequence identity with a peptide segment of the human zalpha11 Ligand (amino acid 13 (Ile) through amino acid 80 (Gln) of the SEQ ID NO:2).

B. PCR Screen of Mouse MARATHON® cDNA Panel

Eleven mouse MARATHON® cDNA (Clontech) samples were screened by PCR described below. The mouse MARATHON® cDNA samples were prepared from brain, pancreas, kidney, placenta, salivary gland, skin, testis, uterus, embryo, and spleen tissues. They were made in-house using a MARATHON® cDNA Amplification Kit (Clontech) according to manufacturer's instructions. Based on the EST sequence, two PCR primers, ZC22,056 (SEQ ID NO:44) and ZC22,057 (SEQ ID NO:45) were used to identify a source of mouse zalpha11 Ligand by PCR. The PCR reaction conditions were as follows: 94° C. for 2 min.; 35 cycles at 94° C. for 30 sec., 68° C. for 2 min.; followed by 68° C. for 4 min.; then a 10° C. soak. The PCR products were run on a 1% agarose gel. A strong 150 bp band representing an amplified cDNA fragment was visualized. This indicated mouse spleen marathon cDNA is the source for mouse zalpha11 Ligand cDNA cloning. The mouse spleen MARATHON® cDNA contained a positive cDNA which was subsequently identified by sequence analysis as a partial cDNA for mouse zalpha11 Ligand.

C. A Composite Sequence for Mouse Full-length cDNA was Generated by 5'- and 3'-RACE The 5' and 3' flanking sequences of the mouse zalpha11 Ligand partial cDNA sequence were obtained by 5' and 3' RACE amplification. Two rounds of nested PCR amplification were performed with additional gene-specific oligo primers ZC22,205 (SEQ ID NO:46) and ZC22,206 (SEQ ID NO:47), ZC22,056 (SEQ ID NO:44) and ZC22,057 (SEQ ID NO:45), and two adapter oligo primers ZC9,739 (SEQ ID NO:48) and ZC9,719 (SEQ ID NO:49). The PCR reactions were run as follows: 94° C. for 2 min; 35 cycles at 94° C. for 30 sec, 68° C. for 2 min; followed by 68° C. for 4 min; then a 10° C. soak. The PCR products were run on a 1% agarose gel, and an approximately 300 bp 5' RACE product and an approximately 800 bp 3' RACE product were identified. These fragments were isolated using PCR purification reagents QIAQUICK® gel extraction kit (Qiagen).

The purified PCR products were sequenced using the following primers: ZC9,719 (SEQ ID NO:49), ZC22,205 (SEQ ID NO:46) and ZC22,206 (SEQ ID NO:47). A preliminary composite full-length mouse zalpha11 Ligand sequence was identified by combining the 5' and 3' RACE fragments. The full length mouse clone was isolated as described in Example 15 below.

Example 15

Isolation of Mouse Zalpha11 cDNA Clone from an Activated Mouse Spleen Library

A. Murine Primary Source Used to Isolate Mouse Zalpha11 Ligand

Mouse spleens from Balb/C mice, were collected and mashed between frosted-end slides to create a cell suspension. The isolated primary mouse cell yield was 6.4×10⁸ cells prior to selection described below.

The spleen cells were suspended in 9.6 ml MACS buffer (PBS, 0.5% EDTA, 2 mM EDTA). 1.6 ml of cell suspension was removed and 0.4 ml CD90 (Thy1.2) microbeads (Miltenyi Biotec) added. The mixture was incubated for 15 min. at 4° C. These cells labeled with CD90 beads were washed with 30 ml MACS buffer, and then resuspended in 2 ml MACS buffer.

A VS+ column (Miltenyi) was prepared according to the manufacturer's instructions. The VS+ column was then placed in a VarioMACS™ magnetic field (Miltenyi). The column was equilibrated with 5 ml MACS buffer. The isolated primary mouse cells were then applied to the column. The CD3 negative cells were allowed to pass through. The column was rinsed with 9 ml (3×3 ml) MACS buffer. The column was then removed from the magnet and placed over a 15 ml falcon tube. CD90+ cells were eluted by adding 5 ml MACS buffer to the column and bound cells flushed out using the plunger provided by the manufacturer. The incubation of the cells with the CD90 magnetic beads, washes, and VS+ column steps (incubation through elution) above were repeated once more. The resulting CD90+ fractions from the 2 column separations were pooled. The yield of CD90+ selected mouse spleen cells were 1×10⁸ total cells.

A sample of the pooled CD90+ selected mouse cells was removed for staining and sorting on a fluorescent antibody cell sorter (FACS) to assess their purity. A PE-conjugated hamster anti-mouse CD3+ antibody (PharMingen) was used for staining and sorting the CD90+ selected cells. The mouse CD90+ selected cells were 93% CD3+ cells, suggesting the cells were 93% T-cells.

The murine CD90+ selected cells were activated by incubating 3×10⁶ cells/ml in RPMI+5% FBS+PMA 10 ng/ml and Ionomycin 0.5 µg/ml (Calbiochem) for overnight at 37□C. The supernatant from these activated CD90+ selected mouse cells was tested for zalpha11 Ligand activity as described below. Moreover, the activated CD90+ selected mouse cells were used to prepare a cDNA library, as described in Example 16, below.

Example 16

Cloning of Mouse Zalpha11 Ligand from a Mouse CD90+ Selected Cell Library

Screening of a primary mouse activated CD90+ selected cell cDNA library revealed an isolated cDNA that is a novel member of the four-helix bundle cytokine family. This cDNA encoded the mouse ortholog of the human zalpha11 Ligand. The cDNA was identified by hybridization screening.

A. The Vector for CD90+ Selected Library Construction

The vector, pZP7N was used for CD3+ selected library construction (See Example 6A)

B. Preparation of Primary Mouse Activated CD90+ Selected Cell cDNA Library

Approximately 1.5×10⁸ primary mouse CD90+ selected cells stimulated in ionomycin/PMA (Example 15) were isolated by centrifugation. Total RNA was isolated from the cell pellet, and converted to double stranded cDNA as described in Example 6B. This DNA was subsequently transfected into BHK cells, as described in Example 6B, and proliferation was assessed using an "ALAMAR BLUE™" fluorescence assay (Example 2B).

For the purpose of screening the library by secretion trap cloning, a complex, amplified form of the library was needed to transfect COS-7 cells. 4.8 million clones were plated on 110 15 cm LB-agar plates supplemented with 100 µg/ml ampicillin, 10 µg/ml methicillin. After growing the plates overnight at 37° C. the bacteria were harvested by scraping and pelleted. Plasmid DNA was extracted from the pelleted bacteria using a an anion exchange matrix plasmid purification method NUCLEOBOND® (Clonetech) following the manufacturer's instructions. This plasmid was then used to transfect COS-7 cells on slides and screened using the secretion trap technique described below (Example 17).

C. Screening the Activated Mouse cDNA Library

Approximately 5×10⁵ clones were plated on 10 LB/Amp Maxi plates. The colonies were lifted, denatured, neutralized, and cross-linked using the standard procedure (Sambrook, J. et al. supra.). Fifty nanograms of the 300 bp 5' RACE PCR fragment (Example 14) was labeled with 32P using PRIME-IT® random primer labeling kit (Stratagene). The 10 filters were hybridized with this labeled probe at 65° C. overnight using EXPRESSHYB™ Hybridization Solution (Clontech). The filters were then washed sequentially at 60° C. for 1 hour three times with 0.2×SSC (30 mM NaCl, 3 mM sodium citrate, pH 7.0), 0.1% SDS; and then at 65° C. for 1 hour. The filters were exposed at −80° C. overnight, and the X-ray film were developed. Agar plugs containing the positive colonies were pulled, and the clones plated on 10-cm LB/Amp plates. The colonies were then filter-lifted and hybridized again following the same procedure described above.

One DNA clone, named M11L/pZP7, was isolated and sequenced using the following primers: ZC14,063 (SEQ ID NO:50), ZC5,020 (SEQ ID NO:51), ZC22,421 (SEQ ID NO:52), ZC22,604 (SEQ ID NO:53), and ZC22,641 (SEQ ID NO:54). The polynucleotide sequence of this clone is full-length mouse zalpha11 Ligand (SEQ ID NO:55) and consistent with the composite sequence obtained from 5' and 3' RACE products. The corresponding amino acid sequence for the mouse zalpha11 Ligand is shown in SEQ ID NO:56.

Example 17

Mouse Zalpha11 Ligand Binds to Human Zalpha11 Soluble Receptor in Secretion Trap Assay The DNA for mouse clone M11L/pZP7 was transfected into COS cells, and the binding of human zalpha11 soluble receptor zalpha11-Fc4 (Example 10C) to the transfected COS cells was tested by a secretion trap assay (Example 12). The assay confirmed that the mouse zalpha11 Ligand binds to human zalpha11 soluble receptor.

The COS cell transfection was performed as per example 12 using 0.7 □g M11L/pZP7 DNA (Example 16) in 3 µl.

The secretion trap was performed as per example 12 using 1 µg/ml zalpha11 soluble receptor Fc4 fusion protein (Example 10C) in TNB, and 1:200 diluted goat-anti-human Ig-HRP (Fc specific) in TNB for the detectable antibody. Positive binding of the soluble human zalpha11 receptor to the prepared fixed cells was detected with fluorescein tyramide reagent as per Example 12. Cells were preserved and visualized according to Example 12.

The positive result indicated the mouse zalpha11 Ligand binds to human zalpha11 soluble receptor.

Example 18

Expression of Mouse Zalpha11 Ligand in Mammalian Cells

A. Construction of Expression Vector M11L/pZP9

An expression vector was prepared for the expression of the mouse zalpha11 Ligand in mammalian cells. A 500 bp PCR generated zalpha11 Ligand DNA fragment was created using ZC22,283 (SEQ ID NO:57) and ZC22,284 (SEQ ID NO:58) as PCR primers to amplify the coding region of mouse zalpha11 Ligand and add XhoI and XbaI restriction sites. The mouse zalpha11 Ligand clone M11L/pZP7 (Example 16) was used as a template. The PCR reaction conditions were as follows: 94° C. for 2 min.; 25 cycles at 94° C. for 30 sec., 68° C. for 2 min.; followed by 68° C. for 4 min.; then a 10° C. soak. A band of the predicted size, about 500 bp, was visualized by 1% agarose gel electrophoresis, excised and the DNA was purified using a QIAEXII® purification system (Qiagen) according to the manufacturer's instructions. The purified DNA was digested with XhoI and XbaI (Boehringer Mannheim) at 37° C. for 2 hours. Then the DNA was gel isolated and purified following the above procedure.

The excised DNA was subcloned into plasmid pZP9 which was cut with XhoI and XbaI (Boehringer Mannheim). Plasmid pZP9 is a mammalian expression vector containing an expression cassette having the mouse metallothionein-1 (MT-1) promoter, multiple restriction sites for insertion of coding sequences, and a human growth hormone terminator. The plasmid also has an *E. coli* origin of replication, a mammalian selective marker expression unit having an SV40 promoter, enhancer and origin of replication, a DHFR gene, and the SV40 terminator.

About 30 ng of the restriction digested mouse zalpha11 Ligand fragment and about 10 ng of the digested pZP9 vector were ligated at room temperature for 2 hours. Two μg of ligation reaction was transformed into INVaF' competent cells (Invitrogen) according to manufacturer's protocol and plated onto LB plates containing 50 μg/ml ampicillin, and incubated at 37° C. overnight. Colonies were screened by restriction analysis using XhoI and XbaI (Boerhinger Mannheim) of DNA prepared from liquid cultures of individual colonies. The insert sequence of positive clones was verified by sequence analysis to be the mouse zalpha11 Ligand sequence. A large scale plasmid preparation was done using a QIAGEN® Maxi prep kit (Qiagen) according to manufacturer's instruction. The expression vector that contains mouse zalpha11 Ligand was named M11L/pZP9.

B. Mammalian Expression of Mouse Zalpha11 Ligand

BHK 570 cells (ATCC No: CRL-10314) were plated in 10 cm tissue culture dishes and allowed to grow to approximately 20% confluence overnight at 37° C., 5% $CO_2$, in DMEM/FBS media (DMEM, Gibco/BRL High Glucose media; Gibco BRL, Gaithersburg, Md.), 5% fetal bovine serum (Hyclone, Logan, Utah), 1 mM L-glutamine (JRH Biosciences, Lenexa, Kans.), 1 mM sodium pyruvate (Gibco BRL)). The cells were then transfected with the plasmid M11L/pZP9 (Example 18A) using a mammalian stable $CaPO_4$ transfection kit (Stratagene) according to the manufacturer's instructions.

One day after transfection, the cells were split 1:10 and 1:20 into the selection media (DMEM/FBS media with the addition of 1 μM methotrexate (Sigma Chemical Co., St. Louis, Mo.)) in 150 mm plates. The media on the cells was replaced with fresh selection media at day 5 post-transfection. Approximately 10 days post-transfection, methotrexate resistant colonies were trypsinized and the cells pooled and plated into large scale culture flasks. Once the cells were grown to approximately 90% confluence, they were rinsed with PBS three times, and cultured with serum-free ESTEP2 media (DMEM (Gibco BRL), 0.11 g/l Na Pyruvate, 3.7 g/l $NaHCO_3$, 2.5 mg/l insulin, 5 mg/l transferrin, pH7.0) conditioned media. The conditioned media were collected three days later, and put into a BaF3 proliferation assay using ALAMAR BLUE™, described in Example 19 below.

Example 19

Mouse Zalpha11 Ligand Activates Human Zalpha11 Receptor in BaF3 Assay using ALAMAR BLUE™

Proliferation of BaF3/zalpha11 cells (Example 4, and 5B) was assessed using serum-free conditioned media from BHK cells expressing mouse zalpha11 Ligand (Example 18).

BaF3/Zalpha11 cells were spun down, washed and plated in mIL-3 free media as described in Example 5B.

Proliferation of the BaF3/Zalpha11 cells was assessed using serum-free conditioned media from BHK cells expressing mouse zalpha11 Ligand (Example 18). Conditioned media was diluted with mIL-3 free media to: 50%, 25%, 12.5%, 6.25%, 3.125%, 1.5%, 0.75% and 0.375% concentrations. The proliferation assay was performed as per Example 5B.

Results confirmed the proliferative response of the BaF3/Zalpha11 cells to mouse zalpha11 Ligand. The response, as measured, was approximately 5-fold over background at the 50% concentration.

Example 20

Zalpha11 Ligand Activates Human Zalpha11 Receptor in Luciferase Assay

A. Construction of BaF3/KZ134/Zalpha11 Cell Line

The KZ134 plasmid was constructed with complementary oligonucleotides ZC12,749 (SEQ ID NO:59) and ZC12,748 (SEQ ID NO:60) that contain STAT transcription factor binding elements from 4 genes. A modified c-fos S is inducible element (m67SIE, or hSIE) (Sadowski, H. et al., *Science* 261:1739-1744, 1993), the p21 SIE1 from the p21 WAF1 gene (Chin, Y. et al., *Science* 272:719-722, 1996), the mammary gland response element of the β-casein gene (Schmitt-Ney, M. et al., *Mol. Cell. Biol.* 11:3745-3755, 1991), and a STAT inducible element of the Fcg RI gene, (Seidel, H. et al., *Proc. Natl. Acad. Sci.* 92:3041-3045, 1995). These oligonucleotides contain Asp718-XhoI compatible ends and were ligated, using standard methods, into a recipient firefly luciferase reporter vector with a c-fos promoter (Poulsen, L. K. et al., *J. Biol. Chem.* 273:6229-6232, 1998) digested with the same enzymes and containing a neomycin selectable marker. The KZ134 plasmid was used to stably transfect BaF3 cells, using standard transfection and selection methods, to make the BaF3/KZ134 cell line.

A stable BaF3/KZ134 indicator cell line, expressing the full-length zalpha11 receptor was constructed as per Example 2A, using about 30 μg of the zalpha11 expression vector, described in Example 3. Clones were diluted, plated and selected using standard techniques. Clones were screened by luciferase assay (see Example 20B, below) using the human zalpha11 Ligand conditioned media as an inducer. Clones with the highest luciferase response (via STAT luciferase) and the lowest background were selected. A stable transfectant cell line was selected. The cell line was called BaF3/KZ134/zalpha11.

B. Human and Mouse Zalpha11 Ligand Activates Human Zalpha11 Receptor in BaF3/KZ134/Zalpha11 Luciferase Assay BaF3/KZ134/Zalpha11 cells were spun down and washed in mIL-3 free media. The cells were spun and washed 3 times to ensure removal of mIL-3. Cells were then counted in a hemacytometer. Cells were plated in a 96-well format at about 30,000 cells per well in a volume of 100 μl per well using the mIL-3 free media. The same procedure was used for untransfected BaF3/KZ134 cells for use as a control in the subsequent assay.

STAT activation of the BaF3/KZ134/Zalpha11 cells was assessed using conditioned media from (1) BHK570 cells transfected with the human zalpha11 Ligand (Example 7) or (2) BHK570 cells transfected with the mouse zalpha11 Ligand (Example 18), or (4) mIL-3 free media to measure media-only control response. Conditioned media was diluted with RPMI mIL-3 free media to 50%, 25%, 12.5%, 6.25%, 3.125%, 1.5%, 0.75% and 0.375% concentrations. 100 µl of the diluted conditioned media was added to the BaF3/KZ134/Zalpha11 cells. The assay using the conditioned media was done in parallel on untransfected BaF3/KZ134 cells as a control. The total assay volume was 200 µl. The assay plates were incubated at 37° C., 5% $CO_2$ for 24 hours at which time the cells were pelleted by centrifugation at 2000 rpm for 10 min., and the media was aspirated and 25 µl of lysis buffer (Promega) was added. After 10 minutes at room temperature, the plates were measured for activation of the STAT reporter construct by reading them on a luminometer (Labsystems Luminoskan, model RS) which added 40 µl of luciferase assay substrate (Promega) at a five second integration.

Results confirmed the STAT reporter response of the BaF3/KZ134/Zalpha11 cells to the human zalpha11 Ligand. The response, as measured, was approximately 50 fold over media-only control at the 50% concentration. STAT activation in response to human zalpha11 Ligand was absent in the untransfected BaF3/KZ134 control cells, showing that the response is mediated through the Zalpha11 receptor.

Results also confirmed the STAT reporter response of the BaF3/KZ134/Zalpha11 cells to the mouse zalpha11 Ligand. The response, as measured, was approximately 40 fold over media-only control at the 50% concentration. Moreover, STAT activation in response to mouse zalpha11 Ligand was evident (about 5-fold) on the untransfected BaF/KZ134 control cells, suggesting that the murine BaF3 cells may have endogenous mouse receptor.

Example 21

Mouse Zalpha11 Ligand is Active in Mouse Bone Marrow Assay

A. Isolation of Non-adherent Low Density Marrow Cells:

Fresh mouse femur aspirate (marrow) was obtained from 6-10 week old male Balb/C or C57BL/6 mice. The marrow was then washed with RPMI+10% FBS (JRH, Lenexa Kans.; Hyclone, Logan Utah) and suspended in RPMI+10% FBS as a whole marrow cell suspension. The whole marrow cell suspension was then subjected to a density gradient (NYCOPREP®, 1.077, Animal; Gibco BRL) to enrich for low density, mostly mononuclear, cells as follows: The whole marrow cell suspension (About 8 ml) was carefully pipetted on top of about 5 ml Nycoprep gradient solution in a 15 ml conical tube, and then centrifuged at 600×g for 20 minutes. The interface layer, containing the low density mononuclear cells, was then removed, washed with excess RPMI+10% FBS, and pelleted by centrifugation at 400×g for 5-10 minutes. This pellet was resuspended in RPMI+10% FBS and plated in a T-75 flask at approximately $10^6$ cells/ml, and incubated at 37° C. 5% $CO_2$ for approximately 2 hours. The resulting cells in suspension were Non-Adherent Low Density (NA LD) Marrow Cells.

B. 96-Well Assay

NA LD Mouse Marrow Cells were plated at 25,000 to 45,000 cells/well in 96 well tissue culture plates in RPMI+10% FBS+1 ng/mL mouse Stem Cell Factor (mSCF) (R&D Systems, Minneapolis, Minn.), plus 5% conditioned medium from one of the following: (1) BHK 570 cells expressing mouse zalpha11 Ligand (Example 18), (2) BHK 570 cells expressing human zalpha11 Ligand (Example 7), or (3) control BHK 570 cells containing vector and not expressing either Ligand. These cells were then subjected to a variety of cytokine treatments to test for expansion or differentiation of hematopoietic cells from the marrow. To test, the plated NA LD mouse marrow cells were subjected to human Interleukin-15 (hIL-15) (R&D Systems), or one of a panel of other cytokines (R&D Systems). Serial dilution of hIl-15, or the other cytokines, were tested, with 2-fold serial dilution from about 50 ng/ml down to about 6025 ng/ml concentration. After 8 to 12 days the 96-well assays were scored for cell proliferation by ALAMAR Blue™ assay as described in Example 5B.

C. Results from the 96-Well NA LD Mouse Marrow Assay

Conditioned media from the BHK cells expressing both mouse and human zalpha11 Ligand acted in synergy with hIL-15 to promote the expansion of a population of hematopoietic cells in the NA LD mouse marrow. This expansion of hematopoietic cells was not shown with control BHK conditioned medium plus IL-15. The population hematopoietic cells expanded by the mouse zalpha11 Ligand with hIL-15, and those hematopoietic cells expanded by the human zalpha11 Ligand with hIL-15, were further propagated in cell culture. These hematopoietic cells were stained with a Phycoerythrin labeled anti-Pan NK cell antibody (Pharmingen) and subjected to flow cytometry analysis, which demonstrated that the expanded cells stained positively for this natural killer (NK) cell marker.

The same 96-well assay was run, using fresh human marrow cells bought from Poietic Technologies, Gaithersburg, Md. Again, in conjunction with IL-15, the mouse and human zalpha11 Ligand expanded a hematopoietic cell population that stained positively for the NK cell marker using the antibody disclosed above.

Example 22

Constructs for Generating Human Zalpha11 Ligand Transgenic Mice

A. Construct for Expressing Human Zalpha11 Ligand from the Liver-specific MT-1 Promoter Oligonucleotides were designed to generate a PCR fragment containing a consensus Kozak sequence and the human zalpha11 Ligand coding region. These oligonucleotides were designed with an FseI site at the 5' end and an AscI site at the 3' end to facilitate cloning into (a) pMT12-8, our standard transgenic vector, or (b) pKFO51, a lymphoid-specific transgenic vector (Example 22B).

PCR reactions were carried out with 200 ng human zalpha11 Ligand template (Example 7) and oligonucleotides ZC22,143 (SEQ ID NO:61) and ZC22,144 (SEQ ID NO:62). PCR reaction conditions were as follows: 95° C. for 5 minutes, wherein ADVANTAGE® cDNA polymerase (Clontech) was added; 15 cycles of 95° C. for 60 seconds, 60° C. for 60 seconds, and 72° C. for 90 seconds; and 72° C. for 7 minutes. PCR products were separated by agarose gel electrophoresis and purified using a PCR purification reagents QIAQUICK® (Qiagen) gel extraction kit. The isolated, 488 bp, DNA fragment was digested with FseI and AscI (Boerhinger-Mannheim), ethanol precipitated and ligated into pMT12-8 previously digested with FseI and AscI. The pMT12-8 plasmid, designed for expressing a gene of interest in liver and other tissues in transgenic mice, contains an expression cassette flanked by 10 kb of MT-1 5' DNA and 7 kb of MT-1 3' DNA. The expression cassette comprises the MT-1 promoter, the rat insulin II intron, a polylinker for the insertion of the desired clone, and the human growth hormone (hGH) poly A sequence.

About one microliter of each ligation reaction was electroporated into *E coli* DH10b™ competent cells ELECTROMAX™ (GIBCO BRL, Gaithersburg, Md.) according to manufacturer's direction and plated onto LB plates containing 100 µg/ml ampicillin, and incubated overnight. Colonies were picked and grown in LB media containing 100 µg/ml ampicillin. Miniprep DNA was prepared from the picked clones and screened for the human zalpha11 Ligand insert by restriction digestion with EcoRI alone, or FseI and AscI combined, and subsequent agarose gel electrophoresis. Maxipreps of the correct pMT-human zalpha11 Ligand were performed. A SalI fragment containing with 5' and 3' flanking sequences, the MT-1 promoter, the rat insulin II intron, human zalpha11 Ligand cDNA and the hGH poly A sequence was prepared to be used for microinjection into fertilized murine oocytes. Microinjection and production of transgenic mice were produced as described in Hogan, B. et al. Manipulating the Mouse Embryo, 2nd ed., Cold Spring Harbor Laboratory Press, NY, 1994.

B. Construct for Expressing Human Zalpha11 Ligand from the Lymphoid-specific E☐LCK Promoter Oligonucleotides were designed to generate a PCR fragment containing a consensus Kozak sequence and the human zalpha11 Ligand coding region. These oligonucleotides were designed with an FseI site at the 5' end and an AscI site at the 3' end to facilitate cloning into pKFO51, a lymphoid-specific transgenic vector.

PCR reactions were carried out with 200 ng human zalpha11 Ligand template (Example 7) and oligonucleotides ZC22,143 (SEQ ID NO:61) and ZC22,144 (SEQ ID NO:62). A PCR reaction was performed using ADVANTAGE® cDNA polymerase (Clontech) under the following conditions: 95° C. for 5 minutes; 15 cycles of 95° C. for 60 seconds, 60° C. for 60 seconds, and 72° C. for 90 seconds; and 72° C. for 7 minutes. PCR products purified as described above. The isolated, 488 bp, DNA fragment was digested with FseI and AscI (Boerhinger-Mannheim), ethanol precipitated and ligated into pKFO51 previously digested with FseI and AscI. The pKFO51 transgenic vector is derived from p1026X (Iritani, B. M., et al., *EMBO J.* 16:7019-31, 1997) and contains the T cell-specific lck proximal promoter, the B/T cell-specific immunoglobulin µ heavy chain enhancer, a polylinker for the insertion of the desired clone, and a mutated hGH gene that encodes an inactive growth hormone protein (providing 3' introns and a polyadenylation signal).

About one microliter of each ligation reaction was electroporated, plated, clones picked and screened for the human zalpha11 Ligand insert by restriction digestion as described above. A correct clone of pKFO51-zalpha11 Ligand was verified by sequencing, and a maxiprep of this clone was performed. A NotI fragment, containing the lck proximal promoter and immunoglobulin 11 enhancer (EµLCK), zalpha11 Ligand cDNA, and the mutated hGH gene was prepared to be used for microinjection into fertilized murine oocytes.

Example 23

Mouse Zalpha11 Ligand Tissue Distribution

Murine Multiple Tissue Northern Blots (Mouse, Mouse Embryo, Clontech; MB1010, MB1012 Origene) were probed to determine the tissue distribution of murine zalpha11 Ligand expression. An approximately 484 bp PCR derived probe was amplified using the plasmid M11L/pZP7 (Example 16) as a template and oligonucleotide ZC22283 (SEQ ID NO:57) and ZC22284 (SEQ ID NO:58) as primers. The PCR amplification was carried out as follows: 1 cycle at 94° C. for 1.0 minutes; 35 cycles of 94° C. for 30 seconds, 50° C. for 30 seconds, and 72° C. for 30 seconds; followed by 1 cycle at 72° C. for 10 minutes. The PCR products were visualized by agarose gel electrophoresis and the approximately 484 bp PCR product was purified using a Gel Extraction Kit (Qiagen) according to manufacturer's instructions. The probe was radioactively labeled using the REDIPRIME™ labeling kit (Amersham) according to the manufacturer's instructions. The probe was purified using a NUCTRAP™ push column (Stratagene). EXPRESSHYB™ (Clontech) solution was used for prehybridization and as a hybridizing solution for the Northern blots. Hybridization took place overnight at 65° C. using $10^6$ cpm/ml of labeled probe. The blots were then washed three times in 2×SSC and 0.1% SDS at room temperature, followed by 2 washes in 0.1×SSC and 0.1% SDS at 55° C. Two transcripts of approximately 1.2 and 3.5 kb were seen in testis. The upper transcript only was seen in thymus.

A murine RNA Master Dot Blot (Clontech) that contained RNAs from various tissues that were normalized to 8 housekeeping genes was also probed and hybridized as described above. Expression was seen in testis.

Example 24

Purification of Untagged Human and Murine Zalpha11 Ligand from BHK 570

Unless other wise stated, all operations were carried out at 4° C. The following procedure was used for purifying human and murine zalpha11 Ligand from conditioned media from BHK 570 cells transfected with a construct expressing either the human zalpha11 Ligand (Example 25) or the mouse zalpha11 Ligand (M11L/pZP9) (Example 18). The conditioned media was concentrated by standard techniques. Concentrated conditioned media (CM) was sterile filtered through 0.45 and 0.22 micron filters. The media was then diluted to low ionic strength (<2 mS) in 0.01 M HEPES (JRH Biosciences, Lenexa, Kans.) at pH 7.0. The low ionic strength diluted CM was then loaded onto a 10×66 mm (6 ml) Poros HS 50 column (PerSeptive BioSystems, Framingham, Mass.) overnight at 4 ml/min using a BioCAD SPRINT (Perceptive BioSystems). The column was washed for 10-20 column volumes (CV) with 0.01 M HEPES pH7.0. The bound proteins were then step eluted with 1 M NaCl (Mallinckrodt, Paris, Ky.) in 0.01 M HEPES pH 7.0 at 5 ml/min; two ml fractions were collected over the entire chromatography and absorbence at 280 and 215 nM were monitored. Peak absorbence fractions were analyzed by bioassay and by SDS-PAGE Silver (Geno Technology, St. Louis, Mo.) and Coomassie (Sigma, St. Louis, Mo.) staining. Peak fractions were pooled, sterile filtered and diluted to <19 mS with Phosphate buffered saline (PBS, Gibco BRL) at pH 7.2.

The diluted sample was then loaded at 2 ml/min using a BioCad SPRINT, onto either a 0.8 ml Poros AL column that had zalpha11CFLAG soluble receptor (Example 10B) or zalpha11-Fc4 fusion soluble receptor (Example 10C) immobilized on the resin (see, below). The column was then washed with at least 20 CV of PBS at 10 ml/min. The column was then rapidly eluted with a 600 µl injection of 0.1 M glycine (Aminoacetic Acid; Glycocol, Spectrum, Gardena, Calif.) pH 2.5 at a flow rate of 10 ml/min with PBS on a BioCAD 700E. The 1 ml fractions were collected for 6 seconds each and immediately pH neutralized with 55 µl of 2 M TRIS (Tris(Hydroxymethyl)Aminomethane, EM Science, Gibbstown, N.J.)

pH 8.8. The absorbence at 280 and 215 nM were monitored over the entire chromatography.

The peak fractions were analyzed by bioassay and by SDS-PAGE Silver (Geno Technology) and Coomassie (Sigma) staining. Two bands, approximately 24 kD and 18 kD, were seen on both Silver and Coomassie gels for mouse zalpha11 Ligand. A single band, at approximately 18 kD, was seen on both Silver and Coomassie gels for human zalpha11 Ligand.

Immobilization of Human Zalpha11 Soluble Receptor Polypeptides on POROS AL Media Poros AL columns having immobilized zalpha11CFLAG soluble receptor (Example 10B) or zalpha11-Fc4 fusion soluble receptor (Example 10C) were prepared. Approximately 3 mg of zalpha11CFLAG soluble receptor and approximately 10 mg of zalpha11-Fc4 fusion soluble receptor were used. All operations were carried out at room temperature on a BioCAD 700E. A 4.5×50 mm column with the POROS AL media was flow packed in 2 M NaCl according to manufactures specifications. The column was then equilibrated in 1.1 M $Na_2SO_4$/50 mM NaPhosphate pH 7.2. The receptor was concentrated to 4 mg/ml using a Millipore 30 MWKO spin concentrator then diluted 1:1 in 1.1 M $Na_2SO_4$/50 mM NaPhosphate pH 7.2. The column was flowed at 2 ml/min in 1.1 M $Na_2SO_4$/50 mM NaPhosphate pH 7.2 and 100 µl injections of the diluted ligand were made ever 9 CVs until a steady state of saturation, or break through, was reached. A 62 CV gradient was then run from 1.1 M $Na_2SO_4$/50 mM NaPhosphate pH 7.2, to 550 mM $Na_2SO_4$/50 mM NaPhosphate pH 7.2/5 mg/ml Sodium Cyanoborohydride. The column was then held for about 2 hours to complete the immobilization chemistry. The column was then equilibrated in 0.2 M TRIS pH 7.2/5 mg/ml Sodium Cyanoborohydride and allowed to rest for about 1 hour to cap the column. Finally the column was equilibrated in PBS/0.02% Sodium Azide, and stored at 4° C. until needed. Prior to use, the column was pre-eluted with 0.1 M glycine to ensure that non-specific proteins were removed and that the column was not leaching the immobilized human zalpha11 soluble receptor.

Example 25

Expression of Human Zalpha11 Ligand in Mammalian Cells

A. Construction of Expression Vector PZMP11/Zalpha11Lig

An expression plasmid containing all or part of a polynucleotide encoding human zalpha11 Ligand was constructed via homologous recombination. A fragment of human zalpha11 Ligand cDNA (SEQ ID NO:63) was isolated using PCR. Two primers were used in the production of the human zalpha11 Ligand fragment in a PCR reaction: (1) Primer ZC22,052 (SEQ ID NO:64), containing 40 bp of the vector flanking sequence and 17 bp corresponding to the amino terminus of the human zalpha11 Ligand, and (2) primer ZC22,053 (SEQ ID NO:65), containing 40 bp of the 3' end corresponding to the flanking vector sequence and 17 bp corresponding to the carboxyl terminus of the human zalpha11 Ligand. The PCR Reaction conditions were as follows: 1 cycle at 94° C. for 2.0 minutes; 25 cycles of 94° C. for 30 seconds, 60° C. for 30 seconds, and 72° C. for 30 seconds; followed by 1 cycle at 72° C. for 5 minutes; 4° C. soak. Ten µl of the 100 µl PCR reaction was run on a 0.8% LMP agarose gel (Seaplaque GTG) with 1×TBE buffer for analysis, and the expected approximately 560 bp fragment seen. The remaining 90 µl of PCR reaction was precipitated with the addition of 5 µl 1 M NaCl and 250 µl of absolute ethanol to be used for recombining onto the recipient vector pZMP11 as described below. The recipient plasmid pZMP11 was previously cut with SmaI.

Plasmid pZMP11 was derived from the plasmid pCZR199 (described herein, e.g., Example 8). The plasmid pCZR199 is a mammalian expression vector containing an expression cassette having the CMV immediate early promoter, a consensus intron from the variable region of mouse immunoglobulin heavy chain locus, multiple restriction sites for insertion of coding sequences, a stop codon and a human growth hormone terminator. The plasmid also has an E. coli origin of replication, a mammalian selectable marker expression unit having an SV40 promoter, enhancer and origin of replication, a DHFR gene and the SV40 terminator. The vector pZMP11 was constructed from pCZR199 and includes the replacement of the metallothionein promoter with the CMV immediate early promoter, and Kozac sequences at the 5' end of the open reading frame.

One hundred microliters of competent yeast cells (S. cerevisiae) were combined with 10 µl of a mixture containing approximately 1 µg of the human zalpha11 Ligand insert, and 100 ng of SmaI digested pZMP11 vector, and transferred to a 0.2 cm electroporation cuvette. The yeast/DNA mixtures were electropulsed at 0.75 kV (5 kV/cm), infinite ohms, 25 µF. To each cuvette was added 600 µl of 1.2 M sorbitol and the yeast was then plated in two 300 µl aliquots onto two URA-D plates and incubated at 30° C.

After about 48 hours, the Ura+ yeast transformants from a single plate were resuspended in 1 ml $H_2O$ and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 µl acid washed glass beads and 200 µl phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 µl ethanol (EtOH), followed by centrifugation for 10 minutes at 4° C. The DNA pellet was resuspended in 100 µl $H_2O$.

Transformation of electrocompetent E. coli cells (DH10B, GibcoBRL) was done with 0.5-2 ml yeast DNA prep and 40 µl of DH10B cells. The cells were electropulsed at 2.0 kV, 25 mF and 400 ohms. Following electroporation, 1 ml SOC (2% Bacto™ Tryptone (Difco, Detroit, Mich.), 0.5% yeast extract (Difco), 10 mM NaCl, 2.5 mM KCl, 10 mM $MgCl_2$, 10 mM $MgSO_4$, 20 mM glucose) was plated in 250 µl aliquots on four LB AMP plates (LB broth (Lennox), 1.8% Bacto™ Agar (Difco), 100 mg/L Ampicillin).

Individual clones harboring the correct expression construct for human zalpha11 Ligand were identified by restriction digest to verify the presence of the insert and to confirm that the various DNA sequences have been joined correctly to one another. The insert of positive clones were subjected to sequence analysis. Larger scale plasmid DNA was isolated using the QIAGEN® Maxi Prep kit (Qiagen) according to manufacturer's instruction.

B. Mammalian Expression of Human Zalpha11 Ligand

BHK 570 cells (ATCC NO: CRL-10314) were plated in 10 cm tissue culture dishes and allowed to grow to approximately 50 to 70% confluence overnight at 37° C., 5% $CO_2$, in DMEM/FBS media (DMEM, Gibco/BRL High Glucose, (Gibco BRL, Gaithersburg, Md.), 5% fetal bovine serum (Hyclone, Logan, Utah), 1 mM L-glutamine (JRH Biosciences, Lenexa, Kans.), 1 mM sodium pyruvate (Gibco BRL). The cells were then transfected with the plasmid PZMP11/zalpha11Lig (Example 25A), using transfection reagent LIPOFECTAMINE™ (Gibco BRL), in serum free (SF) media formulation (DMEM, 10 mg/ml transferrin, 5 mg/ml insulin, 2 mg/ml fetuin, 1% L-glutamine and 1% sodium pyruvate). Zalpha11-Fc4/pZMP6 (Example 8B) was diluted into 15 ml tubes to a total final volume of 640 µl with SF media. 35 µl of transfection reagent LIPOFECTAMINE™ (Gibco BRL) was mixed with 605 µl of SF medium. The transfection reagent LIPOFECTAMINE™ mix was added to the DNA mix and allowed to incubate approximately 30 minutes at room temperature. Five milliliters of SF media was added to the DNA:LIPOFECTAMINE™ mixture. The cells were rinsed once with 5 ml of SF media, aspirated, and the DNA:LIPOFECTAMINE™ mixture was added. The cells were incubated at 37° C. for five hours, then 6.4 ml of DMEM/10% FBS, 1% PSN media was added to each plate. The plates were incubated at 37° C. overnight and the DNA:LIPOFECTAMINE™ mixture was replaced with fresh 5% FBS/DMEM media the next day. On day 5 post-transfection, the cells were split into T-162 flask in selection medium (DMEM/5% FBS, 1% L-GLU, 1% NaPyr). Approximately 10 days post-transfection, two 150 mm culture dishes of methotrexate resistant colonies from each transfection were trypsinized and the cells are pooled and plated into a T-162 flask and transferred to large scale culture. Conditioned media from large scale culture was used to purify human zalpha11 Ligand polypeptide as described in Example 24.

Example 26

Construct for Generating Mouse Zalpha11 Ligand Transgenic Mice

A. Construct for Expressing Mouse Zalpha11 Ligand from the Lymphoid-specific EµLCK Promoter Oligonucleotides were designed to generate a PCR fragment containing a consensus Kozak sequence and the mouse zalpha11 Ligand coding region. These oligonucleotides were designed with an FseI site at the 5' end and an AscI site at the 3' end to facilitate cloning into: (a) pKFO51, a lymphoid-specific transgenic vector, or (b) pTG12-8, our standard transgenic vector.

PCR reactions were carried out with 200 ng mouse zalpha11 Ligand template (SEQ ID NO:55; Example 16) and oligonucleotides ZC23,115 (SEQ ID NO:66) and ZC23,116 (SEQ ID NO:67). A PCR reaction was performed using ADVANTAGE® cDNA polymerase (Clontech) under the PCR conditions described in Example 22B. PCR product was isolated as described in Example 22B. The isolated, 440 bp DNA fragment was digested and ligated into pKFO51 previously digested with FseI and AscI, as described in Example 22B.

About one microliter of each ligation reaction was electroporated, plated, clones picked and screened for the human zalpha11 Ligand insert by restriction digestion as described in Example 22. A correct pKFO51-zalpha11 Ligand clone was verified by sequencing, and a maxiprep of this clone was performed. A NotI fragment, containing the lck proximal promoter, immunoglobulin µ enhancer, zalpha11 Ligand cDNA, and the mutated hGH gene was prepared to be used for microinjection into fertilized murine oocytes.

B. Construct for Expressing Mouse Zalpha11 Ligand from the Liver-specific MT-1 Promoter This same mouse zalpha11 Ligand insert from Example 26A, was subcloned into the pTG12-8 vector, as described in Example 22A. For this construct, about 10 mg of the pKFO51-zalpha11 Ligand maxiprep DNA was digested with FseI and AscI combined, ethanol precipitated, and the mouse zalpha11 Ligand fragment was purified as described in Example 22. This fragment was then ligated into pTG12-8 which had been previously digested with FseI and AscI, as described in Example 22A. Electroporation, screening of clones and a maxiprep was performed as described in Example 22. A SalI fragment containing 5' and 3' flanking sequences, the MT-1 promoter, the rat insulin II intron, mouse zalpha11 Ligand cDNA and the hGH poly A sequence was prepared to be used for microinjection into fertilized murine oocytes.

Example 27

Mouse Zalpha11-ligand Polyclonal Antibodies

Polyclonal antibodies were prepared by immunizing 2 female New Zealand white rabbits with the purified recombinant protein muzalpha11L/MBP-6H (Example 32). The rabbits were each given an initial intraperitoneal (ip) injection of 200 mg of purified protein in Complete Freund's Adjuvant followed by booster ip injections of 100 mg peptide in Incomplete Freund's Adjuvant every three weeks. Seven to ten days after the administration of the second booster injection (3 total injections), the animals were bled and the serum was collected. The animals were then boosted and bled every three weeks.

The muzalpha11L/MBP-6H specific rabbit serum was preadsorbed of anti-MBP antibodies using a CNBr-SEPHAROSE 4B protein column (Pharmacia LKB) that was prepared using 10 mg of purified recombinant maltose binding protein (MBP) per gram of CNBr-SEPHAROSE. Recombinant MBP was made and purified on an amylose column in house, using methods well known in the art. The muzalpha11-ligand-specific polyclonal antibodies were affinity purified from the rabbit serum using a CNBr-SEPHAROSE 4B protein column (Pharmacia LKB) that was prepared using 10 mg of the specific antigen purified recombinant protein muzalpha11L/MBP-6H (Example 32) followed by 20× dialysis in PBS overnight. Muzalpha11-ligand-specific antibodies were characterized by ELISA using 1 ug/ml of the purified recombinant proteins muzalpha11L/MBP-6H (Example 32) or huzalpha11L-MBP/6H (Example 32) as antibody targets. The lower limit of detection (LLD) of the rabbit anti-muzalpha11L/MBP-6H affinity purified antibody is 100 pg/ml on its specific purified recombinant antigen muzalpha11L/MBP-6H and 500 pg/ml on purified recombinant huzalpha11L-MBP/6H.

Example 28

Construction of Mammalian Expression Vector and Large-scale Human zalpha11 Ligand Expression in CHO DG44 Cells A mammalian expression vector for human zalpha11 Ligand (SEQ ID NO:1) designed to add a SalI site at the 5' end and a PmeI site to the 3' end of the cDNA, was constructed via amplification by PCR from a plasmid containing human zalpha11 Ligand (Example 7) with oligonucleotide primers, ZC22,054 (SEQ ID NO:70) and ZC22,055 (SEQ ID NO:71). The PCR reaction conditions were as follows: 94° C. for 4 min.; 25 cycles of 94° C. for 45 sec., 50° C. for 45 seconds, and 72° C. for 3 min.; and 72° C. for 10 minutes. The PCR product was isolated as described herein, and cut with SalI and PmeI then ligated to plasmid pDC312 previously cut at the appropriate restriction sites in the polylinker, using standard methods described herein. The plasmid pDC312 is described in Morris, A. et al., "Expression Augmenting Sequence Element (EASE) isolated from Chinese Hamster Ovary Cells," in *Animal Cell Technology*, Carrondo, M J T et al (eds.) (1997) Kluwer Academic Publishers, The Netherlands, p. 529-534.

The ligated vector was transfected into suspension-adapted CHO DG44 (in house Novo Nordisk, Denmark) cells by lipofection using LIPOFECTAMINEPLUS™ reagent (Gibco/BRL) according to manufacturer's instructions. Transfectants were selected on PFCHO medium (JRH, Lenexa, Kans.) free of thymidine, and hypoxanthine, followed by selection on 200 nM methotrexate (Sigma, St. Louis, Mo.). The methotrexate resistant cells were cloned by dilution and assayed for production of zalpha11 Ligand by a BaF3 activity assay (Example 5B).

A productive clone was scaled up and grown in a 7 to 20 liter bioreactor (Applikon Bioreactors, Schiedam, The Netherlands) in PFCHO medium to produce material for purification (Example 29).

Example 29

Large-scale Purification of Untagged Human and Murine Zalpha11 Ligand from BHK and CHO Mammalian Expression Cell Lines.

A. CHO Expressed Human Zalpha11 Ligand

Unless otherwise stated, all operations were carried out at 4° C. The following procedure was used for purifying human zalpha11 Ligand from at least 30 liters of CHO conditioned media (see, Example 28). Concentrated or non-concentrated conditioned media (CM) was sterile filtered through 0.45 and 0.22 micron filters. The conditioned media was then buffered with 0.01 M MES (Fluka BioChemika, Switzerland)) and the pH adjusted to 6.0, and then loaded onto a 50×100 mm (196 ml) Poros 50 HS column (strong cation exchanger from PerSeptive BioSystems, Framingham, Mass.) overnight at 4-10 ml/min. using a BioCAD SPRINT (Perceptive BioSystems). The column was washed for 10-20 column volumes (CV) with 0.01 M MES/0.130 M NaCl (Mallinckrodt, Paris, Ky.) pH 6.0. The bound proteins were then eluted with a 0.130 M to 1 M NaCl 10 CV gradient in 0.01 M MES pH 6.0 at 30 ml/min.; 25 ml fractions were collected over the entire chromatography and absorbence at 280 and 215 nM were monitored. Peak absorbence fractions were analyzed by SDS-PAGE Silver (Geno Technology, St. Louis, Mo.), Coomassie (Sigma, St. Louis, Mo.) staining and Western immunological blotting using antibodies against the human zalpha11 Ligand (Example 33 and Example 34).

Peak fractions were pooled then concentrated in a stirred cell concentrator on a YM10 membrane (Millipore/Amicon, Bedford, Mass.) to a nominal volume (1-10 ml). The sample was then loaded on an appropriate Sephacryl S-200 (Pharmacia, Uppsala, Sweden) high resolution size exclusion column (52-600 ml) equilibrated in PBS (Gibco BRL) at flow rates 1-2 ml/ml; 1-2 ml fractions were collected over the entire chromatography and absorbence at 280 and 215 nM were monitored. Peak fractions were analyzed by SDS-PAGE Silver (Geno Technology, St. Louis, Mo.), and Coomassie (Sigma, St. Louis, Mo.) staining.

The fractions of interest were pooled and concentrated with Millipore 5 kD MWKO centrifugal spin concentrators to a minimal volume. The final product was then analyzed by SDS PAGE Coomassie staining (Sigma, St. Louis, Mo.), Western Immunological blotting, N-terminal sequencing, Amino Acid Analysis, and BCA (Pierce, Rockford, Ill.) for protein purity and concentration.

B. BHK 570 Expressed Murine Zalpha11 Ligand

Unless otherwise stated, all operations were carried out at 4° C. The following procedure was used for purifying murine zalpha11 Ligand from BHK conditioned media (Example 18). Concentrated or non-concentrated conditioned media (CM) was sterile filtered through 0.45 and 0.22 micron filters. The media was then buffered with 0.01 M MES (Fluka BioChemika, Switzerland)) and the pH adjusted to 6.0. The CM was analyzed, loaded and eluted on an AS column as described in Example 29A.

Fractions of interest were pooled then concentrated in a stirred cell concentrator as in Example 29A, to a volume of 20-30 ml. The pH was adjusted to 7.0 then the sample was loaded onto either a 0.8 ml Poros AL column that had about 3 mg of zalpha11CFLAG tagged soluble receptor (Example 10B) or one with about 10 mg of zalpha11-Fc4 fusion receptor (Example 10C) immobilized on the resin (see method below) at 1 ml/min on a BioCAD SPRINT. The column was then washed with at least 20 CV of 0.3 M NaCl/PBS (Gibco BRL)/0.01 M MES at 10 ml/min. The column was then rapid eluted with a 600 μl injection of 0.1 M glycine (Aminoacetic Acid; Glycocol, Spectrum, Gardena, Calif.) pH 2.5 at a flow rate of 10 ml/min with PBS on a BioCAD SPRINT. The 1 ml fractions were collected for 6 seconds each and immediately pH neutralized with 55 μl of 2 M TRIS pH 8.8 (Tris(Hydroxymethyl)Aminomethane, EM Science, Gibbstown, N.J.). The absorbence at 280 and 215 nM were monitored over the entire chromatography. The peak fractions were analyzed SDS-PAGE Silver (Geno Technology, St. Louis, Mo.), Coomasise (Sigma, St. Louis, Mo.) staining and Western Immunological blotting as above.

Peak fractions were pooled then concentrated in a stirred cell concentrator as in Example 29A to a minimal volume (1-10 ml). The sample was then loaded, equilibrated and analyzed as in Example 29A, on an appropriate Sephacryl S-200 (Pharmacia) high resolution size exclusion column. Peak fractions were analyzed by SDS-PAGE Silver (Geno Technology, St. Louis, Mo.), and Coomasise (Sigma, St. Louis, Mo.) staining. The fractions of interest were pooled and concentrated and analyzed as in Example 29A.

C. Protein Immobilization on POROS AL Media

All operations were carried out at room temperature on a BioCAD 700E. Flow packed a 4.5×50 mm column with the POROS AL media in 2 M NaCl according to manufactures specifications. The column was then equilibrated in 1.1 M $Na_2SO_4$ and 50 mM NaPhosphate pH 7.2. The receptor was concentrated to 4 mg/ml using a Millipore 30 kD MWKO centrifugal spin concentrator then diluted 1:1 in 1.1 M $Na_2SO_4$ and 50 mM NaPhosphate pH 7.2. The column was flowed at 2 ml/min in 1.1 M $Na_2SO_4$ and 50 mM NaPhosphate pH 7.2 and 100 μl injections of the diluted ligand were made ever 9 CVs until a steady state of saturation or break through was reached. A 62 CV gradient was then ran from 1.1 M $Na_2SO_4$ and 50 mM NaPhosphate pH 7.2 to 550 mM $Na_2SO_4$ and 50 mM NaPhosphate pH 7.2 with 5 mg/ml Sodium Cyanoborohydride. Column was held for 2 hr. to complete the immobilization chemistry. The column was then equilibrated in 0.2 M TRIS pH 7.2 with 5 mg/ml Sodium Cyanoborohydride and allowed to rest for 1 hr. Finally the column was equilibrated in PBS with 0.02% Sodium Azide, then stored at 4° C. until needed. Prior to use, the column was pre-eluted with 0.1 M glycine to ensure that non-specific proteins were removed and the column is not leaching the immobilized receptor.

Example 30

Expression Vector Construction Expression and Purification of Untagged Human and Murine Zalpha11 Ligand from Baculovirus.

A. Construct for Expressing Human Zalpha11 Ligand in Baculovirus

An expression vector, pzalpha11L, was prepared to express Human zalpha11 Ligand polypeptides in insect cells. A 517 bp fragment containing sequence for Human zalpha11 Ligand and encoded BamH1 and XhoI restriction sites on the 5' and 3' ends respectively, was generated by PCR amplification from a plasmid containing human zalpha11 Ligand cDNA (Example 7) using primers ZC23,444 (SEQ ID NO:74) and ZC23,445 (SEQ ID NO:75). The PCR reaction conditions were as follows: 1 cycle of 94° C. for 4 minutes, followed by 25 cycles of 94° C. for 45 seconds, 50° C. for 45 seconds, and 72° C. for 2 minutes; 1 cycle at 72° C. for 10 min; followed by a 4° C. soak. The fragment was visualized by gel electrophoresis (1% SeaPlaque/1% NuSieve). The band was excised, diluted to 0.5% agarose with 2 mM $MgCl_2$, melted at 65° C., digested with BamH1 and XhoI (Boerhinger Mannheim), and ligated into an BamH1/XhoI digested baculovirus expression vector, pZBV3L. The pZBV3L vector is a modification of the pFastBac1™ (Life Technologies) expression vector, where the polyhedron promoter has been removed and replaced with the late activating Basic Protein Promoter. About 14 nanograms of the restriction digested zalpha11 Ligand insert and about 40 ng of the corresponding vector were ligated overnight at 16° C.

The ligation mix was diluted 3 fold in TE (10 mM Tris-HCl, pH 7.5 and 1 mM EDTA) and about 4 fmol of the diluted ligation mix was transformed into DH5α LIBRARY EFFICIENCY® competent cells (Life Technologies) according to manufacturer's direction by heat shock for 45 seconds in a 42° C. waterbath. The transformed DNA and cells were diluted in 450 µl of SOC media (2% Bacto™ Tryptone, 0.5% Bacto Yeast Extract, 10 ml 1M NaCl, 1.5 mM KCl, 10 mM $MgCl_2$, 10 mM $MgSO_4$ and 20 mM glucose) and plated onto LB plates containing 100 µg/ml ampicillin. Clones were analyzed by restriction digests and 1 µl of the positive clone was transformed into 20 µl MAX EFFICIENCY® DH5B™ competent cells (GIBCO-BRL, Gaithersburg, Md.) according to manufacturer's instruction, by heat shock as described above. The transformed cells were then diluted in 980 µl SOC media (2% Bacto™ Tryptone, 0.5% Bacto™ Yeast Extract, 10 ml 1M NaCl, 1.5 mM KCl, 10 mM $MgCl_2$, 10 mM $MgSO_4$ and 20 mM glucose) out grown in shaking incubator at 37° C. for four hours and plated onto Luria Agar plates containing 50 µg/ml kanamycin, 7 µg/ml gentamicin (Life Technologies), 10 µg/ml tetracycline, IPTG (Pharmacia Biotech) and Bluo-Gal (Life Technologies). The plated cells were incubated for 48 hours at 37° C. A color selection was used to identify those cells having Human zalpha11 Ligand encoding donor insert that had incorporated into the plasmid (referred to as a "bacmid"). Those colonies, which were white in color, were picked for analysis. Human zalpha11 Ligand Bacmid DNA was isolated from positive colonies using the QiaVac Miniprep8 system (Qiagen) according the manufacturer's directions. Clones were screened for the correct insert by amplifying DNA using primers to the transposable element in the bacmid via PCR using primers ZC447 (SEQ ID NO:76) and ZC976 (SEQ ID NO:77). The PCR reaction conditions were as follows: 35 cycles of 94° C. for 45 seconds, 50° C. for 45 seconds, and 72° C. for 5 minutes; 1 cycle at 72° C. for 10 min.; followed by 4° C. soak. The PCR product was run on a 1% agarose gel to check the insert size. Those clones having the correct insert were used to transfect *Spodoptera frugiperda* (Sf9) cells.

B. Expression and Generation of Material for Purification of Human Zalpha11 Ligand from Baculovirus Sf9 cells were seeded at $5 \times 10^6$ cells per 35 mm plate and allowed to attach for 1 hour at 27° C. Five microliters of human zalpha11 Ligand bacmid DNA (above) was diluted with 100 µl Sf-900 II SFM (Life Technologies). Six µl of CellFECTIN Reagent (Life Technologies) was diluted with 100 µl Sf-900 II SFM. The bacmid DNA and lipid solutions were gently mixed and incubated 30-45 minutes at room temperature. The media from one plate of cells were aspirated, the cells were washed 1× with 2 ml fresh Sf-900 II SFM media. Eight hundred microliters of Sf-900 II SFM was added to the lipid-DNA mixture. The wash media was aspirated and the DNA-lipid mix added to the cells. The cells were incubated at 27° C. for 4-5 hours. The DNA-lipid mix was aspirated and 2 ml of Sf-900 II media was added to each plate. The plates were incubated at 27° C., 90% humidity, for 96 hours after which the virus was harvested.

For Primary Amplification Sf9 cells were grown in 50 ml Sf-900 II SFM in a 125 ml shake flask to an approximate density of $0.41-0.52 \times 10^5$ cells/ml. They were then infected with 150 µl of the virus stock from above and incubated at 27° C. for 3 days after which time the virus was harvested according to standard methods known in the art. A 500 µl sample submitted for activity in a BaF3 assay (Example 5) to show that it was biologically active.

For Secondary Amplification Sf9 cells were grown in 1 L of Sf-900 II SFM in a 2800 ml shake flask to an approximate density of $0.5 \times 10^5$ cells/ml. It was infected with 500 µl of the Primary viral stock from above and incubated at 27° C. for 4 days after which time the virus was harvested according to standard methods known in the art. Virus was titered and grown up large scale for purification of the baculovirus-produced human zalpha11 Ligand (huzalpha11L-Bv), as described in Example 30C and Example 30D, below.

C. Large-scaled Purification of Baculovirus Expressed Human/murine Zalpha11 Ligand Unless otherwise stated, all operations were carried out at 4° C. The following procedure was used for purifying human zalpha11 Ligand (huzalpha11 L-Bv) from BV conditioned media (Example 30B). Conditioned media (CM) was sterile filtered through 0.45 and 0.22 micron filters, then buffered with 0.01 M MES (Fluka BioChemika, Switzerland)) and the pH adjusted to 6.0 The CM was then loaded onto a POROS 50 HS column and run, fractions collected, analyzed, as described in Example 29A.

The above peak fractions were pooled, concentrated run on a high resolution size exclusion column, and analyzed as described in Example 29A.

The fractions of interest from the size exclusion column were pooled and concentrated with 5 kD MWCO Millipore centrifugal spin concentrators to a minimal volume. The final product was then analyzed by SDS-PAGE Coomassie (Sigma, St. Louis, Mo.), Western immunological blotting, N-terminal sequencing, Amino Acid Analysis, and CB (Pierce, Rockford, Ill.) for protein purity and concentration as described in Example 29A. Bulk protein was stored at −80° C.

D. Small Scale (<2 mg) Purification of Baculovirus-expressed Human/murine Zalpha11 Ligand Unless other wise stated, all operations were carried out at 4° C. The following procedure was used for purifying <2 mg of human or murine zalpha11 Ligand from BV conditioned media. The CM was filtered, buffered and pH adjusted as in Example 30C. The CM was then loaded, eluted and the POROS 50 HS chromatography was analyzed as in Example 30C.

Fractions were pooled then concentrated via diafiltration in a stirred cell concentrator on a YM10 membrane (10 kD MWCO) (Millipore/Amicon, Bedford, Mass.) to a nominal volume (20-30 ml). The pH was adjusted to 7.0 then the sample was loaded onto either a 0.8 ml Poros AL column that had about 3 mg of zalpha11CFLAG soluble receptor (Example 10B) or one with about 10 mg of zalpha11-Fc4 fusion soluble receptor (Example 10C) immobilized on the resin (see method in example 29C) at 1 ml/min on a BioCad SPRINT. The column was then washed with at least 20 CV of 0.3 M NaCl/PBS (Gibco BRL)/0.01 M MES at 10 ml/min. The column was then rapid eluted with a 600 µl injection of 0.1 M glycine (Aminoacetic Acid; Glycocol, Spectrum, Gardena, Calif.) pH 2.5 at a flow rate of 10 ml/min with PBS on a BioCAD SPRINT. The 1 ml fractions were collected for 6 seconds each and immediately pH neutralized with 55 µl of 2 M TRIS (Tris(Hydroxymethyl)Aminomethane, EM Science, Gibbstown, N.J.) pH 8.8. The absorbence at 280 and 215 nM were monitored over the entire chromatography. Fractions were analyzed as above.

Peak fractions were pooled then concentrated via diafiltration in a stirred cell concentrator on a YM10 membrane (10 kD MWCO) (Millipore/Amicon, Bedford, Mass.) to 1-2 ml. The sample was then loaded on an appropriate Sephacryl S-200 (Pharmacia, Uppsala, Sweden) high resolution size exclusion column equilibrated in PBS (Gibco BRL) at an optimal flow rate; fractions were collected over the entire chromatography and absorbence at 280 and 215 nM were monitored. Fractions were analyzed as above.

The fractions of interest were pooled and concentrated with 5 Kd MWCO Millipore centrifugal spin concentrators to a nominal volume. The final product was then analyzed by SDS-PAGE Coomassie (Sigma, St. Louis, Mo.), Western immunological blotting, N-terminal sequencing, Amino Acid Analysis, and BCA (Pierce, Rockford, Ill.) for protein purity and concentration. Bulk protein stored as described above.

E. Construct for Expressing Mouse Zalpha11 Ligand in Baculovirus: Pzalpha11lig.M An expression vector, pzalpha11LM, was prepared to express Murine zalpha11 Ligand polypeptides in insect cells. A 413 bp fragment containing sequence for Murine zalpha11 Ligand and encoded BspE1 and Xba1 restriction sites on the 5' and 3' ends, respectively, was generated by PCR amplification from a plasmid containing murine zalpha11 Ligand cDNA (Example 16) using primers ZC25,970 (SEQ ID NO:109) and ZC25,969 (SEQ ID NO:110) utilizing the Expand High Fidelity PCR System (Boerhinger Mannheim) as per manufacturer's instructions. The PCR conditions were as follows: 1 cycle of 94° C. for 2 minutes, followed by 35 cycles of 94° C. for 15 seconds, 50° C. for 30 seconds, and 72° C. for 2 minutes; 1 cycle at 72° C. for 10 min; followed by a 4° C. soak. A small portion of the PCR product was visualized by gel electrophoresis (1% NuSieve agarose). The remainder of the fragment was purified using the QIAGEN® PCR purification kit as per manufacturer's instructions and eluted into 30 µl of $H_2O$. The fragment was then digested with Bspe1 and Xba1 (Boerhinger Mannheim) restriction enzymes at 37 C for about 2 h, then run on an agarose gel as described above. The band was excised, purified and eluted using the QIAGEN® gel extraction kit as per manufacturers instructions. The purified fragment was ligated into an Bspe1/Xba1 digested baculovirus expression vector, pZBV37L. The pZBV37L vector is a modification of the pFastBac1* (Life Technologies) expression vector, where the polyhedron promoter has been removed and replaced with the late activating Basic Protein Promoter followed by the secretory signal sequence from Ecdysteroid UDP-Glucosyltransferase (EGT). About 5 µl of the restriction digested Murine zalpha11 Ligand insert and about 100 ng of the corresponding cut vector were ligated overnight at 16° C. in about 20 µl. Five µl of the ligation mix was electroporated into 50 µl Life Technologies DH12S electrocompetent bacterial cells utilizing a 2 mm cuvette with 2 kV, 25 µF and 400 ohms settings. The electroporated cells were rescued in 1 ml of SOC media (2% Bacto™ Tryptone, 0.5% Bacto Yeast Extract, 10 ml 1M NaCl, 1.5 mM KCl, 10 mM $MgCl_2$, 10 mM $MgSO_4$ and 20 mM glucose (Gibco BRL)) outgrown at 37° C. for about 1 hr and plated onto LB plates containing 100 µg/ml ampicillin. DNA from clones was isolated and analyzed by restriction digests to identify positive clones. About 5 ng DNA from a positive clone was transformed into 20 µl MAX EFFICIENCY® DH5B™ competent cells (GIBCO-BRL, Gaithersburg, Md.) according to manufacturer's instruction, by heat shock for 45 seconds in a 42° C. water bath. The transformed cells were then diluted and grown as described in example 30A. Bacmids containing the murine zalpha11 Ligand insert were identified and isolated as described in Example 30A. Clones were screened for the correct insert by amplifying DNA using primers to the transposable element in the bacmid via PCR using primers ZC447 (SEQ ID NO:76) and ZC976 (SEQ ID NO:77). The PCR reaction conditions were as follows: 35 cycles of 94° C. for 45 seconds, 50° C. for 45 seconds, and 72° C. for 5 minutes; 1 cycle at 72° C. for 10 min.; followed by 4° C. soak. The PCR product was run on a 1% agarose gel to check the insert size. Those having the correct insert were used to transfect *Spodoptera frugiperda* (Sf9) cells.

F. Expression and Generation of Material for Purification of Mouse Zalpha11 from Baculovirus Sf9 cells were seeded at 1 million cells per 35 mm plate and allowed to attach for 1 hour at 27° C. The murine zalpha11 Ligand bacmid DNA was transfected as described in Example 30B and the virus was harvested.

For primary amplification, Sf9 cells were seeded as above and 500 µl of 72 hr post transfection supernatant was added and cultures were allowed to proceed for 96 hr. after which time the virus was harvested according to standard methods.

For Secondary amplification, Sf9 cells were seeded as above and 200 µl of the Primary viral stock was added. Cultures were incubated at 27° C. for 72 hr., after which time the virus was harvested according to standard methods.

For Tertiary amplification, 10 µl of Secondary Amplified virus stock was placed on SF9s at 500,000 cells per well in 50 ml of SF900II media in a 250 ml vol. shake flask for 6 days and virus was harvested as above. Virus was titered and grown up large scale for purification of the baculovirus-produced murine zalpha11 Ligand (muzalpha11L-Bv), as described in Example 30C and Example 30D.

Presence of predicted molecular weight protein in the supernatant was determined by western analysis using an anti-muzalpha11L/MBP-6H polyclonal antibody (Example 27). BaF3 based proliferation assay analysis (Example 5) also showed that the secreted ligand was active.

Example 31

Expression of Human and Mouse Zalpha11 Ligand in *E. coli*

A. Construction of Human Zalpha11 Ligand-MBP Fusion Expression Vector PTAP98/Zalpha11 Ligand An expression plasmid containing a polynucleotide encoding part of the human zalpha11 Ligand fused N-terminally to maltose binding protein (MBP) was constructed via homologous recombination. A fragment of human zalpha11 Ligand cDNA (SEQ ID NO:1) was isolated using PCR. Two primers were used in the production of the human zalpha11 Ligand fragment in a PCR reaction: (1) Primer ZC22,128 (SEQ ID NO:78), containing 40 bp of the vector flanking sequence and 26 bp corresponding to the amino terminus of the human zalpha11 Ligand, and (2) primer ZC22,127 (SEQ ID NO:79), containing 40 bp of the 3' end corresponding to the flanking vector sequence and 28 bp corresponding to the carboxyl terminus of the human zalpha11 Ligand. The PCR reaction conditions were as follows: 25 cycles of 94° C. for 30 seconds, 50° C. for 30 seconds, and 72° C. for 1 minute; followed by 4° C. soak, run in duplicate. Two μl of the 100 μl PCR reaction were run on a 1.0% agarose gel with 1×TBE buffer for analysis, showing the expected band of approximately 472 bp. The remaining 90 μl of PCR reaction was combined with the second PCR tube precipitated with 400 μl of absolute ethanol to be used for recombining into the SmaI cut recipient vector pTAP98 to produce the construct encoding the MBP-zalpha11 Ligand fusion, as described below.

Plasmid pTAP98 was derived from the plasmids pRS316 and pMAL-c2. The plasmid pRS316 is a *Saccharomyces cerevisiae* shuttle vector (Hieter P. and Sikorski, R., *Genetics* 122:19-27, 1989). pMAL-C2 (NEB) is an *E. coli* expression plasmid. It carries the tac promoter driving MalE (gene encoding MBP) followed by a His tag, a thrombin cleavage site, a cloning site, and the rrnB terminator. The vector pTAP98 was constructed using yeast homologous recombination. 100 ng of EcoR1 cut pMAL-c2 was recombined with 1 μg Pvu1 cut pRS316, 1 μg linker, and 1 μg ScaI/EcoR1 cut pRS316. The linker consisted of oligos ZC19,372 (SEQ ID NO:80) (100 pmol): ZC19,351 (SEQ ID NO:81) (1 pmol): ZC19,352 (SEQ ID NO:82) (1 pmol), and ZC19,371 (SEQ ID NO:83) (100 pmol) combined in a PCR reaction. Conditions were as follows: 10 cycles of 94° C. for 30 seconds, 50° C. for 30 seconds, and 72° C. for 30 seconds; followed by 4° C. soak. PCR products were concentrated via 100% ethanol precipitation.

One hundred microliters of competent yeast cells (*S. cerevisiae*) were combined with 10 μl of a mixture containing approximately 1 μg of the human zalpha11 Ligand PCR product, and 100 ng of SmaI digested pTAP98 vector, and transferred to a 0.2 cm electroporation cuvette. The yeast/DNA mixture was electropulsed at 0.75 kV (5 kV/cm), infinite ohms, 25 μF. To each cuvette was added 600 μl of 1.2 M sorbitol. The yeast was then plated in two 300 μl aliquots onto two -URA D plates and incubated at 30° C.

After about 48 hours, the Ura+ yeast transformants from a single plate were resuspended in 1 ml H₂O and spun briefly to pellet the yeast cells. The cell pellet was resuspended in 1 ml of lysis buffer (2% Triton X-100, 1% SDS, 100 mM NaCl, 10 mM Tris, pH 8.0, 1 mM EDTA). Five hundred microliters of the lysis mixture was added to an Eppendorf tube containing 300 μl acid washed glass beads and 200 μl phenol-chloroform, vortexed for 1 minute intervals two or three times, followed by a 5 minute spin in a Eppendorf centrifuge at maximum speed. Three hundred microliters of the aqueous phase was transferred to a fresh tube, and the DNA precipitated with 600 μl ethanol (EtOH), followed by centrifugation for 10 minutes at 4° C. The DNA pellet was resuspended in 100 μl H₂O.

Transformation of electrocompetent *E. coli* cells (MC1061, Casadaban et. al. *J. Mol. Biol.* 138, 179-207) was done with 1 μl yeast DNA prep and 40 μl of MC1061 cells. The cells were electropulsed at 2.0 kV, 25 μF and 400 ohms. Following electroporation, 0.6 ml SOC (2% Bacto™ Tryptone (Difco, Detroit, Mich.), 0.5% yeast extract (Difco), 10 mM NaCl, 2.5 mM KCl, 10 mM MgCl₂, 10 mM MgSO₄, 20 mM glucose) was plated in one aliquot on LB AMP plates (LB broth (Lennox), 1.8% Bacto™ Agar (Difco), 100 mg/L Ampicillin).

Individual clones harboring the correct expression construct for human zalpha11 Ligand were identified by expression. Cells were grown in Superbroth II (Becton Dickinson) with 100 μg/ml of ampicillin overnight. 50 μl of the overnight culture was used to inoculate 2 ml of fresh Superbroth II+100 μg/ml ampicillin. Cultures were grown at 37° C., shaking for 2 hours. 1 ml of the culture was induced with 1 mM IPTG. 2-4 hours later the 250 μl of each culture was mixed with 250 μl acid washed glass beads and 250 μl Thorner buffer with 5% βME and dye (8M urea, 100 mM Tris pH7.0, 10% glycerol, 2 mM EDTA, 5% SDS). Samples were vortexed for one minute and heated to 65° C. for 5-10 minutes. 20 μl were loaded per lane on a 4%-12% PAGE gel (NOVEX). Gels were run in 1×MES buffer. The positive clones were designated pTAP126 and subjected to sequence analysis. The polynucleotide sequence of MBP-human zalpha11 Ligand fusion within pTAP126 is shown in SEQ ID NO:84, and the corresponding polypeptide in SEQ ID NO:85.

B. Bacterial Expression of Human Zalpha11 Ligand.

One microliter of sequencing DNA was used to transform strain W3110 (ATCC). The cells were electropulsed at 2.0 kV, 25 μF and 400 ohms. Following electroporation, 0.6 ml SOC (2% Bacto™ Tryptone (Difco, Detroit, Mich.), 0.5% yeast extract (Difco), 10 mM NaCl, 2.5 mM KCl, 10 mM MgCl₂, 10 mM MgSO₄, 20 mM glucose) was plated in one aliquot on LB AMP plates (LB broth (Lennox), 1.8% Bacto™ Agar (Difco), 100 mg/L Ampicillin).

Individual were expressed. Cells were grown in Superbroth II (Becton Dickinson) with 100 μg/ml of ampicillin overnight. 50 μl of the overnight culture was used to inoculate 2 ml of fresh Superbroth II+100 μg/ml ampicillin. Cultures were grown at 37° C., shaking for 2 hours. 1 ml of the culture was induced with 1 mM IPTG. 2-4 hours later the 250 μl of each culture was mixed with 250 μl acid washed glass beads and 250 μl Thorner buffer with 5% βME and dye (8M urea, 100 mM Tris pH7.0, 10% glycerol, 2 mM EDTA, 5% SDS). Samples were vortexed for one minute and heated to 65° C. for 10 minutes. 20 μl were loaded per lane on a 4%-12% PAGE gel (NOVEX). Gels were run in 1×MES buffer. The positive clones were used to grow up for protein purification of the huzalpha11L/MBP-6H fusion protein (Example 32, below).

C. Construction of Mouse Zalpha11 Ligand-MBP Fusion Expression Vector pTAP98/Mouse Zalpha11 Ligand An expression plasmid containing a polynucleotide encoding part of the mouse zalpha11 Ligand fused N-terminally to maltose binding protein (MBP) was constructed via homologous recombination, as described in Example 31A. A fragment of mouse zalpha11 Ligand cDNA (SEQ ID NO:55) was isolated using PCR. Two primers were used in the production of mouse zalpha11 Ligand fragment in a PCR reaction: (1) Primer ZC22,849 (SEQ ID NO:86), containing 40 bp of the vector flanking sequence and 24 bp corresponding to the amino terminus of the mouse zalpha11 Ligand, and (2) primer ZC22,850 (SEQ ID NO:87), containing 40 bp of the 3' end corresponding to the flanking vector sequence and 21 bp corresponding to the carboxyl terminus of the mouse zalpha11 Ligand. The PCR reaction conditions were as per above. The approximately 450 bp fragment was cloned into pTAP98 as described above. Clones were transformed, identified and grown up as described above. The positive clones were designated pTAP134 and subjected to sequence analysis. The polynucleotide sequence of MBP-mouse zalpha11 Ligand fusion within pTAP134 is shown in SEQ ID NO:88, and the corresponding polypeptide sequence shown in SEQ ID NO:89. The positive clones were used to grow up in *E. coli* as described above for protein purification of the muzalpha11L/MBP-6H fusion protein (Example 32).

Example 32

Purification of Zalpha11-MBP Ligand or Zalpha11-MBP Receptor

Unless otherwise stated, all operations were carried out at 4° C. The following procedure was used for purifying zalpha11-MBP Ligand fusions for human zalpha11-MBP Ligand (huzalpha11L/MBP-6H) or murine zalpha11-MBP Ligand (muzalpha11L/MBP-6H) from E. coli. Human or mouse zalpha11-MBP receptor fusions were carried out using the same method. Pre-spun frozen E. coli paste was thawed and diluted into 2 liters of Buffer B (0.02 M TRIS (EM Science); 0.2 M NaCl (Mallincrodt); 0.01 M 2-mercaptoethanol (EM Science); pH 8.0; with 5 mg/l Pepstatin A (Boerhinger Mannheim); 5 mg/l Aprotinin (Boerhinger Mannheim); and 1 mg/l PMSF (Fluka)) plus 1-2 ml of an antifoaming reagent AF289 antifoam (Sigma). The mixture was processed in a pre-chilled French Press cell disrupter (Constant Systems LTD) with 20-30 kPSI.

The lysate was then centrifuged at 18,000×g for 45 minutes at 4° C.; retained the supernatant. A 200 ml slurry of Amylose resin (New England BioLabs), pre-equilibrated in Buffer A (0.02 M TRIS (EM Science); 0.2 M NaCl (Mallincrodt); 0.01 M 2-mercapto-ethanol (EM Science); pH 8.0), was added to the lysate supernatant and incubated overnight in 21 roller bottles to allow for maximum batch absorption of the MBP fusion protein. The resin was washed in batch column format for >5 column volumes with Buffer A, then batch eluted with Buffer C (Buffer A with 0.02 M Maltose (Sigma)). Crude fractions were collected and monitored by absorbence 280 nm.

The eluted protein was analyzed by SDS NuPAGE (NOVEX) Coomassie (Sigma) staining. Sample and bulk protein were stored at −80° C.

Example 33

Human Zalpha11 Ligand Polyclonal Antibodies

Polyclonal antibodies to Human zalpha11 Ligand were prepared by immunizing 2 female New Zealand white rabbits with the purified recombinant protein huzalpha11L/MBP-6H (Example 32) or the purified CHO recombinant protein huzalpha11L-CHO (Example 29). The rabbits were each given an initial intraperitoneal (ip) injection of 200 mg of purified protein in Complete Freund's Adjuvant followed by booster ip injections of 100 mg purified protein in Incomplete Freund's Adjuvant every three weeks. Seven to ten days after the administration of the second booster injection (3 total injections), the animals were bled and the serum was collected. The animals were then boosted and bled every three weeks.

The rabbit serum raised to huzalpha11L/MBP-6H was pre-adsorbed of anti-MBP antibodies using a CNBr-SEPHAROSE 4B protein column (Pharmacia LKB) that was prepared using 10 mg of purified recombinant MBP per gram of CNBr-SEPHAROSE (Pharmacia). Recombinant MBP was made and purified on an amylose column in house, using methods well known in the art. The huzalpha11-ligand-specific polyclonal antibodies were affinity purified from the rabbit serum using a CNBr-SEPHAROSE 4B protein column (Pharmacia LKB) that was prepared using 10 mg of the specific antigen purified recombinant protein huzalpha11L/MBP-6H or 10 mg of the purified CHO recombinant protein huzalpha11L-CHO per gram of CNBr-SEPHAROSE, followed by 20× dialysis in PBS overnight. Huzalpha11-ligand-specific antibodies were characterized by ELISA using 1 μg/ml of the purified recombinant proteins huzalpha11L/MBP-6H (Example 32), human zalpha11 Ligand (huzalpha11L-CHO) (Example 29), or muzalpha11L-MBP/6H (Example 32) as antibody targets.

The lower limit of detection (LLD) of the rabbit anti-huzalpha11L/MBP-6H affinity purified antibody was 10 ng/ml on its specific purified recombinant antigen huzalpha11L/MBP-6H, 500 pg/ml on purified recombinant huzalpha11L-CHO, and 100 pg/ml on purified recombinant muzalpha11L/MBP-6H (Example 32). The LLD of the rabbit anti-huzalpha11L-CHO affinity purified antibody was 20 pg/ml on its specific purified recombinant antigen huzalpha11L-CHO, 500 pg/ml on purified recombinant huzalpha11L/MBP-6H, and 50 ng/ml on purified recombinant muzalpha11L/MBP-6H.

Example 34

Human Zalpha11 Ligand Anti-Peptide Antibodies

Polyclonal human zalpha11 Ligand anti-peptide antibodies were prepared by immunizing 2 female New Zealand white rabbits with the human zalpha11 Ligand peptide, huzalpha11L-1 (SEQ ID NO:72) or huzalpha11L-3 (SEQ ID NO:73). The peptides were synthesized using an Applied Biosystems Model 431A peptide synthesizer (Applied Biosystems, Inc., Foster City, Calif.) according to manufacturer's instructions. The peptides were then conjugated to the carrier protein keyhole limpet hemocyanin (KLH) with maleimide-activation. The rabbits were each given an initial intraperitoneal (ip) injection of 200 mg of peptide in Complete Freund's Adjuvant followed by booster ip injections of 100 mg peptide in Incomplete Freund's Adjuvant every three weeks. Seven to ten days after the administration of the second booster injection (3 total injections), the animals were bled and the serum was collected. The animals were then boosted and bled every three weeks.

The rabbit sera raised to the human zalpha11 Ligand peptides were characterized by an ELISA titer check using 1 μg/ml of the respective peptide used to make the antibody (SEQ ID NO:72 or SEQ ID NO:73) as an antibody target. The 2 rabbit seras to the huzalpha11L-1 peptide had titer to their specific peptide at a dilution of 1:5,000,000 (1:5E6). The 2 rabbit seras to the huzalpha11L-3 peptide had titer to their specific peptide at a dilution of 1:5E6.

Human zalpha11 Ligand peptide-specific polyclonal antibodies were affinity purified from the rabbit serum using CNBR-SEPHAROSE 4B protein columns (Pharmacia LKB) that were prepared using 10 mg of the respective specific peptide (SEQ. ID. NO:72 or SEQ. ID. NO:73) per gram CNBr-SEPHAROSE, followed by 20× dialysis in PBS overnight. Huzalpha11-ligand-specific antibodies were characterized by an ELISA titer check using 1 μg/ml of the appropriate purified peptide antigen or purified recombinant full-length proteins as antibody targets.

The lower limit of detection (LLD) of the rabbit anti-huzalpha11L-1 affinity purified antibody is 500 pg/ml on its specific peptide antigen (huzalpha11L-1; SEQ ID NO:72), 500 pg/ml on purified recombinant huzalpha11L/MBP-6H (Example 32), and 500 pg/ml on purified CHO recombinant huzalpha11L-CHO (Example 29). No cross-reactivity was seen to the purified recombinant muzalpha11L/MBP-6H (Example 32). The LLD of the rabbit anti-huzalpha11L-3 affinity purified antibody is 50 pg/ml on its specific peptide antigen (huzalpha11L-1; SEQ ID NO:73), 50 pg/ml on purified recombinant huzalpha11L/MBP-6H, 500 pg/ml on purified CHO recombinant huzalpha11L-CHO (Example 29), and 100 pg/ml on purified Baculovirus recombinant huzalpha11L-Bv (Example 30). Cross-reactivity was seen to the purified recombinant muzalpha11L/MBP-6H (Example 32) with an LLD of 5 ng/ml.

Example 35

Human Zalpha11 Receptor Monoclonal Antibodies

Zalpha11 receptor Monoclonal antibodies were prepared by immunizing 5 male BalbC mice (Harlan Sprague Dawley, Indianapolis, Ind.) with the purified recombinant soluble receptor protein, zalpha11CEE (huzalpha11-CEE-BHK) (Example 10A). The mice were each given an initial intraperitoneal (IP) injection of 20 mg of purified protein in Complete Freund's Adjuvant (Pierce, Rockford, Ill.) followed by booster IP injections of 10 mg purified protein in Incomplete Freund's Adjuvant every two weeks. Seven to ten days after the administration of the third booster injection, the animals were bled and the serum was collected.

The mouse sera samples raised to the huzalpha11-CEE-BHK were characterized by an ELISA titer check using purified recombinant CHO huzalpha11-Fc protein (Example 10C) as an antibody target. One mouse serum sample had titer to the specific antibody target at a dilution of 1:1,000,000 (1:1E6). Four mouse serum samples had titer to the specific antibody target at a dilution of 1:100,000 (1:1E5).

Splenocytes were harvested from the 4 high-titer mice and fused to murine SP2/0 myeloma cells using PEG 1500 (Boerhinger Mannheim, UK) in two separate fusion procedures using a 4:1 fusion ratio of splenocytes to myeloma cells (Antibodies: A Laboratory Manual, E. Harlow and D. Lane, Cold Spring Harbor Press). Following 10 days growth post-fusion, specific antibody-producing hybridomas were identified by ELISA using purified recombinant BHK human zalpha11-Fc4 protein (Example 10C) as an antibody target and by FACS using Baf3 cells expressing the huzalpha11 sequence (Example 4, and Example 2) as an antibody target. The resulting 4 hybridomas positive by both methods were cloned three times by limiting dilution. The antibodies were designated: 249.28.2.1.2.2; 247.10.2.15.4.6; 249.19.2.2.3.5; and 249.15.2.4.2.7.

Example 36

Zalpha11 Ligand Transgenic Mice

A. Generation of Transgenic Mice Expressing Human and Mouse Zalpha11 Ligand

DNA fragments from transgenic vectors (Example 22 and Example 26) containing 5' and 3' flanking sequences of the respective promoter (MT-1 liver-specific promoter (mouse zalpha11 Ligand (Example 26B) or lymphoid specific LCK promoter (mouse and human zalpha11 Ligand (Examples 26A and 22B), the rat insulin II intron, zalpha11 Ligand cDNA and the human growth hormone poly A sequence were prepared and used for microinjection into fertilized B6C3fl (Taconic, Germantown, N.Y.) murine oocytes, using a standard microinjection protocol. See, Hogan, B. et al., *Manipulating the Mouse Embryo. A Laboratory Manual*, Cold Spring Harbor Laboratory Press, 1994.

Eight transgenic mice expressing human zalpha11 Ligand from the lymphoid-specific EµLCK promoter were identified among 44 pups. Four of these were pups that died and 4 grew to adulthood. Expression levels were fairly low in these animals. Twenty transgenic mice expressing mouse zalpha11 Ligand from the lymphoid-specific EµLCK promoter were identified among 77 pups. All 20 grew to adulthood. Expression levels were fairly low in these animals. Three transgenic mice expressing mouse zalpha11 Ligand from the liver-specific MT-1 promoter were identified among 60 pups. Two of these pups died and 1 grew to adulthood. Expression levels were fairly low in these animals. Tissues were prepared and histologically examined as describe below.

B. Microscopic Evaluation of Tissues from Transgenic Mice

Spleen, thymus, and mesenteric lymph nodes were collected and prepared for histologic examination from transgenic animals expressing human and mouse zalpha11 Ligand (Example 36A). Other tissues which were routinely harvested included the following: Liver, heart, lung, kidney, skin, mammary gland, pancreas, stomach, small and large intestine, brain, salivary gland, trachea, espohogus, adrenal, pituitary, reproductive tract, accessory male sex glands, skeletal muscle including peripheral nerve, and femur with bone marrow. The tissues were harvested from a neonatal pup which died unexpectedly, and several adult transgenic mice, as described below. Samples were fixed in 10% buffered formalin, routinely processed, embedded in paraffin, sectioned at 5 microns, and stained with hematoxylin and eosin. The slides were examined and scored as to severity of tissue changes (0=none, 1=mild, 2=moderate, 3=severe) by a board certified veterinary pathologist blinded to treatment.

The pup and 2 female adult mice expressing the human zalpha11 Ligand, and 3 of the 6 male adult mice expressing the mouse zalpha11 Ligand showed inflammatory infiltrates in many of the tissues examined. The organs affected varied somewhat from mouse to mouse. The inflammatory infiltrate was composed primarily of neutrophils and macrophages in varying numbers and proportions and was generally mild to moderate degree in severity. Moreover, these animals showed changes in lymphoid organs, including moderate to severe lymphopenia in the spleen and thymus (human and mouse zalpha11 Ligand transgenics); and severe lymphopenia (human zalpha11 Ligand transgenics), or mild to severe suppurative to pyogranulomatous lymphadenitis (mouse zalpha11 Ligand transgenics) in lymph nodes. In addition, increased extramedullary hematopoiesis was evident in the spleens. These changes were not observed in age-matched control mice.

C. Flow Cytometric Analysis of Tissues from Transgenic Mice Over Expressing Zalpha11 Ligand Transgenic animals over expressing either human or mouse zalpha11 ligand (Example 36A) were sacrificed for flow cytometric analysis of peripheral blood, thymus, lymph node, bone marrow, and spleen.

Cell suspensions were made from spleen, thymus and lymph nodes by teasing the organ apart with forceps in ice cold culture media (500 ml RPMI 1640 Medium (JRH Biosciences. Lenexa, Kans.); 5 ml 100× L-glutamine (Gibco BRL. Grand Island, N.Y.); 5 ml 100× Na Pyruvate (Gibco BRL); 5 ml 100× Penicillin, Streptomycin, Neomycin (PSN) (Gibco BRL) and then gently pressing the cells through a cell strainer (Falcon, VWR Seattle, Wash.). Peripheral blood (200 ml) was collected in heparinized tubes and diluted to 10 mls with HBSS containing 10 U Heparin/ml. Erythrocytes were removed from spleen and peripheral blood preparations by hypotonic lysis. Bone marrow cell suspensions were made by flushing marrow from femurs with ice cold culture media. Cells were counted and tested for viability using Trypan Blue (GIBCO BRL, Gaithersburg, Md.). Cells were resuspended in ice cold staining media (HBSS, 1% fetal bovine serum, 0.1% sodium azide) at a concentration of ten million per milliliter. Blocking of Fc receptor and non-specific binding of antibodies to the cells was achieved by adding 10% normal goat sera and Fc Block (Pharmingen, La Jolla, Calif.) to the cell suspension.

Cell suspensions were mixed with equal volumes of fluorochrome labeled monoclonal antibodies (PharMingen), incubated on ice for 60 minutes and then washed twice with ice cold wash buffer (PBS, 1% fetal bovine serum, 0.1% sodium azide) prior to resuspending in 400 ml wash buffer containing 1 mg/ml 7-AAD (Molecular Probes, Eugene, Oreg.) as a viability marker in some samples. Flow data was acquired on a flow cytometer FACSCALIBUR™ flow cytometer (BD Immunocytometry Systems, San Jose, Calif.). Both acquisition and analysis were performed using CellQuest software (BD Immunocytometry Systems).

The transgenic animals that expressed either the human or mouse zalpha11 Ligand at the highest levels had dramatically altered cell populations in all lymphoid organs analyzed. Changes seen included complete loss of thymic cellularity, complete absence of CD45R positive B cells and increased size and cellularity of spleens. Both spleen and bone marrow had increased numbers of myeloid sized cells, which was accounted for by increases in both monocytes and neutrophils. The pan NK cell marker (DX5) was increased in many populations. Moderate expressing founders had less dramatic but still significant changes consistent with the phenotype seen in the high expressers. Mice with the lowest level of expression had neither a significant increase in myeloid cells nor decrease in B cells numbers. They did show significant changes in thymocyte populations with decreases in CD4+ CD8+ double positive cells and increases in both CD4 and CD8 single positive cells.

Example 37

Zalpha11 Ligand Purified Recombinant Human Protein Dose-Response Study in Normal Mice A. Summary Normal six week old female C57B1/6 (Harlan Sprague Dawley, Indianapolis, Ind.). mice were treated by intraperitoneal injection once daily for either four or eight days with one of four dose levels of purified recombinant human zalpha11 Ligand (Example 24) at 0.1, 0.5, 5 or 50 µg/mouse/day or with vehicle as a control. Body weights and body temperatures were monitored daily. On either day four or day nine, four of the eight mice from each protein treatment group and five of the ten mice in the vehicle control group were sacrificed. Blood, bone marrow and tissues were harvested and analyzed. Potential perturbations in lymphoid tissues were examined, as well as general physiologic and toxicological parameters.

There was no evidence of toxicity of human zalpha11 Ligand protein at any of the doses tested. Body weights and temperatures were unchanged. There were no apparent changes in clinical chemistry parameters. However, there were consistent findings relating to increased percentages of myeloid lineage cells in bone marrow, spleen and peripheral blood in mice treated with the highest dose of zalpha11 Ligand compared to the vehicle control. There was a statistically significant increase in myeloid lineage sized cells identified by flow cytometric analysis of spleen homogenate in the high-dose group. The spleens of the two highest dose groups were statistically significantly larger than the other groups. On histopathologic examination, however, only a marginal increase in extramedullary hematopoiesis was seen in the highest dose group. There was a statistically significant increase in the myeloid to erythroid ratio of the bone marrow in the highest dose group compared to the other groups. Finally, there were increases seen in peripheral blood both in total white blood cell counts and in the percentage of monocytes in the same group.

B. Dosing Solution Preparation

Purified recombinant human zalpha11 Ligand (Example 24) was diluted into sterile phosphate buffered saline (GibcoBRL, Grand Island, N.Y.) at concentrations to deliver 50, 5, 0.5 or 0.1 micrograms of protein in 0.1 ml of PBS vehicle. The doses for the first four days were made on day 0 and frozen in a frosty −20° C. freezer prior to use. The doses for days five through eight were made on day five and frozen as above. Aliquots of the same PBS were similarly frozen for the vehicle treated control group. On the day of administration the appropriate aliquots were thawed and 0.1 ml of solution was injected intraperitoneally into the mice each day for either four or eight days.

C. Study Design

The mice were six weeks old at the start of the study. Each treatment group consisted of eight mice, except for the vehicle control group that included ten mice. One half of the mice in each treatment group were sacrificed after four days of treatment and the other half after eight days.

Before treatment each day, each mouse was weighed and her body temperature recorded using the Portable Programmable Notebook System (BMDS, Inc, Maywood, N.J.), by scanning the mouse for identification number and body temperature from transponders implanted subcutaneously (IPTT-100, BMDS, Maywood, N.J.).

At sacrifice, tissues harvested to assess white blood cell populations by flow cytometric analysis included bone marrow, thymus and spleen. FACS analysis of the lymphoid organs and bone marrow was performed with the flow cytometer FACSCALIBUR™, (Becton Dickinson, Mansfield, Mass.). The tissues harvested for histologic examination for signs of toxicity of the protein included: spleen, thymus, liver, kidney, adrenal gland, heart and lungs. All tissues fixed for histology were kept at 4° C. overnight in 10% Normal Buffered Saline (NBF) (Surgipath, Richmond, Ill.). The following day the NBF was replaced with 70% ethanol and the tissues returned to 4° C. until processing for histology.

The tissues were processed and stained for Hematoxylin and Eosin in house, then sent to a contract pathologist for histopathologic analysis. Blood was collected for complete blood cell counts (CBC) and serum chemistry profiles. The CBC's were analyzed in-house with the CELL DYN® 3500 Hematology Analyzer (Abbott Diagnostics Division, Abbott Park, Ill.) and manual differential white blood cell counts were analyzed at Phoenix Central Laboratory, (Everett, Wash.). The serum was kept frozen at −20° C. until submission to Phoenix Central Laboratory for complete serum chemistry panels. To assess myeloid:erythroid ratios, the bone marrow from one femur was applied to CytoSpin slides (CYTOSPIN 3 CYTOCENTRIFUGE and CYTO SLIDES, Shandon, Pittsburgh, Pa.) and sent to Phoenix Central Laboratories for analysis.

D. Study Results

There were no apparent clinical indications of physiologic effects or of toxicity of human zalpha11 Ligand at doses of 50 µg/day or lower. Body weights and temperatures remained normal for the duration of the treatments. Serum chemistry parameters were in normal ranges. Red blood cell and platelet counts appeared normal. In the mice receiving 50 µg/day for 8 days, manual differential white blood cell counts showed that the percentage of monocytes was elevated in the peripheral blood, and an apparent increase in the total white blood cell counts. In bone marrow flushed from a femur, myeloid to erythroid ratios were increased in the 50 µg dose group, and to a lesser degree the 5 µg dose group from the 8-day dose set. In a non-parametric multiple column comparison using INSTAT™ (INSTAT™ MAC; GraphPad Software, Inc., San Diego, Calif.), this difference was statistically significant (p=0.0049). The difference between the highest dose group and vehicle was also significant, (p=0.0286). The increased white blood cells in peripheral blood and the significant increase in myeloid precursors in the marrow may thus be related.

Histologic evaluation of the following tissues showed no apparent evidence of cytologic or structural changes, mitotic events or necrosis: thymus, liver, kidney, adrenal gland, duodenum, pancreas, jejunum, caecum, colon, mesenteric lymph nodes, uterus, ovary, salivary gland, heart, trachea, lung, and brain. There were no apparent differences between the treatment groups in the weights of the thymus, kidney, liver or brain. Of all the tissues examined, only the spleen weights were significantly affected.

Each mouse spleen weight was normalized to her brain weight. In the 50 μg/day treatment group compared to the vehicle, 0.1 μg and 0.5 μg treatment groups, the average of the spleen weights was nearly 50% greater after four days of treatment and almost 100% greater after eight days than the average spleen weights of the other three groups. In the four-day set, the 5 μg/day group also tended to have larger spleens than the control and low dose groups. The difference in the spleen/brain weights with data from the four-day and the eight-day sets combined by treatment group was statistically significant (p=0.0072) by Kruskall-Wallace non-parametric ANOVA, multiple column comparison test using the INSTAT™ program (GraphPad Software).

A marginal increase in extrameduallary hematopoiesis, especially in the red pulp was seen in spleens of mice from the highest dose group, even in the mice treated for four days. Flow cytometric analysis of the spleens showed a significant increase in the proportion of myeloid size cells in the highest dose group (p=0.01, Student's t test), representing increases in both monocytes and neutrophils. This effect may be related to the increased peripheral blood mononuclear cell percentage, as well as the apparent increase in myeloid precursors in the bone marrow, described above. Moreover, the transgenic mice derived from insertion of the human zalpha11 gene had increased extramedullary hematopoiesis in their spleens compared to non-transgenic litter mates.

Several changes were observed in the 50 μg per day dose group compared to the control group that implicate zalpha11 Ligand in production or development of cells of the myeloid lineage. Taken together, the observed changes suggest that zalpha11 may be useful as a therapeutic protein in such medical specialties as cancer and immunologic disorders described herein.

Example 38

Preliminary Elimination and Tissue Distribution Study of Purified Recombinant Human Zalpha11 Ligand Protein A. Summary In order to elucidate tissue distribution and elimination patterns of the purified rhzalpha11 Ligand, a preliminary pharmacokinetic study was undertaken. Nine week old male C57B1/6 mice were given purified recombinant human zalpha11 Ligand protein labeled with $^{111}$Indium ($^{111}$In) (NEN, Boston, Mass.) by one of three routes. A single bolus injection was given to each mouse by either the intravenous (IV), intraperitoneal (IP), or subcutaneous route (SC). The mice injected by either the subcutaneous or intraperitoneal route were sacrificed at either one or three hours after injection. The mice injected intravenously were sacrificed after either ten minutes or one hour following injection. Blood, plasma and selected tissues were harvested at various timepoints and counted by a gamma counter to estimate the approximate half-life and tissue distribution of the exogenous labeled protein. The tissues that were harvested for counting as well as the intervals of sacrifice were selected based on reports of the distribution of other cytokines labeled with radionuclides.

At sacrifice, tissues harvested for counting of radioactivity included thymus, spleen, kidney, a lobe of liver, a lobe of lung, and urinary bladder. In the group receiving the injection intraperitoneally, gut was also counted to assess incidence of injection into the gut, and in the subcutaneously dosed mice, skin with underlying structures in the area of injection was counted. The cpm for whole liver and lung were calculated from a section that was counted and a percentage of the whole organ weight represented by the section.

After the end of the study the collected tissues, whole blood and plasma were counted on the COBRA II AUTO-GAMMA gamma counter (Packard Instrument Company, Meriden, Conn.). An aliquot of the original labeled dosing solution was also counted at the end of the study with the tissues. This allowed calculation of percent total injected radioactivity for each mouse and simultaneous correction of all counts for radioactive decay. Approximations of remaining blood volume and organ weights indicated that the majority of the counts administered were accounted for, and therefore the percentage of counts per tissue were a reasonable representation of distribution of the counts following labeled zalpha11 Ligand administration by each route.

B. $^{111}$Indium Labeling of Zalpha11 Ligand

Purified recombinant human zalpha11 Ligand (Example 29) was conjugated with a 10 fold molar excess of DTPA (Pierce, Rockford, Ill.) by incubating 30 minutes at room temperature in PBS. Unreacted DTPA and hydrolyzates were removed by buffer exchange on a Biomax-5k NMWL (Ultrafree-15, Millipore, Bedford, Mass.). The void volume protein peak was concentrated to 5 mg/ml and an aliquot taken for testing in a bioassay (anti-CD40 stimulation of murine B-cells (Example 44)). Upon confirming that the DTPA-conjugate still had full bioactivity the conjugate was diluted to 0.5 mg/ml with 1M Na Acetate pH6.0. Two mCi of $^{111}$Indium was taken up in 0.5 ml 1M Na Acetate pH6.0 and mixed with the DTPA-human zalpha11 Ligand for 30 min. at room temperature. Unincorporated $^{111}$Indium was removed during buffer exchange to PBS on a PD-10 column (Pharmacia, Piscataway, N.J.). The radio-labeled material was diluted with unlabeled human zalpha11 Ligand to give a specific activity of 100 mCi/mg, sterile filtered and stored at 4° C. overnight. One hundred percent of the labeled protein was retained on a Biomax-5k NMWL membrane (Millipore). The labeled $^{111}$In-human zalpha11 Ligand was administered to mice in the elimination and pharmacokinetic studies. Fifty μg human zalpha11 Ligand protein labeled with 5 μCi of labeled human zalpha11 Ligand in 0.1 ml of PBS vehicle was administered to each animal.

C. Results of Preliminary Distribution Study

After one and three hours following administration by all three routes, the highest concentration of $^{111}$In-human zalpha11 Ligand, was found in kidney and the second highest was in urine and urinary bladder, as evinced by these tissues having the highest cpm. The average counts recovered from kidneys were from 3 to 8 times higher than the whole liver counts, depending on the route of injection and the sacrifice timepoint. For example, the average kidney cpm at 60 minutes following IV injection was 4.5 times greater than the average counts calculated for whole liver from the same group. In the group that was sacrificed ten minutes after intravenous administration, the highest cpm was again in kidney, and the second highest accumulation was equivalent in liver, urinary bladder and urine.

D. Preliminary Pharmacokinetic Study

Blood and plasma collections were done at 10, 30 and 60 minutes following injection by all three routes. Following injection by the IV route, a separate set of mice had blood and plasma samples taken at two, five and ten minutes. Another set of mice who received their injections by either the IP or SC route had blood sampled at one, two and three hours. For the treatment groups see Table 6. The short collection times bracket the reported half-life of IL-2 following intravenous injection. The reported T½ was in the range of 2.5 to 5.1 minutes. For reference to in vivo administration to IL-2, see Donohue J H and Rosenberg S A *J Immunol,* 130:2203, 1983. The long timepoints were chosen to outline the anticipated elimination phase.

TABLE 6

| Route of injection | Bleed Times(min.) | Sacrifice Time |
|---|---|---|
| Intravenous Group 1 | 2, 5, 10 | 10 min. |
| Intravenous Group 2 | 10, 30, 60 | 60 min. |
| Intraperitoneal Group 1 | 10, 30, 60 | 60 min. |
| Intraperitoneal Group 2 | 60, 120, 180 | 180 min. |
| Subcutaneous Group 1 | 10, 30, 60 | 60 min. |
| Subcutaneous Group 2 | 60, 120, 180 | 180 min. |

Un-labeled IL-2 has been shown to be eliminated from the serum with a half-life of approximately three minutes in mice after IV injection. For reference see Donahue, J H and Rosenburg supra. Following IP and SC injection of similar amounts of IL-2, the duration of persistence of IL-2 activity in serum was prolonged from 2 units/ml for less than 30 minutes following IV injection to greater than 2 units/ml for 2 hours following IP and 6 hours following SC injections. The principle route of clearance of IL-2 appears to be the kidney. Zalpha11 ligand has been shown to be structurally similar to IL-2, as discussed herein. Preliminary evaluation of the elimination of zalpha11 Ligand appears to be consistent with the apparent clearance of IL-2 by the kidneys, based on the accumulation of cpm predominantly in the kidneys, followed by the urinary bladder and urine in the present study.

Estimations were made of pharmacokinetic parameters based on non compartmental analysis of the cpm data obtained from the plasma, using the PK analysis program WINNONLIN™, Version 1.1, (Scientific Consulting Inc., Cary, N.C.). Plasma half-lives of zalpha11 Ligand were estimated using the predicted terminal elimination rate constants for intravenous, subcutaneous, and intraperitoneal administration of a 50 µg dose. The pharmacokinetic results were estimations due to limited data points in the terminal elimination region of the plasma concentration vs. time profiles. Moreover, the fit of the terminal elimination phase for SC and IP dosing required use of data from timepoints during which absorption of the $^{111}$In-human zalpha11 Ligand was apparently still occurring. However, estimations of half-lives following intravenous, subcutaneous, and intraperitoneal dosing were 13.6 min., 18.8 min., and 34.3 min., respectively. Since a dosing range was not evaluated it was not apparent whether saturable or active elimination (Michaelis Menten kinetics) was occurring. Therefore, these half-life calculations are estimations.

Estimates of the bioavailability of the labeled protein were made based on the area under the curve (AUC) following subcutaneous or intraperitoneal dosing compared to that of intravenous dosing. The estimated bioavailability following subcutaneous and intraperitoneal injection were 35.8% and 63.9% respectively. Because only one protein dose was studied, the bioavailability was not evaluated as a function of dose. The estimated clearance and volume of distribution (based on the data from the intravenous injection) were 0.48 ml/min. and 6.1 ml, respectively.

Although the data are preliminary, the fate of zalpha11 Ligand administered IV was similar to that reported for IL-2, another 4-helix bundle cytokine (Donahue, J H and Rosenburg, S A supra.). Like 11-2, IV-administered zalpha11 Ligand had a plasma half life of only minutes with the main clearance in the kidney. Three hours after injection, the majority of the labeled material extracted from kidney was still retained in a Biomax 5K NMLW membrane (Millipore). Since it has previously been reported that the indium remains associated with protein even during lysosomal degradation (Staud, F. et al., *J. Pharm. Sciences* 88:577-585, 1999) zalpha11 Ligand is accumulating and may be degraded in the kidney. The current study also showed, as observed with many other proteins, including IL-2 (Donahue, J H and Rosenburg, S A, supra.), that IP and SC administration significantly prolonged the plasma levels of zalpha11 Ligand.

Example 39

Isolation and Expansion of Fresh Human Bone Marrow MNC CD34+ Fraction Using Zalpha11 Ligand for Assessment of NK Activity A. Selection and Isolation of CD34+ Cells from Human Bone Marrow Fresh human bone marrow mononuclear cells (MNC) were prepared to enrich for cells having NK cell activity. Fresh human MNCs were obtained from Poietic Technologies (Gaithersburg, Md.). 10 ml alpha MEM (JRH, Lenexa, Kans.) containing 10% HIA FBS (Hyclone, Logan, Utah) and the antibiotic 1% PSN (Gibco, BRL, Grand Island, N.Y.) was added to the cell suspension and the cells were passed through a 100 µm sieve. The cells were then counted, pelleted, washed with 10 ml PBS containing 2% FBS, then pelleted again and resuspended in 1 ml PBS containing 2% FBS. Cells having a CD34 cell surface marker (CD34+ cells) were magnetically separated using a Detachabead kit with DYNABEADS® M-450 CD34 ((Dynal, Oslo, Norway), as per manufacturer's instructions. Both the CD34+ cell and the CD34– cell fractions were further analyzed below.

B. Expansion of CD34+ Cells Using Zalpha11 Ligand

A CD34+ cell fraction was plated into four wells in a 24-well plate. 50,000 positively selected cells suspended in 1 ml Alpha MEM (JRH) containing 10% HIA FBS (Hyclone) and 1% PSN (Gibco/BRL), plus the various cytokines described below were plated in each of the 4 wells (1-4). Various reagents were used to test for zalpha11 Ligand-induced expansion of the CD34+ selected bone marrow MNCs: Reagents included human flt3 (R&D, Minneapolis, Minn.); purified human zalpha11 Ligand (Example 30C and Example 30D); human IL-15 (R&D). Reagents were combined as follows at day 0: In well #1, 2 ng/ml human flt3 was added. In well #2, 2 ng/ml human flt3 and 15 ng/ml purified human zalpha11 Ligand were added. In well #3, 2 ng/ml human flt3 and 20 ng/ml human IL15 were added. In well #4, 2 ng/ml human flt3, 15 ng/ml purified human zalpha11 Ligand, and 20 ng/ml human IL15 were added. After incubating for 18 days, the suspension cells from each well were pelleted, and then resuspended in 0.5 ml alpha MEM (JRH) containing 10% HIA FBS (Hyclone) and 1% PSN (Gibco/BRL), and counted to assess proliferation of the CD34+ cell fraction. A low level of proliferation was seen in the presence of flt3 alone (control well #1), but the presence of IL-15 or zalpha11 in addition to flt3 had not significant effect on the expansion (wells, #2 and #3). However, expansion beyond the flt3 control was evident in well #4 which contained IL-15 and zalpha11 Ligand in addition to flt3. This result suggested that zalpha11 and IL-15 act in synergy to expand the human CD34+ cell population. Moreover, the results of this experiment supported the results seen with the mouse zalpha11 Ligand in the mouse BM assay (Example 21).

All cell populations were then tested for NK activity and subjected to flow cytometry analysis, as shown below (Example 41).

C. Expansion of CD34+ or CD34− Cells Using Zalpha11 Ligand with Delayed Addition of IL-15

Both CD34 positive and negative (CD34−) fractions were plated separately into six 12 well plate wells (1-6). Each of six wells contained 100,000 positively or negatively selected cells in 2 ml alpha MEM containing 10% HIA FBS and PSN, described above. Reagents used were as described above. In well #1, 2 ng/ml human flt3 was added at day 0. In well #2, 2 ng/ml human flt3 was added at day 0, and after 5 days incubation 20 ng/ml human IL15 was added. In well #3, 2 ng/ml human flt3 and 15 ng/ml human zalpha11 Ligand were added at day 0. In well #4, 2 ng/ml human flt3 and 15 ng/ml human zalpha11 Ligand were added at day 0, and after 5 days incubation 20 ng/ml human IL15 was added. In well #5, 2 ng/ml human flt3 and 20 ng/ml human IL15 were added at day 0. In well #6, 2 ng/ml human flt3, 15 ng/ml human zalpha11 Ligand, and 20 ng/ml human IL15 were added at day 0. After incubating for a total of 15 days from the start of the experiment, the cells from each well were harvested and counted.

In the CD34+ population a low level of proliferation was seen in the presence of flt3 alone (control well #1), but the presence of IL-15 or zalpha11 added at day 0 in addition to flt3 had no significant effect on the expansion (wells, #3 and #5). Addition of IL-15 after 5 days had some proliferative effect in comparison to the flt3 control (well #2 compared to well #1) and a proliferative effect in the presence of zalpha11 (well #4 compared to well #3). However, the greatest expansion was evident in well #6 which contained IL-15 and zalpha11 Ligand in addition to flt3 at day 0.

In the CD34− population, no proliferation was seen in the presence of flt3 alone (control well #1), and in fact a decrease in the cell population was evident. The presence of zalpha11 added at day 0 in addition to flt3 (well #3) was similar to the flt3 control. The presence of IL-15 added at day 5 increased proliferation effect of the cells in the presence (well #4) or absence (well #2) of zalpha11 Ligand. Again, the greatest expansion was evident in well #6 which contained IL-15 and zalpha11 Ligand in addition to flt3 at day 0.

All cell populations were then tested for NK activity and subjected to FACS analysis, as shown below (Example 41).

Example 40

Isolation and Expansion of Fresh Mouse Cells Using Human and Mouse Zalpha11 Ligand for Assessment of NK Activity and NK Cell Markers A. Isolation and Expansion of Fresh Mouse Low Density Bone Marrow Cells Using Human and Mouse Zalpha11 Ligand Fresh mouse marrow cells were isolated by clipping both ends of mouse femurs, and flushing two to three milliliters of growth medium (see below) through the inside of the bone into a collection tube. The growth medium was 500 ml RPMI 1640 Medium (JRH Biosciences. Lenexa, Kans.); 5 ml 100× L-glutamine (Gibco BRL. Grand Island, N.Y.); 5 ml 100× Na Pyruvate (Gibco BRL); 5 ml 100× Penicillin, Streptomycin, Neomycin (PSN) (Gibco BRL); and 50 ml heat-inactivated Fetal Bovine Serum (FBS) (Hyclone Laboratories. Logan, Utah). The marrow cells were then broken-up by pipetting the media up and down several times. The cells were then pelleted and washed once with growth medium, and passed through a 70-micron sieve. The low-density mononuclear cells were then isolated by subjecting the marrow cells to a density gradient. Marrow cells in five to eight milliliters of growth medium were carefully pipetted on top of five to eight milliliters of NYCOPREP® 1.077 Animal (Nycomed. Oslo, Norway) in a centrifuge tube. This gradient was then centrifuged at 600×g for 20 minutes. The low density mononuclear cells were harvested from the interface layer between the NYCOPREP® and the medium. These cells were then diluted to approximately 20 milliliters in growth medium, pelleted and washed. The cells were then plated at approximately 0.5-1.5× $10^6$ cells per milliliter in growth medium in a standard tissue culture flask and incubated at 370 C, 5% CO2 for two hours.

The non-adherent, low density (NA LD) marrow cells were then harvested and plated at 0.5-2.0×105 cells per milliliter in growth medium plus 2.5 nanograms per milliliter mouse flt3 (R and D Systems. Minneapolis, Minn.) plus 25 to 50 nanograms per milliliter human Interleukin 15 (IL-15) (R and D Systems) with or without 50 to 150 nanograms per milliliter human zalpha11 Ligand; or with or without 0.12 to 10 nanograms per milliliter mouse zalpha11 Ligand.

There was no significant expansion without the addition of the human or mouse zalpha11 Ligand. Non-adherent cells were expanded in the cultures containing mouse zalpha11 Ligand as low as 0.12 ng/ml and in the cultures containing human zalpha11 Ligand as low as 22 ng/ml. In cultures containing both the human and mouse zalpha11 Ligand, non-adherent cell expansion increased with increasing dose if zalpha11 Ligand, with the mouse ligand saturating response at about 5-10 ng/ml and the human not reaching a saturating response even at the highest dose of 200 ng/ml. Human zalpha11 Ligand appeared to be approximately 20 to 100 fold less potent on mouse cells as the mouse zalpha11 Ligand. After approximately five to ten days the zalpha11 Ligand expanded mouse cells were harvested and analyzed by flow cytometry (flow cytometer FACSCALIBUR®, Becton Dickinson, Mansfield, Mass.) to determine what percentage of them were positive for NK cell antigens, where 46% were positive for the PanNK cell marker DX5 (Pharmingen).

B. Isolation and Expansion of Fresh lineage Depleted Mouse Marrow Cells

Fresh mouse lineage depleted (lin−) marrow cells were isolated from fresh mouse marrow cells by first incubating the cells with the following antibodies: TER119, Gr-1, B220, MAC-1, CD3e and I-Ab (Pharmingen. San Diego, Calif.). The lin+ cells were then removed with DYNABEADS® M-450 sheep anti-rat IgG (Dynal, Lake Success, N.Y.) as per manufacturer's instructions.

The negatively selected lin− marrow cells were then plated as above in growth medium plus either 2.5 ng/mL flt3 (R&D Systems) and 25 ng/mL IL-15 (R&D Systems); or flt3, IL-15 and mouse zalpha11 Ligand, 2 to 5% BHK mouse zalpha11 Ligand conditioned medium. After six days of growth, the cultures were harvested, counted and submitted to an NK cell activity assay (Example 41). Cells grown with mouse zalpha11 Ligand were approximately two to three times more effective at lysing NK cell target cells (YAC-1 cells) as the cells grown without zalpha11 Ligand.

C. Isolation and Expansion of CD4– CD8– (Double Negative or DN) Thymocytes

Fresh mouse thymocytes were isolated by chopping and sieving thymuses from three to eight week old mice. CD4– CD8– (DN) cells were then negatively selected by incubating the thymocytes with anti-CD4 and anti-CD8 antibodies (PharMingen), then removing the CD4+ CD8+ cells with DYNABEADS® M-450 sheep anti-rat IgG (Dynal) as per manufacturer's instructions.

The DN mouse thymocytes were then grown in growth medium plus 2.5 ng/mL flt3 (R&D Systems), 25 ng/mL IL-15 (R&D Systems) and 10 ng/mL IL-7 (R&D Systems) with or without mouse zalpha11 Ligand as above. Six days later the cells were harvested, counted, analyzed by flow cytometry as described above, and also submitted to an NK cell activity assay (Example 41).

The culture grown with mouse zalpha11 Ligand yielded approximately 480,000 cells while the culture without zalpha11 Ligand yielded only approximately 160,000 cells. The culture grown with mouse zalpha11 Ligand was found to be approximately 16.2% positive for the NK cell antigen Pan NK, DX5 (PharMingen). The culture grown without zalpha11 Ligand was 14.6% positive for DX5. The cells grown with zalpha11 Ligand lysed NK cell target cells, YAC-1, approximately two times better than the cells grown without zalpha11 Ligand. The expanded cells did not lyse significantly a negative control target cell line, EL4. These results suggested that zalpha11 Ligand selectively expands lytic NK cells.

Example 41

Activity of Human and Mouse Zalpha11 Ligand Expanded Cells and Mature Murine NK Cells in NK Cell Cytotoxicity Assays A. NK Cell Assay NK cell-mediated target cytolysis was examined by a standard $^{51}$Cr-release assay. Target cells (K562 cells (ATCC No. CCL-243) in human assays, and YAC-1 cells (ATCC No. TIB-160) in mouse assays) lack expression of major histocompatability complex (MHC) molecules, rendering them susceptible to NK cell-mediated lysis. A negative control target cell line in mouse assays is the MHC+ thymoma EL4 (ATCC No. TIB-39). We grew K562, EL4, and YAC-1 cells in RP10 medium (standard RPMI 1640 (Gibco/BRL, Grand Island, N.Y.) supplemented with 10% FBS (Hyclone, Logan, Utah), as well as 4 mM glutamine (Gibco/BRL), 100 I.U./ml penicillin+100 MCG/ml streptomycin (Gibco/BRL), 50 µM β-mercaptoethanol (Gibco/BRL) and 10 mM HEPES buffer (Gibco/BRL). On the day of assay, 1-2×10$^6$ target cells were harvested and resuspended at 2.5-5×10$^6$ cells/ml in RP10 medium. We added 50-100 µl of 5 mCi/ml $^{51}$Cr-sodium chromate (NEN, Boston, Mass.) directly to the cells and incubated them for 1 hour at 37° C., then washed them twice with 12 ml of PBS and resuspended them in 2 ml of RP10 medium. After counting the cells on a hemacytometer, the target cells were diluted to 0.5-1×10$^5$ cells/ml and 100 µl (0.5-1×10$^4$ cells) were mixed with effector cells as described below.

In human assays, effector cells were prepared from selected and expanded human CD34+ BM cells (Example 39B) which were harvested, washed, counted, mixed at various concentrations with 51Cr-labeled target cells in 96-well round bottomed plates, and incubated for 4 hours at 37° C. After co-incubation of effector cells and the labeled target cells, half of the supernatant from each well was collected and counted in a gamma counter for 1 min/sample. The percentage of specific $^{51}$Cr release was calculated from the formula 100×(X–Y)/(Z–Y), where X is $^{51}$Cr release in the presence of effector cells, Y is the spontaneous release in the absence of effectors, and Z is the total $^{51}$Cr release from target cells incubated with 0.5% Triton X-100. Data were plotted as the % specific lysis versus the effector-to-target ratio in each well.

B. Activity of Human Zalpha11 Ligand Expanded Cells

Isolated CD34+ human HPCs cultured with flt3+/–zalpha11 Ligand and flt3+IL-15+/–zalpha11 Ligand (Example 39), were harvested the cells on day 15 to assess their capacity to lyse MHC– K562 cells in a standard $^{51}$Cr-release assay as described above, and to analyze their surface phenotype by flow cytometry. As expected from previous reports (Mrozek, E et al., *Blood* 87:2632-2640, 1996; and Yu, H et al., *Blood* 92:3647-3657, 1998), simultaneous addition of IL-15 and flt3L did induce the outgrowth of a small population of CD56+ cells. Interestingly, although BM cells cultured simultaneously with zalpha11 Ligand and flt3L did not expand significantly, there was a significant increase in total cell numbers in cultures containing a combination of flt3L, zalpha11 Ligand and IL-15 (see, Example 39).

For an assessment of the surface phenotype of these human BM cultures, we stained small aliquots of the cells for 3-color flow cytometric analysis with anti-CD3-FITC, anti-CD56-PE and anti-CD16-CyChrome mAbs (all from PharMingen, San Diego, Calif.) and analyzed them on a flow cytometer FACSCALIBUR™ using CellQuest software (Becton Dickinson, Mountain View, Calif.). This flow cytometric analysis confirmed that the cells growing out of these cultures were differentiated NK cells, as they were large and granular and expressed both CD56 and CD16, and were CD3– (Lanier, L L *Annu. Rev. Immunol.* 16:359-393, 1998). Furthermore, these cells exhibited significantly higher effector function than those cells grown with IL-15 and flt3. More specifically, cells grown in all three cytokines lysed more than 40% of the K562 targets at an effector-to-target ratio (E:T) of 1.5, whereas cells grown in IL-15+flt3L lysed fewer than 5% of the targets at an E:T of 2. These data demonstrate that, in combination with IL-15, zalpha11 Ligand stimulates the differentiation of NK cells from CD34+ BM cells.

C. Activity of Mouse Zalpha11 Ligand Expanded Cells

To test the effects of zalpha11 Ligand on murine hematopoietic progenitor cells, purified Lineage-negative (Lin–) bone marrow cells from C57B1/6 mice were expanded in flt3+IL-15+/–zalpha11 Ligand, as described in Example 40B. On day 6 of culture, the cells ("effectors") were harvested and counted, then resuspended in 0.4 ml of RP10 medium (Example 41A). Two aliquots (0.15 ml each) of each sample expanded with or without zalpha11 Ligand (Example 41A) were diluted serially 3-fold in duplicate in 96-well round bottomed plates, for a total of 6 wells of 100 µl each. The remaining 100 µl of cells were stained for NK cell surface markers with FITC-anti-2B4 and PE-anti-DX5 mAbs (PharMingen) and analyzed by flow cytometry. Each group of cells exposed to flt3+IL-15 with or without the presence of zalpha11 Ligand had similar fractions of 2B4+DX5+ cells, ranging from 65-75% positive for both NK markers.

For the NK lysis assay, target cells (YAC-1 and EL4) were labeled with $^{51}$Cr as described above. After counting the target cells on a hemacytometer, the target cells were diluted to 0.5-1×105 cells/ml and 100 µl of YAC-1 or EL4 (0.5-1×10$^4$ cells) were mixed with 100 µl effector cells and incubated for 4 hours at 37° C. Specific lysis was determined for each well as described above.

We found that cells grown in the presence of flt3+IL-15+ zalpha11 Ligand exhibited enhanced lytic activity (roughly 2-fold) against the YAC-1 targets (but did not kill the MHC+ control cell line EL4). At an effector-to-target ratio (E:T) of 5, NK cells generated in the presence of all 3 cytokines (zalpha11 Ligand+flt3+IL-15) lysed 12% of the YAC-1 cells, whereas those NK cells expanded with flt3+IL-15 lysed 6% of the YAC-1 targets. Subsequent experiments confirmed this trend.

In a second approach to determine the biological activity of zalpha11 Ligand on murine NK cells, we isolated immature CD4–CD8– ("double negative", DN) mouse thymocytes as described in Example 40C and cultured them with IL-15+ flt3+IL-7 or IL-15+flt3+IL-2, with or without zalpha11 Ligand. On day 6 of culture, the cells were harvested and assayed for NK lytic activity on YAC-1 and EL4 cells as described above. We found that cells cultured in the presence of zalpha11 Ligand had the greatest lytic activity in this assay, with enhanced lytic activity over those cells cultured in the presence of the other cytokines. Specifically, DN thymocytes grown with IL-15+flt3+IL-7 killed 18% of the YAC-1 cells at E:T of 24 while cells grown in the presence of IL-15+flt3+ IL-7 plus zalpha11 Ligand killed 48% of the targets at the same E:T. DN thymocytes grown in IL-15+flt3+IL-2 killed 15% of the YAC-1 targets at an E:T of 6, whereas cells grown with these 3 cytokines and zalpha11 Ligand killed 35% of the YAC-1 cells at an E:T of 9. Flow cytometry was performed on the cultured cells one day before the NK lysis assay. As was true for the bone marrow cultures, despite the proliferative effect of zalpha11 Ligand (cell numbers increase approximately 2-fold when zalpha11 Ligand is added), it did not significantly enhance the fraction of DX5+ cells (17-20% of total cells in the cultures with IL-7, and 35-46% of total in cultures with IL-2). These data imply that zalpha11 Ligand, in combination with IL-15 and flt3, enhances the lytic activity of NK cells generated from murine bone marrow or thymus.

D. Activity of Mouse Zalpha11 Ligand on Mature Murine NK Cells

In order to test the effects of mouse zalpha11 Ligand on mature NK cells, we isolated spleens from four 5-week old C57B1/6 mice (Jackson Laboratories, Bar Harbor, Me.) and mashed them with frosted-end glass slides to create a cell suspension. Red blood cells were removed by hypotonic lysis as follows: cells were pelleted and the supernatant removed by aspiration. We disrupted the pellet with gentle vortexing, then added 900 µl of sterile water while shaking, followed quickly (less than 5 sec later) by 100 µl of 10×HBSS (Gibco/BRL). The cells were then resuspended in 10 ml of 1×HBSS and debris was removed by passing the cells over a nylon mesh-lined cell strainer (Falcon). These RBC-depleted spleen cells were then pelleted and resuspended in MACS buffer (PBS+1% BSA+2 mM EDTA) and counted. We stained $300 \times 10^6$ of the cells with anti-DX5-coated magnetic beads (Miltenyi Biotec) and positively selected DX5+ NK cells over a MACS VS+ separation column, according to the manufacturer's instructions, leading to the recovery of $8.4 \times 10^6$ DX5+ cells and $251 \times 10^6$ DX5– cells. Each of these groups of cells were cultured in 24-well plates ($0.67 \times 10^6$ cells/well, 2 wells per treatment condition) in RP10 medium (Example 41A) alone or with 1) 30 ng/ml mouse zalpha11 Ligand, 2) 30 ng/ml recombinant mouse IL-2 (R&D Systems, Inc., Minneapolis, Minn.), 3) 30 ng/ml recombinant human IL-15 (R&D), 4) 30 ng/ml each of mouse zalpha11 Ligand and hIL-15, or 5) 30 ng/ml each of mIL-2 and hIL-15. The cells were harvested after 21 hours, washed, and resuspended in RP10 medium and counted. The cells were then assayed for their ability to lyse $^{51}$Cr-labeled YAC-1 or EL4 targets cells, as described in Example 41A.

In general, there was little NK activity from the DX5– (non-NK cells) groups, but the DX5– cells cultured with zalpha11 Ligand and hIL-15 did lyse 25% of the YAC-1 target cells at an E:T of 82. By comparison, DX5– cells cultured with hIL-15 alone lysed 14% of the YAC-1 targets at an E:T of 110. This suggests that zalpha11 Ligand and IL-15 are acting together on the residual NK1.1+ NK cells in this cell preparation. As for the DX5+ cell preparation, treatment with mouse zalpha11 Ligand alone did not significantly increase their effector function (their lysis of YAC-1 cells was similar to the untreated group). As expected, both IL-2 and IL-15 significantly improved NK activity. The highest level of lysis, however, was detected in the group treated with zalpha11 Ligand and hIL-15 (65% lysis of YAC-1 cells at an E:T of 3.3, vs. 45% lysis at an E:T of 4 for the hIL-15 treatment group). Taken together, these results suggest that although zalpha11 Ligand alone may not increase NK cell lysis activity, it does enhance NK lysis activity of mature NK cells, when administered with IL-15.

Example 42

Zalpha11 Ligand Proliferation of Human and Mouse T-Cells in a T-Cell Proliferation Assay A. Murine Zalpha11 Ligand Proliferation of Mouse T-Cells T cells from C57B1/6 mice (Jackson Laboratories, Bar Harbor, Me.) were isolated from pooled splenocytes and lymphocytes from axillary, brachial, inguinal, cervical, and mesenteric lymph nodes (LNs). Spleens were mashed with frosted-end glass slides to create a cell suspension. LNs were teased apart with forceps and passed through a cell strainer to remove debris. Pooled splenocytes and LN cells were separated into CD8+ and CD4+ subsets using two successive MACS magnetic separation columns, according to the manufacturer's instructions (Miltenyi Biotec, Auburn, Calif.). Whole thymocytes were collected from the same mice.

Cells were cultured at $3 \times 10^5$ cells/well (thymocytes) or $10^5$ cells/well (mature T cells) with increasing concentrations of purified murine zalpha11 Ligand (0-30 ng/ml) (Example 24 and Example 29) in 96-well flat bottomed plates pre-coated overnight at 4° C. with various concentrations of anti-CD3 mAb 2C11 (PharMingen) for 3 days at 37° C. The anti-CD3 antibody served to activate the murine T-cells through the T-cell receptor. Each well was pulsed with 1µ Ci $^3$H-thymidine on day 2 and plates were harvested and counted 16 hours later to assess proliferation.

When we tested zalpha11 Ligand in T cell proliferation assays, we found that it co-stimulated anti-CD3-activated murine thymocytes, leading to an accelerated outgrowth of CD8+ CD4– cells (the majority of the thymocytes cultured with anti-CD3+zalpha11 Ligand were CD8+ CD4– by day 3 of culture, while cells cultured with anti-CD3 alone did not significantly skew to this phenotype until day 5). We did not observe significant levels of proliferation of thymocytes to zalpha11 Ligand in the absence of anti-CD3.

Interestingly, when we assayed mature peripheral murine T cells for their ability to respond to zalpha11 Ligand+anti-CD3, we found that only the CD8+, but not the CD4+ subset, responded in a dose-dependent manner to zalpha11 Ligand. We also observed weak but reproducible proliferation of CD8+ cells (but not CD4+ cells) in response to zalpha11 Ligand alone. Interestingly, this was not observed for human T cells (see Example 42B, below).

B. Human Zalpha11 Ligand Proliferation of Human T-Cells

Human CD4+ and CD8+ T cells were isolated from PBMC as described in Example 43 (below) Cells were cultured at about 105 cells/well with increasing concentrations of purified human zalpha11 Ligand (0-50 ng/ml) (Example 24) in 96-well flat bottomed plates pre-coated overnight at 4° C. with various concentrations of anti-human CD3 mAb UCHT1 (PharMingen) for 3 days at 37° C. Each well was pulsed with 1 uCi 3H-thymidine on day 2 and plates were harvested and counted 16 hours later. Unlike our results with mouse T cells, our preliminary data suggests that human zalpha11 Ligand co-stimulates CD4+, but not CD8+, human T cells in a dose-dependent fashion.

Example 43

Real Time PCR shows Zalpha11 Ligand Expression in Human CD4+ Cells

A. Purified Human T Cells as a Primary Source Used to Assess Human Zalpha11 Ligand Expression Whole blood (150 ml) was collected from a healthy human donor and mixed 1:1 with PBS in 50 ml conical tubes. Thirty ml of diluted blood was then underlayed with 15 ml of FICOLL-PAQUE PLUS™ (Amersham Pharmacia Biotech, Uppsala, Sweden). These gradients were centrifuged 30 min at 500 g and allowed to stop without braking. The RBC-depleted cells at the interface (PBMC) were collected and washed 3 times with PBS. The isolated human PBMC yield was $200 \times 10^6$ prior to selection described below.

The PBMCs were suspended in 1.5 ml MACS buffer (PBS, 0.5% EDTA, 2 mM EDTA) and $3 \times 10^6$ cells were set aside for control RNA and for flow cytometric analysis. We next added 0.25 ml anti-human CD8 microbeads (Miltenyi Biotec) and the mixture was incubated for 15 min at 4° C. These cells labeled with CD8 beads were washed with 30 ml MACS buffer, and then resuspended in 2 ml MACS buffer.

A VS+ column (Miltenyi) was prepared according to the manufacturer's instructions. The VS+ column was then placed in a VarioMACS magnetic field (Miltenyi). The column was equilibrated with 5 ml MACS buffer. The isolated primary mouse cells were then applied to the column. The CD8 negative cells were allowed to pass through. The column was rinsed with 9 ml (3×3 ml) MACS buffer. The column was then removed from the magnet and placed over a 15 ml falcon tube. CD8+ cells were eluted by adding 5 ml MACS buffer to the column and bound cells flushed out using the plunger provided by the manufacturer. The yield of CD8+ selected human peripheral T cells was about 51×106 total cells. The CD8-negative flow through cells were collected, counted, stained with anti-human CD4 coated beads, then incubated and passed over a new VS+ column at the same concentrations as described above. The yield of CD4+ selected human peripheral T cells was $42 \times 10^6$ total cells.

A sample of each of the CD8+ and CD4+ selected human T cells was removed for staining and sorting on a fluorescence activated cell sorter (FACS) to assess their purity. A PE-conjugated anti-human CD4 antibody, an anti-human CD8-FITC Ab, and an anti-human CD19-CyChrome Ab (all from PharMingen) were used for staining the CD8+ and CD4+ selected cells. The CD8-selected cells in this first experiment were 80% CD8+, and the CD4-selected cells were 85% CD4+. In 2 subsequent experiments (Example 43B), the CD8+ purified cells were 84% and 81% pure, and the CD4+ cells were 85% and 97% pure, respectively. In one experiment, we stained the non-binding (flow-through) cells with anti-human CD19-coated beads (Miltenyi) and ran them over a third magnetic bead column to isolate CD19+ B cells (these were 92% pure).

The human CD8+, CD4+ and CD19+ selected cells were activated by incubating 0.5×106 cells/ml in RPMI+5% human ultraserum (Gemini Bioproducts, Calabasas, Calif.)+ PMA 10 ng/ml and Ionomycin 0.5 μg/ml (Calbiochem) for about 4, 16, or 24 hours at 37° C. The T-cells ($2.5 \times 10^6$/well) were alternately stimulated in 24-well plates pre-coated overnight with 0.5 μg/ml plate-bound anti-CD3 mAb UCHT1 (PharMingen) with or without soluble anti-CD28 mAb (PharMingen) at 5 μg/ml. At each timepoint, the cells were harvested, pelleted, washed once with PBS, and pelleted again. The supernatant was removed and the pellets were snap-frozen in a dry ice/ethanol bath, then stored at −80° C. for RNA preparation at a later date.

Real Time-PCR was performed on these human CD8+, CD4+ and CD19+ selected cells as described in Example 43B and 43C below for assessing human zalpha11 Ligand and receptor expression.

B. Primers and Probes for Quantitative RT-PCR for Human Zalpha11 Ligand Expression Real-time quantitative RT-PCR using the ABI PRISM 7700 Sequence Detection System (PE Applied Biosystems, Inc., Foster City, Calif.) has been previously described (see, Heid, C A et al., *Genome Research* 6:986-994, 1996; Gibson, U E M et al., *Genome Research* 6: 995-1001, 1996; and Sundaresan, S et al., *Endocrinology* 139:4756-4764, 1998). This method incorporates use of a gene specific probe containing both reporter and quencher dyes. When the probe is intact the reporter dye emission is negated due to the proximity of the quencher dye. During PCR extension using additional gene-specific forward and reverse primers, the probe is cleaved by 5' nuclease activity of Taq polymerase which releases the reporter dye resulting in an increase in fluorescent emission.

The primers and probes used for real-time quantitative RT-PCR analyses were designed using the primer design software Primer Express™ (PE Applied Biosystems). Primers for human zalpha11 Ligand were designed spanning an intron-exon junction to eliminate amplification of genomic DNA. The forward primer, ZC22,281 (SEQ ID NO:90) and the reverse primer, ZC22,279 (SEQ ID NO:91) were both used at 300 nM concentration to synthesize an 80 bp product. The corresponding zalpha11 Ligand TaqMan probe, ZG32 (SEQ ID NO:92) was synthesized by PE Applied Biosystems. The probe was labeled with a reporter fluorescent dye (6-carboxy-fluorescein) (FAM) (PE Applied Biosystems) at the 5' end and a quencher fluorescent dye (6-carboxy-tetramethyl-rhodamine) (TAMRA) (PE Applied Biosystems) at the 3' end. In order to test the integrity or quality of all the RNA samples, they were screened for rRNA using the primer and probe set ordered from PE Applied Biosystems (cat No. 4304483). The reporter fluorescent dye for this probe is VIC (PE Applied Biosystems). The rRNA results will allow for the normalization of the zalpha11 Ligand results.

RNA was prepared from pellets provided in Example 43A, using total RNA isolation kit RNEASY® MINI (Qiagen, Valencia, Calif.) per the manufacturer's instructions. Control RNA was prepared from about 10 million BHK cells expressing human zalpha11 Ligand.

C. Primers and Probes for Quantitative RT-PCR for Human Zalpha11 Receptor Expression Real time PCR was performed to assess the expression of zalpha11 receptor as per Example 43B and Example 43D, using the cells prepared under the conditions detailed in 43A, and probes specific for the zalpha11 receptor. The forward primer, ZC22,277 (SEQ ID NO:93) and the reverse primer, ZC22,276 (SEQ ID NO:94) were used in a PCR reaction (above) at about 300 nM concentration to synthesize a 143 bp product. The corresponding zalpha11 TaqMan® probe, designated ZG31 (SEQ ID NO:95) was synthesized and labeled by PE Applied Biosystems. RNA from BaF3 cells expressing human zalpha11 receptor was used to generate appropriate control for standard curves for the real-time PCR described in Example 43D below.

D. Real-Time Quantitative RT-PCR

Relative levels of zalpha11 Ligand RNA were determined by analysis of total RNA samples using the One-Step RT-PCR method (PE Applied Biosystems). RNA from BHK cells expressing human zalpha11 Ligand was used to generate a standard curve. The curve consisted of serial dilutions ranging from 2.5-2.5×10−4 ng for the rRNA screen and 25-0.0025 ng for the zalpha11 Ligand screen with each point analyzed in triplicate. The total RNA samples were also analyzed in triplicate for human zalpha11 Ligand transcript levels and for levels of rRNA as an endogenous control. Each One-step RT-PCR reaction consisted of 25 ng of total RNA in buffer A (50 mM KCL, 10 mM Tris-HCL, and the internal standard dye, ROX (PE Applied Biosystems)), appropriate primers (50 nM for rRNA samples, 300 nM for zalpha11 Ligand samples) and probe (50 nM for rRNA, 100 nM for zalpha11 Ligand), 5.5 mM MgCl2, 300 µM each d-CTP, d-ATP, and d-GTP and 600 µM of d-UTP, reverse transcriptase (0.25 U/µl), AmpliTaq DNA polymerase (0.025 U/µl) and RNase Inhibitor (0.4 U/µl) in a total volume of 25 µl. Thermal cycling conditions consisted of an initial RT step at 48° C. for 30 minutes, an AmpliTaq Gold activation step of 95° C. for 10 minutes, followed by 40 cycles of amplification for 15 seconds at 95° C. and 1 minute at 60° C. Relative zalpha11 Ligand RNA levels were determined by the Standard Curve Method as described in User Bulletin No. 2 (PE Biosystems; User Bulletin #2: ABI Prism 7700 Sequence Detection System, Relative Quantitation of Gene Expression, Dec. 11, 1997) using the rRNA measurements to normalize the zalpha11 Ligand levels. Samples were compared relative to the calibrator within each experiment. The calibrator was arbitrarily chosen based on good quality RNA and an expression level to which other samples could significantly be compared. Results of the experiments analyzing the expression of the zalpha11 Ligand and zalpha receptor in stimulated and unstimulated cells (Example 43A) are as described in Example 43E below.

E. Expression of Human Zalpha11 Receptor and Ligand in CD4+, CD8+ and CD19+ Cells The first experiment used RT-PCR, described above, to assess zalpha11 receptor expression in unstimulated and anti-CD3 stimulated CD4+ and CD8+ samples at timepoints of 0 h (unstimulated ("resting") cells), and at 4 h, 15.5 h and 24 h, after stimulation. The resting CD4+ sample was arbitrarily chosen as the calibrator and given a value of 1.00. There was approximately a 4-fold increase in receptor expression in unstimulated CD4+ cells from 4 h to 24 h of culture and about an 8-fold increase over the same time period in anti-CD3 stimulated CD4+ cells. The CD8+ cells showed a 7-fold increase in zalpha11 receptor expression that peaked at 4 hrs and decreased over time. With anti-CD3 stimulation, the CD8+ cells had a constant 8-fold increase in receptor expression.

This first experiment also used RT-PCR to assess zalpha11 Ligand expression in the same anti-CD3 stimulated and unstimulated CD4+ and CD8+ samples. The 4 hr anti-CD3 stimulated CD8+ sample was arbitrarily chosen as the calibrator and given a value of 1.00. The results showed that unstimulated CD4+ and CD8+ cells do not express zalpha11 Ligand. We observed a significant elevation of expression in the anti-CD3 stimulated CD4+ cells at 4 h, with about a 300-fold increase in signal observed at 15.5 h. The CD8+ cells expressed a small amount of ligand upon anti-CD3 stimulation, however this is probably due to contamination of the CD8+ population with a small number of CD4+ cells.

The second experiment used RT-PCR to assess zalpha11 receptor expression in anti-CD3-stimulated, PMA+Ionomycin-stimulated and unstimulated CD4+ and CD8+ samples at timepoints of 0 h, and at 3.5 h, 16 h and 24 h after activation. The resting CD8+ sample was arbitrarily chosen as the calibrator and given a value of 1.00. The resting CD4+ and CD8+ cells did not have significant amounts of receptor expression. The expression was about 3 fold higher in the PMA+Ionomycin-stimulated CD4+ samples at 3.5 h, 16 h and 24 h after stimulation. The expression in anti-CD3 activated CD4+ cells peaked at 10-fold above background levels at 3.5 h after stimulation, then fell back to levels 4-fold above background at 16 h after stimulation. The CD8+ cells showed a 4-fold expression increase at 3.5 h after PMA+Ionomycin stimulation, with expression decreasing at subsequent timepoints. As in the first experiment, the anti-CD3 stimulated CD8+ cells again exhibited an 8-fold above background induction of receptor expression.

These samples from the second experiment were also used to assess zalpha11 Ligand expression. The 24 hr PMA+Ionomycin stimulated CD4+ sample was arbitrarily chosen as the calibrator and given a value of 1.00. The results showed that again none of the unstimulated cells expressed zalpha11 Ligand. There was about a 30-fold induction of ligand expression in the CD4+ cells stimulated with anti-CD3 at 3.5 h, as seen in the previous experiment (at 4 h). However, there was only about a 5-fold induction with PMA+Ionomycin stimulation at 3.5 h that went down at subsequent timepoints. Again, the CD8+ cells expressed a very small amount of Ligand that was probably attributed to contaminating CD4+ cells.

The final experiment used RT-PCR to assess zalpha11 receptor expression in anti-CD3- and anti-CD3/anti-CD28-stimulated and unstimulated CD4+ and CD8+ samples at timepoints of 0 h, and at 2 h, 4 h, and 16 h after stimulation. CD19+ cells activated with PMA+Ionomycin were also screened for receptor expression at the same time intervals. The resting CD4+ sample was arbitrarily chosen as the calibrator and given a value of 1.00. The 2 h anti-CD3 stimulated CD4+ cells only had a 4-fold induction of receptor, compared to the 10-fold induction seen at 3.5 h in the previous experiment. The combination of anti-CD3 and anti-CD28 increased zalpha11 receptor expression to 8-fold above background. The 16 h anti-CD3/anti-CD28 stimulated CD8+ cells had very low zalpha11 receptor expression levels, as seen in the CD8+ cells in previous experiments (above). The CD19+ cells stimulated with PMA+Ionomycin had the most significant zalpha11 receptor expression with a 19-fold increase at 2 h, but the expression levels decreased back to those of resting cells by 16 h.

These samples from the final experiment were also used to assess zalpha11 Ligand by RT-PCR. The 16 h anti-CD3/anti-CD28 stimulated CD8+ sample was arbitrarily chosen as the calibrator and given a value of 1.00. The results showed that at 2 h the CD4+ cells had about a 2-fold induction of zalpha11 Ligand expression with anti-CD3 stimulation and a 5-fold induction with anti-CD3 plus anti-CD28 stimulation. These stimulation conditions induced Ligand expression over time, with the 16 h stimulated CD4+ cells exhibiting Ligand expression levels 70-fold above background. CD8+ and CD19+ cells showed no zalpha11 Ligand expression.

A certain amount of variation was expected between blood draws (i.e. multiple samples at different times from the same patient and between multiple patients). Therefore, data trends were analyzed within each study or from a single blood sample and the three experiments above were compared for an overall conclusion. The trend from the Real Time PCR experiments described above is that of all the cell types tested, CD19+ B cells activated with PMA+ ionomycin expressed the highest levels of zalpha11 receptor RNA. CD4+ and CD8+ cells can also be stimulated to express receptor, but at lower levels than in B cells. Zalpha11 Ligand was expressed almost exclusively in stimulated CD4+ T cells (and not by CD8+ T cells or CD19+ B cells). Although stimulation with PMA+Ionomycin induced a good zalpha11 Ligand signal in this assay, a significantly higher signal was obtained from CD4+ T cells stimulated with anti-CD3 mAb or a combination of anti-CD3 and anti-CD28 mAbs, conditions that better mimic an antigen encounter in vivo.

Example 44

Zalpha11 Ligand-Dependent Proliferation of B-Cell Cells Stimulated Anti-CD40 or Anti-IgM A. Purification of Human B Cells A vial containing 1×10$^8$ frozen, apheresed human peripheral blood mononuclear cells (PBMCs) was quickly thawed in a 37° C. water bath and resuspended in 25 ml B cell medium (RPMI Medium 1640 (JRH Biosciences. Lenexa, Kans.), 10% Heat inactivated fetal bovine serum, 5% L-glutamine, 5% Pen/Strep) (Gibco BRL)) in a 50 ml tube (Falcon VWR, Seattle, Wash.). Cells were tested for viability using Trypan Blue (Gibco BRL). Ten milliliters of Ficoll/Hypaque Plus (Pharmacia LKB Biotechnology Inc., Piscataway, N.J.) was layered under the cell suspension and spun for 30 minutes at 1800 rpm and allowed to stop with the brake off. The interface was then removed and transferred to a fresh 50 ml Falcon tube, brought up to a final volume of 40 ml with PBS and spun for 10 minutes at 1200 rpm with the brake on. The viability of the isolated cells was again tested using Trypan Blue. Alternately fresh drawn human blood was diluted 1:1 with PBS (Gibco BRL) and layered over Ficoll/Hypaque Plus (Pharmacia), spun and washed as above. Cells isolated from either fresh or frozen sources gave equivalent results.

B cells were purified from the Ficoll floated peripheral blood cells of normal human donors (above) with anti-CD19 magnetic beads (Miltenyi Biotec, Auburn, Calif.) following the manufacturer's instructions. The purity of the resulting preparations was monitored by flow cytometric analysis with anti-CD22 FITC Ab (Pharmingen, San Diego, Calif.). B cell preparations were typically >90% pure.

B. Purification of Murine B Cells

A suspension of murine splenocytes was prepared by teasing adult C57B1/6 mouse (Charles River Laboratories, Wilmington, Mass.) spleens apart with bent needles in B cell medium. RBCs were removed by hypotonic lysis. CD43 positive cells were removed with CD43 magnetic beads (Miltenyi Biotec) following the manufacturer's instructions. The purity of the resulting preparations was monitored by flow cytometric analysis with anti-CD45R FITC Ab (Pharmingen). B cell preparations were typically >90% pure.

C. Proliferation of Anti-CD40-Stimulated B-Cells in the Presence of Human or Murine Zalpha11 Ligand The B cells from either the human or mouse source were resuspended at a final concentration of 1×10$^6$ cells/ml in B cell medium and plated at 100 µl/well in a 96 well U bottom plate (Falcon, VWR) containing various stimulation conditions to bring the final volume to 200 µl/well. For anti-CD40 stimulation human cultures were supplemented with 1 µg/ml anti-human CD40 (Genzyme, Cambridge, Mass.) and mouse cultures were supplemented with 1 µg/ml anti-murine CD40 (Serotec, UK). Human or murine zalpha11 Ligand was added at dilutions ranging from 1 µg/ml-100 ng/ml. The specificity of the effect of zalpha11 Ligand was confirmed by inhibition of zalpha11 Ligand with 25 mg/ml soluble human zalpha11CEE (Example 10A). All treatments were performed in triplicate. The cells were then incubated at 37° C. in a humidified incubator for 120 hours (human) or 72 hours (mouse). Sixteen hours prior to harvesting, 1 µCi 3H-thymidine (Amersham, Piscataway, N.J.) was added to all wells to assess whether the B-cells had proliferated. The cells were harvested into a 96 well filter plate (UniFilter GF/C, Packard, Meriden, Conn.) using a cell harvester (Packard) and collected according to manufacturer's instructions. The plates were dried at 55° C. for 20-30 minutes and the bottom of the wells were sealed with an opaque plate sealer. To each well was added 0.25 ml of scintillation fluid (Microscint-O, Packard) and the plate was read using a TopCount Microplate Scintillation Counter (Packard).

Incubation with Zalpha11 Ligand at concentrations of 3 ng/ml or more enhanced the proliferation induced by soluble anti-CD40 in a dose dependent manner in both murine and human B cells by as much as 30 fold. The murine and human B cells responded equally as well to their respective zalpha11 Ligand. In both species, the stimulation was specific to zalpha11 Ligand, as it was reversed by the presence of soluble zalpha11 receptor in the culture.

D. Proliferation of Anti-IgM-Stimulated B-Cells in the Presence of Human or Murine Zalpha11 Ligand The B cells from either human or mouse source as described above (Example 44A and Example 44B) were plated as described above (Example 44C). For anti-IgM stimulation of human cells the plates were pre-coated overnight with 10 mg/ml F(ab')2 anti-human IgM Abs (Southern Biotech Associates, Birmingham, Ala.) and washed with sterile media just prior to use. The cultures were supplemented with 0-10 ng/ml hu rIL-4 (R&D Systems, Minneapolis, Minn.). For anti-IgM stimulation of murine cells soluble anti-IgM (Biosource, Camarillo, Calif.) was added to the cultures at 10 mg/ml. To each of the preceding anti-IgM/IL-4 conditions, human or murine Zalpha11 ligand was added at dilutions ranging from 1 pg/ml-100 ng/ml as described above. The specificity of the effect of zalpha11 Ligand was confirmed by inhibition with soluble human zalpha11 receptor as described above (Example 44C). All treatments were performed in triplicate. The cells were incubated, labeled with 3H-thymidine, harvested, and analyzed as described in Example 44C.

Incubation with Zalpha11 ligand at concentrations of 0.3 ng/ml or more inhibited the proliferation induced by insoluble anti-IgM (mouse) or anti-IgM and IL-4 (human) in a dose-dependent manner. This inhibition was specific to zalpha11 Ligand, as it was reversed by the presence of soluble zalpha11 receptor in the culture.

Example 45

Expression of Human Zalpha11 Soluble Receptor in *E. coli*

A. Construction of Expression Vector pCZR225 that Expresses Huzalpha11/MBP-6H Fusion Polypeptide An expression plasmid containing a polynucleotide encoding a human zalpha11 soluble receptor fused C-terminally to maltose binding protein (MBP) was constructed via homologous recombination. A fragment of human zalpha11 cDNA (SEQ ID NO:7) was isolated using PCR. The polynucleotide sequence for the MBP-zalpha11 soluble receptor fusion polypeptide is shown in SEQ ID NO:96. Two primers were used in the production of the human zalpha11 fragment in a PCR reaction: (1) Primer ZC20,187 (SEQ ID NO:98), containing 40 bp of the vector flanking sequence and 25 bp corresponding to the amino terminus of the human zalpha11, and (2) primer ZC20,185 (SEQ ID NO:99), containing 40 bp of the 3' end corresponding to the flanking vector sequence and 25 bp corresponding to the carboxyl terminus of the human zalpha11. The PCR Reaction conditions were as follows: 25 cycles of 94° C. for 30 seconds, 50° C. for 30 seconds, and 72° C. for 1 minute; followed by 4° C. soak, run in duplicate. Two μl of the 100 μl PCR reaction was run on a 1.0% agarose gel with 1×TBE buffer for analysis, and the expected approximately 660 bp fragment was seen. The remaining 90 μl of PCR reaction was combined with the second PCR tube precipitated with 400 μl of absolute ethanol. The precipitated DNA used for recombining into the SmaI cut recipient vector pTAP98 (Example 31) to produce the construct encoding the MBP-zalpha11 fusion. Clones were transformed, identified and grown up as described in Example 31. The positive clones were designated pCZR225 and subjected to sequence analysis. The polynucleotide sequence for the MBP-zalpha11 soluble receptor fusion polypeptide is shown in SEQ ID NO:96, and corresponding polypeptide sequence is shown in SEQ ID NO:97. The positive clones were used to grow up in *E. coli* as described in Example 31 for protein purification of the huzalpha11/MBP-6H fusion protein (Example 46, below).

Example 46

Purification of Huzalpha11/MBP-6H Soluble Receptor from *E. coli* Fermentation

Unless otherwise noted, all operations were carried out at 4° C. The following procedure was used for purifying huzalpha11/MBP-6H soluble receptor polypeptide. *E. coli* cells containing the pCZR225 construct and expressing huzalpha11/MBP-6H soluble receptor (Example 45) were grown up in SuperBroth II (12 g/L Casein, 24 g/L Yeast Extract, 11.4 g/L di-potassium phosphate, 1.7 g/L Mono-potassium phosphate; Becton Dickenson, Cockeysville, Md.), and frozen in 0.5% glycerol. Twenty grams of the frozen cells in SuperBroth II+Glycerol were used to purify the protein. The frozen cells were thawed and diluted 1:10 in a protease inhibitor solution (Extraction buffer) prior to lysing the cells and releasing the huzalpha11/MBP-6H soluble receptor protein. The diluted cells contained final concentrations of 20 mM Tris (JT Baker, Philipsburg, N.J.) 100 mM Sodium Chloride (NaCl, Mallinkrodt, Paris, Ky.), 0.5 mM phenylmethylsulfonyl fluoride (PMSF, Sigma Chemical Co., St. Louis, Mo.), 2 μg/ml Leupeptin (Fluka, Switzerland), and 2 μg/ml Aprotinin (Sigma). A French Press cell breaking system (Constant Systems Ltd., Warwick, UK) with temperature of −7 to −10° C. and 30K PSI was used to lyse the cells. The diluted cells were checked for breakage by A600 readings before and after the French Press. The lysed cells were centrifuged at 18,000 G for 45 minutes to remove the broken cell debris, and the supernatant used to purify the protein. Total target protein concentrations of the supernatant was determined via BCA Protein Assay (Pierce, Rockford, Ill.), according to manufacturer's instructions.

A 25 ml column of Talon Metal Affinity resin (Clontech, Palo Alto, Calif.) (prepared as described below) was poured in a Bio-Rad, 2.5 cm D×10 cm H glass column. The column was packed and equilibrated by gravity with 10 column volumes (CVs) of Talon Equilibration buffer (20 mM Tris, 100 mM NaCl, pH 8.0). The supernatant was batch loaded to Talon metal affinity resin and was rocked overnight. The resin was poured back into the column and was washed with 10 CV's of Talon Equilibration buffer by gravity, then gravity eluted with 140 ml of Elution buffer (Talon Equilibration buffer+200 mM Imidazole-Fluka Chemical). The talon column was cleaned with 5 CVs of 20 mM 2-(N-Morhpholino) ethanesulfonic acid pH 5.0 (MES, Sigma), 5 CVs of distilled H2O, then stored in 20% Ethanol/0.1% Sodium Azide. Fourteen ml fractions were collected over the entire elution chromatography and the fractions were read with absorbance at 280 and 320 nM and BCA protein assay; the pass through and wash pools were also saved and analyzed. The protein elution fractions of interest were pooled and loaded straight to Amylose resin (New England Biolabs, Beverly, Mass.).

To obtain more pure huzalpha11/MBP-6H polypeptide, the talon affinity elution pooled fractions were subjected to Amylose resin (22 mls) at pH 7.4. A 2.5 cm D×10 cm H Bio-Rad column was poured, packed and equilibrated in 10 CVs of Amylose equilibration buffer-20 mM Tris (JT Baker), 100 mM NaCl (Mallinkrodt), 1 mM PMSF (Sigma), 10 mM beta-Mercaptoethanol (BME, ICN Biomedicals Inc., Aurora, Ohio) pH 7.4. The sample was loaded by gravity flow rate of 0.5 ml/min. The column was washed for 10 CVs with Amylose equilibration buffer, then eluted with about 2 CV of Amylose equilibration buffer+10 mM Maltose (Fluka Biochemical, Switzerland) by gravity. 5 ml fractions were collected over the entire chromatography and absorbance at 280 and 320 nM were read. The Amylose column was regenerated with 1 CV of distilled $H_2O$, 5 CVs of 0.1% (w/v) SDS (Sigma), 5 CVs of distilled H2O, and then 5 CVs of Amylose equilibration buffer.

Fractions of interest were pooled and dialyzed in a Slide-A-Lyzer (Pierce) with 4×4 L PBS pH 7.4 (Sigma) to remove low molecular weight contaminants, buffer exchange and desalt. After the changes of PBS, the material harvested represented the purified huzalpha11/MBP-6H polypeptide. The purified huzalpha11/MBP-6H polypeptide was analyzed via SDS-PAGE Coomassie staining and Western blot analysis with the anti-rabbit HRP conjugated antibody (Rockland, Gilbertsville, Pa.). The concentration of the huzalpha11/MBP-6H polypeptide was 1.92 mg/ml as determined by BCA analysis.

Purified huzalpha11/MBP-6H polypeptide was prepared for injection into rabbits and sent to R & R Research and Development (Stanwood, Wash.) for antibody production. Rabbits were injected to produce anti anti-huzalpha11/MBP-6H serum (Example 47, below).

Example 47

Zalpha11 Receptor Polyclonal Antibodies

Polyclonal antibodies were prepared by immunizing two female New Zealand white rabbits with the purified huzalpha11/MBP-6H polypeptide (Example 46), or the purified recombinant zalpha11CEE soluble receptor (Example 110A). Corresponding polyclonal antibodies were designated rabbit anti-huzalpha11/MBP-6H and rabbit anti-huzalpha11-CEE-BHK respectively. The rabbits were each given an initial intraperitoneal (IP) injection of 200 mg of purified protein in Complete Freund's Adjuvant (Pierce, Rockford, Ill.) followed by booster IP injections of 100 mg purified protein in Incomplete Freund's Adjuvant every three weeks. Seven to ten days after the administration of the third booster injection, the animals were bled and the serum was collected. The rabbits were then boosted and bled every three weeks.

The zalpha11-specific polyclonal antibodies were affinity purified from the rabbit serum using an CNBr-SEPHAROSE 4B protein column (Pharmacia LKB) that was prepared using 10 mg of the purified huzalpha11/MBP-6H polypeptide (Example 32) per gram CNBr-SEPHAROSE, followed by 20× dialysis in PBS overnight. Zalpha11-specific antibodies were characterized by an ELISA titer check using 1 mg/ml of the appropriate protein antigen as an antibody target. The lower limit of detection (LLD) of the rabbit anti-huzalpha11/MBP-6H affinity purified antibody is a dilution of 500 pg/ml. The LLD of the rabbit anti-huzalpha11-CEE-BHK affinity purified antibody is a dilution of 50 pg/ml.

Example 48

Zalpha11 Receptor Distribution

To assess zalpha11 receptor distribution on various cells types, we generated both rabbit polyclonal and mouse monoclonal antibodies (mAbs) directed against the human receptor (Example 35 and Example 47) and conjugated these antibodies to biotin for use in flow cytometry. We initially used the polyclonal antibodies, which were of relatively low affinity, to stain a panel of cell lines: IL-3 dependent murine pre-B cell line wild-type BaF3 cells (Palacios and Steinmetz, ibid.; Mathey-Prevot et al., ibid.); BaF3 cells transfected with human zalpha11 (Example 4); human Burkitt's lymphoma cell lines Raji (ATCC No. CCL-86), Ramos (ATCC No. CRL-1596), RPMI 8226 (ATCC No. CCL-155), and Daudi (ATCC No. CCL-213); human T cell leukemia cell line Jurkat (ATCC No. TIB-152); human myelomonocytic leukemia cell lines Thp-1 (ATCC No. TIB-202) and UT937 (ATCC No. CRL-1593.2); human pro-myelomonocytic cells HLT60 (ATCC No. CCL-240); murine B cell lymphoma cell line A20 (ATCC No TIB-208); and murine thymoma cell line EL4 (ATCC No. TIB-39).

The cells were harvested, washed once with FACS wash buffer with serum (WBS). WBS consisted of Hank's balanced salt solution (Gibco/BRL)+10 mM HEPES (Gibco/BRL)+1% BSA (Sigma)+10% normal goat serum (Gemini Bioproducts, Woodland, Calif.)+10% normal rabbit serum (Sigma). Wash buffer (WB) was identical to WBS except that it was serum free. After washing, the cells were resuspended in 100 µl WB containing 10 µg/ml rabbit anti-zalpha11 polyclonal antibodies (Example 47). The cells were kept on ice with Ab for 20 min, then washed with WB and resuspended in WB containing goat anti-rabbit-FITC (BioSource, International), incubated another 20 min on ice, then washed and resuspended in 400 µl WB for analysis on a flow cytometer FACSCALIBUR™ flow cytometer (Becton Dickinson). Control samples were stained with the secondary goat anti-rabbit-FITC Ab only. Positive staining was defined as a shift above the staining with secondary alone. Although the polyclonal antibodies were of low affinity, we confidently detected zalpha11 expression on the BaF3/zalpha11 transfectant, on all four human Burkitt's lymphomas (Raji, Ramos, Daudi, and RPMI 8226), and on Jurkat T cells. Resting (undifferentiated) HL-60 cells did not bind the anti-zalpha11 antibodies, but we did detect a positive signal on HL-60 cells activated for 24 hours with PMA (Calbiochem, La Jolla, Calif.) which induces HL-60 cell differentiation into a monocyte-like cell. We also saw a positive signal on UT937 and Thp-1 cells, although this signal may have been due to non-specific binding. The polyclonal antibodies weakly cross-reacted on the mouse B cell line A20, but we saw no staining of the EL4 murine thymoma.

The four anti-zalpha11 monoclonal antibodies (Example 35) were conjugated to biotin, and a subset of the cells described above were screened for zalpha11 receptor expression (BaF3, BaF3/zalpha11, Raji, Jurkat, and resting HL-60). Cells were harvested, washed, then resuspended in 100 µl WB containing 15 µg/ml of one of each of the 4 biotinylated mAbs. The cells were incubated with mAb for 20 min on ice, then washed with 1.5 ml WB and pelleted in a centrifuge. The supernatant was removed by aspiration and the pellets were resuspended in 100 µl of CyChrome-conjugated streptavidin (CyC-SA; PharMingen), then incubated on ice for another 20 min and washed and pelleted as before. Control tubes contained cells stained only with CyC-SA. Pellets were resuspended in 400 µl WB and flow cytometry performed as above. Positive staining was defined as a signal exceeding the background level of staining with CyC-SA alone. Using the BaF3/zalpha11 transfectant as a control, we were able to rank the 4 mAbs in terms of their respective mean fluorescence intensities (MFI), which can reflect antibody affinity and/or the extent of biotinylation of the mAbs. The mAbs were ranked as follows, from highest to lowest MFI: 249.28.2.1.2.2, 247.10.2.15.4.6, 249.19.2.2.3.5, and 249.15.2.4.2.7. The Raji cells stained positive with the zalpha11 monoclonal antibodies. The Jurkats cells positively stained with the zalpha11 monoclonal antibodies, but not as strongly as that on B cells (Raji). Thus the, zalpha11 receptor was expressed on these B and T cell lines. The staining patterns on non-activated HL60 cells were identical for all the mAbs, and the signal was very weak. We believe that this signal does not reflect actual expression of zalpha11 by HL-60 cells, but rather may be due to non-specific binding of the mouse mAbs to the human cells, probably via Fc-receptors.

Example 49

Human Zalpha11 Ligand Effect on B-Cells and Zalpha11 Ligand Toxic Saporin Fusion The effects of human zalpha11 Ligand were tested on the following human B-cell lines: and human Burkitt's lymphoma cell lines Raji (ATCC No. CCL-86), and Ramos (ATCC No. CRL-1596); human EBV B-cell lymphoma cell line RPMI 1788 (ATCC No. CRL-156); human myeloma/plasmacytoma cell line IM-9 (ATCC No. CRL159); and human EBV transformed B-cell line DAKIKI (ATCC No. TIB-206), and HS Sultan cells (ATCC No. CRL-1484). Following about 2-5 days treatment with zalpha11 Ligand, changes in surface marker expression were found in IM-9, Raji, Ramos, and RPMI1788 cell lines, showing that these cells can respond to zalpha11 Ligand. Human B-cell lines treated with zalpha11 Ligand grew much more slowly than untreated cells when re-plated in cell culture dishes. These cells also had an increased expression of FAS ligand, as assessed by flow cytometry (Example 49D and Example 49E), and moderately increased sensitivity to an activating FAS antibody (Example 49A). This results indicate that zalpha11 Ligand could control some types of B-cell neoplasms by inducing them to differentiate to a less proliferative and or more FAS ligand sensitive state. Moreover, zalpha11 receptor is expressed on the surface of several of these cell lines (See Example 48). Thus, zalpha11 Ligand and the human zalpha11 Ligand-saporin immunotoxin conjugate (Example 49B, below), or other zalpha11 Ligand-toxin fusion could be therapeutically used in B-cell leukemias and lymphomas.

A. The Effect of Human Zalpha11 Ligand on B-Cell Lines.

IM-9 cells were seeded at about 50,000 cells per ml+/-50 µg/ml purified human zalpha11 Ligand (Example 29). After 3 days growth the cells were harvested, washed and counted then re-plated at about 2500 cells/ml in 96 well plates in to wells with 0, 0.033, 0.1 or 0.33 µg/ml anti-FAS antibody (R&D Systems, Minneapolis). After 2 days an ALAMAR Blue™ fluorescence assay was performed (Example 2B) to assess proliferation of the cells.

Zalpha11 Ligand-treated IM-9 cells grew to only 27% the density of the untreated cells in the absence of anti-FAS antibody. In the presence of 0.33 µg/ml anti-FAS antibody, the zalpha11 Ligand-treated cells were inhibited an additional 52% while the untreated cells were inhibited by only 30%. The overall inhibition of cell growth with both zalpha11 Ligand and 0.33 µg/ml anti-FAS antibody treatment was 86%.

When the IM-9 cells were pretreated for three days with or without zalpha11 Ligand and then re-plated at 100 cells per well and grown with or without anti-FAS antibody for 6 days, the growth of untreated cells assessed by ALAMAR BLUE™ assay (Example 2B) was inhibited only 25% by anti-FAS antibody while the growth of zalpha11 Ligand-treated cells was inhibited 95% relative to the growth of untreated cells in zero anti-FAS antibody.

B. The Effect of Human Zalpha11 Ligand-Saporin Immunotoxin on B-Cell Lines.

The human zalpha11 Ligand-saporin immunotoxin conjugate (zalpha11L-sap) construction and purification is described in Example 50. The human zalpha11L-sap was far more potent than the saporin alone in inhibiting cell growth. When the treated cell are re-plated after a three or four day treatment the human zalpha11L-sap treated cells grew very poorly.

IM-9, Ramos and K562 (ATCC No. CCL-243) cells were seeded at about 2500 cells/well in 96 well plates with zero to 250 ng/ml human zalpha11L-sap conjugate or 0-250 ng/ml saporin (Stirpe et al., Biotechnology 10:405-412, 1992) only as a control. The plates were incubated 4 days then an ALAMAR BLUE™ proliferation assay was performed (Example 5B). At the maximal concentration of human zalpha11-sap conjugate, the growth of IM-9 cells and RAMOS cells was inhibited by 79% and 65% respectively. K562 cells which are low/negative by flow for expression of the zalpha11 receptor were not affected by the zalpha11-sap, thus showing the specificity of the conjugate's effect.

IM-9 cells were seeded a 50,000 cells/ml into 6 well plates at zero and 50 ng/ml human zalpha11L-sap conjugate. After 3 days the cells were harvested and counted then re-plated from 100 to 0.8 cells per well in 2 fold serial dilutions, and 12 wells per cell dilution without the human zalpha11 Ligand-saporin immunotoxin. After 6 days the number of wells with growth at each cell dilution was scored according to the results of an ALAMAR BLUE™ proliferation assay (Example 2B).

When cell number was assessed, by ALAMAR BLUE™ assay (Example 2B), after 6 days of growth control cells seeded at about 12.5 and 6.25 cells per well had equivalent growth to zalpha11-sap treated cells seeded at 100 and 50 cells/well respectively. Thus, the growth of the surviving treated IM-9 cells was markedly impaired even after the removal, by re-plating, of the zalpha11-sap immunotoxin.

The limited tissue distribution of the human zalpha11 receptor (Example 48), and the specificity of action of the zalpha11-sap to receptor-expressing cell lines suggest that this conjugate may be tolerated in vivo.

C. The Effect of Human Zalpha11 Ligand-Saporin Immunotoxin on B-Cell Line Viability.

HS Sultan cells (ATCC No. CRL-1484) were seeded at about 40,000 cells per ml into 12 well plates and grown for five days with either no added cytokines or 40 ng/ml purified human zalpha11 Ligand (Example 29) or 25 ng/ml human zalpha11L-sap conjugate (Example 50, below) or with 20 ng/ml IFN-alpha (RDI) or zalpha11 Ligand and IFN-alpha. Zalpha11 ligand inhibited the outgrowth of Hs Sultan cells by 63%. IFN-alpha inhibited the growth by 38%. Zalpha11 ligand plus IFN-alpha inhibited growth 78%, indicating that the growth inhibitory effects of human zalpha11 Ligand and IFN-alpha may be additive. The human zalpha11L-sap inhibited growth of the HS Sultans by 92%.

The results above support the possible use of zalpha11 Ligand or human zalpha11L-sap in the treatment of malignancies or other diseases that express the zalpha11 receptor, particularly those of B-cell origin. The combination of zalpha11 Ligand with IFN-alpha is specifically suggested by their additive effect in the inhibition of HS Sultan cells. Some other types of lymphoid malignancies and diseases may also express the zalpha11 receptor, as activated T-cells also express the receptor mRNA (Example 48), and some of these diseases may also be responsive to zalpha11 Ligand of zalpha11 Ligand-toxic fusion therapy.

D. FAS (CD95) Expression on Human B-Cell Lines is Increased by Human Zalpha11 Ligand Stimulation Human B-cell lines HS Sultan (ATCC No. CRL-1484), IM-9 (ATCC No. CRL159), RPMI 8226 (ATCC No. CCL-155), RAMOS (ATCC No. CRL-1596), DAKIKI (ATCC No. TIB-206), and RPMI 1788 (ATCC No. CRL-156), were all treated with or without purified 10 to 50 ng/ml human zalpha11 Ligand (Example 29) for 2 to 8 days. The cells were then stained with anti-CD95 PE-conjugated antibody (PharMingen, San Diego, Calif.), per manufacturer's protocol, and analyzed on a flow cytometer FACSCALIBUR™ (Becton Dickinson, San Jose, Calif.). In all cell lines, anti-CD95 (FAS or APO-1) staining was increased, in some cases more than two fold, upon treatment with human zalpha11 Ligand.

E. FAS (CD95) Expression on Primary Mouse Spleen B-Cells is Increased by Human Zalpha11 Ligand Stimulation Primary mouse splenocytes were obtained by chopping up spleens from 8 to 12 week old C57/BL6 mice. Erythrocytes were lysed by treating the preparation for 5 seconds with water then put through a 70 micron sieve. The remaining splenocytes were washed and plated in RPMI (JRH Bioscience) plus 10% HIA-FBS (Hyclone, Logan, Utah). Interleukin 2 (IL-2) (R and D Systems) with or without human zalpha11 Ligand, as described above. They were then incubated at 37° C., in 5% CO2 for 5 days. The splenocytes were harvested and stained with anti-CD95 PE conjugated antibody (PharMingen) and anti-CD19 FITC conjugated antibody (PharMingen) per manufacturer's protocol. The cells were analyzed by flow cytometry on a flow cytometer FACSCALIBUR™ (Becton Dickinson). Upon gating on the CD19+ mouse B-cells, it was found that anti-CD95 staining was increased on B-cells treated with IL-2 plus human zalpha11 Ligand compared to those in IL-2 alone. The anti-CD95 staining was 37 relative fluorescent units (RFU) on the B-cells in IL-2 alone and 55 RFU on the B-cells cultured in IL-2 and human zalpha11 Ligand.

Example 50

Construction and Purification of Zalpha11 Ligand Toxic Fusion

Under a supply contract, 10 mg human zalpha11 Ligand (Example 29) was sent to Advanced Targeting Systems (ATS, San Diego, Calif.) for conjugation to the plant toxin saporin (Stirpe et al., *Biotechnology* 10:405-412, 1992). ZymoGenetics received from ATS 1.3 mg of a protein conjugate comprised of 1.1 molecules saporin per molecule of human zalpha11 Ligand, formulated at a concentration of 1.14 mg/ml in 20 nM Sodium phosphate, 300 nM sodium chloride, pH 7.2.

Example 51

Zalpha11 Ligand Toxic Fusion In Vivo

A. Testing Zalpha11-Saporin Conjugate in Mice

Zalpha11-saporin conjugate (Example 49) was administered to C57BL6 mice (female, 12 weeks of age, purchased from Taconic) at two different dosages: 0.5 and 0.05 mg/kg.

Injections were given i.v. in vehicle consisting of 0.1% BSA (ICN, Costa Mesa, Calif.). Three injections were given over a period of one week (day 0, 2, and 7). Blood samples were taken from the mice on day 0 (pre-injection) and on days 2 and 8 (post-injection). Blood was collected into heparinized tubes (Bectin Dickenson, Franklin Lakes, N.J.), and cell counts were determined using an automated hematology analyzer (Abbot Cell-Dyn model No. CD-3500CS, Abbot Park, Ill.). Animals were euthanized and necropsied on day 8 following blood collection. Spleen, thymus, liver, kidney and bone marrow were collected for histopathology. Spleen and thymus were weighed, and additional blood sample was collected in serum separator tubes. Serum was sent to Phoenix Central Labs, Everett, Wash., for testing in a standard chemistry panel. Samples were also collected for flow cytometric analysis as described herein.

Circulating blood cell counts and serum chemistry measurements did not differ significantly between zalpha11 conjugate treated mice and mice treated with an equivalent dose of unconjugated toxin (saporin). Histological analysis of tissues in zalpha11-saporin treated mice showed no significant changes relative to mice treated with an equivalent dose of unconjugated toxin. These results indicated that the saporin conjugate was not toxic in vivo.

B. Testing Zalpha11 Ligand Toxic Saporin Fusion on B-Cell Derived Tumors In Vivo The effects of human zalpha11 Ligand and the human zalpha11 Ligand toxic saporin fusion (Example 50) on human tumor cells are tested in vivo using a mouse tumor xenograft model described herein. The xenograft models are initially tested using cell lines selected on the basis of in vitro experiments, such as those described in Example 49. These cell lines include, but are not limited to: human Burkitt's lymphoma cell lines Raji (ATCC No. CCL-86), and Ramos (ATCC No. CRL-1596); human cell line RPMI 1788 (ATCC No. CRL-156); human myeloma/plasmacytoma cell line IM-9 (ATCC No. CRL159); human cell line DAKIKI (ATCC No. TIB-206), and HS Sultan cells (ATCC No. CRL-1484). Cells derived directly from human tumors can also be used in this type of model. In this way, screening of patient samples for sensitivity to treatment with zalpha11 Ligand or with a zalpha11 Ligand toxic saporin fusion can be used to select optimal indications for use of zalpha11 in anti-tumor therapy.

After selection of the appropriate zenograft in vivo model, described above, zalpha11 Ligand-induced activity of natural killer cells and/or zalpha11 Ligand effects on B-cell derived tumors are assessed in vivo. Human zalpha11 Ligand is tested for its ability to generate cytotoxic effector cells (e.g. NK cells) with activity against B-cell derived tumors using mouse tumor xenograft models described herein. Moreover, direct affects of human zalpha11 Ligand on tumors can be assessed. The xenograft models to be carried out are selected as described above. A protocol using zalpha11 Ligand stimulated human cells is developed and tested for efficacy in depleting tumor cells and promoting survival in mice innoculated with cell lines or primary tumors.

Example 52

Identification of P1 Artificial Chromosome Clones Containing Genomic Human Zalpha11 Ligand DNA The human zalpha11 Ligand cDNA insert was amplified by PCR using vector-based primers. The PCR product was $^{32}$P-labeled and hybridized to high-density filters representing a PAC (P1 Artificial Chromosome) library. Filters and frozen library stocks were obtained from Roswell Park Cancer Institute, Buffalo, N.Y.; the library segment was RPCI6, with a four-fold depth of coverage. Filters were hybridized overnight at 65° C. in EXPRESSHYB™ (Clontech) and were washed according to manufacturer's suggestions. Decoding the positive signals resulted in identification of four PAC clones, designated 23H17, 34A9, 105G9, and 236H14. PCR analysis using primers specific for the 5' end (ZC22,452 (SEQ ID NO:100) and ZC 22,451 (SEQ ID NO:101)) and 3' end (ZC 22,450 (SEQ ID NO:102) and ZC 22,449 (SEQ ID NO:103)) of the coding region showed that PACs 34A9 and 105G9 contained both ends, while PACs 23H17 and 236H14 contained the 5' end only. PAC 23H17 was digested with Eco RI and Not I, and a 9 kb fragment was identified which hybridized with the zalpha11 Ligand cDNA probe. This fragment was isolated and subcloned, using methods described herein, into phagemid kit pBLUESCRIPT® II SK (+) (Stratagene) previously digested with Eco RI and Not I. Sequencing revealed that this fragment contained about 380 base pairs of the promoter region, exons 1, 2, and 3, all of introns 1 and 2, and ended within intron 3.

The 3' end of the human zalpha11 Ligand gene was obtained by PCR using DNA from PAC 34A9 as template, with primers ZC23,771 (SEQ ID NO:104) and ZC22,449. (SEQ ID NO:103). Taq DNA polymerase was used, with buffer provided, with the addition of 4% DMSO. Reaction conditions were as follows: 94° C., 5 min.; followed by 35 cycles of 94° C. for 30 sec., 52° C. for 1 min., 72° C. for 3 min.; then 72° C. for 7 min. This generated a 2.9 kb fragment which contained part of exon 3, all of introns 3 and 4, all of exon 4, and the coding portion of exon 5.

The genomic structure of the human zalpha11 Ligand gene is as follows from 5' to 3': SEQ ID NO:105, containing about 240 bp of the promoter, exon 1 (nucleotide number 240-455 of SEQ ID NO:105), intron 1 (nucleotide number 456-562 of SEQ ID NO:105), exon 2 (nucleotide number 563-598 of SEQ ID NO:105), and part of intron 2 containing the 5' 748 base pairs (nucleotide number 599-1347 of SEQ ID NO:105); a gap of approximately 3 kb; SEQ ID NO:106, containing the 3' 718 bp of intron 2, exon 3 (nucleotide number 719-874 of SEQ ID NO:106), and part of the 5' end of intron 3 (nucleotide number 875-1656 of SEQ ID NO:106); a gap of less than about 800 bp; SEQ ID NO:107, containing 644 bp of intron 3; a gap of less than about 800 bp; and SEQ ID NO:108, containing the 3' 435 bp of intron 3, exon 4 (nucleotide number 436-513 of SEQ ID NO:108), intron 4 (nucleotide number 514-603 of SEQ ID NO:108), and part of the 5' end of exon 5 (nucleotide number 604-645 of SEQ ID NO:108).

Example 53

$^{125}$I-Labeled Human Zalpha11 Ligand Binding Study in Cell Lines 25 micrograms of purified human zalpha11 Ligand (Example 29) was labeled with 2 mCI $^{125}$I using iodobeads (Pierce, Rockford Ill.), according to manufacturer's instructions. This labeled protein was used to assess human zalpha11 Ligand binding to human Raji cells (ATCC No. CCL-86), using binding to wild-type murine BaF3 cells, and BaF3 cells transfected with zalpha11 receptor (BaF3/hzalpha11 cells) as controls. Zalpha11 Ligand binding to BaF3/hzalpha11 cells was expected (positive control), while no binding to wild-type BaF3 cells was expected (negative control), based on proliferation assay results (Example 5). About $5 \times 10^5$ Raji cells/well, $1 \times 10^6$ BaF3/hzalpha11 and $1 \times 10^6$ BaF3 cells cells/well, were each plated in 96-well plates. Ten ng/ml of labeled human zalpha11 Ligand was added in duplicate to wells, with a dilution series of unlabeled human zalpha11 Ligand competitor added from 250 fold molar excess in 1:4 dilutions down to 0.061 fold molar excess. Each point was run in duplicate. After the labeled human zalpha11 Ligand was added to wells, it was allowed to incubate at 4° C. for 2 h to allow for binding of Ligand to the cells. The cells were then washed 3× in binding buffer (RPMI-1710 (JRH Bioscience) with 1% BSA (Sigma)), and counted on the COBRA II AUTO-GAMMA gamma counter (Packard Instrument Company, Meriden, Conn.).

Binding of the labeled zalpha11 Ligand to cells was evident in the Raji and the BaF3/hzalpha11 cells. In addition, for Raji cells, an average 250 fold molar excess of unlabeled zalpha11 Ligand decreased binding 3 fold in the presence of a non-specific unlabeled competitor (Interferon Gamma from R&D Systems, Minneapolis, Minn.), and 3.7 fold relative to no competitor. Competition was observed in a dose dependent fashion for the specific unlabeled competitor, human zalpha11 Ligand. Thus, the zalpha11 Ligand binding to Raji cells was specific. Similarly, for positive control BaF3/zalpha11 cells, the 250 fold molar excess of unlabeled zalpha11 Ligand decreased binding 2 fold relative to the non-specific competitor and 3.06 fold relative to no competitor. Thus, the zalpha11 Ligand binding to BaF3/zalpha11 cells also was specific. No compeatable binding was observed with the wild-type BaF3 cells. Thus, the zalpha11 Ligand was shown to bind specifically to Raji cells, and to Baf3/hzalpha11 cells, but not to the negative control Baf3 cells.

Example 54

Zalpha11 Receptor Expression on Human Blood Cells

A. Preparation and Culture of Human Peripheral Blood Cells

Fresh drawn human blood was diluted 1:1 with PBS (GIBCO BRL) and layered over Ficoll/Hypaque Plus (Pharmacia LKB Biotechnology Inc., Piscataway, N.J.) and spun for 30 minutes at 1800 rpm and allowed to stop with the brake off. The interface layer was removed and transferred to a fresh 50 ml Falcon tube (Falcon, VWR, Seattle, Wash.), brought up to a final volume of 40 ml with PBS and spun for 10 minutes at 1200 rpm with the brake on. The viability of the isolated cells was tested using Trypan Blue (GIBCO BRL) and the cells were resuspended at a final concentration of 1×106 cells/ml cell medium (RPMI Medium 1640, 10% Heat inactivated fetal bovine serum, 5% L-glutamine, 5% Pen/Strep) (GIBCO BRL).

Cells were cultured in 6 well plates (Falcon, VWR) for 0, 4 or 24 hours with a variety of different stimuli described below. Anti-IgM, anti-CD40 and anti-CD3 stimulation were done as in Example 44 and Example 42. Phorbol myristate acetate (PMA) and ionomycin (Sigma, St. Louis, Mo.) (Example 5C) were added to appropriate wells at 10 ng/ml and 0.5 mg/ml respectively. The cells were incubated at 37° C. in a humidified incubator for various times.

B. Antibody Staining and Analysis

Cells were collected out of the plates, washed and resuspended in ice cold staining media (HBSS, 1% fetal bovine serum, 0.1% sodium azide) at a concentration of about ten million cells per milliliter. Blocking of Fc receptor and non-specific binding of antibodies to the cells was achieved by adding 10% normal goat serum (Gemini Bioproducts, Woodland, Calif.) and 10% normal human serum (Ultraserum, Gemini) to the cell suspension. Aliquots of the cell suspensions were mixed with a FITC labeled monoclonal antibody against one of the lineage markers CD3, CD19 or CD14 (PharMingen, La Jolla, Calif.) and a biotinylated monoclonal antibody against the human zalpha11 receptor (hu-zalpha11) (Example 35). Staining specificity was determined by competition using zalpha11CEE soluble receptor (Example 10A) at a ten fold mass excess. After incubation on ice for 60 minutes the cells were washed twice with ice cold staining media and resuspended in 50 ml staining media containing streptavidin-PE (Caltag, Burlingame, Calif.). After a 30 minute incubation on ice, the cells were washed twice with ice cold wash buffer (PBS, 1% fetal bovine serum, 0.1% sodium azide) and resuspended in wash buffer containing 1 mg/ml 7-AAD (Molecular Probes, Eugene, Oreg.) as a viability marker. Flow data was acquired on living cells using a flow cytometer FACSCALIBUR™ flow cytometer (BD Immunocytometry Systems, San Jose, Calif.). Both acquisition and analysis were performed using CellQuest software (BD Immunocytometry Systems).

Results of staining by anti-zalpha11 antibody showed that the human zalpha11 receptor is expressed on human peripheral blood cells expressing either CD3, CD19 or CD14. Staining on CD3 and CD19 cells was specific, as evidenced by absolute competion with the zalpha11 soluble receptor. Staining on CD14 cells showed some specificity for the Ligand, as evidenced by partial competion with the soluble receptor. Activation of either T cells with anti-CD3 or B cells with anti-CD40 resulted in an increased level of cell surface zalpha11 at 24 hours. No increase in the level of expression of zalpha11 was seen at 4 hours with any stimulus on either cell population. Treatment of the cells with zalpha11ligand resulted in a decrease of zalpha11 staining on CD3 positive and CD19 positive cells but not CD14 positive cells at both 4 and 24 hours.

Example 55

Preliminary Evaluation of the Aqueous Stability of Human Zalpha11 Ligand

Preliminary studies were conducted to evaluate the aqueous stability characteristics of human zalpha11 Ligand in support of bioprocessing, formulation, and in vivo administration. The objectives were to: 1) verify the stability and recovery from Alzet Minipumps & general storage and handling, 2) determine the stability-indicating nature of several analytical methods including cation-exchange HPLC (CX-HPLC), reverse-phase HPLC (RP-HPLC), size exclusion HPLC (SEC-HPLC), & bioassay (BaF3/zalpha11R proliferation (e.g., Example 2 and Example 4), and 3) determine the stability-limiting degradation pathways and their kinetic dependencies.

Aliquots of purified human zalpha11 Ligand (Example 29) were prepared by dilution to 2 mg/mL in PBS (pH 7.4) and stored in low density polyethylene (LDPE) cryovials (Nalgene, 1.8 mL) at −80° C. (control), 5° C., 30° C., and 37° C. Samples were assayed intermittently over 29 days by CX-, RP-, SEC-HPLC, and bioassay. Aliquots were also stored at −80° C. and subjected to freeze-thaw (f/t) cycling (−80° C./RT; 5×f/t, 10×f/t). Recovery of human zalpha11 Ligand was determined relative to the −80° C. control (1 f/t) in all assays.

The remaining human zalpha11 Ligand solution from the −80° C. control samples were refrozen (80° C.) after analysis. This aliquot (2 f/t) was used to evaluate the thermal and conformational stability of human zalpha11 Ligand as a function of pH using circular dichroism (CD). The 2 mg/mL solution was diluted to 100 µg/mL in PBS buffers ranging from pH 3.3-8.8. The far-UV CD spectra was monitored over the temperature range 5-90° C. in 5° C. intervals (n=3/pH). The CD spectropolarimeter used was a Jasco 715 (Jasco, Easton, Md.). The thermal unfolding was monitored by changes in ellipticity at 222 nm as a function of temperature.

Estimates of the Tm were estimated assuming a two-state unfolding model. The data was fit (sigmoidal) using Slide-Write Plus for Windows v4.1 (Advanced Graphics Software; Encinitas, Calif.).

Recovery and stability from Alzet Minipumps (Model No. 1007D; ALZA Corporation, Mountain View, Calif.) was assessed by filling pumps with 100 μL of the 2 mg/mL human zalpha11 Ligand solution, placing the pumps in 1.8 mL LDPE containing 1 mL of PBS (pH 7.4), and storing them at 37° C. The release/recovery of human zalpha11 Ligand from the minipumps was assessed by CX-, RP-, and SEC-HPLC on days 2, 4, and 7. The activity was assessed by bioassay on day 7. The study was designed to evaluate the release from 3 pumps per sampling time.

The chromatographic data suggested that the CX- & SEC-HPLC methods were stability-indicating, whereas the RP-HPLC method was not. At least 3 additional peaks indicating apparent degradation products were observed by CX-HPLC. The SEC-HPLC method resolved an apparent human zalpha11 Ligand aggregate, eluting prior to human zalpha11 Ligand. However, no significant additional peaks were observed eluting after the human zalpha11 Ligand peak. This suggests that the degradation products observed by CX-HPLC most probably result from amino acid modifications such as deamidation, rather than hydrolysis/proteolysis processes leading to clipped variants. A small degree of fronting/tailing was observed by RP-HPLC (relative to control) in samples which had been shown to have undergone significant degradation by SEC- & CX-HPLC. However, apparent degradation products were not resolved by RP-HPLC. The degradation observed by CX-HPLC increased as a function of time-temperature, and followed apparent first-order kinetics. The % human zalpha11 Ligand recovered by CX-HPLC after 29 days at 37° C., 30° C., and 5° C. was 39%, 63%, and 98%, respectively. Aggregation also increased in a time-temperature dependent fashion. The % aggregate found in preparations stored for 29 days at 37° C., 30° C., and 5° C. was 7.4, 3.4, and below detectable limits (BDL), respectively. No significant differences were observed by bioassay in any sample, suggesting the degradation products have equivalent activity to intact human zalpha11 Ligand. No degradation was observed by any assay in samples subjected to up to 10 f/t cycles.

The release of human zalpha11 Ligand from Alzet Minipumps was consistent with the theoretical expected volume release. This suggests that significant surface adsorption would not impair the delivery of human zalpha11 Ligand using the Alzet Minipumps with a 2 mg/mL fill concentration. The degradation consistent with that previously noted was observed. The % purity determined by CX-HPLC of human zalpha11 Ligand released after 2, 4, and 7 days was 96%, 90%, and 79%, respectively. It should be recognized that degradation also occurs after human zalpha11 Ligand is released into or diluted with release medium. Therefore, the % purity within the minipump may be somewhat different than that determined to be in the release medium. The bioactivity of each sample was consistent with the expected amount of human zalpha11 Ligand released from the minipumps.

The human zalpha11 Ligand far-UV CD spectra, as expected, was consistent with interleukins, such as IL-3 (*J. Biochem.*, 23:352-360, 1991), IL-4 (*Biochemistry*, 30:1259-1264, 1991), and IL-6 mutants (*Biochemistry*, 35:11503-11511, 1996). Gross changes in the far-uv CD spectra as a function of pH were not observed. Results showed that the pH of maximum thermal/conformational stability was ~pH 7.4. Analysis of the unfolding curves were based on a two-state unfolding mechanism to allow comparison of the thermal/conformational stability as a function of pH/composition. However, one or more intermediates may exist during the unfolding process since the cooperativity was relatively low, based on the shallowness of the unfolding curve. Although studies were not specifically designed to determine whether human zalpha11 Ligand refolds following thermal unfolding to 90° C., preliminary data suggests that at least partial refolding occurs after the temperature of the sample is cooled back to 20° C.

These studies allow an analytical paradigm to be identified to evaluate the purity and verify the stability of human zalpha11 Ligand. For instance, SEC-HPLC can be used to characterize the extent and rate of aggregation in aqueous solution. Likewise, CX-HPLC can be used to characterize the extent and rate of degradation of human zalpha11 Ligand by mechanisms other than aggregation. The bioassay can be used to verify activity of human zalpha11 Ligand and it's aqueous degradation products. For instance, the human zalpha11 Ligand variants generated in aqueous solution & resolved by CX-HPLC may themselves be useful as therapeutic agents, since they have equivalent bioactivity. Also, the fact that human zalpha11 Ligand degrades by several different processes (aggregation, amino acid modifications) suggests a preferred or unique formulation which minimizes the rate of each degradation process may be necessary for long-term stability of a solution product.

Identification of the nature of the aqueous degradation products and determination of their kinetic dependencies (pH, concentration, excipients) is underway. Human zalpha11 Ligand stability in serum/plasma is determined to support the design and interpretation of in vivo studies.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

SEQUENCE LISTING

<160> NUMBER OF SEQ ID NOS: 115

<210> SEQ ID NO 1
<211> LENGTH: 642
<212> TYPE: DNA
<213> ORGANISM: Homo sapiens
<220> FEATURE:
<221> NAME/KEY: CDS
<222> LOCATION: (47)...(532)

<400> SEQUENCE: 1

```
gctgaagtga aaacgagacc aaggtctagc tctactgttg gtactt atg aga tcc      55
                                                Met Arg Ser
                                                  1 agt cct ggc aac atg gag agg att gtc atc tgt ctg atg gtc atc ttc    103
Ser Pro Gly Asn Met Glu Arg Ile Val Ile Cys Leu Met Val Ile Phe
  5                  10                  15 ttg ggg aca ctg gtc cac aaa tca agc tcc caa ggt caa gat cgc cac    151
Leu Gly Thr Leu Val His Lys Ser Ser Ser Gln Gly Gln Asp Arg His
 20                  25                  30                  35 atg att aga atg cgt caa ctt ata gat att gtt gat cag ctg aaa aat    199
Met Ile Arg Met Arg Gln Leu Ile Asp Ile Val Asp Gln Leu Lys Asn
                 40                  45                  50 tat gtg aat gac ttg gtc cct gaa ttt ctg cca gct cca gaa gat gta    247
Tyr Val Asn Asp Leu Val Pro Glu Phe Leu Pro Ala Pro Glu Asp Val
                     55                  60                  65 gag aca aac tgt gag tgg tca gct ttt tcc tgt ttt cag aag gcc caa    295
Glu Thr Asn Cys Glu Trp Ser Ala Phe Ser Cys Phe Gln Lys Ala Gln
             70                  75                  80 cta aag tca gca aat aca gga aac aat gaa agg ata atc aat gta tca    343
Leu Lys Ser Ala Asn Thr Gly Asn Asn Glu Arg Ile Ile Asn Val Ser
 85                  90                  95 att aaa aag ctg aag agg aaa cca cct tcc aca aat gca ggg aga aga    391
Ile Lys Lys Leu Lys Arg Lys Pro Pro Ser Thr Asn Ala Gly Arg Arg
100                 105                 110                 115 cag aaa cac aga cta aca tgc cct tca tgt gat tct tat gag aaa aaa    439
Gln Lys His Arg Leu Thr Cys Pro Ser Cys Asp Ser Tyr Glu Lys Lys
                120                 125                 130 cca ccc aaa gaa ttc cta gaa aga ttc aaa tca ctc ctc caa aag atg    487
Pro Pro Lys Glu Phe Leu Glu Arg Phe Lys Ser Leu Leu Gln Lys Met
                135                 140                 145 att cat cag cat ctg tcc tct aga aca cac gga agt gaa gat tcc        532
Ile His Gln His Leu Ser Ser Arg Thr His Gly Ser Glu Asp Ser
                150                 155                 160 tgaggatcta acttgcagtt ggacactatg ttcatactc taatatagta gtgaaagtca   592
tttctttgta ttccaagtgg aggagcccta ttaaattata taaagaaata             642
```

<210> SEQ ID NO 2
<211> LENGTH: 162
<212> TYPE: PRT
<213> ORGANISM: Homo sapiens

<400> SEQUENCE: 2

```
Met Arg Ser Ser Pro Gly Asn Met Glu Arg Ile Val Ile Cys Leu Met
  1               5                  10                  15

Val Ile Phe Leu Gly Thr Leu Val His Lys Ser Ser Ser Gln Gly Gln
             20                  25                  30

Asp Arg His Met Ile Arg Met Arg Gln Leu Ile Asp Ile Val Asp Gln
         35                  40                  45

Leu Lys Asn Tyr Val Asn Asp Leu Val Pro Glu Phe Leu Pro Ala Pro
 50                  55                  60

Glu Asp Val Glu Thr Asn Cys Glu Trp Ser Ala Phe Ser Cys Phe Gln
65                  70                  75                  80

Lys Ala Gln Leu Lys Ser Ala Asn Thr Gly Asn Asn Glu Arg Ile Ile
                 85                  90                  95

Asn Val Ser Ile Lys Lys Leu Lys Arg Lys Pro Pro Ser Thr Asn Ala
            100                 105                 110
```

Gly Arg Arg Gln Lys His Arg Leu Thr Cys Pro Ser Cys Asp Ser Tyr
    115                 120                 125

Glu Lys Lys Pro Pro Lys Glu Phe Leu Glu Arg Phe Lys Ser Leu Leu
    130                 135                 140

Gln Lys Met Ile His Gln His Leu Ser Ser Arg Thr His Gly Ser Glu
145                 150                 155                 160

Asp Ser

<210> SEQ ID NO 3
<211> LENGTH: 486
<212> TYPE: DNA
<213> ORGANISM: Artificial Sequence
<220> FEATURE:
<223> OTHER INFORMATION: Degenerate polynucleotide sequence for human
      zalpha11 ligand
<220> FEATURE:
<221> NAME/KEY: misc_feature
<222> LOCATION: (1)...(486)
<223> OTHER INFORMATION: n = A,T,C or G

<400> SEQUENCE: 3
atgmgnwsnw snccnggnaa yatggarmgn athgtnatht gyytnatggt nathttyytn     60
ggnacnytng tncayaarws nwsnwsncar ggncargaym gncayatgat hmgnatgmgn    120
carytnathg ayathgtnga ycarytnaar aaytaygtna aygayytngt nccngartty    180
ytnccngcnc cngargaygt ngaracnaay tgygartggw sngcnttyws ntgyttycar    240
aargcncary tnaarwsngc naayacnggn aayaaygarm gnathathaa ygtnwsnath    300
aaraarytna armgnaarcc nccnwsnacn aaygcnggnm gnmgncaraa rcaymgnytn    360
acntgyccnw sntgygayws ntaygaraar aarccnccna argarttyyt ngarmgntty    420
aarwsnytny tncaraarat gathcaycar cayytnwsnw snmgnacnca yggnwsngar    480 gaywsn                                                               486

<210> SEQ ID NO 4
<211> LENGTH: 535
<212> TYPE: DNA
<213> ORGANISM: Mus musculus
<220> FEATURE:
<221> NAME/KEY: source
<222> LOCATION: (0)...(0)
<223> OTHER INFORMATION: EST1483966 ;  GenBank Acc #AA764063

<400> SEQUENCE: 4
taaacatgta tcatataagg atatgtcata ataaggatta atattatata attataaata     60
atttataata cttataatat cattgtttgg ttcactaata aatctatgga tacatggtca    120
aaatggaaat gaatattttg ccaattatta atccccaaag tcattgaaaa taagcataac    180
cattctactg acttgttaga ctctaaacta acataaaata cattttcaga aataaattca    240
accgatctta cctttacatc ttgtggagct gatagaagtt caggatccta agaaaattaa    300
ccaaagagta ttagttctga gttggtgata caagtcaaaa ggctcctttt gcattaatta    360
aaaaaatatt atttaaattg cattgtgaca acatggcct taccaagtca ttttcataga    420
ttttcagctg ttcaacaatg tcataaggt gacgaagtct aatcaggagg cgatctggcc    480
cttgggggct tgatttatgg gccactgtcc ccaagaagat gactaccaga cagac         535

<210> SEQ ID NO 5
<211> LENGTH: 33
<212> TYPE: DNA

```
<213> ORGANISM: Artificial Sequence
<220> FEATURE:
<223> OTHER INFORMATION: Oligonucleotide primer ZC17212

<400> SEQUENCE: 5
ggggaattcg aagccatgcc ctcttgggcc ctc                           33

<210> SEQ ID NO 6
<211> LENGTH: 30
<212> TYPE: DNA
<213> ORGANISM: Artificial Sequence
<220> FEATURE:
<223> OTHER INFORMATION: Oligonucleotide primer ZC19914

<400> SEQUENCE: 6
caatggatgg gtctttagca gcagtaggcc                               30

<210> SEQ ID NO 7
<211> LENGTH: 1614
<212> TYPE: DNA
<213> ORGANISM: Homo sapiens

<400> SEQUENCE: 7
atgccgcgtg gctgggccgc ccccttgctc ctgctgctgc tccagggagg ctggggctgc    60
cccgacctcg tctgctacac cgattacctc cagacggtca tctgcatcct ggaaatgtgg   120
aacctccacc ccagcacgct caccccttac ctggcaagac cagtatgaaga gctgaaggac   180 gaggccacct cctgcagcct ccacaggtcg gcccacaatg ccacgcatgc cacctacacc   240
tgccacatgg atgtattcca cttcatggcc gacgacattt tcagtgtcaa catcacagac   300
cagtctggca actactccca ggagtgtggc agctttctcc tggctgagag catcaagccg   360
gctccccctt tcaacgtgac tgtgaccttc tcaggacagt ataatatctc ctggcgctca   420
gattacgaag accctgcctt ctacatgctg aagggcaagc ttcagtatga gctgcagtac   480
aggaaccggg gagacccctg gctgtgagt ccgaggagaa agctgatctc agtggactca   540
agaagtgtct ccctcctccc cctggagttc cgcaaagact cgagctatga gctgcaggtg   600
cgggcagggc ccatgcctgg ctcctcctac caggggacct ggagtgaatg gagtgacccg   660
gtcatctttc agacccagtc agaggagtta aaggaaggct ggaacccctca cctgctgctt   720 ctcctcctgc ttgtcatagt cttcattcct gccttctgga gcctgaagac ccatccattg   780
tggaggctat ggaagaagat atgggccgtc cccagccctg agcggttctt catgcccctg   840
tacaagggct gcagcggaga cttcaagaaa tgggtgggtg cacccttcac tggctccagc   900
ctggagctgg acccctggag cccagaggtg ccctccaccc tggaggtgta cagctgccac   960
ccaccacgga gcccggccaa gaggctgcag ctcacggagc tacaagaacc agcagagctg  1020
gtggagtctg acgtgtgcc caagcccagc ttctggccga cagcccagaa ctcgggggc   1080 tcagcttaca gtgaggagag ggatcggcca tacgcctgg tgtccattga cacagtgact  1140
gtgctagatg cagaggggcc atgcacctgg ccctgcagct gtgaggatga cggctaccca  1200
gccctggacc tggatgctgg cctggagccc agcccaggcc tagaggaccc actcttggat  1260
gcagggacca cagtcctgtc ctgtggctgt gtctcagctg gcagccctgg gctaggaggg  1320
cccctgggaa gctcctggga cagactaaag ccaccccttg cagatgggga ggactgggct  1380
gggggactgc cctggggtgg ccggtcacct ggaggggtct cagagagtga ggcgggctca  1440 ccctggccg gcctggatat ggacacgttt gacagtggct ttgtgggctc tgactgcagc  1500
agccctgtgg agtgtgactt caccagcccc ggggacgaag acccccccg gagctacctc  1560
```

```
cgccagtggg tggtcattcc tccgccactt tcgagccctg acccccaggc cagc         1614
```

<210> SEQ ID NO 8
<211> LENGTH: 30
<212> TYPE: DNA
<213> ORGANISM: Artificial Sequence
<220> FEATURE:
<223> OTHER INFORMATION: Oligonucleotide primer ZC19913

<400> SEQUENCE: 8

```
ggcctactgc tgctaaagac ccatccattg                                      30
```

<210> SEQ ID NO 9
<211> LENGTH: 33
<212> TYPE: DNA
<213> ORGANISM: Artificial Sequence
<220> FEATURE:
<223> OTHER INFORMATION: Oligonucleotide primer ZC20097

<400> SEQUENCE: 9

```
acatctagat tagctggcct ggggtccagg cgt                                  33
```

<210> SEQ ID NO 10
<211> LENGTH: 21
<212> TYPE: DNA
<213> ORGANISM: Artificial Sequence
<220> FEATURE:
<223> OTHER INFORMATION: Oligonucleotide primer ZC12700

<400> SEQUENCE: 10

```
ggaggtctat ataagcagag c                                               21
```

<210> SEQ ID NO 11
<211> LENGTH: 21
TYPE: NA
<213> ORGANISM: Artificial Sequence
<220> FEATURE:
<223> OTHER INFORMATION: Oligonucleotide primer ZC5020

<400> SEQUENCE: 11

```
cactggagtg gcaacttcca g                                               21
```

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide primer ZC6675

<400> SEQUENCE: 12

```
gtggatgccg aacccagtcc                                                 20
```

<210> SEQ ID NO 13
<211> LENGTH: 21
<212> TYPE: DNA
<213> ORGANISM: Artificial Sequence
<220> FEATURE:
<223> OTHER INFORMATION: Oligonucleotide primer ZC7727

<400> SEQUENCE: 13

```
tgttcacagc tacctgggct c                                               21
```

<210> SEQ ID NO 14
<211> LENGTH: 26
<212> TYPE: DNA
<213> ORGANISM: Artificial Sequence

```
<220> FEATURE:
<223> OTHER INFORMATION: Oligonucleotide primer ZC8290

<400> SEQUENCE: 14
ccaccgagac tgcttggatc accttg                                          26

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primer ZC19572

<400> SEQUENCE: 15
gtcctgtggc tgtgtctcag                                                 20

<210> SEQ ID NO 16
<211> LENGTH: 21
<212> TYPE: DNA
<213> ORGANISM: Artificial Sequence
<220> FEATURE:
<223> OTHER INFORMATION: Oligonucleotide primer ZC6622

<400> SEQUENCE: 16
ctgggctgga aactggcaca c                                               21

<210> SEQ ID NO 17
<211> LENGTH: 18
<212> TYPE: DNA
<213> ORGANISM: Artificial Sequence
<220> FEATURE:
<223> OTHER INFORMATION: Oligonucleotide primer ZC7736

<400> SEQUENCE: 17
cactgtcaga aatggagc                                                   18

<210> SEQ ID NO 18
<211> LENGTH: 24
<212> TYPE: DNA
<213> ORGANISM: Artificial Sequence
<220> FEATURE:
<223> OTHER INFORMATION: Oligonucleotide primer ZC9273

<400> SEQUENCE: 18
ggtccctccc cgggcaccga gaga                                            24

<210> SEQ ID NO 19
<211> LENGTH: 36
<212> TYPE: DNA
<213> ORGANISM: Artificial Sequence
<220> FEATURE:
<223> OTHER INFORMATION: Oligonucleotide primer ZC19905

<400> SEQUENCE: 19
acaggatccg tcagcatgcc gcgtggctgg gccgcc                               36

<210> SEQ ID NO 20
<211> LENGTH: 33
<212> TYPE: DNA
<213> ORGANISM: Artificial Sequence
<220> FEATURE:
<223> OTHER INFORMATION: Oligonucleotide primer ZC19906

<400> SEQUENCE: 20
acagaattct tagctggcct ggggtccagg cgt                                  33
```

<210> SEQ ID NO 21
<211> LENGTH: 22
<212> TYPE: DNA
<213> ORGANISM: Artificial Sequence
<220> FEATURE:
<223> OTHER INFORMATION: Oligonucleotide primer ZC20114

<400> SEQUENCE: 21
cctgccttct acatgctgaa gg                                          22

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide primer ZC19459

<400> SEQUENCE: 22
ctcctcctgc ttgtcatagt c                                           21

<210> SEQ ID NO 23
<211> LENGTH: 18
<212> TYPE: DNA
<213> ORGANISM: Artificial Sequence
<220> FEATURE:
<223> OTHER INFORMATION: Oligonucleotide primer ZC19954

<400> SEQUENCE: 23
actgggctgg gggactgc                                               18

<210> SEQ ID NO 24
<211> LENGTH: 22
<212> TYPE: DNA
<213> ORGANISM: Artificial Sequence
<220> FEATURE:
<223> OTHER INFORMATION: Oligonucleotide primer ZC20116

<400> SEQUENCE: 24
agcacagtca ctgtgtcaat gg                                          22

<210> SEQ ID NO 25
<211> LENGTH: 40
<212> TYPE: DNA
<213> ORGANISM: Artificial Sequence
<220> FEATURE:
<223> OTHER INFORMATION: Oligonucleotide primer ZC13946

<400> SEQUENCE: 25
ccctgcagtg atcaacatgg ccaagttgac cagtgccgtt                       40

<210> SEQ ID NO 26
<211> LENGTH: 45
<212> TYPE: DNA
<213> ORGANISM: Artificial Sequence
<220> FEATURE:
<223> OTHER INFORMATION: Oligonucleotide primer ZC13945

<400> SEQUENCE: 26
gcccatggac tagtttcgaa aggtcgagtg tcagtcctgc tcctc                 45

<210> SEQ ID NO 27
<211> LENGTH: 34
<212> TYPE: DNA
<213> ORGANISM: Artificial Sequence
<220> FEATURE:
<223> OTHER INFORMATION: Oligonucleotide primer ZC18698

<400> SEQUENCE: 27
tttttttctc gagactttt tttttttttt tttt                            34

<210> SEQ ID NO 28
<211> LENGTH: 25
<212> TYPE: DNA
<213> ORGANISM: Artificial Sequence
<220> FEATURE:
<223> OTHER INFORMATION: Oligonucleotide primer ZC14063

<400> SEQUENCE: 28
caccagacat aatagctgac agact                                    25

<210> SEQ ID NO 29
<211> LENGTH: 6
<212> TYPE: PRT
<213> ORGANISM: Artificial Sequence
<220> FEATURE:
<223> OTHER INFORMATION: Glu-Glu (CEE) Tag amino acid sequence

<400> SEQUENCE: 29

Glu Tyr Met Pro Met Glu
 1               5

<210> SEQ ID NO 30
<211> LENGTH: 36
<212> TYPE: DNA
<213> ORGANISM: Artificial Sequence
<220> FEATURE:
<223> OTHER INFORMATION: Oligonucleotide primer ZC19931

<400> SEQUENCE: 30
ggttggtacc gcaagatgcc gcgtggctgg gccgcc                        36

<210> SEQ ID NO 31
<211> LENGTH: 29
<212> TYPE: DNA
<213> ORGANISM: Artificial Sequence
<220> FEATURE:
<223> OTHER INFORMATION: Oligonucleotide primer ZC19932

<400> SEQUENCE: 31
cggaggatcc gtgagggttc cagccttcc                                29

<210> SEQ ID NO 32
<211> LENGTH: 66
<212> TYPE: DNA
<213> ORGANISM: Artificial Sequence
<220> FEATURE:
<223> OTHER INFORMATION: Oligonucleotide primer spanning vector flanking
      region and the 5' end of the zalpha11
      extracellular domain

<400> SEQUENCE: 32
tccactttgc ctttctctcc acaggtgtcc agggaattca tcgataatgc cgcgtggctg    60
ggccgc                                                              66

<210> SEQ ID NO 33
<211> LENGTH: 699
<212> TYPE: DNA
<213> ORGANISM: Homo sapiens

<400> SEQUENCE: 33
gagcccagat cttcagacaa aactcacaca tgcccaccgt gcccagcacc tgaagccgag    60

```
ggggcaccgt cagtcttcct cttcccccca aacccaagg acaccctcat gatctcccgg    120
acccctgagg tcacatgcgt ggtggtggac gtgagccacg aagaccctga ggtcaagttc    180
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc catcctccat cgagaaaacc    360
atctccaaag ccaaagggca gccccgagaa ccacaggtgt acaccctgcc cccatcccgg    420
gatgagctga ccaagaacca ggtcagcctg acctgcctgg tcaaaggctt ctatcccagc    480
gacatcgccg tggagtggga gagcaatggg cagccggaga caactacaa gaccacgcct    540 cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga agagcctctc cctgtctccg ggtaaataa                          699

<210> SEQ ID NO 34
<211> LENGTH: 62
<212> TYPE: DNA
<213> ORGANISM: Artificial Sequence
<220> FEATURE:
<223> OTHER INFORMATION: First Oligonucleotide primer spanning 3' end of
      the zalpha11 extracellular domain and the 5' end
      of Fc4

<400> SEQUENCE: 34
gcacggtggg catgtgtgag ttttgtctga agatctgggc tcgtgagggt tccagccttc    60
ct                                                                   62

<210> SEQ ID NO 35
<211> LENGTH: 61
<212> TYPE: DNA
<213> ORGANISM: Artificial Sequence
<220> FEATURE:
<223> OTHER INFORMATION: Second Oligonucleotide primer spanning 3' end
      of the zalpha11 extracellular domain and the 5' end of Fc4

<400> SEQUENCE: 35
agacccagtc agaggagtta aaggaaggct ggaaccctca cgagcccaga tcttcagaca    60
a                                                                    61

<210> SEQ ID NO 36
<211> LENGTH: 67
<212> TYPE: DNA
<213> ORGANISM: Artificial Sequence
<220> FEATURE:
<223> OTHER INFORMATION: Oligonucleotide primer spanning  the 3' end of
      Fc4 and the vector flanking region

<400> SEQUENCE: 36
gtgggcctct ggggtgggta caaccccaga gctgttttaa tctagattat ttacccggag    60
acaggga                                                              67

<210> SEQ ID NO 37
<211> LENGTH: 8
<212> TYPE: PRT
<213> ORGANISM: Artificial Sequence
<220> FEATURE:
<223> OTHER INFORMATION: C-terminal FLAG amino acid sequence

<400> SEQUENCE: 37
```

```
Asp Tyr Lys Asp Asp Asp Lys
  1               5
```

<210> SEQ ID NO 38
<211> LENGTH: 26
<212> TYPE: DNA
<213> ORGANISM: Artificial Sequence
<220> FEATURE:
<223> OTHER INFORMATION: Oligonucleotide primer ZC7764a

<400> SEQUENCE: 38
tttttttttt tttttttttt tttta                                    26

<210> SEQ ID NO 39
<211> LENGTH: 26
<212> TYPE: DNA
<213> ORGANISM: Artificial Sequence
<220> FEATURE:
<223> OTHER INFORMATION: Oligonucleotide primer ZC7764b

<400> SEQUENCE: 39
tttttttttt tttttttttt tttttc                                   26

<210> SEQ ID NO 40
<211> LENGTH: 19
<212> TYPE: DNA
<213> ORGANISM: Artificial Sequence
<220> FEATURE:
<223> OTHER INFORMATION: Oligonucleotide primer ZC22034

<400> SEQUENCE: 40
ttcaaatcac ttctccaaa                                           19

<210> SEQ ID NO 41
<211> LENGTH: 20
<212> TYPE: DNA
<213> ORGANISM: Artificial Sequence
<220> FEATURE:
<223> OTHER INFORMATION: Oligonucleotide primer ZC22035

<400> SEQUENCE: 41
ttttggagaa gtgatttgaa                                          20

<210> SEQ ID NO 42
<211> LENGTH: 16
<212> TYPE: DNA
<213> ORGANISM: Artificial Sequence
<220> FEATURE:
<223> OTHER INFORMATION: Oligonucleotide primer ZC22050

<400> SEQUENCE: 42
gaatgcgtca acttat                                              16

<210> SEQ ID NO 43
<211> LENGTH: 16
<212> TYPE: DNA
<213> ORGANISM: Artificial Sequence
<220> FEATURE:
<223> OTHER INFORMATION: Oligonucleotide primer ZC22051

<400> SEQUENCE: 43
ggaccaagtc attcac                                              16

<210> SEQ ID NO 44
<211> LENGTH: 25
<212> TYPE: DNA

<213> ORGANISM: Artificial Sequence
<220> FEATURE:
<223> OTHER INFORMATION: Oligonucleotide primer ZC22056

<400> SEQUENCE: 44
gtctgtctgg tagtcatctt cttgg                                25

<210> SEQ ID NO 45
<211> LENGTH: 25
<212> TYPE: DNA
<213> ORGANISM: Artificial Sequence
<220> FEATURE:
<223> OTHER INFORMATION: Oligonucleotide primer ZC22057

<400> SEQUENCE: 45
cttgtggagc tgatagaagt tcagg                                25

<210> SEQ ID NO 46
<211> LENGTH: 26
<212> TYPE: DNA
<213> ORGANISM: Artificial Sequence
<220> FEATURE:
<223> OTHER INFORMATION: Oligonucleotide primer ZC22205

<400> SEQUENCE: 46
agctgttcaa caatgtcaat aaggtg                               26

<210> SEQ ID NO 47
<211> LENGTH: 24
<212> TYPE: DNA
<213> ORGANISM: Artificial Sequence
<220> FEATURE:
<223> OTHER INFORMATION: Oligonucleotide primer ZC22206

<400> SEQUENCE: 47
cctcctgatt agacttcgtc acct                                 24

<210> SEQ ID NO 48
<211> LENGTH: 27
<212> TYPE: DNA
<213> ORGANISM: Artificial Sequence
<220> FEATURE:
<223> OTHER INFORMATION: Oligonucleotide primer ZC9739

<400> SEQUENCE: 48
ccatcctaat acgactcact atagggc                              27

<210> SEQ ID NO 49
<211> LENGTH: 23
<212> TYPE: DNA
<213> ORGANISM: Artificial Sequence
<220> FEATURE:
<223> OTHER INFORMATION: Oligonucleotide primer ZC9719

<400> SEQUENCE: 49
actcactata gggctcgagc ggc                                  23

<210> SEQ ID NO 50
<211> LENGTH: 25
<212> TYPE: DNA
<213> ORGANISM: Artificial Sequence
<220> FEATURE:
<223> OTHER INFORMATION: Oligonucleotide primer ZC14063

<400> SEQUENCE: 50
caccagacat aatagctgac agact                                25

<210> SEQ ID NO 51
<211> LENGTH: 21
<212> TYPE: DNA
<213> ORGANISM: Artificial Sequence
<220> FEATURE:
<223> OTHER INFORMATION: Oligonucleotide primer ZC5020

<400> SEQUENCE: 51
cactggagtg gcaacttcca g                                             21

<210> SEQ ID NO 52
<211> LENGTH: 20
<212> TYPE: DNA
<213> ORGANISM: Artificial Sequence
<220> FEATURE:
<223> OTHER INFORMATION: Oligonucleotide primer ZC22421

<400> SEQUENCE: 52
ctaaaatggc tccttcaaaa                                               20

<210> SEQ ID NO 53
<211> LENGTH: 40
<212> TYPE: DNA
<213> ORGANISM: Artificial Sequence
<220> FEATURE:
<223> OTHER INFORMATION: Oligonucleotide primer ZC22604

<400> SEQUENCE: 53
cacacaggcc ggccaccatg ggcttccagc ctccggccgc                         40

<210> SEQ ID NO 54
<211> LENGTH: 20
<212> TYPE: DNA
<213> ORGANISM: Artificial Sequence
<220> FEATURE:
<223> OTHER INFORMATION: Oligonucleotide primer ZC22641

<400> SEQUENCE: 54
atgcgttggt tctgattgtg                                               20

<210> SEQ ID NO 55
<211> LENGTH: 3072
<212> TYPE: DNA
<213> ORGANISM: mus musculus
<220> FEATURE:
<221> NAME/KEY: CDS
<222> LOCATION: (54)...(491)

<400> SEQUENCE: 55
gagaaccaga ccaaggccct gtcatcagct cctggagact cagttctggt ggc atg      56
                                                          Met
                                                          1 gag agg acc ctt gtc tgt ctg gta gtc atc ttc ttg ggg aca gtg gcc    104
Glu Arg Thr Leu Val Cys Leu Val Val Ile Phe Leu Gly Thr Val Ala
         5                  10                  15 cat aaa tca agc ccc caa ggg cca gat cgc ctc ctg att aga ctt cgt    152
His Lys Ser Ser Pro Gln Gly Pro Asp Arg Leu Leu Ile Arg Leu Arg
             20                  25                  30 cac ctt att gac att gtt gaa cag ctg aaa atc tat gaa aat gac ttg    200
His Leu Ile Asp Ile Val Glu Gln Leu Lys Ile Tyr Glu Asn Asp Leu
         35                  40                  45 gat cct gaa ctt cta tca gct cca caa gat gta aag ggg cac tgt gag    248
Asp Pro Glu Leu Leu Ser Ala Pro Gln Asp Val Lys Gly His Cys Glu
50                  55                  60                  65

```
cat gca gct ttt gcc tgt ttt cag aag gcc aaa ctc aag cca tca aac        296
His Ala Ala Phe Ala Cys Phe Gln Lys Ala Lys Leu Lys Pro Ser Asn
             70                  75                  80 cct gga aac aat aag aca ttc atc att gac ctc gtg gcc cag ctc agg        344
Pro Gly Asn Asn Lys Thr Phe Ile Ile Asp Leu Val Ala Gln Leu Arg
             85                  90                  95 agg agg ctg cct gcc agg agg gga gga aag aaa cag aag cac ata gct        392
Arg Arg Leu Pro Ala Arg Arg Gly Gly Lys Lys Gln Lys His Ile Ala
            100                 105                 110 aaa tgc cct tcc tgt gat tcg tat gag aaa agg aca ccc aaa gaa ttc        440
Lys Cys Pro Ser Cys Asp Ser Tyr Glu Lys Arg Thr Pro Lys Glu Phe
    115                 120                 125 cta gaa aga cta aaa tgg ctc ctt caa aag atg att cat cag cat ctc        488
Leu Glu Arg Leu Lys Trp Leu Leu Gln Lys Met Ile His Gln His Leu
130                 135                 140                 145 tcc tagaacacat aggacccgaa gattcctgag gatccgagaa gattcccgag             541
Ser gactgaggag acgccggaca ctatagacgc tcacgaatgc aggagtacat cttgcctctt      601
gggattgcaa gtggagaagt acgatacgtt atgataagaa caactcagaa aagctatagg      661
ttaagatcct ttcgcccatt aactaagcag acattgtggt tccctgcaca gactccatgc      721
tgtcaacatg gaaaatctca actcaacaag agcccagctt ccgtgtcag ggatttctgg       781 tgcttctcaa gctgtggctt catcttattg cccaactgtg acattctttg attggaaggg      841
gaaaactaaa gcttttagca aaatacagc tagggaattt gtcgatctgc gagagtaaga      901
cctcttatga tcctaacgga atgatgtaag ctggaaataa taagcataag atgaaattga     961
aaattgaagt ctttattctt taagaaaaac tttgtacttg aaagcatgtc tgaagagttt     1021
actcattacc acaaacatct agcatattga taactaacat ctttatactc tacaagagag     1081
gctttccaga taggtacagt ttttcttctc tattaggtct atcaaaattt aacctattat     1141
gagggtcacc cctggctttc actgtttttc taaagaggca agggtgtagt aagaagcagg     1201
cttaagttgc cttcctccca atgtcaagtt cctttataag ctaatagttt aatcttgtga     1261
agatggcaat gaaagcctgt ggaagtgcaa acctcactat cttctggagc caagtagaat     1321
tttcaagttt gtagctctca cctcaagtgg ttatgggtgt cctgtgatga atctgctagc     1381
tccagcctca gtctcctctc ccacatcctt tcctttcttt cctctttgaa acttctaaga     1441
aaaagcaatc caaacaagtt cagcacttaa gacacattgc atgcacactt ttgataagtt     1501
aaatccaacc atctatttaa aatcaaaatc aggagatgag ccaagagacc agaggttctg     1561
ttccagtttt aaacagactt ttactgaaca tcccaatctt ttaaccacag aggctaaatt     1621
gagcaaatag ttttgccatt tgatataatt ccaacagta tgtttcaatg tcaagttaaa     1681
aagtctacaa agctatttc cctggagtgg tatcatcgct ttgagaattt cttatggtta     1741
aaatggatct gagatccaag catggcctgg gggatggttt tgatctaagg aaaaggtgt     1801 ctgtacctca cagtgccttt aaaacaagca gagatcccgt gtaccgccct aagatagcac     1861
agactagtgt taactgattc ccagaaaagt gtcacaatca gaaccaacgc attctcttaa     1921
actttaaaaa tatgtattgc aaagaacttg tgtaactgta aatgtgtgac tgttgatgac     1981
attatacaca catagcccac gtaagtgtcc aatggtgcta gcattggttg ctgagtttgc     2041
tgctcgaaag ctgaagcaga gatgcagtcc ttcacaaagc aatgatggac agagagggga     2101
gtctccatgt tttattcttt tgttgttcct ggctgtgtaa ctgttgactt cttgacattg     2161 tgattttta atttaagaca atgtattat tttggtgtgt ttattgttct agccttttaa       2221
```

```
atcactgaca atttctaatc aagaagtaca aataattcaa tgcagcacag gctaagagct    2281
tgtatcgttt ggaaaagcca gtgaaggctt ctccactagc catgggaaag ctacgcttta    2341
gagtaaacta gacaaaattg cacagcagtc ttgaacctct ctgtgctcaa gactcagcca    2401
gtcctttgac attattgttc actgtgggtg ggaacacatt ggacctgaca cactgttgtg    2461
tgtccatgaa ggttgccact ggtgtaagct ttttttggtt ttcattctct tatctgtaga    2521
acaagaatgt ggggctttcc taagtctatt ctgtatttta ttctgaactt cgtatgtctg    2581
agttttaatg ttttgagtac tcttacagga acacctgacc acactttga gttaaatttt      2641 atcccaagtg tgatatttag ttgttcaaaa agggaaggga tatacataca tacatacata    2701
catacataca tatatatata tatatataca tatatatata tatatatatg tatatatata    2761
tatatataga gagagagaga gagagagaga gagaaagaga gagaggttgt tgtaggtcat    2821
aggagttcag aggaaatcag ttatggccgt taatactgta gctgaaagtg ttttctttgt    2881
gaataaattc atagcattat tgatctatgt tattgctctg ttttatttac agtcacacct    2941
gagaatttag ttttaatatg aatgatgtac tttataactt aatgattatt tattatgtat    3001
ttggttttga atgtttgtgt tcatggcttc ttatttaaga cctgatcata ttaaatgcta    3061
cccagtccgg a                                                         3072
```

<210> SEQ ID NO 56
<211> LENGTH: 146
<212> TYPE: PRT
<213> ORGANISM: mus musculus

<400> SEQUENCE: 56

```
Met Glu Arg Thr Leu Val Cys Leu Val Val Ile Phe Leu Gly Thr Val
 1               5                  10                  15

Ala His Lys Ser Ser Pro Gln Gly Pro Asp Arg Leu Leu Ile Arg Leu
            20                  25                  30

Arg His Leu Ile Asp Ile Val Glu Gln Leu Lys Ile Tyr Glu Asn Asp
        35                  40                  45

Leu Asp Pro Glu Leu Leu Ser Ala Pro Gln Asp Val Lys Gly His Cys
    50                  55                  60

Glu His Ala Ala Phe Ala Cys Phe Gln Lys Ala Lys Leu Lys Pro Ser
65                  70                  75                  80

Asn Pro Gly Asn Asn Lys Thr Phe Ile Ile Asp Leu Val Ala Gln Leu
                85                  90                  95

Arg Arg Arg Leu Pro Ala Arg Arg Gly Gly Lys Lys Gln Lys His Ile
            100                 105                 110

Ala Lys Cys Pro Ser Cys Asp Ser Tyr Glu Lys Arg Thr Pro Lys Glu
        115                 120                 125

Phe Leu Glu Arg Leu Lys Trp Leu Leu Gln Lys Met Ile His Gln His
    130                 135                 140

Leu Ser
145
```

<210> SEQ ID NO 57
<211> LENGTH: 34
<212> TYPE: DNA
<213> ORGANISM: Artificial Sequence
<220> FEATURE:
<223> OTHER INFORMATION: Oligonucleotide primer ZC22283

<400> SEQUENCE: 57
cgctcgagac catggagagg acccttgtct gtct                                    34

<210> SEQ ID NO 58
<211> LENGTH: 31
<212> TYPE: DNA
<213> ORGANISM: Artificial Sequence
<220> FEATURE:
<223> OTHER INFORMATION: Oligonucleotide primer ZC22284

<400> SEQUENCE: 58
gctctagaat cttctcggat cctcaggaat c                                       31

<210> SEQ ID NO 59
<211> LENGTH: 100
<212> TYPE: DNA
<213> ORGANISM: Artificial Sequence
<220> FEATURE:
<223> OTHER INFORMATION: Oligonucleotide ZC12749

<400> SEQUENCE: 59
gtaccttccc gtaaatccct cccttcccg gaattacaca cgcgtatttc ccagaaaagg         60
aactgtagat ttctaggaat tcaatccttg gccacgcgtc                              00

<210> SEQ ID NO 60
<211> LENGTH: 100
<212> TYPE: DNA
<213> ORGANISM: Artificial Sequence
<220> FEATURE:
<223> OTHER INFORMATION: Oligonucleotide ZC12748

<400> SEQUENCE: 60
tcgagacgcg tggccaagga ttgaattcct agaaatctac agttcctttt ctgggaaata       60
cgcgtgtgta attccgggaa ggggagggat ttacgggaag                              00

<210> SEQ ID NO 61
<211> LENGTH: 32
<212> TYPE: DNA
<213> ORGANISM: Artificial Sequence
<220> FEATURE:
<223> OTHER INFORMATION: Oligonucleotide primer ZC22143

<400> SEQUENCE: 61
cgtatcggcc ggccaccatg agatccagtc ct                                      32

<210> SEQ ID NO 62
<211> LENGTH: 32
<212> TYPE: DNA
<213> ORGANISM: Artificial Sequence
<220> FEATURE:
<223> OTHER INFORMATION: Oligonucleotide primer ZC22144

<400> SEQUENCE: 62
cgtacgggcg cgcctcagga atcttcactt cc                                      32

<210> SEQ ID NO 63
<211> LENGTH: 483
<212> TYPE: DNA
<213> ORGANISM: homo sapiens

<400> SEQUENCE: 63
tccagtcctg gcaacatgga gaggattgtc atctgtctga tggtcatctt cttggggaca       60
ctggtccaca aatcaagctc ccaaggtcaa gatcgccaca tgattagaat gcgtcaactt      120
atagatattg ttgatcagct gaaaaattat gtgaatgact tggtccctga atttctgcca      180

```
gctccagaag atgtagagac aaactgtgag tggtcagctt tttcctgttt tcagaaggcc    240
caactaaagt cagcaaatac aggaaacaat gaaaggataa tcaatgtatc aattaaaaag    300
ctgaagagga aaccaccttc cacaaatgca gggagaagac agaaacacag actaacatgc    360
ccttcatgtg attcttatga gaaaaaacca cccaagaat tcctagaaag attcaaatca     420
cttctccaaa agatgattca tcagcatctg tcctctagaa cacacggaag tgaagattcc    480
tga                                                                  483
```

```
<210> SEQ ID NO 64
<211> LENGTH: 57
<212> TYPE: DNA
<213> ORGANISM: Artificial Sequence
<220> FEATURE:
<223> OTHER INFORMATION: Oligonucleotide primer ZC22052

<400> SEQUENCE: 64
tcatataggc cggccatatg cccgggcgcc accatggatt ccagtcctgg caacatg        57

<210> SEQ ID NO 65
<211> LENGTH: 57
<212> TYPE: DNA
<213> ORGANISM: Artificial Sequence
<220> FEATURE:
<223> OTHER INFORMATION: Oligonucleotide primer ZC22053

<400> SEQUENCE: 65
gtacaacccc agagctgttt taaggcgcgc ctctagatca ggaatcttca cttccgt        57

<210> SEQ ID NO 66
<211> LENGTH: 32
<212> TYPE: DNA
<213> ORGANISM: Artificial Sequence
<220> FEATURE:
<223> OTHER INFORMATION: Oligonucleotide primer ZC23115

<400> SEQUENCE: 66
gtatacggcc ggccaccatg gagaggaccc tt                                   32

<210> SEQ ID NO 67
<211> LENGTH: 32
<212> TYPE: DNA
<213> ORGANISM: Artificial Sequence
<220> FEATURE:
<223> OTHER INFORMATION: Oligonucleotide primer ZC23116

<400> SEQUENCE: 67
cgtatcggcg cgccctagga gagatgctga tg                                   32

<210> SEQ ID NO 68
<211> LENGTH: 35
<212> TYPE: DNA
<213> ORGANISM: Artificial Sequence
<220> FEATURE:
<223> OTHER INFORMATION: Oligonucleotide primer ZC20892

<400> SEQUENCE: 68
gtatacgttt aaacgccacc atgccgcgtg gctgg                                35

<210> SEQ ID NO 69
<211> LENGTH: 32
<212> TYPE: DNA
<213> ORGANISM: Artificial Sequence
<220> FEATURE:
```

<223> OTHER INFORMATION: Oligonucleotide primer ZC20893

<400> SEQUENCE: 69
cgtatcggcg cgccttacaa tggatgggtc tt        32

<210> SEQ ID NO 70
<211> LENGTH: 39
<212> TYPE: DNA
<213> ORGANISM: Artificial Sequence
<220> FEATURE:
<223> OTHER INFORMATION: Oligonucleotide primer ZC22054

<400> SEQUENCE: 70
cccggggtcg acaccatgga ttccagtcct ggcaacatg        39

<210> SEQ ID NO 71
<211> LENGTH: 32
<212> TYPE: DNA
<213> ORGANISM: Artificial Sequence
<220> FEATURE:
<223> OTHER INFORMATION: Oligonucleotide primer ZC22055

<400> SEQUENCE: 71
tgcagtttaa actcaggaat cttcacttcc gt        32

<210> SEQ ID NO 72
<211> LENGTH: 40
<212> TYPE: PRT
<213> ORGANISM: Artificial Sequence
<220> FEATURE:
<223> OTHER INFORMATION: Huzalpha11L-1 peptide

<400> SEQUENCE: 72

Gln Asp Arg His Met Ile Arg Met Arg Gln Leu Ile Asp Ile Val Asp
1               5                   10                  15
Gln Leu Lys Asn Tyr Val Asn Asp Leu Val Pro Glu Phe Leu Pro Ala
            20                  25                  30
Pro Glu Asp Val Glu Thr Asn Cys
        35                  40

<210> SEQ ID NO 73
<211> LENGTH: 32
<212> TYPE: PRT
<213> ORGANISM: Artificial Sequence
<220> FEATURE:
<223> OTHER INFORMATION: Huzalpha11L-3 peptide

<400> SEQUENCE: 73

Cys Pro Ser Cys Asp Ser Tyr Glu Lys Lys Pro Pro Lys Glu Phe Leu
1               5                   10                  15
Glu Arg Phe Lys Ser Leu Leu Gln Lys Met Ile His Gln His Leu Ser
            20                  25                  30

<210> SEQ ID NO 74
<211> LENGTH: 29
<212> TYPE: DNA
<213> ORGANISM: Artificial Sequence
<220> FEATURE:
<223> OTHER INFORMATION: Oligonucleotide primer ZC23444

<400> SEQUENCE: 74
gcccgggcgg atccatggat tccagtcct        29

<210> SEQ ID NO 75

```
<211> LENGTH: 32
<212> TYPE: DNA
<213> ORGANISM: Artificial Sequence
<220> FEATURE:
<223> OTHER INFORMATION: Oligonucleotide primer ZC23445

<400> SEQUENCE: 75
cgcgccctcg agtcaggaat cttcacttcc gt                                   32

<210> SEQ ID NO 76
<211> LENGTH: 17
<212> TYPE: DNA
<213> ORGANISM: Artificial Sequence
<220> FEATURE:
<223> OTHER INFORMATION: Oligonucleotide primer ZC447

<400> SEQUENCE: 76
taacaatttc acacagg                                                    17

<210> SEQ ID NO 77
<211> LENGTH: 18
<212> TYPE: DNA
<213> ORGANISM: Artificial Sequence
<220> FEATURE:
<223> OTHER INFORMATION: Oligonucleotide primer ZC976

<400> SEQUENCE: 77
cgttgtaaaa cgacggcc                                                   18

<210> SEQ ID NO 78
<211> LENGTH: 66
<212> TYPE: DNA
<213> ORGANISM: Artificial Sequence
<220> FEATURE:
<223> OTHER INFORMATION: Oligonucleotide primer ZC22128

<400> SEQUENCE: 78
tcaccacgcg aattcggtac cgctggttcc gcgtggatcc caagatcgcc acatgattag     60
aatgcg                                                                66

<210> SEQ ID NO 79
<211> LENGTH: 68
<212> TYPE: DNA
<213> ORGANISM: Artificial Sequence
<220> FEATURE:
<223> OTHER INFORMATION: Oligonucleotide primer ZC22127

<400> SEQUENCE: 79
tctgtatcag gctgaaaatc ttatctcatc cgccaaaaca tcaggaatct tcacttccgt     60
gtgttcta                                                              68

<210> SEQ ID NO 80
<211> LENGTH: 40
<212> TYPE: DNA
<213> ORGANISM: Artificial Sequence
<220> FEATURE:
<223> OTHER INFORMATION: Oligonucleotide primer ZC19372

<400> SEQUENCE: 80
tgtcgatgaa gccctgaaag acgcgcagac taattcgagc                           40

<210> SEQ ID NO 81
<211> LENGTH: 60
<212> TYPE: DNA
<213> ORGANISM: Artificial Sequence
```

```
<220> FEATURE:
<223> OTHER INFORMATION: Oligonucleotide primer ZC19351

<400> SEQUENCE: 81
acgcgcagac taattcgagc tcccaccatc accatcacca cgcgaattcg gtaccgctgg    60

<210> SEQ ID NO 82
<211> LENGTH: 60
<212> TYPE: DNA
<213> ORGANISM: Artificial Sequence
<220> FEATURE:
<223> OTHER INFORMATION: Oligonucleotide primer ZC19352

<400> SEQUENCE: 82
actcactata gggcgaattg cccgggggat ccacgcggaa ccagcggtac cgaattcgcg    60

<210> SEQ ID NO 83
<211> LENGTH: 42
<212> TYPE: DNA
<213> ORGANISM: Artificial Sequence
<220> FEATURE:
<223> OTHER INFORMATION: Oligonucleotide primer ZC19371

<400> SEQUENCE: 83
acggccagtg aattgtaata cgactcacta tagggcgaat tg                       42

<210> SEQ ID NO 84
<211> LENGTH: 1560
<212> TYPE: DNA
<213> ORGANISM: Artificial Sequence
<220> FEATURE:
<221> NAME/KEY: CDS
<222> LOCATION: (1)...(1560)
<223> OTHER INFORMATION: MBP-human zalpha11 Ligand fusion polynucleotide

<400> SEQUENCE: 84
```

| | | | | | | | | | | | | | | | | |
|---|---|---|---|---|---|---|---|---|---|---|---|---|---|---|---|---|
| atg | aaa | act | gaa | gaa | ggt | aaa | ctg | gta | atc | tgg | att | aac | ggc | gat | aaa | 48 |
| Met | Lys | Thr | Glu | Glu | Gly | Lys | Leu | Val | Ile | Trp | Ile | Asn | Gly | Asp | Lys | |
| 1 | | | | 5 | | | | | 10 | | | | | 15 | | |

```
ggc tat aac ggt ctc gct gaa gtc ggt aag aaa ttc gag aaa gat acc    96
Gly Tyr Asn Gly Leu Ala Glu Val Gly Lys Lys Phe Glu Lys Asp Thr
             20                  25                  30 gga att aaa gtc acc gtt gag cat ccg gat aaa ctg gaa gag aaa ttc   144
Gly Ile Lys Val Thr Val Glu His Pro Asp Lys Leu Glu Glu Lys Phe
         35                  40                  45 cca cag gtt gcg gca act ggc gat ggc cct gac att atc ttc tgg gca   192
Pro Gln Val Ala Ala Thr Gly Asp Gly Pro Asp Ile Ile Phe Trp Ala
     50                  55                  60 cac gac cgc ttt ggt ggc tac gct caa tct ggc ctg ttg gct gaa atc   240
His Asp Arg Phe Gly Gly Tyr Ala Gln Ser Gly Leu Leu Ala Glu Ile
 65                  70                  75                  80 acc ccg gac aaa gcg ttc cag gac aag ctg tat ccg ttt acc tgg gat   288
Thr Pro Asp Lys Ala Phe Gln Asp Lys Leu Tyr Pro Phe Thr Trp Asp
                 85                  90                  95 gcc gta cgt tac aac ggc aag ctg att gct tac ccg atc gct gtt gaa   336
Ala Val Arg Tyr Asn Gly Lys Leu Ile Ala Tyr Pro Ile Ala Val Glu
            100                 105                 110 gcg tta tcg ctg att tat aac aaa gat ctg ctg ccg aac ccg cca aaa   384
Ala Leu Ser Leu Ile Tyr Asn Lys Asp Leu Leu Pro Asn Pro Pro Lys
        115                 120                 125 acc tgg gaa gag atc ccg gcg ctg gat aaa gaa ctg aaa gcg aaa ggt   432
Thr Trp Glu Glu Ile Pro Ala Leu Asp Lys Glu Leu Lys Ala Lys Gly
    130                 135                 140
```

```
aag agc gcg ctg atg ttc aac ctg caa gaa ccg tac ttc acc tgg ccg      480
Lys Ser Ala Leu Met Phe Asn Leu Gln Glu Pro Tyr Phe Thr Trp Pro
145                 150                 155                 160 ctg att gct gct gac ggg ggt tat gcg ttc aag tat gaa aac ggc aag      528
Leu Ile Ala Ala Asp Gly Gly Tyr Ala Phe Lys Tyr Glu Asn Gly Lys
                165                 170                 175 tac gac att aaa gac gtg ggc gtg gat aac gct ggc gcg aaa gcg ggt      576
Tyr Asp Ile Lys Asp Val Gly Val Asp Asn Ala Gly Ala Lys Ala Gly
            180                 185                 190 ctg acc ttc ctg gtt gac ctg att aaa aac aaa cac atg aat gca gac      624
Leu Thr Phe Leu Val Asp Leu Ile Lys Asn Lys His Met Asn Ala Asp
        195                 200                 205 acc gat tac tcc atc gca gaa gct gcc ttt aat aaa ggc gaa aca gcg      672
Thr Asp Tyr Ser Ile Ala Glu Ala Ala Phe Asn Lys Gly Glu Thr Ala
    210                 215                 220 atg acc atc aac ggc ccg tgg gca tgg tcc aac atc gac acc agc aaa      720
Met Thr Ile Asn Gly Pro Trp Ala Trp Ser Asn Ile Asp Thr Ser Lys
225                 230                 235                 240 gtg aat tat ggt gta acg gta ctg ccg acc ttc aag ggt caa cca tcc      768
Val Asn Tyr Gly Val Thr Val Leu Pro Thr Phe Lys Gly Gln Pro Ser
                245                 250                 255 aaa ccg ttc gtt ggc gtg ctg agc gca ggt att aac gcc gcc agt ccg      816
Lys Pro Phe Val Gly Val Leu Ser Ala Gly Ile Asn Ala Ala Ser Pro
            260                 265                 270 aac aaa gag ctg gca aaa gag ttc ctc gaa aac tat ctg ctg act gat      864
Asn Lys Glu Leu Ala Lys Glu Phe Leu Glu Asn Tyr Leu Leu Thr Asp
        275                 280                 285 gaa ggt ctg gaa gcg gtt aat aaa gac aaa ccg ctg ggt gcc gta gcg      912
Glu Gly Leu Glu Ala Val Asn Lys Asp Lys Pro Leu Gly Ala Val Ala
    290                 295                 300 ctg aag tct tac gag gaa gag ttg gcg aaa gat cca cgt att gcc gcc      960
Leu Lys Ser Tyr Glu Glu Glu Leu Ala Lys Asp Pro Arg Ile Ala Ala
305                 310                 315                 320 acc atg gaa aac gcc cag aaa ggt gaa atc atg ccg aac atc ccg cag     1008
Thr Met Glu Asn Ala Gln Lys Gly Glu Ile Met Pro Asn Ile Pro Gln
                325                 330                 335 atg tcc gct ttc tgg tat gcc gtg cgt act gcg gtg atc aac gcc gcc     1056
Met Ser Ala Phe Trp Tyr Ala Val Arg Thr Ala Val Ile Asn Ala Ala
            340                 345                 350 agc ggt cgt cag act gtc gat gaa gcc ctg aaa gac gcg cag act aat     1104
Ser Gly Arg Gln Thr Val Asp Glu Ala Leu Lys Asp Ala Gln Thr Asn
        355                 360                 365 tcg agc tcc cac cat cac cat cac cac gcg aat tcg gta ccg ctg gtt     1152
Ser Ser Ser His His His His His His Ala Asn Ser Val Pro Leu Val
    370                 375                 380 ccg cgt gga tcc caa gat cgc cac atg att aga atg cgt caa ctt ata     1200
Pro Arg Gly Ser Gln Asp Arg His Met Ile Arg Met Arg Gln Leu Ile
385                 390                 395                 400 gat att gtt gat cag ctg aaa aat tat gtg aat gac ttg gtc cct gaa     1248
Asp Ile Val Asp Gln Leu Lys Asn Tyr Val Asn Asp Leu Val Pro Glu
                405                 410                 415 ttt ctg cca gct cca gaa gat gta gag aca aac tgt gag tgg tca gct     1296
Phe Leu Pro Ala Pro Glu Asp Val Glu Thr Asn Cys Glu Trp Ser Ala
            420                 425                 430 ttt tcc tgt ttt cag aag gcc caa cta aag tca gca aat aca gga aac     1344
Phe Ser Cys Phe Gln Lys Ala Gln Leu Lys Ser Ala Asn Thr Gly Asn
        435                 440                 445 aat gaa agg ata atc aat gta tca att aaa aag ctg aag agg aaa cca     1392
Asn Glu Arg Ile Ile Asn Val Ser Ile Lys Lys Leu Lys Arg Lys Pro
    450                 455                 460
```

```
cct tcc aca aat gca ggg aga aga cag aaa cac aga cta aca tgc cct    1440
Pro Ser Thr Asn Ala Gly Arg Arg Gln Lys His Arg Leu Thr Cys Pro
465                 470                 475                 480 tca tgt gat tct tat gag aaa aaa cca ccc aaa gaa ttc cta gaa aga    1488
Ser Cys Asp Ser Tyr Glu Lys Lys Pro Pro Lys Glu Phe Leu Glu Arg
            485                 490                 495 ttc aaa tca ctt ctc caa aag atg att cat cag cat ctg tcc tct aga    1536
Phe Lys Ser Leu Leu Gln Lys Met Ile His Gln His Leu Ser Ser Arg
        500                 505                 510 aca cac gga agt gaa gat tcc tga                                    1560
Thr His Gly Ser Glu Asp Ser
            515
```

<210> SEQ ID NO 85
<211> LENGTH: 519
<212> TYPE: PRT
<213> ORGANISM: Artificial Sequence
<220> FEATURE:
<223> OTHER INFORMATION: MBP-human zalpha11 Ligand fusion polypeptide

<400> SEQUENCE: 85

```
Met Lys Thr Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60

His Asp Arg Phe Gly Gly Tyr Ala Gln Ser Gly Leu Leu Ala Glu Ile
65                  70                  75                  80

Thr Pro Asp Lys Ala Phe Gln Asp Lys Leu Tyr Pro Phe Thr Trp Asp
                85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
```

```
                275                 280                 285
Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser His His His His His His Ala Asn Ser Val Pro Leu Val
370                 375                 380

Pro Arg Gly Ser Gln Asp Arg His Met Ile Arg Met Arg Gln Leu Ile
385                 390                 395                 400

Asp Ile Val Asp Gln Leu Lys Asn Tyr Val Asn Asp Leu Val Pro Glu
                405                 410                 415

Phe Leu Pro Ala Pro Glu Asp Val Glu Thr Asn Cys Glu Trp Ser Ala
            420                 425                 430

Phe Ser Cys Phe Gln Lys Ala Gln Leu Lys Ser Ala Asn Thr Gly Asn
        435                 440                 445

Asn Glu Arg Ile Ile Asn Val Ser Ile Lys Lys Leu Lys Arg Lys Pro
    450                 455                 460

Pro Ser Thr Asn Ala Gly Arg Arg Gln Lys His Arg Leu Thr Cys Pro
465                 470                 475                 480

Ser Cys Asp Ser Tyr Glu Lys Lys Pro Pro Lys Glu Phe Leu Glu Arg
                485                 490                 495

Phe Lys Ser Leu Leu Gln Lys Met Ile His Gln His Leu Ser Ser Arg
            500                 505                 510

Thr His Gly Ser Glu Asp Ser
        515

<210> SEQ ID NO 86
<211> LENGTH: 64
<212> TYPE: DNA
<213> ORGANISM: Artificial Sequence
<220> FEATURE:
<223> OTHER INFORMATION: Oligonucleotide primer ZC22849

<400> SEQUENCE: 86
tcaccacgcg aattcggtac cgctggttcc gcgtggatcc ccagatcgcc tcctgattag   60
actt                                                                64

<210> SEQ ID NO 87
<211> LENGTH: 64
<212> TYPE: DNA
<213> ORGANISM: Artificial Sequence
<220> FEATURE:
<223> OTHER INFORMATION: Oligonucleotide primer ZC22850

<400> SEQUENCE: 87
tctgtatcag gctgaaaatc ttatctcatc cgccaaaaca ctaggagaga tgctgatgaa   60
tcat                                                                64

<210> SEQ ID NO 88
<211> LENGTH: 1533
<212> TYPE: DNA
```

-continued

```
<213> ORGANISM: Artificial Sequence
<220> FEATURE:
<223> OTHER INFORMATION: MBP-mouse zalpha11 Ligand fusion polynucleotide
<220> FEATURE:
<221> NAME/KEY: CDS
<222> LOCATION: (1)...(1533)

<400> SEQUENCE: 88 atg aaa act gaa gaa ggt aaa ctg gta atc tgg att aac ggc gat aaa         48
Met Lys Thr Glu Glu Gly Lys Leu Val Ile Trp Ile Asn Gly Asp Lys
 1               5                  10                  15 ggc tat aac ggt ctc gct gaa gtc ggt aag aaa ttc gag aaa gat acc         96
Gly Tyr Asn Gly Leu Ala Glu Val Gly Lys Lys Phe Glu Lys Asp Thr
             20                  25                  30 gga att aaa gtc acc gtt gag cat ccg gat aaa ctg gaa gag aaa ttc        144
Gly Ile Lys Val Thr Val Glu His Pro Asp Lys Leu Glu Glu Lys Phe
         35                  40                  45 cca cag gtt gcg gca act ggc gat ggc cct gac att atc ttc tgg gca        192
Pro Gln Val Ala Ala Thr Gly Asp Gly Pro Asp Ile Ile Phe Trp Ala
     50                  55                  60 cac gac cgc ttt ggt ggc tac gct caa tct ggc ctg ttg gct gaa atc        240
His Asp Arg Phe Gly Gly Tyr Ala Gln Ser Gly Leu Leu Ala Glu Ile
 65                  70                  75                  80 acc ccg gac aaa gcg ttc cag gac aag ctg tat ccg ttt acc tgg gat        288
Thr Pro Asp Lys Ala Phe Gln Asp Lys Leu Tyr Pro Phe Thr Trp Asp
                 85                  90                  95 gcc gta cgt tac aac ggc aag ctg att gct tac ccg atc gct gtt gaa        336
Ala Val Arg Tyr Asn Gly Lys Leu Ile Ala Tyr Pro Ile Ala Val Glu
            100                 105                 110 gcg tta tcg ctg att tat aac aaa gat ctg ctg ccg aac ccg cca aaa        384
Ala Leu Ser Leu Ile Tyr Asn Lys Asp Leu Leu Pro Asn Pro Pro Lys
        115                 120                 125 acc tgg gaa gag atc ccg gcg ctg gat aaa gaa ctg aaa gcg aaa ggt        432
Thr Trp Glu Glu Ile Pro Ala Leu Asp Lys Glu Leu Lys Ala Lys Gly
    130                 135                 140 aag agc gcg ctg atg ttc aac ctg caa gaa ccg tac ttc acc tgg ccg        480
Lys Ser Ala Leu Met Phe Asn Leu Gln Glu Pro Tyr Phe Thr Trp Pro
145                 150                 155                 160 ctg att gct gct gac ggg ggt tat gcg ttc aag tat gaa aac ggc aag        528
Leu Ile Ala Ala Asp Gly Gly Tyr Ala Phe Lys Tyr Glu Asn Gly Lys
                165                 170                 175 tac gac att aaa gac gtg ggc gtg gat aac gct ggc gcg aaa gcg ggt        576
Tyr Asp Ile Lys Asp Val Gly Val Asp Asn Ala Gly Ala Lys Ala Gly
            180                 185                 190 ctg acc ttc ctg gtt gac ctg att aaa aac aaa cac atg aat gca gac        624
Leu Thr Phe Leu Val Asp Leu Ile Lys Asn Lys His Met Asn Ala Asp
        195                 200                 205 acc gat tac tcc atc gca gaa gct gcc ttt aat aaa ggc gaa aca gcg        672
Thr Asp Tyr Ser Ile Ala Glu Ala Ala Phe Asn Lys Gly Glu Thr Ala
    210                 215                 220 atg acc atc aac ggc ccg tgg gca tgg tcc aac atc gac acc agc aaa        720
Met Thr Ile Asn Gly Pro Trp Ala Trp Ser Asn Ile Asp Thr Ser Lys
225                 230                 235                 240 gtg aat tat ggt gta acg gta ctg ccg acc ttc aag ggt caa cca tcc        768
Val Asn Tyr Gly Val Thr Val Leu Pro Thr Phe Lys Gly Gln Pro Ser
                245                 250                 255 aaa ccg ttc gtt ggc gtg ctg agc gca ggt att aac gcc gcc agt ccg        816
Lys Pro Phe Val Gly Val Leu Ser Ala Gly Ile Asn Ala Ala Ser Pro
            260                 265                 270 aac aaa gag ctg gca aaa gag ttc ctc gaa aac tat ctg ctg act gat        864
Asn Lys Glu Leu Ala Lys Glu Phe Leu Glu Asn Tyr Leu Leu Thr Asp
```

```
                275                 280                 285
gaa ggt ctg gaa gcg gtt aat aaa gac aaa ccg ctg ggt gcc gta gcg      912
Glu Gly Leu Glu Ala Val Asn Lys Asp Lys Pro Leu Gly Ala Val Ala
290                 295                 300 ctg aag tct tac gag gaa gag ttg gcg aaa gat cca cgt att gcc gcc      960
Leu Lys Ser Tyr Glu Glu Glu Leu Ala Lys Asp Pro Arg Ile Ala Ala
305                 310                 315                 320 acc atg gaa aac gcc cag aaa ggt gaa atc atg ccg aac atc ccg cag     1008
Thr Met Glu Asn Ala Gln Lys Gly Glu Ile Met Pro Asn Ile Pro Gln
                325                 330                 335 atg tcc gct ttc tgg tat gcc gtg cgt act gcg gtg atc aac gcc gcc     1056
Met Ser Ala Phe Trp Tyr Ala Val Arg Thr Ala Val Ile Asn Ala Ala
            340                 345                 350 agc ggt cgt cag act gtc gat gaa gcc ctg aaa gac gcg cag act aat     1104
Ser Gly Arg Gln Thr Val Asp Glu Ala Leu Lys Asp Ala Gln Thr Asn
        355                 360                 365 tcg agc tcc cac cat cac cat cac cac gcg aat tcg gta ccg ctg gtt     1152
Ser Ser Ser His His His His His His Ala Asn Ser Val Pro Leu Val
    370                 375                 380 ccg cgt gga tcc cca gat cgc ctc ctg att aga ctt cgt cac ctt att     1200
Pro Arg Gly Ser Pro Asp Arg Leu Leu Ile Arg Leu Arg His Leu Ile
385                 390                 395                 400 gac att gtt gaa cag ctg aaa atc tat gaa aat gac ttg gat cct gaa     1248
Asp Ile Val Glu Gln Leu Lys Ile Tyr Glu Asn Asp Leu Asp Pro Glu
                405                 410                 415 ctt cta tca gct cca caa gat gta aag ggg cac tgt gag cat gca gct     1296
Leu Leu Ser Ala Pro Gln Asp Val Lys Gly His Cys Glu His Ala Ala
            420                 425                 430 ttt gcc tgt ttt cag aag gcc aaa ctc aag cca tca aac cct gga aac     1344
Phe Ala Cys Phe Gln Lys Ala Lys Leu Lys Pro Ser Asn Pro Gly Asn
        435                 440                 445 aat aag aca ttc atc att gac ctc gtg gcc cag ctc agg agg agg ctg     1392
Asn Lys Thr Phe Ile Ile Asp Leu Val Ala Gln Leu Arg Arg Arg Leu
    450                 455                 460 cct gcc agg agg gga gga aag aaa cag aag cac ata gct aaa tgc cct     1440
Pro Ala Arg Arg Gly Gly Lys Lys Gln Lys His Ile Ala Lys Cys Pro
465                 470                 475                 480 tcc tgt gat tcg tat gag aaa agg aca ccc aaa gaa ttc cta gaa aga     1488
Ser Cys Asp Ser Tyr Glu Lys Arg Thr Pro Lys Glu Phe Leu Glu Arg
                485                 490                 495 cta aaa tgg ctc ctt caa aag atg att cat cag cat ctc tcc tga         1533
Leu Lys Trp Leu Leu Gln Lys Met Ile His Gln His Leu Ser
            500                 505                 510

<210> SEQ ID NO 89
<211> LENGTH: 510
<212> TYPE: PRT
<213> ORGANISM: Artificial Sequence
<220> FEATURE:
<223> OTHER INFORMATION: MBP-mouse zalpha11 Ligand fusion polypeptide

<400> SEQUENCE: 89

Met Lys Thr Glu Glu Gly Lys Leu Val Ile Trp Ile Asn Gly Asp Lys
1               5                   10                  15

Gly Tyr Asn Gly Leu Ala Glu Val Gly Lys Lys Phe Glu Lys Asp Thr
            20                  25                  30

Gly Ile Lys Val Thr Val Glu His Pro Asp Lys Leu Glu Glu Lys Phe
        35                  40                  45

Pro Gln Val Ala Ala Thr Gly Asp Gly Pro Asp Ile Ile Phe Trp Ala
    50                  55                  60
```

-continued

```
His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
                100                 105                 110

Ala Leu Ser Leu Ile Tyr Asn Lys Asp Leu Leu Pro Asn Pro Pro Lys
            115                 120                 125

Thr Trp Glu Glu Ile Pro Ala Leu Asp Lys Glu Leu Lys Ala Lys Gly
        130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
                180                 185                 190

Leu Thr Phe Leu Val Asp Leu Ile Lys Asn Lys His Met Asn Ala Asp
            195                 200                 205

Thr Asp Tyr Ser Ile Ala Glu Ala Ala Phe Asn Lys Gly Glu Thr Ala
        210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
                260                 265                 270

Asn Lys Glu Leu Ala Lys Glu Phe Leu Glu Asn Tyr Leu Leu Thr Asp
            275                 280                 285

Glu Gly Leu Glu Ala Val Asn Lys Asp Lys Pro Leu Gly Ala Val Ala
        290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335

Met Ser Ala Phe Trp Tyr Ala Val Arg Thr Ala Val Ile Asn Ala Ala
                340                 345                 350

Ser Gly Arg Gln Thr Val Asp Glu Ala Leu Lys Asp Ala Gln Thr Asn
            355                 360                 365

Ser Ser Ser His His His His His His Ala Asn Ser Val Pro Leu Val
        370                 375                 380

Pro Arg Gly Ser Pro Asp Arg Leu Leu Ile Arg Leu Arg His Leu Ile
385                 390                 395                 400

Asp Ile Val Glu Gln Leu Lys Ile Tyr Glu Asn Asp Leu Asp Pro Glu
                405                 410                 415

Leu Leu Ser Ala Pro Gln Asp Val Lys Gly His Cys Glu His Ala Ala
                420                 425                 430

Phe Ala Cys Phe Gln Lys Ala Lys Leu Lys Pro Ser Asn Pro Gly Asn
            435                 440                 445

Asn Lys Thr Phe Ile Ile Asp Leu Val Ala Gln Leu Arg Arg Arg Leu
        450                 455                 460

Pro Ala Arg Arg Gly Gly Lys Lys Gln Lys His Ile Ala Lys Cys Pro
465                 470                 475                 480
```

```
Ser Cys Asp Ser Tyr Glu Lys Arg Thr Pro Lys Glu Phe Leu Glu Arg
            485                 490                 495

Leu Lys Trp Leu Leu Gln Lys Met Ile His Gln His Leu Ser
        500                 505                 510

<210> SEQ ID NO 90
<211> LENGTH: 22
<212> TYPE: DNA
<213> ORGANISM: Artificial Sequence
<220> FEATURE:
<223> OTHER INFORMATION: Oligonucleotide primer ZC22281

<400> SEQUENCE: 90
tgtgaatgac ttggtccctg aa                                          22

<210> SEQ ID NO 91
<211> LENGTH: 23
<212> TYPE: DNA
<213> ORGANISM: Artificial Sequence
<220> FEATURE:
<223> OTHER INFORMATION: Oligonucleotide primer ZC22279

<400> SEQUENCE: 91
aacaggaaaa agctgaccac tca                                         23

<210> SEQ ID NO 92
<211> LENGTH: 31
<212> TYPE: DNA
<213> ORGANISM: Artificial Sequence
<220> FEATURE:
<223> OTHER INFORMATION: Human zalpha11 Ligand TaqMan probe, ZG32

<400> SEQUENCE: 92
tctgccagct ccagaagatg tagagacaaa c                                31

<210> SEQ ID NO 93
<211> LENGTH: 20
<212> TYPE: DNA
<213> ORGANISM: Artificial Sequence
<220> FEATURE:
<223> OTHER INFORMATION: Oligonucleotide primer ZC22277

<400> SEQUENCE: 93
ccaggagtgt ggcagctttc                                             20

<210> SEQ ID NO 94
<211> LENGTH: 21
<212> TYPE: DNA
<213> ORGANISM: Artificial Sequence
<220> FEATURE:
<223> OTHER INFORMATION: Oligonucleotide primer ZC22276

<400> SEQUENCE: 94
gcttgccctt cagcatgtag a                                           21

<210> SEQ ID NO 95
<211> LENGTH: 23
<212> TYPE: DNA
<213> ORGANISM: Artificial Sequence
<220> FEATURE:
<223> OTHER INFORMATION: Human zalpha11 TaqMan probe, ZG31

<400> SEQUENCE: 95
cggctccccc tttcaacgtg act                                         23
```

-continued

```
<210> SEQ ID NO 96
<211> LENGTH: 1821
<212> TYPE: DNA
<213> ORGANISM: Artificial Sequence
<220> FEATURE:
<221> NAME/KEY: CDS
<222> LOCATION: (1)...(1821)
<223> OTHER INFORMATION: MBP-zalpha11 soluble receptor polynucleotide
      sequence

<400> SEQUENCE: 96 atg aaa atc gaa gaa ggt aaa ctg gta atc tgg att aac ggc gat aaa        48
Met Lys Ile Glu Glu Gly Lys Leu Val Ile Trp Ile Asn Gly Asp Lys
1               5                   10                  15 ggc tat aac ggt ctc gct gaa gtc ggt aag aaa ttc gag aaa gat acc        96
Gly Tyr Asn Gly Leu Ala Glu Val Gly Lys Lys Phe Glu Lys Asp Thr
            20                  25                  30 gga att aaa gtc acc gtt gag cat ccg gat aaa ctg gaa gag aaa ttc       144
Gly Ile Lys Val Thr Val Glu His Pro Asp Lys Leu Glu Glu Lys Phe
        35                  40                  45 cca cag gtt gcg gca act ggc gat ggc cct gac att atc ttc tgg gca       192
Pro Gln Val Ala Ala Thr Gly Asp Gly Pro Asp Ile Ile Phe Trp Ala
    50                  55                  60 cac gac cgc ttt ggt ggc tac gct caa tct ggc ctg ttg gct gaa atc       240
His Asp Arg Phe Gly Gly Tyr Ala Gln Ser Gly Leu Leu Ala Glu Ile
65                  70                  75                  80 acc ccg gac aaa gcg ttc cag gac aag ctg tat ccg ttt acc tgg gat       288
Thr Pro Asp Lys Ala Phe Gln Asp Lys Leu Tyr Pro Phe Thr Trp Asp
                85                  90                  95 gcc gta cgt tac aac ggc aag ctg att gct tac ccg atc gct gtt gaa       336
Ala Val Arg Tyr Asn Gly Lys Leu Ile Ala Tyr Pro Ile Ala Val Glu
            100                 105                 110 gcg tta tcg ctg att tat aac aaa gat ctg ctg ccc aac ccg cca aaa       384
Ala Leu Ser Leu Ile Tyr Asn Lys Asp Leu Leu Pro Asn Pro Pro Lys
        115                 120                 125 acc tgg gaa gag atc ccg gcg ctg gat aaa gaa ctg aaa gcg aaa ggt       432
Thr Trp Glu Glu Ile Pro Ala Leu Asp Lys Glu Leu Lys Ala Lys Gly
    130                 135                 140 aag agc gcg ctg atg ttc aac ctg caa gaa ccg tac ttc acc tgg ccg       480
Lys Ser Ala Leu Met Phe Asn Leu Gln Glu Pro Tyr Phe Thr Trp Pro
145                 150                 155                 160 ctg att gct gct gac ggg ggt tat gcg ttc aag tat gaa aac ggc aag       528
Leu Ile Ala Ala Asp Gly Gly Tyr Ala Phe Lys Tyr Glu Asn Gly Lys
                165                 170                 175 tac gac att aaa gac gtg ggc gtg gat aac gct ggc gcg aaa gcg ggt       576
Tyr Asp Ile Lys Asp Val Gly Val Asp Asn Ala Gly Ala Lys Ala Gly
            180                 185                 190 ctg acc ttc ctg gtt gac ctg att aaa aac aaa cac atg aat gca gac       624
Leu Thr Phe Leu Val Asp Leu Ile Lys Asn Lys His Met Asn Ala Asp
        195                 200                 205 acc gat tac tcc atc gca gaa gct gcc ttt aat aaa ggc gaa aca gcg       672
Thr Asp Tyr Ser Ile Ala Glu Ala Ala Phe Asn Lys Gly Glu Thr Ala
    210                 215                 220 atg acc atc aac ggc ccg tgg gca tgg tcc aac atc gac acc agc aaa       720
Met Thr Ile Asn Gly Pro Trp Ala Trp Ser Asn Ile Asp Thr Ser Lys
225                 230                 235                 240 gtg aat tat ggt gta acg gta ctg ccc acc ttc aag ggt caa cca tcc       768
Val Asn Tyr Gly Val Thr Val Leu Pro Thr Phe Lys Gly Gln Pro Ser
                245                 250                 255 aaa ccg ttc gtt ggc gtg ctg agc gca ggt att aac gcc gcc agt ccg       816
Lys Pro Phe Val Gly Val Leu Ser Ala Gly Ile Asn Ala Ala Ser Pro
            260                 265                 270
```

|  |  |
|---|---:|
| aac aaa gag ctg gca aaa gag ttc ctc gaa aac tat ctg ctg act gat<br>Asn Lys Glu Leu Ala Lys Glu Phe Leu Glu Asn Tyr Leu Leu Thr Asp<br>275                    280                    285 | 864 |
| gaa ggt ctg gaa gcg gtt aat aaa gac aaa ccg ctg ggt gcc gta gcg<br>Glu Gly Leu Glu Ala Val Asn Lys Asp Lys Pro Leu Gly Ala Val Ala<br>290                    295                    300 | 912 |
| ctg aag tct tac gag gaa gag ttg gcg aaa gat cca cgt att gcc gcc<br>Leu Lys Ser Tyr Glu Glu Glu Leu Ala Lys Asp Pro Arg Ile Ala Ala<br>305                    310                    315                    320 | 960 |
| acc atg gaa aac gcc cag aaa ggt gaa atc atg ccg aac atc ccg cag<br>Thr Met Glu Asn Ala Gln Lys Gly Glu Ile Met Pro Asn Ile Pro Gln<br>                    325                    330                    335 | 1008 |
| atg tcc gct ttc tgg tat gcc gtg cgt act gcg gtg atc aac gcc gcc<br>Met Ser Ala Phe Trp Tyr Ala Val Arg Thr Ala Val Ile Asn Ala Ala<br>              340                    345                    350 | 1056 |
| agc ggt cgt cag act gtc gat gaa gcc ctg aaa gac gcg cag act aat<br>Ser Gly Arg Gln Thr Val Asp Glu Ala Leu Lys Asp Ala Gln Thr Asn<br>              355                    360                    365 | 1104 |
| tcg agc tcc cac cat cac cat cac cac gcg aat tcg gta ccg ctg gtt<br>Ser Ser Ser His His His His His His Ala Asn Ser Val Pro Leu Val<br>370                    375                    380 | 1152 |
| ccg cgt gga tcc tgc ccc gac ctc gtc tgc tac acc gat tac ctc cag<br>Pro Arg Gly Ser Cys Pro Asp Leu Val Cys Tyr Thr Asp Tyr Leu Gln<br>385                    390                  395                    400 | 1200 |
| acg gtc atc tgc atc ctg gaa atg tgg aac ctc cac ccc agc acg ctc<br>Thr Val Ile Cys Ile Leu Glu Met Trp Asn Leu His Pro Ser Thr Leu<br>                    405                    410                    415 | 1248 |
| acc ctt acc tgg caa gac cag tat gaa gag ctg aag gac gag gcc acc<br>Thr Leu Thr Trp Gln Asp Gln Tyr Glu Glu Leu Lys Asp Glu Ala Thr<br>                       420                    425                    430 | 1296 |
| tcc tgc agc ctc cac agg tcg gcc cac aat gcc acg cat gcc acc tac<br>Ser Cys Ser Leu His Arg Ser Ala His Asn Ala Thr His Ala Thr Tyr<br>              435                    440                    445 | 1344 |
| acc tgc cac atg gat gta ttc cac ttc atg gcc gac gac att ttc agt<br>Thr Cys His Met Asp Val Phe His Phe Met Ala Asp Asp Ile Phe Ser<br>450                    455                    460 | 1392 |
| gtc aac atc aca gac cag tct ggc aac tac tcc cag gag tgt ggc agc<br>Val Asn Ile Thr Asp Gln Ser Gly Asn Tyr Ser Gln Glu Cys Gly Ser<br>465                    470                    475                    480 | 1440 |
| ttt ctc ctg gct gag agc atc aag ccg gct ccc cct ttc aac gtg act<br>Phe Leu Leu Ala Glu Ser Ile Lys Pro Ala Pro Pro Phe Asn Val Thr<br>                    485                    490                    495 | 1488 |
| gtg acc ttc tca gga cag tat aat atc tcc tgg cgc tca gat tac gaa<br>Val Thr Phe Ser Gly Gln Tyr Asn Ile Ser Trp Arg Ser Asp Tyr Glu<br>                     500                    505                    510 | 1536 |
| gac cct gcc ttc tac atg ctg aag ggc aag ctt cag tat gag ctg cag<br>Asp Pro Ala Phe Tyr Met Leu Lys Gly Lys Leu Gln Tyr Glu Leu Gln<br>              515                    520                    525 | 1584 |
| tac agg aac cgg gga gac ccc tgg gct gtg agt ccg agg aga aag ctg<br>Tyr Arg Asn Arg Gly Asp Pro Trp Ala Val Ser Pro Arg Arg Lys Leu<br>530                    535                    540 | 1632 |
| atc tca gtg gac tca aga agt gtc tcc ctc ctc ccc ctg gag ttc cgc<br>Ile Ser Val Asp Ser Arg Ser Val Ser Leu Leu Pro Leu Glu Phe Arg<br>545                    550                    555                    560 | 1680 |
| aaa gac tcg agc tat gag ctg cag gtg cgg gca ggg ccc atg cct ggc<br>Lys Asp Ser Ser Tyr Glu Leu Gln Val Arg Ala Gly Pro Met Pro Gly<br>                    565                    570                    575 | 1728 |
| tcc tcc tac cag ggg acc tgg agt gaa tgg agt gac ccg gtc atc ttt<br>Ser Ser Tyr Gln Gly Thr Trp Ser Glu Trp Ser Asp Pro Val Ile Phe | 1776 |

-continued

```
                     580                 585                 590
      cag acc cag tca gag gag tta aag gaa ggc tgg aac cct cac tag      1821
      Gln Thr Gln Ser Glu Glu Leu Lys Glu Gly Trp Asn Pro His
              595                 600                 605
```

<210> SEQ ID NO 97
<211> LENGTH: 606
<212> TYPE: PRT
<213> ORGANISM: Artificial Sequence
<220> FEATURE:
<223> OTHER INFORMATION: MBP-zalpha11 soluble receptor polypeptide sequence

<400> SEQUENCE: 97

```
Met Lys Ile Glu Glu Gly Lys Leu Val Ile Trp Ile Asn Gly Asp Lys
 1               5                  10                  15

Gly Tyr Asn Gly Leu Ala Glu Val Gly Lys Lys Phe Glu Lys Asp Thr
             20                  25                  30

Gly Ile Lys Val Thr Val Glu His Pro Asp Lys Leu Glu Glu Lys Phe
         35                  40                  45

Pro Gln Val Ala Ala Thr Gly Asp Gly Pro Asp Ile Ile Phe Trp Ala
     50                  55                  60

His Asp Arg Phe Gly Gly Tyr Ala Gln Ser Gly Leu Leu Ala Glu Ile
 65                  70                  75                  80

Thr Pro Asp Lys Ala Phe Gln Asp Lys Leu Tyr Pro Phe Thr Trp Asp
                 85                  90                  95

Ala Val Arg Tyr Asn Gly Lys Leu Ile Ala Tyr Pro Ile Ala Val Glu
            100                 105                 110

Ala Leu Ser Leu Ile Tyr Asn Lys Asp Leu Leu Pro Asn Pro Pro Lys
        115                 120                 125

Thr Trp Glu Glu Ile Pro Ala Leu Asp Lys Glu Leu Lys Ala Lys Gly
    130                 135                 140

Lys Ser Ala Leu Met Phe Asn Leu Gln Glu Pro Tyr Phe Thr Trp Pro
145                 150                 155                 160

Leu Ile Ala Ala Asp Gly Gly Tyr Ala Phe Lys Tyr Glu Asn Gly Lys
                165                 170                 175

Tyr Asp Ile Lys Asp Val Gly Val Asp Asn Ala Gly Ala Lys Ala Gly
            180                 185                 190

Leu Thr Phe Leu Val Asp Leu Ile Lys Asn Lys His Met Asn Ala Asp
        195                 200                 205

Thr Asp Tyr Ser Ile Ala Glu Ala Ala Phe Asn Lys Gly Glu Thr Ala
    210                 215                 220

Met Thr Ile Asn Gly Pro Trp Ala Trp Ser Asn Ile Asp Thr Ser Lys
225                 230                 235                 240

Val Asn Tyr Gly Val Thr Val Leu Pro Thr Phe Lys Gly Gln Pro Ser
                245                 250                 255

Lys Pro Phe Val Gly Val Leu Ser Ala Gly Ile Asn Ala Ala Ser Pro
            260                 265                 270

Asn Lys Glu Leu Ala Lys Glu Phe Leu Glu Asn Tyr Leu Leu Thr Asp
        275                 280                 285

Glu Gly Leu Glu Ala Val Asn Lys Asp Lys Pro Leu Gly Ala Val Ala
    290                 295                 300

Leu Lys Ser Tyr Glu Glu Leu Ala Lys Asp Pro Arg Ile Ala Ala
305                 310                 315                 320

Thr Met Glu Asn Ala Gln Lys Gly Glu Ile Met Pro Asn Ile Pro Gln
                325                 330                 335
```

```
Met Ser Ala Phe Trp Tyr Ala Val Arg Thr Ala Val Ile Asn Ala Ala
            340                 345                 350

Ser Gly Arg Gln Thr Val Asp Glu Ala Leu Lys Asp Ala Gln Thr Asn
        355                 360                 365

Ser Ser Ser His His His His His His Ala Asn Ser Val Pro Leu Val
    370                 375                 380

Pro Arg Gly Ser Cys Pro Asp Leu Val Cys Tyr Thr Asp Tyr Leu Gln
385                 390                 395                 400

Thr Val Ile Cys Ile Leu Glu Met Trp Asn Leu His Pro Ser Thr Leu
                405                 410                 415

Thr Leu Thr Trp Gln Asp Gln Tyr Glu Glu Leu Lys Asp Glu Ala Thr
            420                 425                 430

Ser Cys Ser Leu His Arg Ser Ala His Asn Ala Thr His Ala Thr Tyr
        435                 440                 445

Thr Cys His Met Asp Val Phe His Phe Met Ala Asp Asp Ile Phe Ser
    450                 455                 460

Val Asn Ile Thr Asp Gln Ser Gly Asn Tyr Ser Gln Glu Cys Gly Ser
465                 470                 475                 480

Phe Leu Leu Ala Glu Ser Ile Lys Pro Ala Pro Phe Asn Val Thr
                485                 490                 495

Val Thr Phe Ser Gly Gln Tyr Asn Ile Ser Trp Arg Ser Asp Tyr Glu
            500                 505                 510

Asp Pro Ala Phe Tyr Met Leu Lys Gly Lys Leu Gln Tyr Glu Leu Gln
        515                 520                 525

Tyr Arg Asn Arg Gly Asp Pro Trp Ala Val Ser Pro Arg Arg Lys Leu
    530                 535                 540

Ile Ser Val Asp Ser Arg Ser Val Ser Leu Leu Pro Leu Glu Phe Arg
545                 550                 555                 560

Lys Asp Ser Ser Tyr Glu Leu Gln Val Arg Ala Gly Pro Met Pro Gly
                565                 570                 575

Ser Ser Tyr Gln Gly Thr Trp Ser Glu Trp Ser Asp Pro Val Ile Phe
            580                 585                 590

Gln Thr Gln Ser Glu Glu Leu Lys Glu Gly Trp Asn Pro His
        595                 600                 605

<210> SEQ ID NO 98
<211> LENGTH: 65
<212> TYPE: DNA
<213> ORGANISM: Artificial Sequence
<220> FEATURE:
<223> OTHER INFORMATION: Oligonucleotide primer ZC20187

<400> SEQUENCE: 98
tcaccacgcg aattcggtac cgctggttcc gcgtggatcc tgccccgacc tcgtctgcta    60
caccg                                                                65

<210> SEQ ID NO 99
<211> LENGTH: 68
<212> TYPE: DNA
<213> ORGANISM: Artificial Sequence
<220> FEATURE:
<223> OTHER INFORMATION: Oligonucleotide primer ZC20185

<400> SEQUENCE: 99
tctgtatcag gctgaaaatc ttatctcatc cgccaaaaca ctagtgaggg ttccagcctt    60
cctttaac                                                             68
```

```
<210> SEQ ID NO 100
<211> LENGTH: 21
<212> TYPE: DNA
<213> ORGANISM: Artificial Sequence
<220> FEATURE:
<223> OTHER INFORMATION: Oligonucleotide primer ZC22452

<400> SEQUENCE: 100
tcttcttggg gacactggtc c                                              21

<210> SEQ ID NO 101
<211> LENGTH: 21
<212> TYPE: DNA
<213> ORGANISM: Artificial Sequence
<220> FEATURE:
<223> OTHER INFORMATION: Oligonucleotide primer ZC22451

<400> SEQUENCE: 101
aatcatgtgg cgatcttgac c                                              21

<210> SEQ ID NO 102
<211> LENGTH: 21
<212> TYPE: DNA
<213> ORGANISM: Artificial Sequence
<220> FEATURE:
<223> OTHER INFORMATION: Oligonucleotide primer ZC22450

<400> SEQUENCE: 102
cagactaaca tgcccttcat g                                              21

<210> SEQ ID NO 103
<211> LENGTH: 23
<212> TYPE: DNA
<213> ORGANISM: Artificial Sequence
<220> FEATURE:
<223> OTHER INFORMATION: Oligonucleotide primer ZC22449

<400> SEQUENCE: 103
ttcacttccg tgtgttctag agg                                            23

<210> SEQ ID NO 104
<211> LENGTH: 18
<212> TYPE: DNA
<213> ORGANISM: Artificial Sequence
<220> FEATURE:
<223> OTHER INFORMATION: Oligonucleotide primer ZC23771

<400> SEQUENCE: 104
accaccttcc acaaatgc                                                  18

<210> SEQ ID NO 105
<211> LENGTH: 1347
<212> TYPE: DNA
<213> ORGANISM: Homo sapiens

<400> SEQUENCE: 105
gaattcaccc attctctctt tttcctgtca aagatgcaga tggggcacat ttcgttgact     60
ccatcaatcc ctgccccac acattagcac atgcacacgt ataccctagcc agtggaaaag    120 aaaaaagagt tactcacatt catccatttt acaaagattt ccaggctgca atgggagggc   180
tttacctctc cctgaaggat gaataaatag gtagcttaac tgacaacctg ttctcagtca   240
agctgaagtg aaaacgagac caaggtctag ctctactgtt ggtacttatg agatccagtc   300
```

```
ctggcaacat ggagaggatt gtcatctgtc tgatggtcat cttcttgggg acactggtcc      360
acaaatcaag ctcccaaggt caagatcgcc acatgattag aatgcgtcaa cttatagata      420
ttgttgatca gctgaaaaat tatgtgaatg acttggtaag actatatttg tcacaacaaa      480
atctaaatca tacttttcaa ttaatataaa aggagggttt ggcttataaa aataactcag      540
aacaaatttt cttttgctct aggtccctga atttctgcca gctccagaag atgtagaggt      600
aagaccagtt gaatttattt ctgaaaatac attggacata agttttttaaa tccaataaga     660 aagacattag catgattata taggagtata ctgaattttta atgaacttag cggtctaata     720
attgatgaaa tatttatttta tattttggtt aaattcattg atttaccaaa aaccaactaa    780
aaaatgctat attatattcc tcataaacta tgtttatctt caagaatctc taagagtact      840
cctaagtagt attgctgaga cagaataaca aaactagaaa cgaaatctat actctgatca      900
gtttctgaac aatgcacagc tagttactct ttaagagccc ttgggcatga aagcttttga      960
gccttctttg ttatcctacc gaagaaacat agatacatac agtaggaagc agaattaacc     1020
ttttaataac aaacttaaaa aagaaagaaa gaaagaatta gattacaggg acagcatgga     1080
gaaatggtgg tgtggaaatc aaagctgtcc tttagaatat aattcacata accttggcc      1140 tcagtgagtc ttgtctttgg ccttccgtga ggtcttttga aagaaccatt ttcaacaatt     1200
catcccgtct cttaagccat ttaaatccat tagagttcca ggaagaagag gcctggcatg     1260
agttcagagt gctgtcccgc tgatcttttt ctcagtaact tctacgatct gatcttctgg     1320
tctggtaccc tgaggtataa atgcaat                                          1347

<210> SEQ ID NO 106
<211> LENGTH: 1656
<212> TYPE: DNA
<213> ORGANISM: Homo sapiens

<400> SEQUENCE: 106
cctcaactgc ttgattcagg cagaatccta accctaaact gagctgggag tatgaaaagg       60
gttttagaaa agtcatggtg tgatctatgg caagtatatt gattcttaga tgtaaaatat      120
gctatcagag ggaggtaccc acttcctttc tccaaaggag gggctttaat tcattttctt      180
catctgttaa ctttacaaat atatgttgat cattaactgg caagacacta tgcctggcgc      240
tgtacagaat aaaatgctgc tcaagacatg tcatgataga tacattaaca gaaaccacaa      300
acaaatgaaa aatgttcttc atcagactat aacataattt acccaaagct gccactagtc      360
acagtgtaag ttttagagcc tcataactca gcaaatgtgt cctaaaccga actaactctc      420
ctttataaaa cacaaggtc ttgtccacca cccagacatc aaaatggtcc tctgtgtagc       480
atcaggaata aagcattgtg aagaagtgag gctcctttct ctcttatctg cgaagcaggg     540
gattgtccct ttttcccatc ccaaagatta agtaggaggt gaaatcatac ctcactcatc      600
tgttgaaacg atgtaatgca cgacattgca gaagagatag aaatagagga ttgggaaagc     660 tatctttttac tttctgaata atgtttgtta acatatatac aaattgttta tctttcagac    720
aaactgtgag tggtcagctt tttcctgttt tcagaaggcc caactaaagt cagcaaatac     780
aggaaacaat gaaaggataa taaatgtatc aattaaaaag ctgaagagga aaccaccttc    840
cacaaatgca gggagaagac agaaacacag actagtaaga ttgtcatttg tcatctctct    900
tatttgtact tataaactat atatcttgca ttacataaac atacacacac acctgtagcc     960
agggctgctg gtgtcttcct tacctatagt tatgccttat tatacatggt gcttttttt     1020
tttaagacag agtctcactc tgtcacccag gctggagtgc agtggcgtga tctctgctca     1080
ccgcaagatc cacctcccgg tttcacgcca ttctcctcct acctcagcct cctgagtacc     1140
```

-continued

```
tgggactaca ggtgcccgcc accatgcccg gctaattttg ttttttgtatt tttagtaaag   1200
acagggtttc accatgttag ccaggatggt ctcgatctcc tgaccccgtg atccgcccgc   1260
cttggcctcc caaagtgtgg ggattacagg catgagccac cgcacccggc ctacgtgtgg   1320
tgcattttaa gaagtagggt cactctttta agcccacaga cttgaaagta ttcaaaaacc   1380
caattataat ttcctagtag tccttggcag ctgaatatg ttaatatagc ttctcaaggt   1440
gaggaagtca ttaggcagag aatccaactg tgatttggga gttaagaact atttcctctc   1500
atatggtcac agataacttg tattcttatt aacaggagct agatcctagc tttctaacaa   1560
gaaaagagcc tacaagaaga ctagggcaaa tcttaaactt tgcctcctct ctaaatcata   1620
ttactatctg tacatcagca gagtcagtat tgaatt                             1656
```

<210> SEQ ID NO 107
<211> LENGTH: 644
<212> TYPE: DNA
<213> ORGANISM: Homo sapiens

<400> SEQUENCE: 107

```
agctaaactt agaactctcc agttaagcat gttcatctta tagatgagga aaagtgagat    60
ctacaaagga gttaagtcac tagccccaag ttccataaat agtgtcagaa tgagaattag   120
aacgtatatc tactatcttt tagtgaaatg ctctcactac aacatcacac tggcattgag   180
atgctaacta ccaagcaatg gcttggtgtt tggatctaaa tagggataaa gacaaagagc   240
ataaactaag aaagcttttt aaaaatctaa gtgagcaatc catatatgaa aaactgttca   300
atctccctag taatcacata aatgcgagtt aaaacaagga aatcctgttt tttccaatta   360
aacatttttaa acaatacct ataataataa gaatgctcca agtgaaaaga gtaaaaccc   420
tttataatgt atatcaaagc cttaaaattt ttatccctttt aatttagtaa ttctacttct   480
aggaatatat caaataagca aagatatata tgaaaaatta tttacagaga tgttctttgg   540
agtaatgtag acaaaaataa aaagttagat acagctgggt gtggtggctc atgcctgtat   600
tcccagcact ttgggaggcc gaggcaggcg gatcacctga gatc                    644
```

<210> SEQ ID NO 108
<211> LENGTH: 645
<212> TYPE: DNA
<213> ORGANISM: Homo sapiens
<220> FEATURE:
<221> NAME/KEY: misc_feature
<222> LOCATION: (1)...(645)
<223> OTHER INFORMATION: n = A,T,C or G

<400> SEQUENCE: 108

```
aaaaaaaaaa aaaaaaaaaa gttagatgca ccnttgggtc caaaaatagt aagagtgcat    60
cctatgtgga aacagaccaa ccactacatg tcatattttt gaagattatt taacacttag   120
gaaatcctgt gatatgttaa gtgtgaaaaa aaaaagcaa atcaccaact ggtataaata   180
atgtaaatgc acaataataa ttaaaaatac ccaaaacaca gagagaatat acattaaaac   240
attgcagtgg gattcctatc tctgggaatg ggattacaag gacttttttcc attgttactt   300 tccaaacagt tttatgtact tctcgaatgt ttttcagtga acataattta tgttttaat    360 gaaaaaaat tttaagaaac attttattac gaaaaaaatt ttaaagaaga ctgttacttt   420
ttcattgatt tctagacatg cccttcatgt gattcttatg agaaaaaacc acccaaagaa   480
ttcctagaaa gattcaaatc acttctccaa aaggtatcta ccttaagttt catttgattt   540
tctgctttat ctttacctat ccagatttgc ttccttagtta ctcacggtat actatttcca   600
cagatgattc atcagcatct gtcctctaga acacacggaa gtgaa                   645
```

<210> SEQ ID NO 109
<211> LENGTH: 36
<212> TYPE: DNA
<213> ORGANISM: Artificial Sequence
<220> FEATURE:
<223> OTHER INFORMATION: Oligonucleotide primer ZC25970

<400> SEQUENCE: 109

```
atgcattcta gactaggaga gatgctgatg aatcat                              36
```

<210> SEQ ID NO 110
<211> LENGTH: 36

```
<212> TYPE: DNA
<213> ORGANISM: Artificial Sequence
<220> FEATURE:
<223> OTHER INFORMATION: Oligonucleotide primer ZC25969

<400> SEQUENCE: 110
atgcattccg gacataaatc aagcccccaa gggcca                              36

<210> SEQ ID NO 111
<211> LENGTH: 153
<212> TYPE: PRT
<213> ORGANISM: Homo sapiens

<400> SEQUENCE: 111
```

Met Tyr Arg Met Gln Leu Leu Ser Cys Ile Ala Leu Ser Leu Ala Leu
1               5                   10                  15

Val Thr Asn Ser Ala Pro Thr Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
50                  55                  60

Tyr Met Pro Lys Lys Ala Thr Glu Leu Lys His Leu Gln Cys Leu Glu
65                  70                  75                  80

Glu Glu Leu Lys Pro Leu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150

```
<210> SEQ ID NO 112
<211> LENGTH: 153
<212> TYPE: PRT
<213> ORGANISM: Homo sapiens

<400> SEQUENCE: 112
```

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
    50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95

Phe His Arg His Lys Gln Leu Ile Arg Phe Leu Lys Arg Leu Asp Arg
            100                 105                 110

Asn Leu Trp Gly Leu Ala Gly Leu Asn Ser Cys Pro Val Lys Glu Ala
        115                 120                 125

Asn Gln Ser Thr Leu Glu Asn Phe Leu Glu Arg Leu Lys Thr Ile Met
            130                 135                 140

Arg Glu Lys Tyr Ser Lys Cys Ser Ser
145                 150

<210> SEQ ID NO 113
<211> LENGTH: 162
<212> TYPE: PRT
<213> ORGANISM: Homo sapiens

<400> SEQUENCE: 113

Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140

Lys Glu Phe Leu Gln Ser Phe Val His Ile Val Gln Met Phe Ile Asn
145                 150                 155                 160

Thr Ser

<210> SEQ ID NO 114
<211> LENGTH: 144
<212> TYPE: PRT
<213> ORGANISM: Homo sapiens

<400> SEQUENCE: 114

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Arg Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu 130                 135                 140

<210> SEQ ID NO 115
<211> LENGTH: 538
<212> TYPE: PRT
<213> ORGANISM: Homo sapiens

<400> SEQUENCE: 115

Met Pro Arg Gly Trp Ala Ala Pro Leu Leu Leu Leu Leu Gln Gly
1               5                   10                  15

Gly Trp Gly Cys Pro Asp Leu Val Cys Tyr Thr Asp Tyr Leu Gln Thr
                20                  25                  30

Val Ile Cys Ile Leu Glu Met Trp Asn Leu His Pro Ser Thr Leu Thr
            35                  40                  45

Leu Thr Trp Gln Asp Gln Tyr Glu Glu Leu Lys Asp Glu Ala Thr Ser
    50                  55                  60

Cys Ser Leu His Arg Ser Ala His Asn Ala Thr His Ala Thr Tyr Thr
65                  70                  75                  80

Cys His Met Asp Val Phe His Phe Met Ala Asp Ile Phe Ser Val
                85                  90                  95

Asn Ile Thr Asp Gln Ser Gly Asn Tyr Ser Gln Glu Cys Gly Ser Phe
                100                 105                 110

Leu Leu Ala Glu Ser Ile Lys Pro Ala Pro Phe Asn Val Thr Val
            115                 120                 125

Thr Phe Ser Gly Gln Tyr Asn Ile Ser Trp Arg Ser Asp Tyr Glu Asp
    130                 135                 140

Pro Ala Phe Tyr Met Leu Lys Gly Lys Leu Gln Tyr Glu Leu Gln Tyr
145                 150                 155                 160

Arg Asn Arg Gly Asp Pro Trp Ala Val Ser Pro Arg Arg Lys Leu Ile
                165                 170                 175

Ser Val Asp Ser Arg Ser Val Ser Leu Leu Pro Leu Glu Phe Arg Lys
                180                 185                 190

Asp Ser Ser Tyr Glu Leu Gln Val Arg Ala Gly Pro Met Pro Gly Ser
                195                 200                 205

Ser Tyr Gln Gly Thr Trp Ser Glu Trp Ser Asp Pro Val Ile Phe Gln
    210                 215                 220

Thr Gln Ser Glu Glu Leu Lys Glu Gly Trp Asn Pro His Leu Leu Leu
225                 230                 235                 240

Leu Leu Leu Leu Val Ile Val Phe Ile Pro Ala Phe Trp Ser Leu Lys
                245                 250                 255

Thr His Pro Leu Trp Arg Leu Trp Lys Lys Ile Trp Ala Val Pro Ser
                260                 265                 270

Pro Glu Arg Phe Phe Met Pro Leu Tyr Lys Gly Cys Ser Gly Asp Phe
            275                 280                 285

Lys Lys Trp Val Gly Ala Pro Phe Thr Gly Ser Ser Leu Glu Leu Gly
            290                 295                 300

Pro Trp Ser Pro Glu Val Pro Ser Thr Leu Glu Val Tyr Ser Cys His
305                 310                 315                 320

Pro Pro Arg Ser Pro Ala Lys Arg Leu Gln Leu Thr Glu Leu Gln Glu
                325                 330                 335

Pro Ala Glu Leu Val Glu Ser Asp Gly Val Pro Lys Pro Ser Phe Trp
                340                 345                 350

Pro Thr Ala Gln Asn Ser Gly Gly Ser Ala Tyr Ser Glu Glu Arg Asp
                355                 360                 365

-continued

```
Arg Pro Tyr Gly Leu Val Ser Ile Asp Thr Val Thr Val Leu Asp Ala
    370                 375                 380

Glu Gly Pro Cys Thr Trp Pro Cys Ser Cys Glu Asp Asp Gly Tyr Pro
385                 390                 395                 400

Ala Leu Asp Leu Asp Ala Gly Leu Glu Pro Ser Pro Gly Leu Glu Asp
                405                 410                 415

Pro Leu Leu Asp Ala Gly Thr Thr Val Leu Ser Cys Gly Cys Val Ser
            420                 425                 430

Ala Gly Ser Pro Gly Leu Gly Gly Pro Leu Gly Ser Leu Leu Asp Arg
        435                 440                 445

Leu Lys Pro Pro Leu Ala Asp Gly Glu Asp Trp Ala Gly Gly Leu Pro
    450                 455                 460

Trp Gly Gly Arg Ser Pro Gly Gly Val Ser Glu Ser Glu Ala Gly Ser
465                 470                 475                 480

Pro Leu Ala Gly Leu Asp Met Asp Thr Phe Asp Ser Gly Phe Val Gly
                485                 490                 495

Ser Asp Cys Ser Ser Pro Val Glu Cys Asp Phe Thr Ser Pro Gly Asp
            500                 505                 510

Glu Gly Pro Pro Arg Ser Tyr Leu Arg Gln Trp Val Val Ile Pro Pro
        515                 520                 525

Pro Leu Ser Ser Pro Gly Pro Gln Ala Ser
    530                 535
```

What is claimed is:

1. A fusion protein comprising a first polypeptide comprising a sequence of amino acid residues that is at least 90% identical to residues 41 to 148 of SEQ ID NO:2 and comprising a second GMCSF polypeptide as shown in SEQ ID NO:114 or fragment thereof, wherein the fusion protein binds the receptor as shown in SEQ ID NO:115.

2. The fusion protein of claim 1, wherein the first polypeptide is of at least 95% identity to residues 41 to 148 of SEQ ID NO:2.

3. The fusion protein of claim 1, wherein the first polypeptide comprises amino acid residues 41 to 148 of SEQ ID NO:2.

4. A fusion protein comprising a first polypeptide comprising amino acid residues 32 to 162 of SEQ ID NO:2 and comprising a second GMSCF polypeptide as shown in SEQ ID NO:114 or fragment thereof, wherein the fusion protein binds the receptor as shown in SEQ ID NO:115.

* * * * *